US006613743B2

(12) United States Patent
Hale et al.

(10) Patent No.: US 6,613,743 B2
(45) Date of Patent: Sep. 2, 2003

(54) SULFONAMIDE INHIBITORS OF ASPARTYL PROTEASE

(75) Inventors: Michael Robin Hale, Bedford, MA (US); Clarence Webster Andrews, III, Durham, NC (US); Eric Steven Furfine, Durham, NC (US); Ronald George Sherrill, Cary, NC (US); Andrew Spaltenstein, Raleigh, NC (US); Gregory Thomas Lowen, Williamsburg, VA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/731,129

(22) Filed: Dec. 6, 2000

(65) Prior Publication Data

US 2002/0049201 A1 Apr. 25, 2002

Related U.S. Application Data

(63) Continuation of application No. PCT/US99/13744, filed on Jun. 17, 1999.
(60) Provisional application No. 60/090,094, filed on Jun. 19, 1998.

(51) Int. Cl.[7] ...................... C07C 303/00; A61K 31/18; A61P 31/18

(52) U.S. Cl. .................. 514/12; 514/120; 514/221; 514/263.38; 514/274; 514/233.8; 514/314; 514/357; 514/367; 514/38; 514/387; 514/403; 514/452; 514/456; 514/465; 514/471; 544/168; 546/169; 546/355; 548/163; 548/164; 548/306.4; 548/307.7; 548/309.1; 548/311.2; 548/362.1; 548/362.5; 549/220; 549/366; 549/372; 549/396; 549/414; 549/464; 549/475

(58) Field of Search ............... 514/233.8, 314, 514/357, 367, 381, 387, 403, 452, 456, 465, 471; 544/168; 546/169, 355; 548/163, 164, 306.4, 307.7, 308.1, 311.2, 362.1, 362.5; 549/220, 366, 372, 396, 414, 464, 475

(56) References Cited

U.S. PATENT DOCUMENTS

| | | |
|---|---|---|
| 3,743,722 A | 7/1973 | Mohrs et al. .................. 424/98 |
| 4,330,542 A | 5/1982 | Descamps et al. ........ 424/248.5 |
| 4,629,724 A | 12/1986 | Ryono et al. .................. 514/18 |
| 5,196,438 A | 3/1993 | Martin et al. ............... 514/311 |
| 5,354,866 A | 10/1994 | Kempf et al. ............... 546/265 |
| 5,622,949 A | 4/1997 | Talley et al. ............. 514/237.8 |
| 5,723,490 A | 3/1998 | Tung ......................... 514/478 |
| 5,744,481 A | 4/1998 | Vazquez et al. ............ 514/311 |
| 5,843,946 A | 12/1998 | Vazquez et al. ....... 514/252.11 |

FOREIGN PATENT DOCUMENTS

| | | |
|---|---|---|
| DE | 3542567 | 6/1986 |
| EP | 0 022 118 | 1/1981 |
| EP | 0 181 071 | 5/1986 |
| EP | 0 264 795 | 4/1988 |
| EP | 0 346 847 | 12/1989 |
| EP | 0 364 804 | 4/1990 |
| EP | 0 434 365 | 6/1991 |
| EP | 0 468 641 | 1/1992 |
| EP | 0 486 948 | 5/1992 |
| EP | 0 541 168 | 5/1993 |
| EP | 0 594 540 | 4/1994 |
| GB | 2167759 | 6/1986 |
| GB | 2200115 | 7/1988 |
| JP | 59-46252 | 3/1984 |
| JP | 59-48449 | 3/1984 |
| JP | 61-71830 | 4/1986 |
| WO | WO90/07329 | 7/1990 |
| WO | WO91/00725 | 1/1991 |
| WO | WO91/18866 | 12/1991 |
| WO | WO92/08688 | 5/1992 |
| WO | WO92/08698 | 5/1992 |
| WO | WO92/08699 | 5/1992 |
| WO | WO92/08700 | 5/1992 |

(List continued on next page.)

OTHER PUBLICATIONS

Thompson, L.A. etal, Ann, Reports Med. Chem., 36, 247–257, 2001.*
Polman, C.H. et al, BMJ 2000, 321, 490–4.*

(List continued on next page.)

*Primary Examiner*—Richard L. Raymond
*Assistant Examiner*—Thomas McKenzie
(74) *Attorney, Agent, or Firm*—Fish & Neave; James F. Haley, Jr.; Min Wang

(57) ABSTRACT

The present invention relates to a novel class of sulfonamides of formula I which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity. The sulfonamides of formula I have the structure:

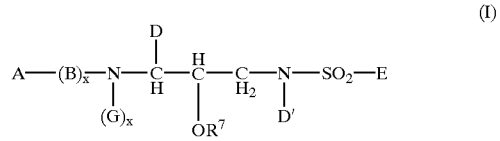

(I)

wherein A, B, D, D', E, G and R[7] are as defined above.

25 Claims, No Drawings

FOREIGN PATENT DOCUMENTS

| | | |
|---|---|---|
| WO | WO92/08701 | 5/1992 |
| WO | WO92/17176 | 10/1992 |
| WO | WO93/23368 | 11/1993 |
| WO | WO93/23379 | 11/1993 |
| WO | WO93/23388 | 11/1993 |
| WO | WO94/04491 | 3/1994 |
| WO | WO94/04492 | 3/1994 |
| WO | WO94/04493 | 3/1994 |
| WO | WO94/05639 | 3/1994 |
| WO | WO94/10134 | 5/1994 |
| WO | WO94/10136 | 5/1994 |
| WO | WO94/18192 | 8/1994 |
| WO | WO94/19322 | 9/1994 |
| WO | WO95/06030 | 3/1995 |
| WO | WO95/07269 | 3/1995 |
| WO | WO95/09843 | 4/1995 |
| WO | WO95/14016 | 5/1995 |
| WO | WO95/32185 | 11/1995 |
| WO | WO96/33184 | 10/1996 |
| WO | WO96/33187 | 10/1996 |
| WO | WO 2000/76961 A1 * | 12/2000 |

OTHER PUBLICATIONS

Cohen, J.A. et al, J. Neuroimmun., 1999, 98 29–36.*

Menendez–Arias et al., "Moloney Murine Leukemia Virus Protease: Bacterial Expression and Characterization of the Purified Enzyme, " *Virology* , 1996, pp. 557–563 (1993).

Berger et al., "Multiple–sclerosis–like Illness Occurring with Human Immunodeficiency Virus Infection, " *Neurology*, 39 , pp. 324–329 (1989).

Facchini et al., "Human Immunodeficiency Virus–1 Infection and Multiple Sclerosis–like Illness in a Child," *Pediatr. Neurol.*, 26, pp. 231–235 (2002).

Banker et al., *Modern Pharmaceutics*, pp. 627–629 (1996).

R. Bone et al., "X–ray Crystal Structure of the HIV Protease complex with L–700,417, an Inhibitor with Pseudo $C_2$ Symmetry ", *J. Am. Chem. Soc.* , 113, pp. 9382–9384 (1991).

J.C. Craig et al., "Antiviral Synergy Between Inhibitors of HIV Proteinase and Reverse Transcriptase",*Antiviral Chem. and Chemotherapy*, 4(3), pp. 161–166 (1990).

S. Crawford et al., "A Deletion Mutation in the 5' Part of the pol Gene of Moloney Murine Leukemia Virus Blocks Proteolytic Processing of the gag and pol Polyproteins ", *J. Virol.*, 53, pp. 899–907 (1985).

M. Cushman et al., "Delvelopment of Methodology for the Synthesis of Stereochemically Pure Pheψ[CH$_2$N]Pro Linkages in HIV Protease Inhibitors", *J. Org. Chem.*, 56, pp. 4161–4167 (1991).

D.S. Dhanoa et al., "The Synthesis of Potent Macrocyclic Renin Inhibitors", *Tetrahedron Lett.*, 33, pp. 1725–1728 (1992).

G.B. Dreyer et al., "Hydroxyethylene Isostere Inhibitors of Human Immunodeficiency Virus–1 Protease: Structure–Activity Analysis Using Enzyme Kinetics, X–ray Crystallography, and Infected T–Cell Assays", *Biochemistry*, 31, pp. 6646–6659 (1992).

G.A. Flynn et al., "An Acyl–Iminium Ion Cyclization Route to a Novel Conformationally Restricted Dipeptide Mimic: Applications to Angiotensin–Converting Enzyme Inhibition", *J. Am. Chem. Soc.*, 109, pp. 7914–7915 (1989).

G. Fontenot et al., "PCR Amplification of HIV–1 Proteinase Sequences Directly from Lab Isolates Allows Determination of Five Conserved Domains", *Virology*, 190, pp. 1–10 (1992).

J. Freskos et al., "(Hydroxyethyl)sulfonamide HIV–1 Protease Inhibitors: Indentification of the 2– Methylbenzoyl Moiety at P–2 ", *Bio. & Med. Chem. Lett.*, 6, pp. 445–450 (1996).

A. Ghosh et al., "Potent HIV Protease Inhibitors Incorporating High–Affinity $P_2$–Ligands and (R)–(Hydroxyethylamino)sulfonamide Isostere", *Bio. & Med. Chem. Lett.*, 8, pp. 687–690 (1998).

E.E. Gilbert, "Recent Developments in Preparative Sulfonation and Sulfation ", *Synthesis*, 1969, pp. 3–10 (1969).

A. Goldblum, "Modulation of the Affinity of Aspartic Proteases by the Mutated Residues in Active Site Models ", *FEBS*, 261, pp. 241–244 (1990).

D. Grobelny et al., "Selective Phosphinate Transition–State Analogue Inhibitors of the Protease of Human Immunodeficiency Virus", *Biochem. Biophys, Res. Commun.*, 169, pp. 1111–1116 (1990).

G. D. Hartman et al., "4–Substituted Thiophene– and Furan–2 sulfonamides as Topical Carbonic Anhydrase Inhibitors", *J. Med. Chem.*, 35, pp. 3822–3831 (1992).

S. J. Hays et al., "Synthesis of cis–4–(Phosphonooxy)–2–piperidinecarboxylic Acid, an N–Methyl–D–aspartate Antagonist", J. Org. Chem., 56, pp. 4984–4086 (1991).

J.R. Huff, "HIV Protease: A Novel Chemotherapeutic Target for AIDS", *Journal of medicinal Chemistry*, 34(8), pp. 2305–2314 (1991).

K.Y. Hui et al., "A Rational Approach in the Search for Potent Inhibitors Against HIV Proteinase", *FASEB*, 5, pp. 2606–2610 (1991).

Y. Kiso Et al., "O→N Intramolecular Acyl Migration'–type Prodrugs of Tripeptide Inhibitors of HIV Protease", *Peptides: Chemistry, Structure and Biology*, 61, pp. 157–159 (1996.)

N.E. Kohl Et al., "Active HIV Protease Is Required for Viral Infectivity", *Proc. Natl. Acad. Sci. USA*, 85, pp. 4686–4690 (1988).

X. Lin et al., "Enzymic Activities of Two–Chain Pepsinogen, Two–Chain Pepsin, and the Amino– Terminal Lobe of Pepsinogen", *J. Biol. Chem.*, 267(24), pp. 17257–17263 (1992).

K.P. Manfredi et al., "Examination of HIV–1 Protease Secondary Structure Specificity Using Conformationally Constrained Inhibitors", *J. Med. Chem.*, 34, pp. 3395–3399 (1991).

G.R. Marshall, "Computer–Aided Drug Design ", *Ann. Ref. Pharmacol. Toxicol.*, 27, pp. 193–213 (1987).

J.A. Martin, "Recent Advances in the Design of HIV Proteinase Inhibitors", *Antiviral Research*, 17 pp. 265–278 (1992).

T.D. Meek et al., "Inhibition of HIV–1 Protease in Infected T–Lymphocytes by Synthetic Peptide Analogues", *Nature*, 343, pp. 90–92 (1990).

M. Miller et al., "Structure of Complex of Synthetic HIV–1 Protease with a Substrate–Based Inhibitor at 2.3 Å Resolution", *Science*, 246, pp. 1149–1152 (1989).

M. Miller et al., "Crystal Structure of a Retroviral Protease Proves Relationship to Aspartic Protease Family", *Nature*, 337, pp. 576–576 (1989).

K.H.M. Murthy et al., "The Crystal Structures at 2.2–Å Resolution of Hydroxyethylene–Based Inhibitors Bound to Human Immunodeficiency Virus type 1 Protease Show That the Inhibitors Are Present in Two Distinct Orientations", *J. Biol. Chem.*, 267, pp. 22770–22778 (1992).

J.B. Nichols et al., "A Molecular Mechnics Valence Force Field for Sulfonamides Derived by *ab initio* Methods", *J. Phys, Chem.*, 95, pp. 9803–9811 (1991).

J. Palca, "Shooting at a New HIV Target", *Science*, 247, p. 410 (1990).

L.H. Pearl et al., "A Structural Model for the Retroviral Proteases ", *Nature*, 329, pp. 329–351 (1987).

J.W. Percih et al., "The Synthesis of Multiple O–Phosphoseryl–Containing Peptides via Phenyl Phosphate Protection", *J. Org. Chem.*, 53, pp. 4103–4105 (1988).

M.S. Plummer et al., "Design of Peptidomimetic Ligands for the pp60$^{src}$ SH2 Domain", *Bioorganic* & Medicinal Chemistry, 5, pp. 41–47 (1997).

M. Popvic et al., "Detection, Isolation, and Continuous Production of Cytopathic Retroviruses (HTLV–III) from Patients with AIDS and Pre–AIDS", *Science*, 224, pp. 497–500(1984).

M.D. Power et al., "Nucleotide Sequence of SRV–1, a Type D Simian Acquired Immune Deficiency Syndrome Retrovirus", *Science* , 231, pp. 1567–1573 (1986).

N.A. Roberts, "Rational Design of Peptide–Based HIV Proteinase Inhibitors", *Science*, 248, pp. 358–361 (1990).

S. Scharpe et al., "Proteases and Their Inhibitors: Today and Tomorrow", *Biochimie*, 73, pp. 131–126 (1991).

S.K. Sharma et al., "Could Angiotensin I Be Produced from a Renin Substrate by the HIV–1 Protease?", *Anal. Biochem.*, 198, pp. 363–367 (1991).

S. Yamaguchi et al., "Synthesis of HIV Protease Dipeptide Inhibitors and Prodrugs", *Peptide Chemistry 1996* , pp. 297–300 (1997).

* cited by examiner

SULFONAMIDE INHIBITORS OF ASPARTYL PROTEASE

CROSS-REFERENCE TO RELATED APPLICATIONS

This application is a continuing application of co-pending International patent application PCT/US99/13744, filed Jun. 17, 1999, designating the United States, which claims priority from United States provisional patent application No. 60/090,094, filed Jun. 19, 1998.

TECHNICAL FIELD OF THE INVENTION

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARdfgC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", *Nature*, pp. 329–351 (1987); M.D. Power et al., "Nucleotide Sequence of SRV-1, a Type D Simian Acquired Immune Deficiency Syndrome Retrovirus", *Science*, 231, p. 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aqulia, "Therapy for Human Immunodeficiency Virus Infection", *New Eng. J. Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration.

Accordingly, the need still exists for compounds that can effectively inhibit the action of viral proteases, for use as agents for preventing and treating chronic and acute viral infections.

SUMMARY OF THE INVENTION

The present invention provides a novel class of compounds, and pharmaceutically acceptable derivatives thereof, that are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ T-cells. These compounds are useful as therapeutic and prophylactic agents to treat or prevent infection by HIV-1 and related viruses which may result in a symptomatic infection, AIDS-related complex ("ARC"), acquired immunodeficiency syndrome ("AIDS"), or similar disease of the immune system.

It is a principal object of this invention to provide a novel class of sulfonamides which are aspartyl protease inhibitors, and particularly, HIV aspartyl protease inhibitors. The novel sulfonamides of this invention are those of formula I:

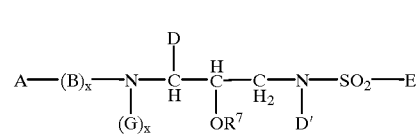

(I)

wherein:

A is selected from H; Ht; —$R^1$—Ht; —$R_1$—C—$C_6$ alkyl, which is optionally substituted with one or more groups independently selected from hydroxy, $C_1$–$C_4$ alkoxy, Ht, —O—Ht, —$NR_1$—CO—$N(R^2)_2$ or —CO—$N(R^2)$ 2; —$R^1$—$C_2$—$C_6$ alkenyl, which is optionally substituted with one or more groups independently selected from hydroxy, $C_1$—$C_4$ alkoxy, Ht, —O—Ht, —$NR^2$—CO—$N(R^2)_2$ or —CO—$N(R^2)_2$; or $R^7$;

each $R^1$ is independently selected from —C(O)—, —$S(O)_2$—, —C(O)—C(O)—, —O—C(O)—, —O—$S(O)_2$, —$NR^2$—$S(O)_2$, —$NR^2$—C(O)— or —$NR^2$—C(O)—C(O)—;

each Ht is independently selected from $C_3$—C— cycloalkyl; $C_5$—$C_7$ cycloalkenyl; $C_6$-$C_{14}$ aryl; or a 5–7 membered saturated or unsaturated heterocycle, containing one or more heteroatoms selected from N, $N(R^2)$, O, S and $S(O)_n$; wherein said aryl or said heterocycle is optionally fused to Q; and wherein any member of said Ht is optionally substituted with one or more substituents independently selected from oxo, —$OR^2$, $SR^2$, —R—, —$N(R^2)(R^2)$, —$R^2$—OH, —CN, —$CO_2R^2$, —C(O)—N $(R_2)_2$, —$S(O)_2$—N $(R^2)_2$, —$N(R^2)$—C(O)—$R^2$, —C(O)—$R^2$, —$S(O)_n$—$R^2$, —$OCF_3$, —$S(O)_n$—Q, methylenedioxy, —$N(R^2)$—S$(O)_2(R^2)$ halo, —$CF_3$, —$NO_2$, Q, —OQ, —$OR^7$, —$SR^7$, —$R^7$, —$N(R^2)(R^7)$ or —$N(R^7)_2$;

each $R^2$ is independently selected from H, or $C_1$—$C_6$ alkyl optionally substituted with Q or $R^{10}$;

B, when present, is —$N(R^2)$—$C(R^3)_2$—C(O)—;

each x is independently 0 or 1;

each $R^3$ is independently selected from H, Ht, $C_1$—$C_6$ alkyl, $C_2$—$C_6$ alkenyl, $C_3$—$C_6$ cycloalkyl or $C_5$—$C_6$ cycloalkenyl; wherein any member of said $R^3$, except H, is optionally substituted with one or more substituents selected from —$OR^2$, —C(O)—NH—$R^2$, —S(O)—N $(R^2)(R^2)$ Ht, —CN, —$SR^2$, —$CO_2R^2$, $NR^2$—C(O)—$R^2$;

each n is independently 1 or 2;

G, when present, is selected from H, $R^7$ or $C_1$—$C_4$ alkyl, or, when G is $C_1$-$C_4$ alkyl, G and $R^7$ are bound to one another either directly or through a $C_1$—$C_3$ linker to form a heterocyclic ring; or when G is not present (i.e., when x in $(G)_x$ is 0), then the nitrogen to which G is attached is bound directly to the $R^7$ group in —$OR^7$ with the concomitant displacement of one —ZM group from $R^7$;

D is selected from Q; $C_1$—$C_6$ alkyl, which is optionally substituted with one or more groups selected from $C_3$—$C_6$ cycloalkyl, —OR, —S—Ht, —$R^3$, —O—Q or Q; $C_2$—$C_4$ alkenyl, which is optionally substituted with one or more groups selected from —$OR^2$, —S—Ht, —$R^3$, —O—Q or Q; $C_3$—$C_6$ cycloalkyl, which is optionally substituted with or fused to Q; or $C_5$—$C_6$ cycloalkenyl, which is optionally substituted with or fused to Q;

each Q is independently selected from a 3–7 membered saturated, partially saturated or unsaturated carbocyclic ring system; or a 5–7 membered saturated, partially saturated or unsaturated heterocyclic ring containing one or more heteroatoms selected from O, N, S, $S(O)_n$, or $N(R^2)$; wherein Q is optionally substituted with one or more groups selected from oxo, —$OR^2$, —$R^2$, —$SO_2$—$R^2$, —$SO_2$—$N(R^2)_2$, —$N(R^2)_2$, —$N(R^2)$—C(O)—$R^2$, —R—OH, —CN, —$CO_2R^2$, —C(O)—N $(R^2)_2$, halo or —$CF_3$;

D' is selected from —$OR^{10}$, —N=$R^{10}$ or —$N(R^{10})$—$R^1$—$R^3$;

E is selected from Ht; O—Ht; Ht—Ht; —O—$R^3$; —$N(R^2)(R^3)$; $C_1$—$C_6$ alkyl, which is optionally substituted with one or more groups selected from $R^4$ or Ht; $C_2$—$C_6$ alkenyl, which is optionally substituted with one or more groups selected from $R^4$ or Ht; $C_3$—$C_6$ saturated carbocycle, which is optionally substituted with one or more groups selected from $R_4$ or Ht; or $C_3$—$C_6$ unsaturated carbocycle, which is optionally substituted with one or more groups selected from $R^4$ or Ht;

each $R^4$ is independently selected from —OR—, —SR—, —SOR—, —$SO_2R^2$, —$CO_2R^2$, —C(O)—$NHR^2$, —C(O)—$N(R^2)_2$, —C(O)—$NR^2(OR^2)$, —$S(O)_2$—$NHR^2$, halo, —$NR^2$—C(O)—$R^2$, —$N(R^2)_2$ or —CN;

each $R^7$ is independently selected from hydrogen,

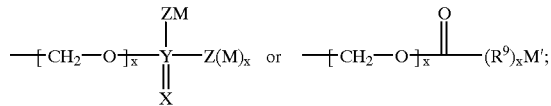

wherein each M is independently selected from H, Li, Na, K, Mg, Ca, Ba, —$N(R^2)_4$, $C_2$—$C_{12}$—alkyl, $C_2$—$C_{12}$-alkenyl, or —$R^6$; wherein 1 to 4 —$CH_2$ radicals of the alkyl or alkenyl group, other than the —$CH_2$ that is bound to Z, is optionally replaced by a heteroatom group selected from O, S, S(O), S $(O_2)$, or $N(R^2)$; and wherein any hydrogen in said alkyl, alkenyl or Re is optionally replaced with a substituent selected from oxo, —OR—, —$R^2$, $N(R^2)_2$, $N(R^2)_3$, R—OH, —CN, —$CO_2R^2$, —C(O)—$N(R^2)_2$, $S(O)_2$—$N(R^2)_2$, $N(R^2)$—C(O)—$R_2$, $C(O)R^2$, —$S(O)_n$—$R^2$, $OCF_3$, —$S(O)_n$—$R^6$, N $(R^2)$—$S(O)_2(R^2)$, halo, —$CF_3$, or —$NO_2$;

M' is H, $C_1$–$C_{12}$-alkyl, $C_2$–$C_{12}$-alkenyl, or —$R^6$; wherein 1 to 4 —$CH_2$ radicals of the alkyl or alkenyl group is optionally replaced by a heteroatom group selected from O, S, S(O), $S(O_2)$, or $N(R^2)$; and wherein any hydrogen in said alkyl, alkenyl or $R^6$ is optionally replaced with a substituent selected from oxo, —$OR^2$, —$R^2$, —$N(R^2)_2$, $N(R^2)_3$, —R—OH, —CN, —$CO_2R^2$, —C(O)—$N(R^2)_2$, —$S(O)_2$—N $(R^2)_2$, —$N(R^2)$—C(O)—$R_2$, —$C(O)R^2$, —$S(O)_n$—$R^2$, —$OCF_3$, —$S(O)_n$—$R^6$, —$N(R^2)$—$S(O)_2(R^2)$, halo, —$CF_3$, or —$NO_2$;

Z is O, S, $N(R^2)_2$, or, when M is not present, H.

Y is P or S;

X is O or S; and $R^9$ is $C(R^2)_2$, O or $N(R^2)$; and wherein when Y is S, Z is not S; and $R^6$ is a 5–6 membered saturated, partially saturated or unsaturated carbocyclic or heterocyclic ring system, or an 8–10 membered saturated, partially saturated or unsaturated bicyclic ring system; wherein any of said heterocyclic ring systems contains one or more heteroatoms selected from O, N, S, $S(O)_n$ or $N(R^2)$; and wherein any of said ring systems optionally contains 1 to 4 substituents independently selected from OH, $C_1$-$C_4$ alkyl, —O—$C_1$-$C_4$ alkyl or —O—C(O)—$C_1$-$C_4$ alkyl;

$R^{10}$ is selected from $C_1$-$C_8$ alkyl, $C_2$-$C_6$ alkenyl, $C_6$-$C_{14}$ aryl or Ht, wherein $R^{10}$ optionally contains up to three substituents independently selected from —$R^3$, —CN, —$SR^5$, —$SOR^5$, —$SO_2R^5$, —SR—$NR^5$—C(O) $R^6$, —$NR^5$—$(SO_2)$ $R^5$, —$C(O)N(R^5)_2$, —$C(S)N(R^5)_2$, —$S(O)_2N(R^5)_2$, —$C(O)R^6$, —$C(S)R^6$, —$N(R^5)_2$,—$NR^5$ —$C(O)R^5$, —$NR^5$—$C(O)OR^5$, —$NR^5$—C(O)N $(R^5)_2$, —$NR^5$—$C(S)R^5$, —$NR^5$—C(S)OR, —$NR^5$—C$(S)N(R^5)_2$, —$NR^5$—C[=$N(R^5)$]—$N(R^5)_2$, —NH—C[=N—$NO_2$]—$NH_2$, —NH—C[=N—$NO_2$]—$OR^5$, —$N(R^8)_2$—$C(O)R^8$, —$OC(O)R^6$, —OC(O)$N(R^5)_2$, —$OC(S)N(R^5)_2$, wherein any one of the —$CH_2$ groups of said alkyl or alkenyl chains of $R^{10}$ may be optionally replaced by O, S, SO, $SO_2$, C(O) or $NR^5$; wherein each $R^5$ is independently selected from hydrogen, $C_1$-$C_8$ alkyl, $C_2$-$C_6$ alkenyl, $C_2$-$C_6$ alkynyl or Ht, wherein each $R^5$, except for hydrogen, is optionally substituted with —$CF_3$, —$PO_3R^3$, azido or halo.

It is also an object of this invention to provide pharmaceutical compositions comprising the sulfonamides of formula (I) and methods for their use as inhibitors of HIV aspartyl protease.

DETAILED DESCRIPTION OF THE INVENTION

In order that the invention herein described may be more fully understood, the following detailed description is set forth. In the description, the following terms are employed herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

For the compounds of formula I, and intermediates thereof, the stereochemistry of OR$^7$ is defined relative to D on the adjacent carbon atom, when the molecule is drawn in an extended zig-zag representation (such as that drawn for compound of formula I). If both OR$^7$ and D reside on the same side of the plane defined by the extended backbone of the compound, the stereochemistry of OR$^7$ will be referred to as "syn". If OR$^7$ and D reside on opposite sides of that plane, the stereochemistry of OR$^7$ will be referred to as "anti".

The term "alkyl", alone or in combination with any other term, refers to a straight-chain or branch-chain saturated aliphatic hydrocarbon radical containing the specified number of carbon atoms, or where no number is specified, preferably from 1 to about 10 and more preferably from 1 to about 8 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl" alone or in combination with any other term, refers to a straight-chain or branched-chain mono- or poly-unsaturated aliphatic hydrocarbon radical containing the specified number of carbon atoms, or where no number is specified, preferably from 2 to about 18 carbon atoms and more preferably, from 2 to about 8 carbon atoms. Examples of alkenyl radicals include, but are not limited to, ethenyl, propenyl, isopropenyl, 1,4-butadienyl, pentenyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like. The term "aryl" alone or in combination with any other term, refers to a carbocyclic aromatic radical (such as phenyl or naphthyl) containing the specified number of carbon atoms, preferably from 6–14 carbon atoms, and more preferably from 6–10 carbon atoms, optionally substituted with one or more substituents selected from $C_1$–6 alkoxy, (for example methoxy), nitro, halogen, (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocyclyl" or "heterocycle" refers to a stable 3–7 membered monocyclic heterocyclic ring or 8–11 membered bicyclic heterocyclcic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5–7 membered monocyclic heterocycles and 8–10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, c3 athiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 asparryl protease.

The term "thiocarbamates" refers to compounds containing the functional group N—SO$_2$—O.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides.

Water or oil-soluble or dispersible products may be obtained by such quaternlzation.

The novel sulfonamides of this invention are those of formula I:

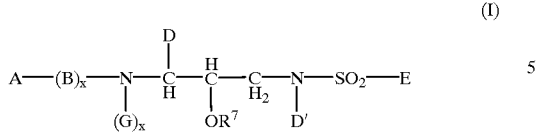

(I)

wherein:
A is selected from H; Ht; —R$^1$—Ht; —R$^1$-C$_1$-C$_6$ alkyl, which is optionally substituted with one or more groups independently selected from hydroxy, C$_1$-C$_4$ alkoxy, Ht, —O—Ht, —NR$^2$—CO—N(R$^2$) or —CO—N(R$^2$)$_2$; —R$^1$-C$_1$-C$_6$ alkenyl, which is optionally substituted with one or more groups independently selected from hydroxy, C$_1$-C$_4$ alkoxy, Ht, —O—Ht, —NR$^2$—CO—N(R$^2$)$_2$ or —CO—N(R$^2$)$_2$; or R$^7$;

each R$^1$ is independently selected from —C(O)—, —S(O)$_2$—, —C(O)—C(O)—, —O—C (O)—, —O—S(O)$_2$, —NR$^2$—S(O)$_2$—, —NR$^2$—C(O)— or —NR$^2$—C(O)—C(O)—;

each Ht is independently selected from C$_3$-C$_7$ cycloalkyl; C$_3$-C$_7$, cycloalkenyl; C$_6$-C$_{14}$ aryl; or a 5–7 membered saturated or unsaturated heterocycle, containing one or more heteroatoms selected from N, N(R$^2$), O, S and S(O)$_n$; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)(R$^2$), —R$^2$—OH, —CN, —CO$_2$—R$^2$, —C(O)—N (R$^2$)$_2$, —S(O)$_2$—N(R$^2$)$_2$, —N(R$^2$)—C (O)—R$^2$, —C(O)—R$^2$, —S(O)$_n$—R$^2$, —OCF$_3$, —S(O)$_n$—Q, methylenedioxy, —N(R$^2$)—S(O)$_2$ (R$^2$), halo, —CF$_3$, —NO2, Q, —OQ, —OR$^7$, —SR$^7$, —R$^7$, —N(R$^2$)(R$^7$) or —N(R$^7$)2;

each R$^2$ is independently selected from H, or C$_1$-C$_6$ alkyl optionally substituted with Q or R$^{10}$;

B, when present, is —N(R$^2$)—C(R$^3$)$_2$—C(O)—;

each x is independently 0 or 1;

each R$^3$ is independently selected from H, Ht, C$_1$—C$_6$ alkyl, C$_2$-C$_6$ alkenyl, C$_3$-C$_6$ cycloalkyl or C$_5$-C$_6$ cycloalkenyl; wherein any member of said R$^3$, except H, is optionally substituted with one or more substituents selected from —OR$^2$, —C(O)—NH—R$^2$, —S(O)$_n$—N(R$^2$)(R$^2$), Ht, —NSR$^2$, —CO$_2$R$^2$, NR$^2$—C(O)—R $^2$;

each n is independently 1 or 2;

G, when present, is selected from H, R$^7$ or C$_1$-C$_4$ alkyl, or, when G is C$_1$-C$_4$ alkyl, G and R$^7$ are bound to one another either directly or through a C$_1$-C$_3$ linker to form a heterocyclic ring; or when G is not present (i.e., when x in (G)$_x$ is 0), then the nitrogen to which G is attached is bound directly to the R group in —OR$^7$ with the concomitant displacement of one —ZM group from R$^7$;

D is selected from Q; C$_1$-C$_6$ alkyl, which is optionally substituted with one or more groups selected from C$_3$-C$_6$ cycloalkyl, —OR$^2$, —S—Ht, —R$^3$, —O—Q or Q; C$_2$-C$_4$ alkenyl, which is optionally substituted with one or more groups selected from —OR$^2$, —S—Ht, —R$^3$, —O—Q or Q, C$_3$-C$_6$ cycloalkyl, which is optionally substituted with or fused to Q; or C$_5$-C$_6$ cycloalkenyl, which is optionally substituted with or fused to Q;

each Q is independently selected from a 3–7 membered saturated, partially saturated or unsaturated carbocyclic ring system; or a 5–7 membered saturated, partially saturated or unsaturated heterocyclic ring containing one or more heteroatoms selected from O, N, S, S(O)$_n$, or N(R$^2$); wherein Q is optionally substituted with one or more groups selected from oxc, —OR$^2$, —R$^2$, —SO$_2$R$^2$, —SO$_2$—N(R$^2$)$_2$, —N(R$^2$)—C(O)—R$^2$, —R$^2$—OH, —CN, —CO$_2$R$^2$, —C(O)—N(R$^2$)$_2$, halo or —CF$_3$;

D' is selected from —OR$^{10}$, —N=R$^{10}$ or —N(R$^{10}$)—R$^1$—R$^3$;

E is selected from Ht; O—Ht; Ht—Ht; —O—R$^3$; —N(R$^2$)(R$^3$); C$_1$-C$_6$ alkyl, which is optionally substituted with one or more groups selected from R$^4$ or Ht; C$_2$-C$_6$ alkenyl, which is optionally substituted with one or more groups selected from R$^4$ or Ht; C$_3$-C$_6$ saturated carbocycle, which is optionally substituted with one or more groups selected from R$^4$ or Ht; or C$_5$-C$_6$ unsaturated carbocycle, which is optionally substituted with one or more groups selected from R$^4$ or Ht;

each R$^4$ is independently selected from —OR$^2$, —SR$^2$, —SOR$^2$, —SO$_2$R$^2$, —CO$_2$R$^2$, —C(O)—NHR$^2$, —C(O)—N(R$^2$)$_2$, —C(O)—NR$^2$—(OR$^2$), —S(O)$_2$—NHR$^2$, halo, —NR$^2$—C(O)—R$^2$, —N(R$^2$)$_2$ or —CN;

each R$^7$ is independently selected from hydrogen,

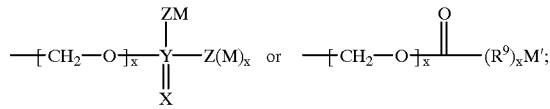

wherein each M is independently selected from H, Li, Na, K, Mg, Ca, Ba, —N(R$^2$)$_4$, C$_2$-C$_{12}$-alkyl, C$_2$-C$_2$-alkenyl, or —R$^6$; wherein 1 to 4 —CH$_2$ radicals of the alkyl or alkenyl group, other than the —CH$_2$ that is bound to Z, is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, —R$^2$, N(R$^2$)$_2$, N(R$^2$)$_3$, R$^2$OH, —CN, —CO$_2$R$^2$, —C(O)—N(R$^2$)$_2$, S(O)$_2$—N(R)$_2$, N(R$^2$)—C(O)—R$_2$, C(O)R$^2$, —S(O)$_n$—R$^2$, OCF$_3$, —S(O)$_n$—R$^6$, N(R$^2$)—S(O)$_2$ (R$^2$), halo, —CF$_3$, or —NO$_2$;

M' is H, C$_1$-C$_{12}$-alkyl, C$_2$-C$_{12}$-alkenyl, or —R$^6$; wherein 1 to 4 —CH$_2$ radicals of the alkyl or alkenyl group is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, R$^2$, —N(R$^2$)$_2$, N(R$^2$)$_3$, —R$^2$OH, —CN, —CO$_2$R$^2$, —C(O)—N(R$^2$)$_2$, —S(O)$_2$—N(R$^2$)$_2$, —N (R$^2$)—C (O)—R$_2$, —C(O)R$^2$, —S(O)$_n$—R$^2$, —OCF$_3$, —S(O) $_n$—R$^6$, —N(R$^2$)—S(O)$_2$ (R$^2$), halo, —CF$_3$, or —NO$_2$;

Z is O, S, N(R$^2$)$_2$, or, when M is not present, H.

Y is P or S;

X is O or S; and

R$^9$ is C(R$^2$)$_2$, O or N(R$^2$); and wherein when Y is S, Z is not S; and

R$^6$ is a 5–6 membered saturated, partially saturated or unsaturated carbocyclic or heterocyclic ring system, or an 8–10 membered saturated, partially saturated or unsaturated bicyclic ring system; wherein any of said heterocyclic ring systems contains one or more heteroatoms selected from O, N, S, S(O)$_n$ or N(R$^2$); and wherein any of said ring systems optionally contains 1 to 4 substituents independently selected from OH, C$_1$-C$_4$ alkyl, —O—C$_1$-C$_4$ alkyl or —O—C(O)—C$_1$-C$_4$ alkyl;

$R^{10}$ is selected from $C_1$–$C_8$ alkyl, $C_2$–$C_6$ alkenyl, $C_6$–$C_{14}$ aryl or Ht, wherein $R^{10}$ optionally contains up to three substituents independently selected from —$R^3$, —CN, —$SR^5$, —$SOR^5$, —$SO_2R^5$, —SR—$NR^5$—$O(O)R^6$, —NR—$(SO_2)R^5$, —$C(O)N(R^5)_2$, —$C(S)N(R^5)_2$, —$S(O)_2N(R^5)_2$, —$C(O)R^6$, —$C(S)R^6$, —$N(R^5)_2$, —NR—$C(O)R^5$, —$NR^5$—$C(O)OR^5$, —$NR^5$—$C(O)N(R^5)_2$, —$NR^5$—$C(S)R^5$, —$NR^5$—$C(S)OR$—, —$NR^5$—$C(S)N(R^5)2$, —NR5—$C[=N(R^5)]$—$N(R^5)2$, —NH—$O[=N$—$NO_2]$—$NH_2$, —NH—$C[=N$—$NO_2]$—$OR^5$, —$N(R^8)_2$—$C(O)R^8$, —$OC(O)R^6$, —OC$(O)N(R^5)_2$, —$OC(S)N(R^5)_2$, wherein any one of the —$CH_2$ groups of said alkyl or alkenyl chains of $R^{10}$ may be optionally replaced by O, S, SO, $SO_2$, C(O) or $NR^5$;

wherein each $R^5$ is independently selected from hydrogen, $C_1$–$C_6$ alkyl, $C_2$–$C_6$ alkenyl, $C_2$–$C_6$ alkynyl or Ht, wherein each $R^5$, except for hydrogen, is optionally substituted with —CF3, —$PO_3R^3$, azido or halo;

Preferably, at least one R is selected from:

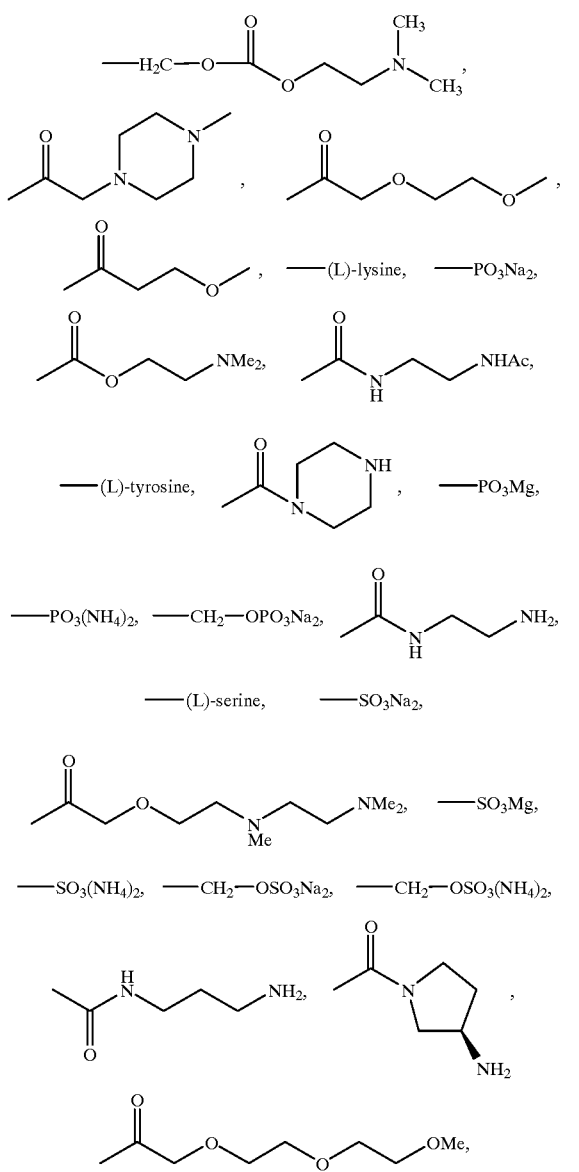

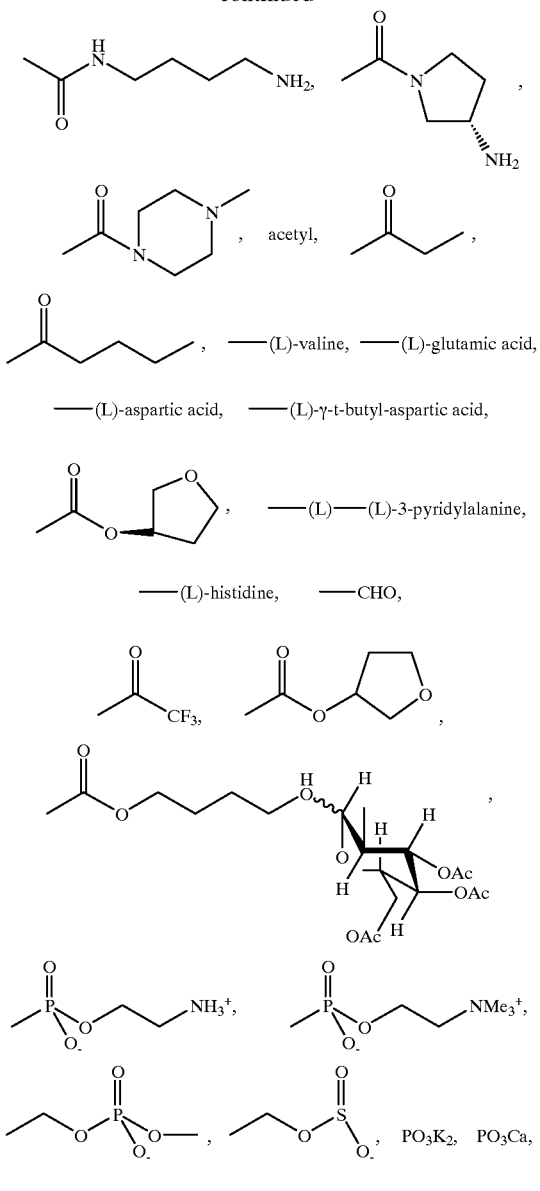

$PO_3$-spermine, $PO_3$-(spermidine)$_3$ or $PO_3$-(meglamine)$_2$.

It will be understood by those of skill in the art that component M or M' in the formulae set forth herein will have either a covalent, a covalent/zwitterionic, or an ionic association with either Z or $R^9$ depending upon the actual choice for M or M'. When M or M' is hydrogen, alkyl, alkenyl, or $R^6$, M or M' is covalently bound to $R^9$ or Z. If M is a mono- or bivalent metal or other charged species (i.e., $NH_4^+$), there is an ionic interaction between M and Z and the resulting compound is a salt.

When x is 0 in $(M)_x$, Z may be a charged species. When that occurs, the other M may be oppositely charged to produce a 0 net charge on the molecule. Alternatively, the counter ion may located elsewhere in the molecule.

Except where expressly provided to the contrary, as used herein, the definitions of variables A, $R^1$—$R^4$, $R^6$—$R^9$, Ht, B. x, n, D, D', M, Q, X, Y, Z and E are to be taken as they are defined above for the compounds of formula I.

According to a preferred embodiment, the compounds of this invention are those represented by formula II, formula III or formula IV:

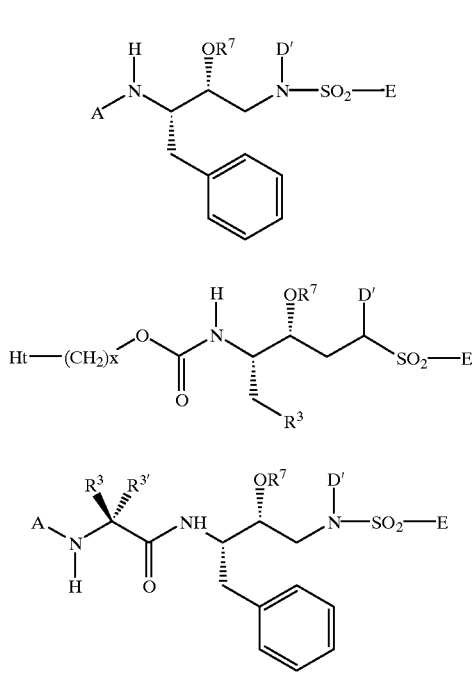

(II)

(III)

(IV)

wherein A, $R^3$, $R^7$, Ht, D, D', x, E are as defined above for compounds of formula I. For ease of reference, the two $R^3$ moieties present in formula IV have been labeled $R^3$ and $R^{3'}$.

For compounds of formula II, more preferred compounds are those wherein:

A is —C(O)Ht;

D' is —O—$R^{10}$;

E is $C_6$–$C_{10}$ aryl optionally substituted with one or more substituents selected from oxo, —$OR^2$, $SR^2$, —$R^2$, —$N(R^2)_2$, —$R^2$—OH, —CN, —$CO_2R^2$, —C(O)—N$(R^2)_2$, —S(O)$_2$—N$(R^2)_2$, —N$(R^2)$—C(O)—$R^2$, —C(O)—$R^2$, —S(O)$_n$—$R^2$, —$OCF_3$, —S(O)$_n$—Q, methylenedioxy, —N$(R^2)$—S(O)$_2$ $(R^2)$, halo, —$CF_3$, —NO2, Q, —OQ, —$OR^7$, —$SR^7$, —$R_7$, —N$(R^2)(R^7)$ or —N$(R^7)_2$; or a 5-membered heterocyclic ring containing one S and optionally containing N as an additional heteroatom, wherein said heterocyclic ring is optionally substituted with one to two groups independently selected from —$CH_3$, $R^4$, or Ht.

all other variables are as defined for formula I.

Another preferred embodiment for the formula II compounds are those wherein:

E is a 5-membered heterocyclic ring containing one S and optionally containing N as an additional heteroatom, wherein said heterocyclic ring is optionally substituted with one to two groups independently selected from —$CH_3$, $R^4$, or Ht; and all other variables are as defined for formula I.

More preferred are any of the formula II compounds set forth above, wherein $R^7$ in —$OR^7$ is —PO(OM)$_2$ or C(O)CH$_2$OCH$_2$CH$_2$OCH$_2$CH$_2$OCH$_3$ and both $R^7$ in —N$(R^7)_2$ are H, wherein M is H, Li, Na, K or $C_1$–$C_4$ alkyl; or wherein R in —OR is C(O)CH$_2$OCH$_2$CH$_2$OCH$_3$, one $R^7$ in —N$(R^7)_2$ is C(O)CH$_2$OCH$_2$CH$_2$OCH$_3$ and the other is H.

According to another preferred embodiment of the present invention, there is provided compounds of formula (V):

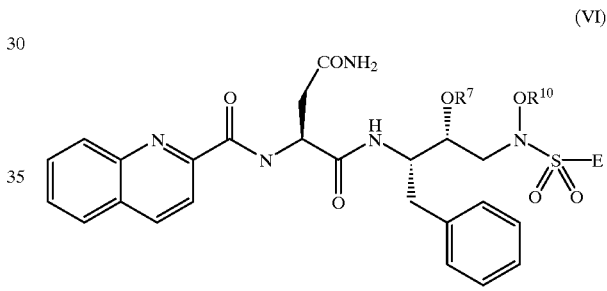

(V)

wherein:

A is $C_6$–$C_{14}$ aryl optionally substituted with one or more groups independently selected from the group consisting of $C_1$–$C_8$ alkyl or hydroxy, or $OR^4$, wherein $R^4$ is $C_1$–$C_8$ alkyl, $C_3$–$C_7$ cycloalkyl, $C_1$–$C_6$ alkyl substituted with $C_6$–$C_4$, $C_6$–$C_{14}$ aryl optionally substituted with $C_1$–$C_6$ alkyl, heterocyclyl or heterocyclylalkyl;

E is $C_6$–$C_4$ aryl, optionally substituted with one or more groups selected from nitro, oxo, alkoxy, amino, hydroxyamino; heterocyclcyl, optionally substituted with one or more groups selected from the group consisting of nitro, oxo, alkoxy, amino, hydroxyamino or N(CO)OCH$_3$;

$R^{10}$ and $R^7$ are as defined above; or a pharmaceutically acceptable derivative thereof.

According to yet another preferred embodiment, there is provided compounds of Formula (VI):

(VI)

[Structure VI diagram]

wherein:

$R^7$ and $R^{10}$ are as defined above for formula I;

E is $C_6$–$C_4$ aryl, optionally substituted with one or more groups selected from the group consisting of nitro, oxo, alkoxy, amino, hydroxyamino; heterocyclcyl, optionally substituted with one or more groups selected from the group consisting of nitro, oxo, alkoxy, amino, hydroxyamino or N(CO)OCH$_3$;

or a pharmaceutically acceptable derivative thereof.

According to yet another preferred embodiment, there is provided a compound of Formula (VII):

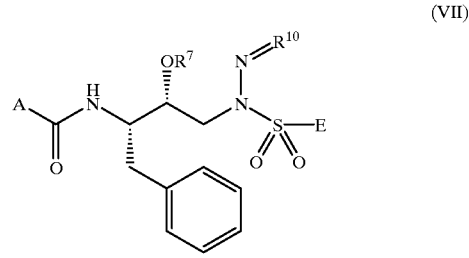

(VII)

wherein:

A, E, $R^7$ and $R^{10}$ are as defined in formula (I); or a pharmaceutically acceptable derivative thereof.

According to yet another preferred embodiment, there is provided a compound of formula (VIII):
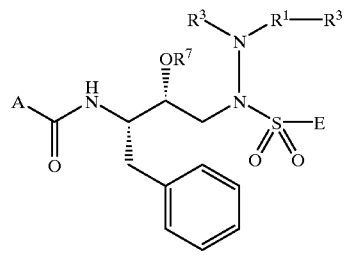
(VIII)
wherein A, $R^1$, $R^3$, $R^7$ and E are as defined in formula (I).
According to yet another embodiment of the present invention, there are provided compounds of the formula:
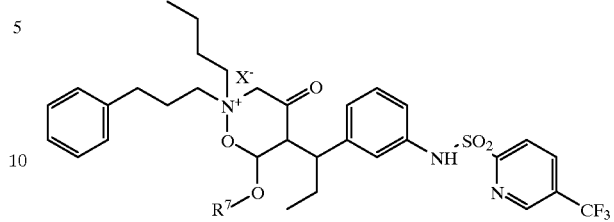
wherein $X^-$ is a pharmaceutically suitable counterion;
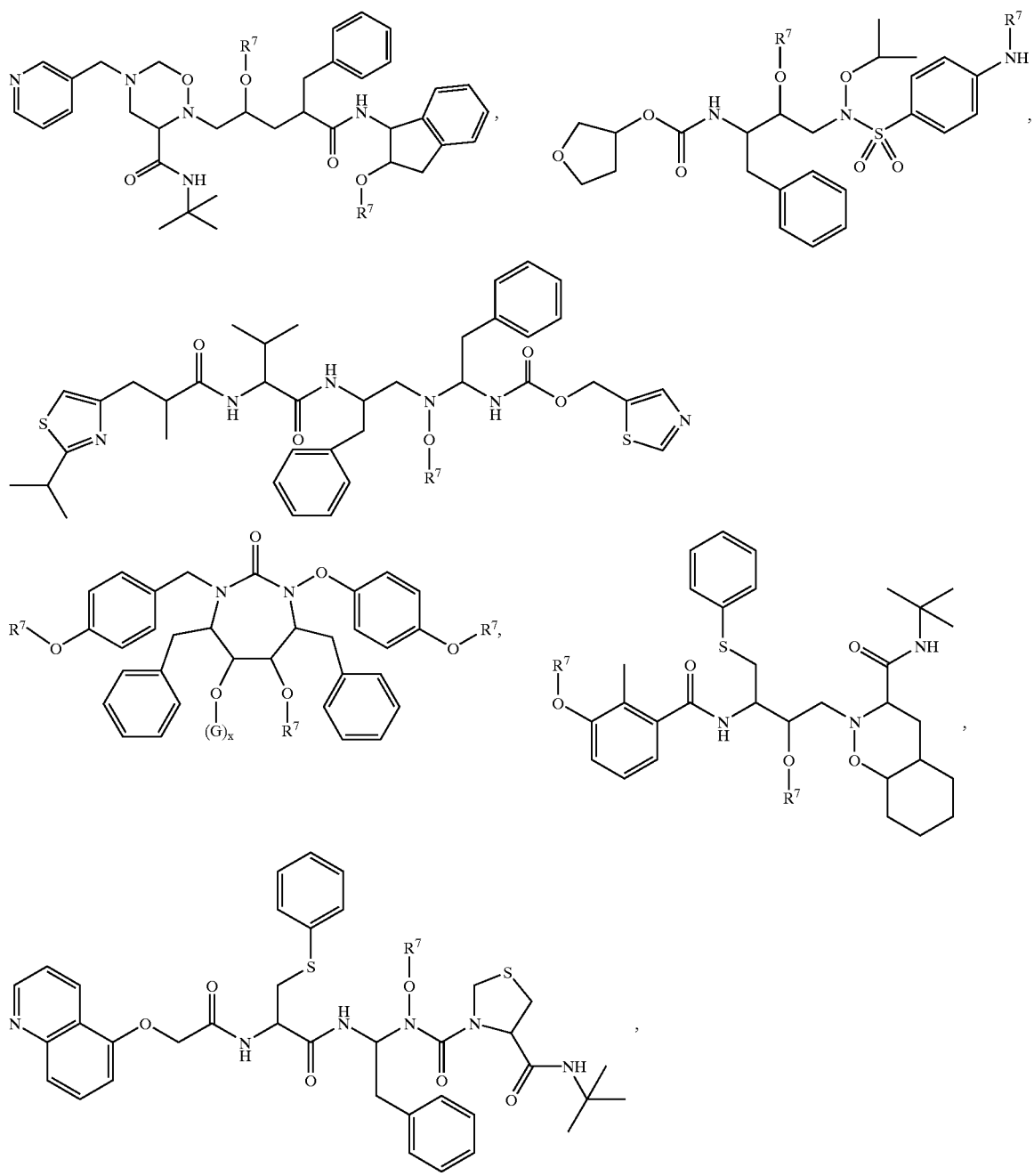

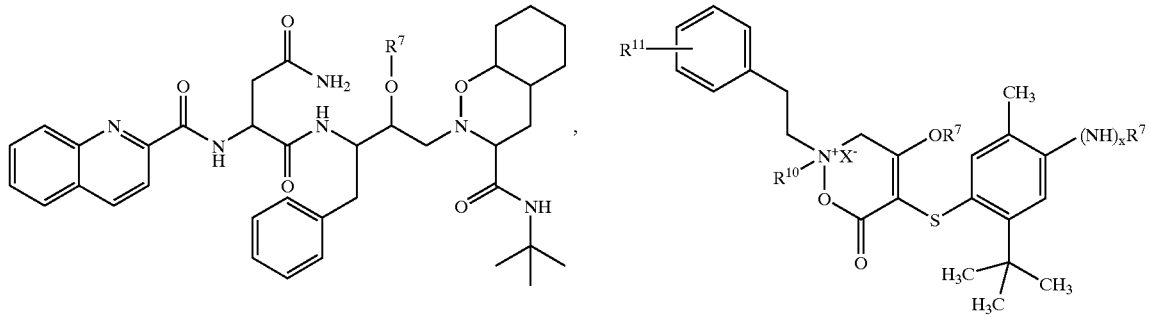

wherein $R^{10}$ is selected from isopropyl or cyclopentyl; $R^{11}$ is selected from $NHR^7$ or $OR^7$; x, $R^7$ and G are as defined above; and $X^-$ is a pharmaceutically acceptable counterion.

The compounds according to the invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

More preferred compounds of formula (I) of the present invention are set forth below in Table 1.

TABLE 1

| Compound | A | $R^{10}$ | E |
|---|---|---|---|
| 1 | *t*-BuO– | *t*-Bu– | 3-aminophenyl |
| 2 | *t*-BuO– | *t*-Bu– | 3,4-diaminophenyl |
| 3 | *t*-BuO– | *t*-Bu– | 1H-benzimidazol-6-yl |
| 4 | *t*-BuO– | *t*-Bu– | 2-oxo-2,3-dihydro-1H-benzimidazol-5-yl |

TABLE 1-continued
| Compound | A | R¹⁰ | E |
|---|---|---|---|
| 5 | 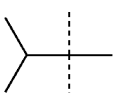 | 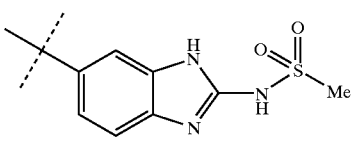 | 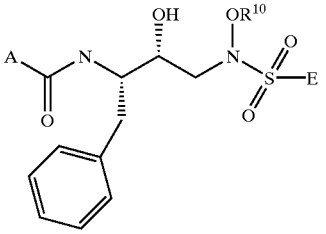 |
| 6 | 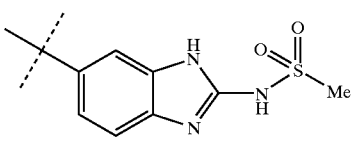 |  | 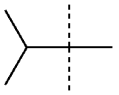 |
| 7 | 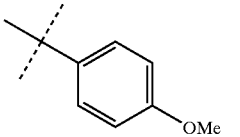 | 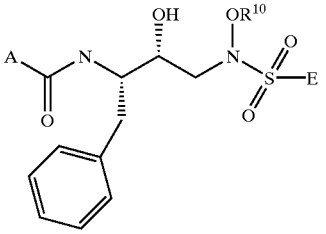 | 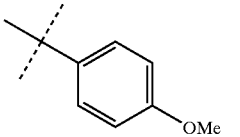 |
| 8 |  | 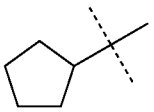 | 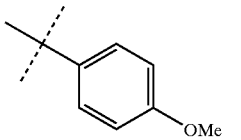 |
| 9 | 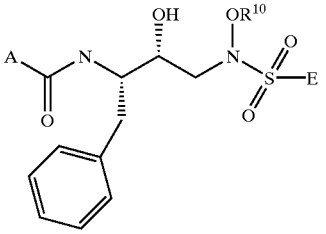 | 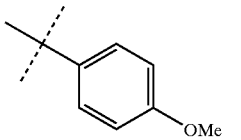 |  |
| 10 | 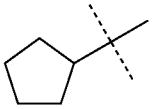 | 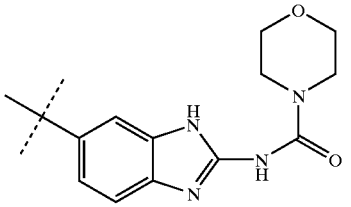 | 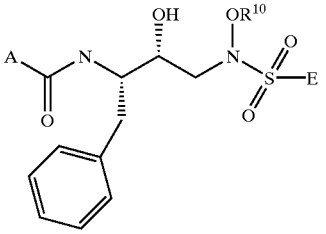 |
| 11 | 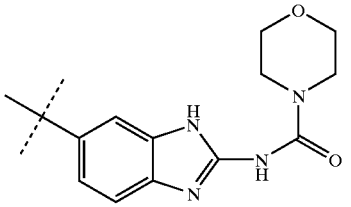 |  |  |

TABLE 1-continued

| Compound | A | R¹⁰ | E |
|---|---|---|---|
| 12 | tBu-O- | cyclopentyl-CH₂- | 5-tBu-benzimidazol-2-yl-NHC(O)-(3,4,5-trimethoxyphenyl) |
| 13 | tBu-O- | cyclopentyl-CH₂- | 5-tBu-benzimidazol-2-yl-NHC(O)CH₂-COOMe |
| 14 | tBu-O- | cyclopentyl-CH₂- | 5-tBu-benzimidazol-2-yl-NHC(O)-N(Me)₂ |
| 15 | tBu-O- | sec-butyl-CH₂- | 4-MeO-C₆H₄- |
| 16 | tBu-O- | cyclohexyl-CH₂- | 4-MeO-C₆H₄- |
| 17 | tBu-O- | phenyl-CH₂- | 4-MeO-C₆H₄- |
| 18 | tBu-O- | tetrahydropyran-4-yl-CH₂- | 4-MeO-C₆H₄- |
| 19 | tBu-O- | (tetrahydropyran-2-yl)-CH₂- | 4-MeO-C₆H₄- |

TABLE 1-continued

| Compound | A | R¹⁰ | E |
|---|---|---|---|
| 20 | tBuO— | 3-tetrahydrofuranyl-CMe₂— | 4-MeO-C₆H₄-CMe₂— |
| 21 | tBuO— | PhCH₂-CMe₂— | 4-MeO-C₆H₄-CMe₂— |
| 22 | tBuO— | iBu-CMe₂— | 4-MeO-C₆H₄-CMe₂— |
| 23 | tBuO— | cyclohexyl-CMe₂— | 4-MeO-C₆H₄-CMe₂— |
| 24 | PhCH₂O— | cyclopentyl-CMe₂— | 4-MeO-C₆H₄-CMe₂— |
| 25 | (pyridin-3-yl)CH₂O— | cyclopentyl-CMe₂— | 4-MeO-C₆H₄-CMe₂— |
| 26 | 2-Me-C₆H₄-CMe₂— | cyclopentyl-CMe₂— | 4-HO-C₆H₄-CMe₂— |
| 27 | (S)-tetrahydrofuran-3-yl-O— | cyclopentyl-CMe₂— | 3-NH₂-C₆H₄-CMe₂— |

TABLE 1-continued

| Compound | A | R¹⁰ | E |
|----------|---|-----|---|
| 28 | bis(tetrahydropyran-tetrahydrofuran) fused bicyclic system | cyclopentyl | 4-methoxyphenyl |
| 29 | bis(tetrahydrofuran) fused bicyclic system | cyclopentyl | 4-methoxyphenyl |
| 30 | bis(tetrahydrofuran) fused bicyclic system | cyclopentyl | 3-(NHCH₂C(O)O-tBu)phenyl |
| 31 | bis(tetrahydrofuran) fused bicyclic system | cyclopentyl | 3-aminophenyl |
| 32 | bis(tetrahydrofuran) fused bicyclic system | cyclopentyl | 3-(NHCH₂C(O)NHMe)phenyl |

TABLE 1-continued

| Compound | A | R¹⁰ | E |
|---|---|---|---|
| 33 | bis-tetrahydrofuran-3-yl (dioxabicyclic diol) | cyclopentyl | 3-(2-(dimethylamino)ethylamino)phenyl |
| 34 | bis-tetrahydrofuran-3-yl (dioxabicyclic diol) | cyclopentyl | 3-(4-methylpiperazin-1-yl)phenyl |
| 35 | bis-tetrahydrofuran-3-yl (dioxabicyclic diol) | cyclopentyl | 3-(carboxymethylamino)phenyl |
| 36 | bis-tetrahydrofuran-3-yl (dioxabicyclic diol) | cyclopentyl | 3-(2-hydroxyethylamino)phenyl |
| 37 | bis-tetrahydrofuran-3-yl (dioxabicyclic diol) | cyclopentyl | 3-[N-(isobutoxycarbonyl)-N-(2-hydroxyethylcarbamoylmethyl)amino]phenyl |

TABLE 1-continued

| Compound | A | R¹⁰ | E |
|---|---|---|---|
| 38 | bicyclic furan-ol | tert-pentyl | 3-aminophenyl |
| 39 | bicyclic furan-ol | cyclopentylmethyl | 6-(methylsulfonylamino)-1H-benzimidazol-2-yl |
| 40 | bicyclic furan-ol | cyclopentylmethyl | 6-(methylsulfonylamino)-1H-benzimidazol-2-yl |
| 41 | bicyclic furan-ol | cyclopentylmethyl | 4-hydroxyphenyl |
| 42 | bicyclic furan-ol | cyclopentylmethyl | 4-(2-hydroxyethoxy)phenyl |
| 43 | bicyclic furan-ol | cyclopentylmethyl | 3-(dimethylamino)phenyl |
| 44 | bicyclic furan-ol | cyclopentylmethyl | 3-hydroxyphenyl |
| 45 | bicyclic furan-ol | cyclopentylmethyl | 3-(methylamino)phenyl |

TABLE 1-continued

| Compound | A | R¹⁰ | E |
|---|---|---|---|
| 46 | hexahydrofuro[2,3-b]furan-3-yl-oxy | cyclopentyl | 1H-benzimidazol-5-yl |
| 47 | (S)-tetrahydrofuran-3-yl-oxy | cyclopentyl | 4-methoxyphenyl |
| 48 | 1,3-dioxan-5-yl-oxy | cyclopentyl | 4-methoxyphenyl |
| 49 | quinoline-2-carbonyl-NH-CH(CH₂CONH₂)-C(CH₃)₂- | cyclopentyl | 3-aminophenyl |
| 50 | quinoline-2-carbonyl-NH-CH(CH₂CONH₂)-C(CH₃)₂- | cyclopentyl | 4-methoxyphenyl |
| 51 | quinoline-2-carbonyl-NH-CH(CH₂CONH₂)-C(CH₃)₂- | cyclopentyl | 2-(methoxycarbonylamino)-1H-benzimidazol-5-yl |
| 52 | quinoline-2-carbonyl-NH-CH(CH₂CONH₂)-C(CH₃)₂- | cyclopentyl | 1H-indazol-6-yl |
| 53 | (S)-tetrahydrofuran-3-yl-oxy | cyclopentyl | 2-(methoxycarbonylamino)-1H-benzimidazol-5-yl |

TABLE 1-continued
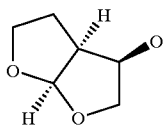
| Compound | A | R¹⁰ | E |
|---|---|---|---|
| 54 | 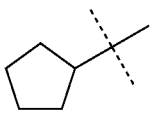 | 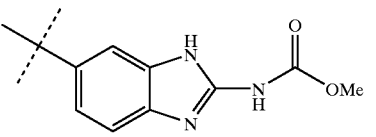 | 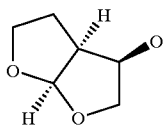 |
| 55 | 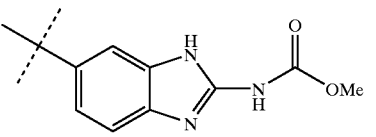 | 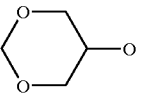 | 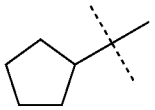 |
| 56 | 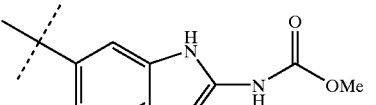 | 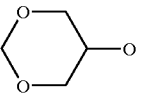 | 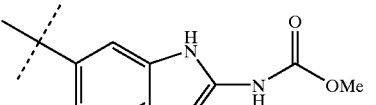 |
| 57 | 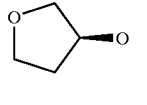 | 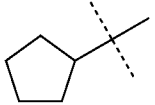 | 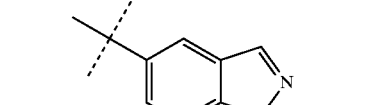 |
| 58 | 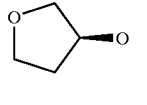 | 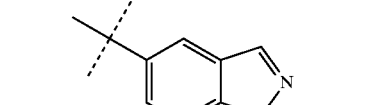 | 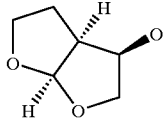 |
| 59 | 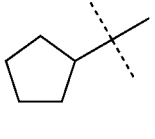 | 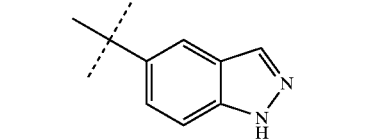 | 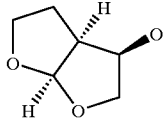 |
| 60 | 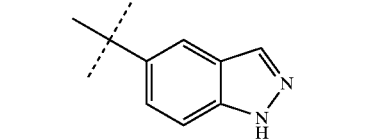 | 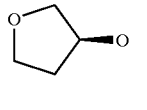 | 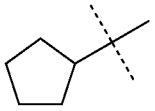 |
| 61 | 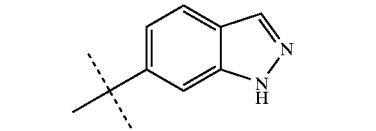 | 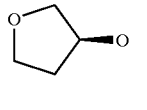 | 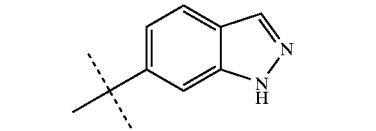 |

TABLE 1-continued

| Compound | A | R¹⁰ | E |
|---|---|---|---|
| 62 | (S)-tetrahydrofuran-3-yl | neopentyl (tert-butylmethyl) | 5-(2-oxo-2,3-dihydro-1H-benzimidazolyl) |
| 63 | (R)-tetrahydrofuran-3-yl | neopentyl (tert-butylmethyl) | 5-(2-oxo-2,3-dihydro-1H-benzimidazolyl) |
| 64 | (S)-tetrahydrofuran-3-yl | cyclohexylmethyl | 4-methoxyphenyl |
| 65 | 1,3-dioxan-5-yl | cyclohexylmethyl | 4-methoxyphenyl |
| 66 | quinoline-2-carbonyl-NH-CH(CH₂CONH₂)-C(CH₃)₂- | cyclohexylmethyl | 4-methoxyphenyl |
| 67 | (S)-tetrahydrofuran-3-yl | 2-methylbutyl | 4-methoxyphenyl |
| 68 | (3R,3aS,6aR)-hexahydrofuro[2,3-b]furan-3-yl | 2-methylbutyl | 4-methoxyphenyl |
| 69 | 1,3-dioxan-5-yl | 2-methylbutyl | 4-methoxyphenyl |

TABLE 1-continued
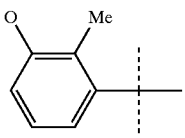
| Compound | A | R¹⁰ | E |
|---|---|---|---|
| 70 |  | 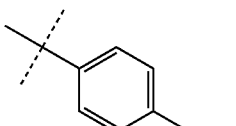 | 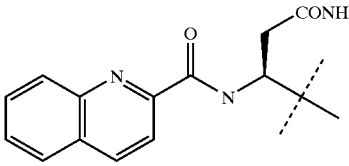 |
| 71 |  | 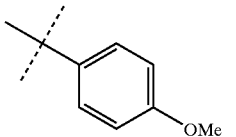 | 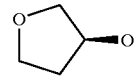 |
| 72 | 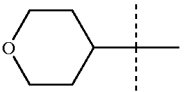 | 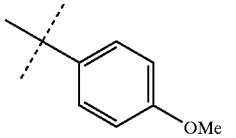 | 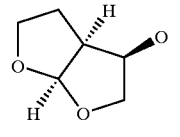 |
| 73 | 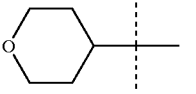 | 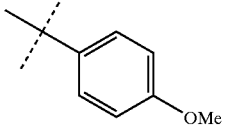 | 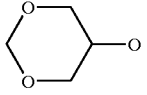 |
| 74 | 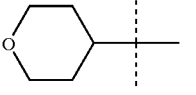 | 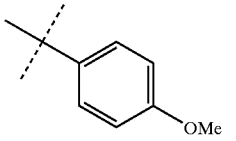 | 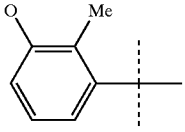 |
| 75 | 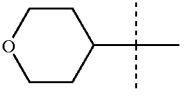 | 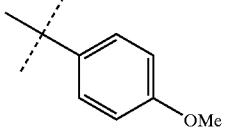 | 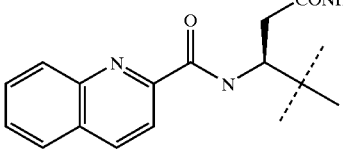 |
| 76 | 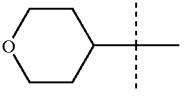 | 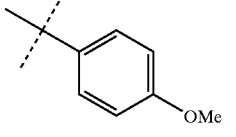 | 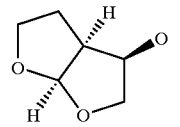 |
| 77 | 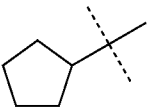 | 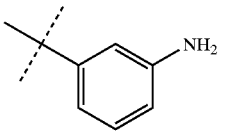 |  |

TABLE 1-continued
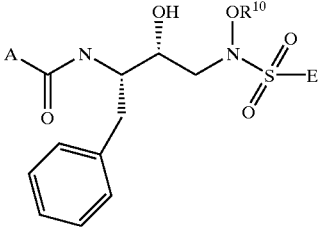
| Compound | A | R¹⁰ | E |
|---|---|---|---|
| 78 | 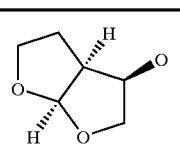 | 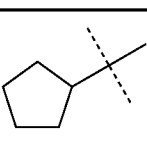 | 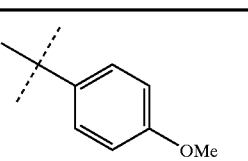 |
| 79 | 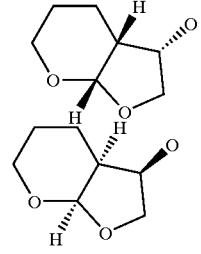 | 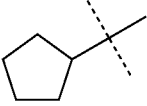 | 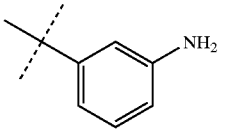 |
| 82 | 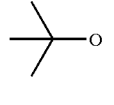 | 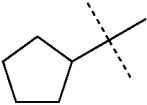 | 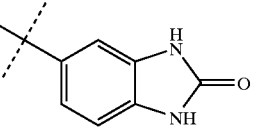 |
| 83 | 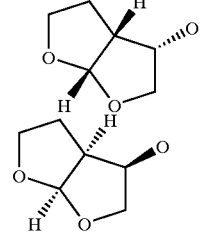 | 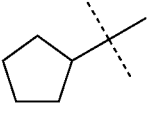 | 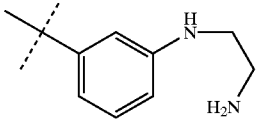 |
| 84 | 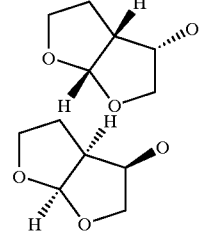 | 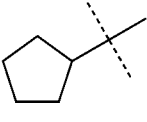 | 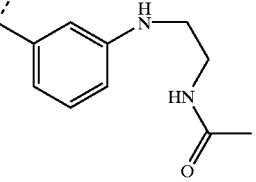 |
| 85 | 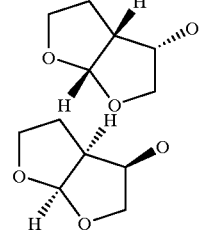 | 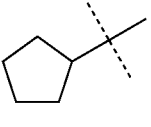 | 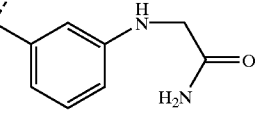 |

TABLE 1-continued
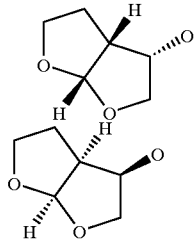
| Compound | A | R¹⁰ | E |
|---|---|---|---|
| 86 |  | 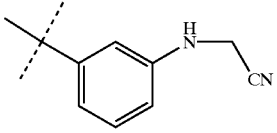 | 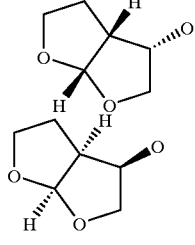 |
| 87 | 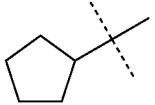 | 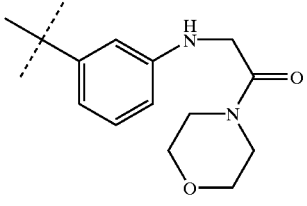 | 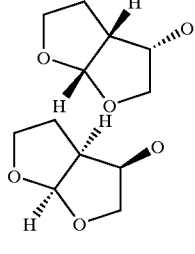 |
| 88 | 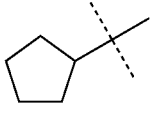 | 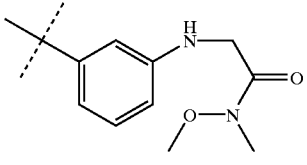 | 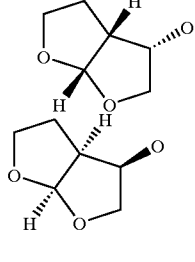 |
| 89 | 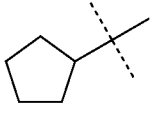 | 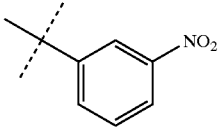 | 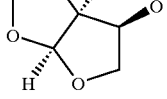 |
| 90 | 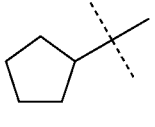 | 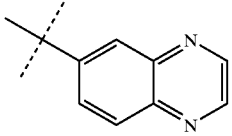 | |

TABLE 1-continued
| Compound | A | R¹⁰ | E |
|---|---|---|---|
| 91 | 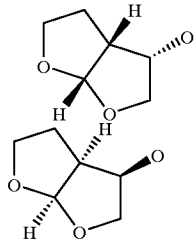 | 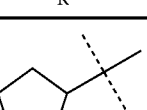 | 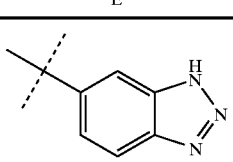 |
| 92 | 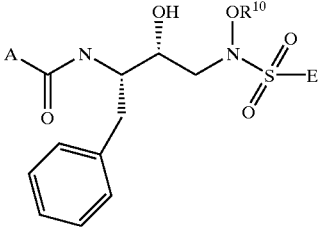 | 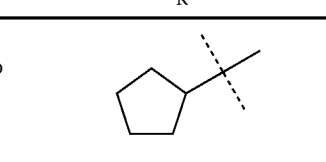 | 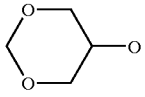 |
| 93 | 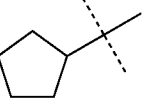 | 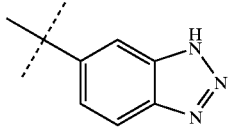 | 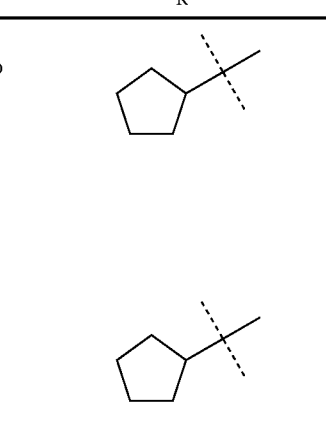 |
| 94 | 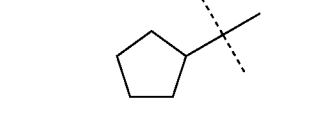 |  | 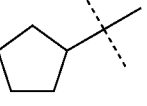 |
| 95 | 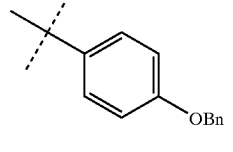 | 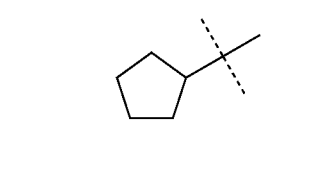 | 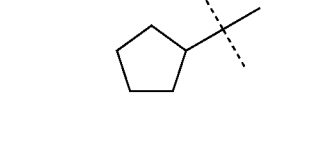 |
| 96 |  | 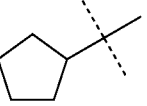 | 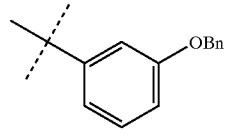 |
| 97 | 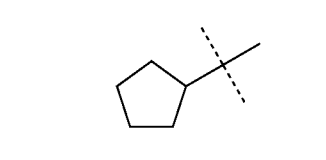 | 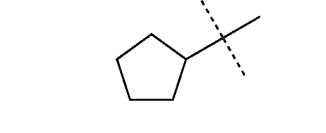 | 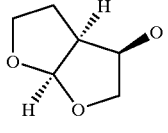 |
| 98 | 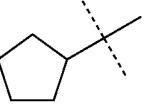 | 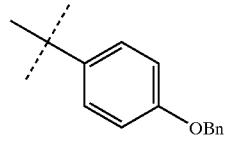 | 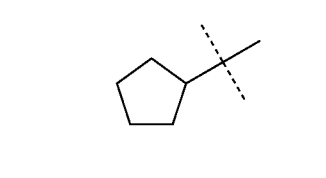 |

TABLE 1-continued

| Compound | A | R¹⁰ | E |
|---|---|---|---|
| 99 | hexahydrofuro[3,2-b]furan-3-yl (H,H stereo) | cyclopentyl | 3-(2-morpholinoethoxy)phenyl |
| 102 | hexahydrofuro[3,2-b]furan-3-yl (H,H stereo) | cyclopentyl | 4-methoxyphenyl |
| 103 | hexahydrofuro[3,2-b]furan-3-yl (H,H stereo) | cyclopentyl | 3-(cyanomethylamino)phenyl |
| 104 | hexahydrofuro[3,2-b]furan-3-yl (H,H stereo) | cyclohexyl | phenyl |
| 105 | tert-butoxy | cyclopentyl | 5-(3-chloropropanamido)-1H-benzimidazol-2-yl (linked via benzimidazole 5-position; 2-NHC(O)CH₂CH₂Cl) |
| 106 | tert-butoxy | cyclopentyl | 2-amino-1H-benzimidazol-5-yl |
| 107 | tert-butoxy | cyclopentyl | 2-(methylamino)-1H-benzimidazol-5-yl |

TABLE 1-continued

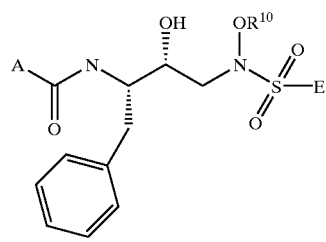

| Compound | A | R¹⁰ | E |
|---|---|---|---|
| 108 | tBu-O- | cyclopentyl | 6-tBu-benzimidazol-2-yl-NHCO-CH₂CH₂-Cl |
| 109 | tBu-O- | cyclopentyl | 4-(MOM-O)-phenyl |
| 110 | (S)-tetrahydrofuran-3-yl-O- | cyclopentyl | quinoxalin-6-yl |
| 111 | (S)-tetrahydrofuran-3-yl-O- | tBu-CH< (neopentyl branched) | phenyl |
| 112 | (S)-tetrahydrofuran-3-yl-O- | tBu-CH< | phenyl |
| 113 | hexahydrofuro[3,2-b]furan-3-yl-O- | cyclopentyl | 3-[N-(ethoxycarbonylmethyl)-N-(2-aminoethyl)carbamoylamino]phenyl |
| 114 | 1,3-dioxan-5-yl-O- | cyclopentyl | 5-(NHCOCH₃)-benzothiazol-2-yl |
| 115 | MeSO₂-CH₂-C(CH₃)₂- | cyclopentyl | 4-OMe-phenyl |

TABLE 1-continued
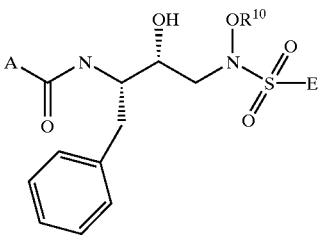
| Compound | A | R¹⁰ | E |
|---|---|---|---|
| 116 | 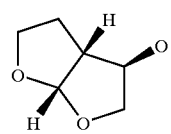 | 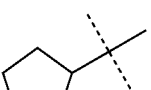 | 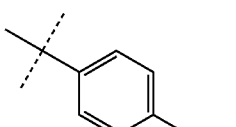 |
| 117 | 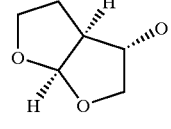 | 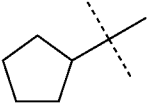 | 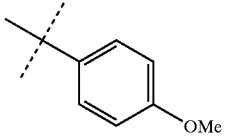 |
| 118 | 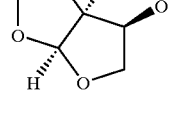 |  | 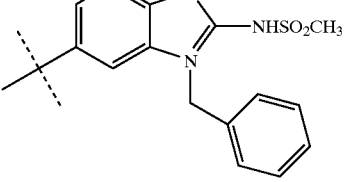 |
| 120 | 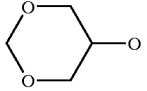 | 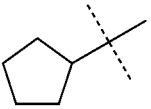 | 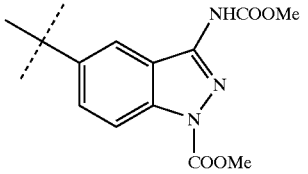 |
| 121 | 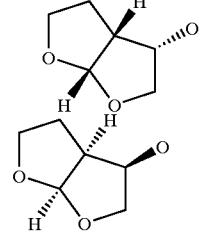 | 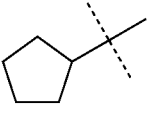 | 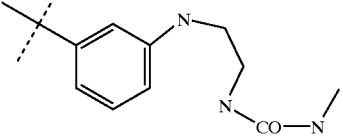 |
| 122 | 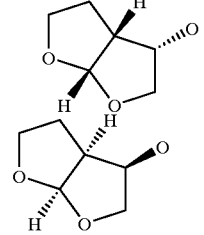 | 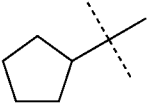 | 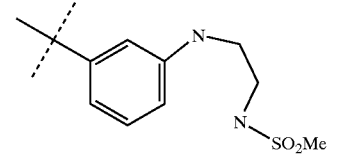 |

TABLE 1-continued
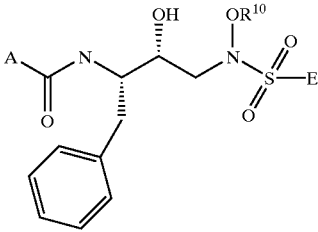
| Compound | A | R[10] | E |
|---|---|---|---|
| 123 | 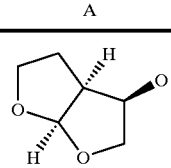 | 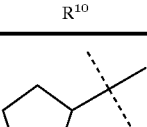 | 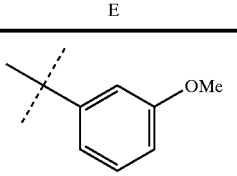 |
| 124 | 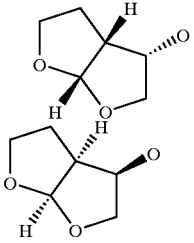 | 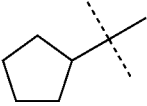 | 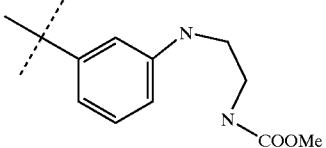 |
| 125 | 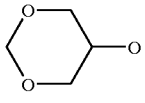 | 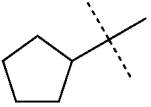 | 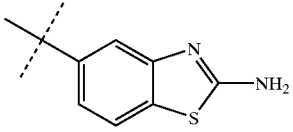 |
| 126 | 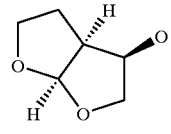 |  | 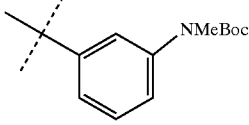 |
| 127 | 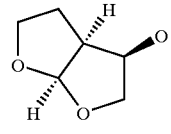 |  | 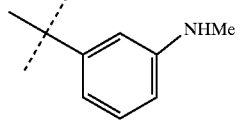 |
| 128 | 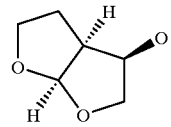 | 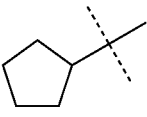 | 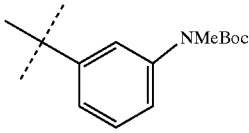 |
| 129 | 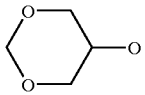 | 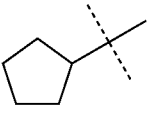 | 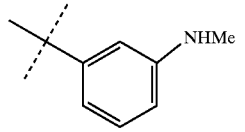 |
| 130 | 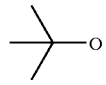 | 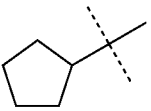 | 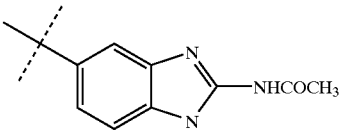 |

TABLE 1-continued
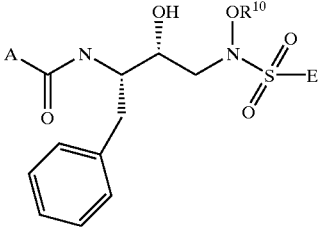
| Compound | A | R10 | E |
|---|---|---|---|
| 131 | 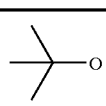 | 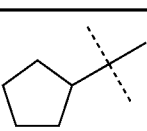 | 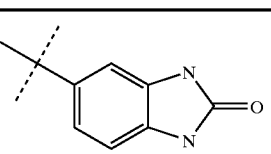 |
| 132 | 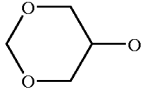 |  | 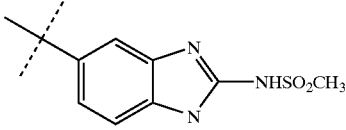 |
| 133 | 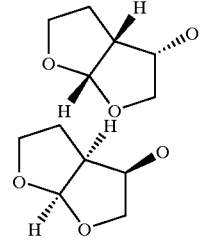 | 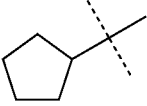 | 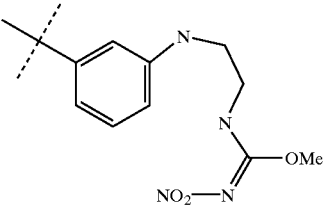 |
| 134 | 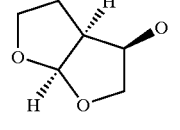 | 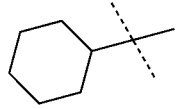 | 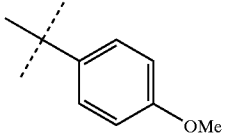 |
| 135 | 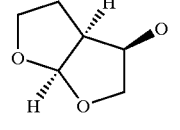 | 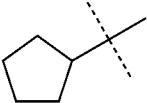 | 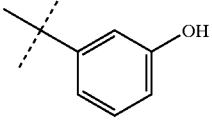 |
| 136 | 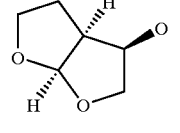 | 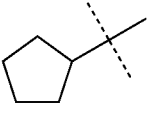 | 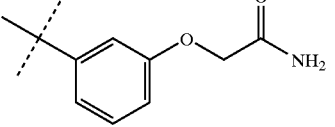 |
| 137 | 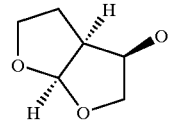 | 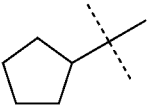 | 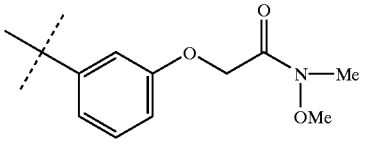 |
| 138 | 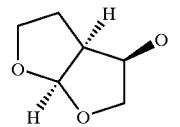 | 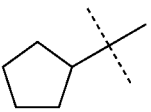 | 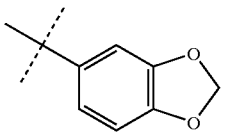 |

TABLE 1-continued

| Compound | A | R¹⁰ | E |
|---|---|---|---|
| 139 | hexahydrofuro[3,2-b]furan-3-yl | cyclopentyl | 2,3-dihydro-1,4-benzodioxin-6-yl |
| 140 | hexahydrofuro[3,2-b]furan-3-yl | cyclopentyl | 3,4-dimethoxyphenyl |
| 141 | hexahydrofuro[3,2-b]furan-3-yl | cyclopentyl | 4-(isopropoxy)phenyl |
| 142 | hexahydrofuro[3,2-b]furan-3-yl | cyclopentyl | 3-(isopropoxy)phenyl |
| 145 | hexahydrofuro[3,2-b]furan-3-yl | isobutyl (branched) | 4-methoxyphenyl |
| 146 | hexahydrofuro[3,2-b]furan-3-yl | tetrahydropyran-4-yl | 4-aminophenyl |
| 147 | hexahydrofuro[3,2-b]furan-3-yl | tetrahydropyran-4-yl | 3-aminophenyl |

TABLE 1-continued

| Compound | A | R¹⁰ | E |
|---|---|---|---|
| 148 | hexahydrofuro[2,3-b]furan-3-yl | tetrahydro-2H-pyran-4-yl | 3-hydroxyphenyl |
| 149 | hexahydrofuro[2,3-b]furan-3-yl | tetrahydro-2H-pyran-4-yl | 4-hydroxyphenyl |
| 150 | hexahydrofuro[2,3-b]furan-3-yl | tetrahydro-2H-pyran-4-yl | 2,3-dihydro-1,4-benzodioxin-6-yl |
| 151 | hexahydrofuro[2,3-b]furan-3-yl | tetrahydro-2H-pyran-4-yl | 1,3-benzodioxol-5-yl |
| 152 | hexahydrofuro[2,3-b]furan-3-yl | 3-cyano-1-methylpropyl | 4-methoxyphenyl |
| 153 | hexahydrofuro[2,3-b]furan-3-yl | cyclohexyl | 4-aminophenyl |

TABLE 1-continued
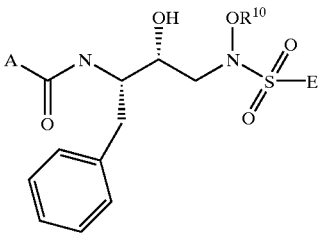
| Compound | A | R10 | E |
|---|---|---|---|
| 154 | 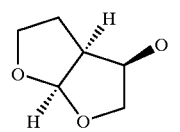 | 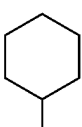 | 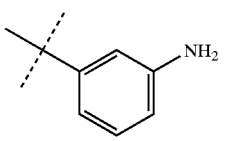 |
| 155 | 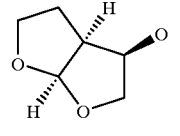 | 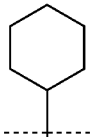 | 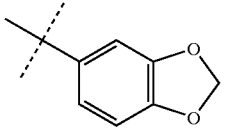 |
| 156 | 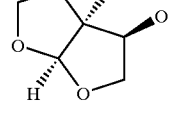 | 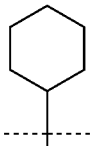 | 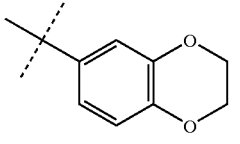 |
| 157 | 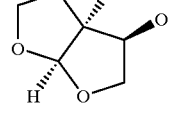 | 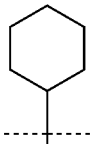 | 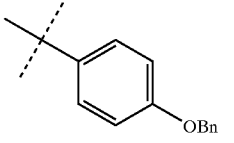 |
| 158 | 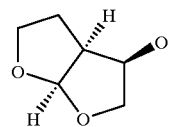 | 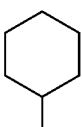 | 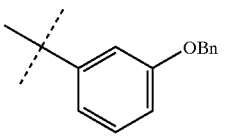 |
| 159 | 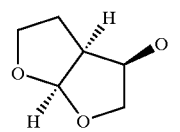 | 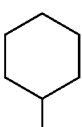 | 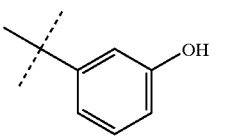 |

TABLE 1-continued

| Compound | A | R¹⁰ | E |
|---|---|---|---|
| 160 | hexahydrofuro[3,2-b]furan-3-yl-O- | cyclohexylmethyl- | 4-hydroxyphenyl |
| 161 | tert-butyl-O- | 3-ethylpentan-3-yl | 4-methoxyphenyl |
| 162 | hexahydrofuro[3,2-b]furan-3-yl-O- | 3-ethylpentan-3-yl | benzo[1,3]dioxol-5-yl |
| 163 | hexahydrofuro[3,2-b]furan-3-yl-O- | 3-ethylpentan-3-yl | 4-aminophenyl |
| 164 | hexahydrofuro[3,2-b]furan-3-yl-O- | 3-ethylpentan-3-yl | 3-aminophenyl |
| 165 | hexahydrofuro[3,2-b]furan-3-yl-O- | 3-ethylpentan-3-yl | 4-benzyloxyphenyl |
| 166 | hexahydrofuro[3,2-b]furan-3-yl-O- | 3-ethylpentan-3-yl | 4-hydroxyphenyl |

TABLE 1-continued

| Compound | A | R¹⁰ | E |
|---|---|---|---|
| 167 | bis-tetrahydrofuran diol | cyclopentyl | 3-(NHCH₂CH₂NHC(O)NHCH₂CONHMe)phenyl |
| 168 | bis-tetrahydrofuran diol | cyclopentyl | 3-(NHCH₂C(O)NHOMe)phenyl |
| 169 | bis-tetrahydrofuran diol | cyclopentyl | 3-(NHCH₂C(O)NMe₂)phenyl |
| 170 | bis-tetrahydrofuran diol | cyclopentyl | 3-(NHCH₂C(O)N(Et)Me)phenyl |
| 171 | hexahydrofuro[2,3-b]furan-3-ol | cyclopentyl | 4-aminophenyl |
| 172 | hexahydrofuro[2,3-b]furan-3-ol | cyclopentyl | 4-aminophenyl |

TABLE 1-continued

| Compound | A | R[10] | E |
|---|---|---|---|
| 173 | hexahydrofuro[2,3-b]furan-3-yl | cyclopentyl-C(CH3)2- | 3-CONH2-C6H4-C(CH3)2- |

| Compound | A | R[8] | E |
|---|---|---|---|
| 80 | tert-butoxy | cyclopentylidene-CH- | 4-OMe-C6H4-C(CH3)2- |

| Compound | A | R[8] | E |
|---|---|---|---|
| 81 | tert-butoxy | (CH3)2CH-C(CH3)= | 4-OMe-C6H4-C(CH3)2- |

| Compound | A | R[10] | E |
|---|---|---|---|
| 100 | hexahydrofuro[2,3-b]furan-3-yl | cyclopentyl-C(CH3)2- | 3-NH2-C6H4-C(CH3)2- |

-continued

| Compound | A | R¹⁰ | E |
|---|---|---|---|
| 101 | hexahydrofuro[2,3-b]furan-3-yl | cyclopentyl | 4-methoxyphenyl |
| 119 | hexahydrofuro[2,3-b]furan-3-yl | cyclopentyl | 3-(NHMe)phenyl |
| 143 | hexahydrofuro[2,3-b]furan-3-yl | cyclopentyl | benzo[1,3]dioxol-5-yl |
| 144 | hexahydrofuro[2,3-b]furan-3-yl | cyclopentyl | 2,3-dihydro-1,4-benzodioxin-6-yl |

Most preferred compounds of the present invention include the following:

(3R,3aS,6aR)hexahydrofuro[2,3-b]furan-3-yl N-((1S,2R)-1-benzyl-3-(cyclopentyloxy)[(3-[2-(dimethylamino)ethyl]aminophenyl)sulfonyl]amino-2-hydroxypropyl)carbamate;

(3S,3aR,6aS)hexahydrofuro[2,3-b]furan-3-yl N-((1S,2R)-1-benzyl-3-(cyclopentyloxy)[(3-[2-(dimethylamino)ethyl]aminophenyl)sulfonyl]amino-2-hydroxypropyl)carbamate;

(3R,3aS,6aR)Hexahydrofuro[2,3-b]furan-3-yl-N-((1S,2R)-1-benzyl-3-(cyclopentyloxy)(2-[(methylsulfonyl)amino] benzimidazol-5-ylsulfonyl)amino-2-hydroxypropyl)carbamate;

(3R,3aS,6aR)hexahydrofuro[2,3-b]furan-3-yl N-(1S, 2R)-3-[[(3-N-methylaminophenyl)sulfonyl](cyclopentyloxy)amino]-1-benzyl-2-hydroxypropylcarbamate;

1,3-Dioxan-5-yl N-(1S,2R)-1-benzyl-3-[(cyclopentyloxy) (2-{(methoxycarbonyl)amino}-1H-benzimidazol-5-ylsulfonyl) amino]-2-hydroxypropylcarbamate;

(3R,3aS,6aR)hexahydrofuro[2,3-b]furan-3-yl N-(1S,2R)-1-benzyl-2-hydroxy-3-[[(4-methoxyphenyl)sulfonyl] (tetrahydro-2H-pyran-4-yloxy)amino] propylcarbamate;

(3R,3aS,6aR)hexahydrofuro[2,3-b]furan-3-yl N-(1S,2R)-3-[[(3-aminophenyl)sulfonyl](cyclopentyloxy)amino]-1-benzyl-2-hydroxypropylcarbamate;

(3R,3aS,6aR)hexahydrofuro[2,3-b]furan-3-yl AT-[(1S, 2R)-1-benzyl-3-((cyclopentyloxy)[3-(2-[methoxy (methyl)amino]-2-oxoethylamino) phenyl]sulfonylamino)-2-hydroxypropyl] carbamate;

(3R,3aS,6aR)hexahydrofuro[2,3-b]furan-3-yl N-[(1S, 2R)-1-benzyl-4-(cyclopentyloxy)-2-hydroxy-4-(6-quinoxalinyl sulfonyl)butyl]carbamate;

(3R,3aS,6aR)hexahydrofuro[2,3-b]furan-3-yl N-((1S, 2R)-1-benzyl-3-(cyclopentyloxy)[(4-methoxyphenyl) sulfonyl]amino-2-hydroxypropyl)carbamate;

(3R,3aS,6aR)hexahydrofuro[2,3-b]furan-3-yl N-[(1S, 2R)-1-benzyl-3-((cyclopentyloxy)[3-(2-

[(methylsulfonyl)amino] ethylamino)phenyl] sulfonylamino)-2-hydroxypropyl]carbamate;

(3R,3aS,6aR)hexahydrofuro[2,3-b]furan-3-yl N-(1S,2R)-3-[[(3-N-methylaminophenyl)sulfonyl](cyclopentyloxy)amino]-1-benzyl-2-hydroxypropylcarbamate phosphate ester;

(3R,3aS,6aR)hexahydrofuro[2,3-b]furan-3-yl N-(1S,2R)-3-[[(3-aminophenyl)sulfonyl](cyclopentyloxy)amino]-1-benzyl-2-hydroxypropylcarbamate phosphate ester;

(3R,3aS,6aR) hexahydrofuro [2,3-b]furan-3-yi N-(1S,2R)-3-[[(4-aminophenyl)sulfonyl](cyclopentyloxy)amino]-1-benzyl-2-hydroxypropyl carbamate;

(3R,3aS,6aR)hexahydrofuro[2,3-b]furan-3-yl (1S,2R)-1-benzyl-3-{(1-ethylpropoxy)[(4-hydroxyphenyl)sulfonyl]amino}-2-hydroxypropylcarbamate;

(3R,3aS,6aR)hexahydrofuro[2,3-b]furan-3-yl (1S,2R)-3-[(1,3-benzodioxol-5-ylsulfonyl)(1-ethylpropoxy)amino]-1-benzyl-2-hydroxypropylcarbamate;

(3R,3aS,6aR)hexahydrofuro[2,3-b]furan-3-yl N-[(1S,2R)-3-[(1,3-benzodioxol-5-ylsulfonyl)(cyclopentyloxy)amino]-1-benzyl-2-(phosphonooxy)propyl]carbamate;

(3R,3aS,6aR)hexahydrofuro[2,3-b]furan-3-yl (1S,2R)-3-[(1,3-benzodioxol-5-ylsulfonyl)(cyclohexyloxy)amino]-1-benzyl-2-hydroxypropylcarbamate;

(3R,3aS,6aR)hexahydrofuro[2,3-b]furan-3-yl 3-[(1,3-benzodioxol-5-ylsulfonyl)(tetrahydro-2H-pyran-4-yloxy)amino]-1-benzyl-2-hydroxypropylcarbamate;

(3R,3aS,6aR)hexahydrofuro[2,3-b]furan-3-yl N-[(1S,2R)-3-[(1,3-benzodioxol-5-ylsulfonyl)(cyclopentyloxy)amino]-1-benzyl-2-(phosphonooxy)propyl]carbamate; or a pharmaceutically acceptable derivative thereof.

The compounds of the present invention can be readily prepared by techniques known in the art. Scheme I illustrates a general synthetic route to compounds of formula (V), a preferred sub-genus of formula (I).

According to Scheme I, commercially available N-hydroxyphthalimide is reacted with $R^{10}$-Br or $R^{10}$ OH under displacement or Mitsonobu-type conditions respectively, followed by hydrazinolysis in ethanol to produce the amine of formula (I). Amine of formula (I) is further utilized in two synthetic routes, Path 1 and Path 2.

Path 1

Step 1: Amine of formula (I) is reacted with a sulfonyl chloride of formula (A) to produce sulfonamide of formula (II').

Step 2: Sulfonamide of formula (II') is reacted with intermediate of formula (B), which bears an amine protecting group P, such as t-butoxycarbonyl, to produce compound of formula (III'). Suitable amine protecting groups are described in numerous references, including T. W. Greene and P. G. M. Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995). Examples of such amino protecting groups include, but are not limited to, Cbz or Alloc.

Step 3: Compound of formula (III') is then reacted with A-L, wherein L is a leaving group, to produce compound of formula (IV). A leaving group is an atom or group which is displaceable upon reaction with an appropriate amine or sulfonamide. Suitable leaving groups would be obvious to one of skill in the art and include but are not limited to hydroxyls, carboxylates and halides.

SCHEME I

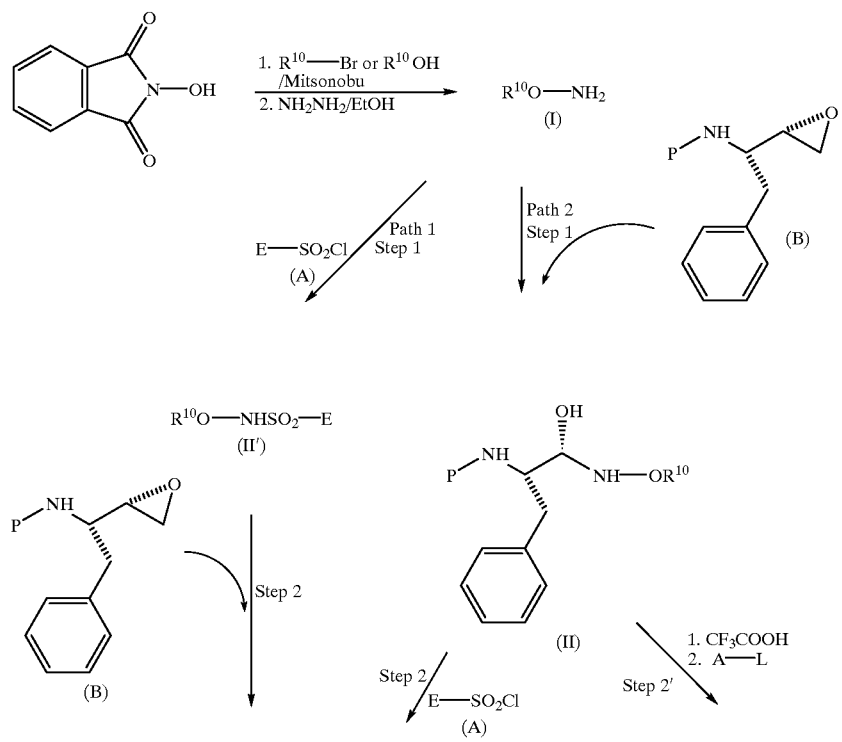

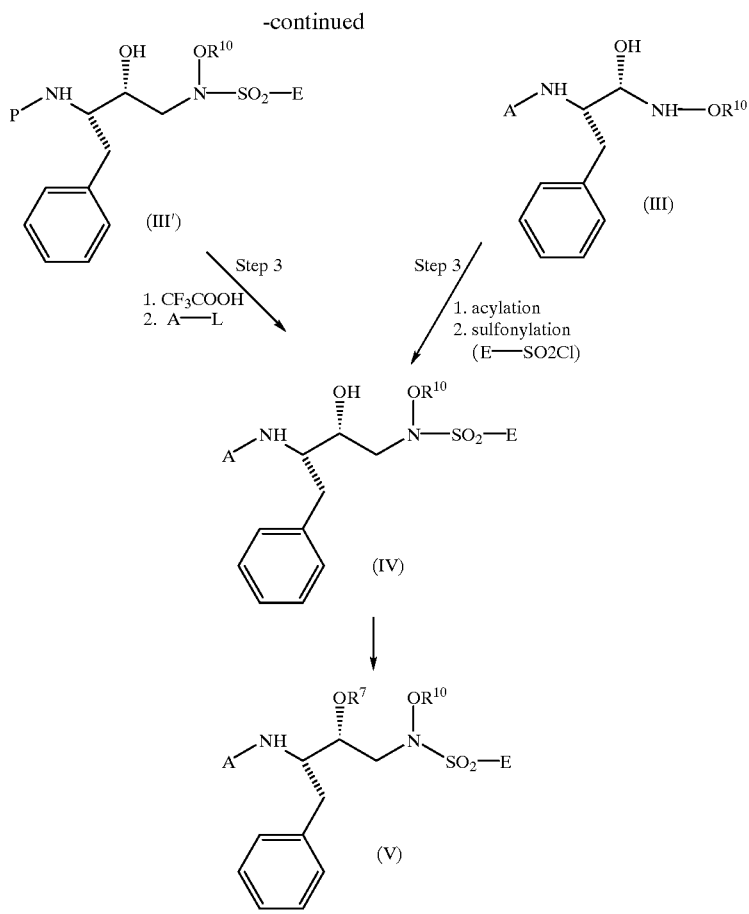

Step 4: Compound of formula (IV) is then converted to compound of formula (V) by functional transformation of the hydroxy group.

Path 2 differs from Path 1 only in the sequence of reagents employed to convert compound of formula (I) to compound of formula (IV).

The synthetic approach illustrated in Scheme I can be readily extended to produce other compounds of the present invention. The above synthetic scheme is not intended to comprise a comprehensive list of all means by which compounds described and claimed in this application may be synthesized. Further methods will be evident to those of ordinary skill in the art.

As discussed above, the novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other anti-viral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of Eprotease inhibitors in vaccines. For example, a compound of this invention may be combined with pharmaceutically acceptable adjuvants conventionally employed in vaccines and administered in prophylactically effective amounts to protect individuals over an extended period time against HIV infection. As such, the novel protease inhibitors of this invention can be administered as agents for treating or preventing HIV infection in a mammal.

The compounds of formula I, especially those having a molecular weight of less than about 700 g/mole, may be readily absorbed by the bloodstream of mammals upon oral administration. Compounds of formula I having a molecular weight of less than about 600 g/mole are most likely to demonstrate oral availability. This surprisingly impressive oral availability makes such compounds excellent agents for orally-administered treatment and prevention regimens against HIV infection.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), alcitabine (ddC), d4T, zidovudine 3AZT), polysulfated polysaccharides, sT4 (soluble CD4), 3TC, 935U83, 1592U89, 524W91, ganciclovir, dideoxycytidine, trisodium phosphonoformate, eflornithine, ribavirin, acyclovir, alpha interferon and trimenotrexate. Ribonucleotide reductase inhibitors such as hydroxyurea may also be used. Additionally, non-nucleoside inhibitors of reverse transcriptase, such as TIBO, delavirine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent which would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that these compounds act synergistically in preventing the replication of HIV in human T cells. Preferred combination therapies include the administration of a compound of this invention with AZT, ddI, ddC or d4T.

Alternatively, the compounds of this invention may also be co-administered with other HIV protease inhibitors such as Agenerase (VX-478, Vertex), saquinavir, Ro 31-8959 (Roche), L-735,524 (Merck), XM 323 (Du-Pont Merck) A-80,987 (Abbott), MK 639 (Merck), ABT 538 (A-80538, Abbott), AG 1343(Agouron), XM 412 (Du-Pont Merck), XM 450 (Du-Pont Merck), BMS 186318 (Bristol-Meyers Squibb), ABT 378 (Abbott) and CPG 53,437 (Ciba Geigy) to increase the effect of therapy or prophylaxis against various viral mutants or members of other HIV quasi species.

We prefer administering the compounds of this invention as single agents or in combination with retroviral reverse transcriptase inhibitors, such as derivatives of AZT, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone, tuscarasol and rEPO); and antibiotics (e.g., pentamidine isethiorate) to prevent or combat infection and disease associated with HIV infections, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include, as well as other AIDS-like diseases caused by retroviruses, such as simian immunodeficiency viruses, but are not limited to, HTLV-I and HTLV-II. In addition, the compounds of this invention may also be used to inhibit other aspartyl proteases, and in particular, other human aspartyl proteases, including renin and aspartyl proteases that process endothelin precursors. Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 50 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. These and other uses which characterize commercial aspartyl protease inhibitors will be evident to those of ordinary skill in the art.

As used herein, the compounds according to the invention are defined to include pharmaceutically acceptable derivatives or prodrugs thereof. A "pharmaceutically acceptable derivative" or "pharmaceutically acceptable prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The compounds according to the invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium and $^+NW_4$ (wherein W is Cl-4 alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$ alkyl group)

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds according to the invention will be pharmaceutically acceptable. However, salts of acids and bases which are non-pharmaceutically acceptable may also find use, for example, in the preparation or purification of a pharmaceutically acceptable compound.

Preferred salts include salts formed from hydrochloric, sulfuric, acetic, succinic, citric and ascorbic acids.

Preferred esters of the compounds according to the invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Any reference to any of the above compounds also includes a reference to a pharmaceutically acceptable salts thereof.

The compounds according to the invention are especially useful for the treatment of AIDS and related clinical conditions such as AIDS related complex (ARC), progressive generalized lymphadenopathy (PGL), Kaposi's sarcoma, thrombocytopenic purpura, AIDS-related neurological conditions such as AIDS dementia complex, multiple sclerosis or tropical paraperesis, and also anti-HIV antibody-positive and HIV-positive conditions, including such conditions in asymptomatic patients.

In a further aspect of the invention there are provided the compounds according to the invention for use in medical therapy particularly for the treatment or prophylaxis of viral infections such as HIV infections.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is an HIV infection. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions. It will be appreciated that of compounds of Formula (I), (II), (III), (IV), and (V) and one or more other HIV protease inhibitors, reverse transcriptase inhibitors, or non-nucleoside reverse transcriptase inhibitors may be used in the manufacture of the above medicament.

Reference herein to treatment extends to prophylaxis as well as the treatment of established infections or symptoms.

The above compounds according to the invention and their pharmaceutically acceptable derivatives may be employed in combination with other therapeutic agents for the treatment of the above infections or conditions. Combination therapies according to the present invention comprise the administration of at least one compound of the formula (I) or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmacuetically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as (1 alpha, 2 beta, 3 alpha)-9-[2,3-bis(hydroxymethyl)cyclobutyl]guanine [(-)BHCG, SQ-34514], oxetanocin-G (3,4-bis-(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2- phosphonyl-methoxypropyl)cytosine (HPMPC), ribonucleotide reductase inhibitors such as 2-acetylpyridine 5-[(2-chloroanilino)thiocarbonyl) thiocarbonohydrazone, 3'azido-3'-deoxythymidine, hydroxyurea, other 2',3'-dideoxynucleosides such as 2', 3'-dideoxycytidine, 2',3'-dideoxyadenosine, 2', 3'-dideoxyinosine, 2',3'-didehydrothymidine, protease inhibitors such as agenerase, indinavir, ritonavir, nelfinavir, [3S-[3R*(1R*, 2S*)]]-[3[[(4-aminophenyl)sulfonyl](2-methylpropyl)amino]-2-hydroxy-1-(phenylmethyl)propyl]-tetrahydro-3-furanyl ester (141W94), oxathiolane nucleoside analogues such as (-)-cis-1-(2-hydroxymethyl)-1,3-oxathiolane 5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (-)-cis-4-[2-amino-6-(cyclopropylamino)-9H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrcl-2yl)-3H-1,4-benzodiazepin-2-amine (Ro24-7429), interferons such as a-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3,1-benzoxazin-2-ones NNRTIs such as (-)-6-chloro-4-cyclopropylethynyl-4-trifluoromethyl-1,4-dihydro-2H-3,1-benzoxazin-2-one (L-743,726 or DMP-266), and quinoxaline NNRTIs such as isopropyl (2S)-7-fluoro-3,4-dihydro-2-ethyl-3-oxo-1(2H)-quinoxalinecarboxylate (HBY1293).

More preferably the combination therapy involves the administration of one of the above mentioned agents and a compound within one of the preferred or particularly preferred sub-groups within formula (I) as described above. Most preferably the combination therapy involves the joint use of one of the above named agents together with one of the compounds of formula (I) specifically named herein.

The present invention further includes the use of a compound according to the invention in the manufacture of a medicament for simultaneous or sequential administration with at least one other therapeutic agent, such as those defined hereinbefore.

In order that this invention may be more fully understood, the following examples are set forth. These examples are for the purpose of illustration only and are not to be construed as limiting the scope of the invention in any way.

EXAMPLES

General Methods and Conditions

All temperatures are recorded in degrees Celsius. Thin layer chromatography (TLC) was carried out using 0.25 mm thick E. Merck silica gel 60 $F_{25}4$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 F254 plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5;M silica, $C_{18}$ reversed-phase column, 3.9 mm ID×15 cm L with a flow rate of 1.5 mL/min using the following table:

| Mobile phase: | A = 0.1% $CF_3CO_2H$ in $H_2O$ |
| --- | --- |
| | B = 0.1% $CF_3CO_2H$ in $CH_3CN$ |
| Gradient: | T = 0 min., A (95%), B (5%) |
| | T = 20 min., A (0%), B (100%) |
| | T = 22.5 min., A (0%), B (100%) |

Preparative HPLC was also carried out using $C_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., Peptides 1990, Gimet, E. and D. Andrew, Eds., Escom, Leiden, Netherlands (1990); and the method described essentially by Partaledis et al., J. Virol., 69, pp. 5228–35 (1995).

Compounds of invention were tested for their antiviral potency in several virological assays.

Insofar as the compounds of this invention are able to inhibit the replication of the HIV virus in $CD_4^+$ cells of human lineage, they are of evident clinical utility for the treatment of HIV infection. These tests are predictive of the compounds ability to inhibit HIV protease in vivo.

Example 1

Step 1

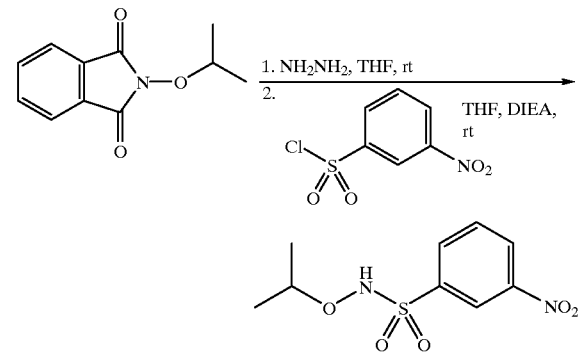

$N^1$-isopropoxy-3-nitro-1-benzenesulfonamide. To a cooled solution (0° C.) of O-isopropyl hydroxyphthalimide (4.10 g, 0.02 mol) in anhydrous THF (45 mL) was added anhydrous hydrazine(0.69 mL, 0.022 mmol) with stirring. The solution was allowed to warm to RT and stir for 20.0h, filtered and the ppt. was washed with anhydrous THF (20 mL). To the filtrate was added 3-nitro-benzenesulfonylchloride (4.86 g, 0.022 mol) and diiosopropylethylamine (4.17 mL, 0.024 mol) at RT and the mixture was stirred at RT for 20 h. The solution was evaporated and the reside was partioned between ethyl acetate (200 mL) and Aq. 1.0 N HCl (30 mL). The organic layer was washed with 1.0 N HCl (2 x 50 mL), 5% Aq. $NaHCO_3$ (2×50 mL), brine (2×25 mL), dried ($MgSO_4$), filtered, and evaporated to give a yellow oil. The oil was purified by column chromatography: hexane/ethyl acetate (80/20) to give 3.58g (69%) of the product as a white solid. 1HNMR ($CDCl_3$): 1.20(d,6H); 4.27 (m, 1H); 7.05(s, 1H); 7.75(1,1H); 8.22 (d,1H); 8.48 (dd,1H); 8.74(t, 1H).

Step 2

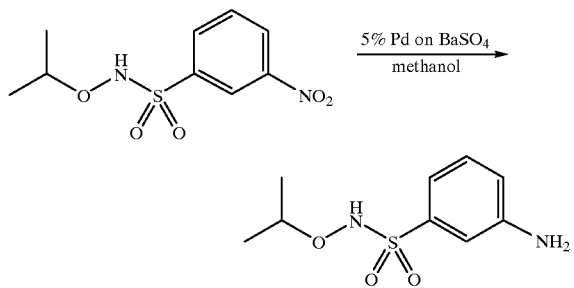

3-amino-N[1]-isopropoxy-1-benzenesulfonamide. To a Parr H$_2$ vessel containing 5% Pd/BaSO$_4$ (0.350g) was added a methanolic solution (125 mL) of N[1]-isopropoxy-3-nitro-1-benzenesulfonamide (3.50 g, 0.0135 mol) at rt under Ar atm. The solution was hydrogenated at 45psi for approx. 1.0 h. The reaction mixtire was filtered (1/2" celite pad) and evaporated to give the product as yellow crystalline solid 2.90 g (96%). $^1$H NMR (CDCl$_3$) 1.20(d,25H); 4.27(m,1H) 7.05(s,1H); 7.75(1,1H); 8.22(d,1H); 8.48 (dd,1H); 8.74(t, 1H).

Step 3

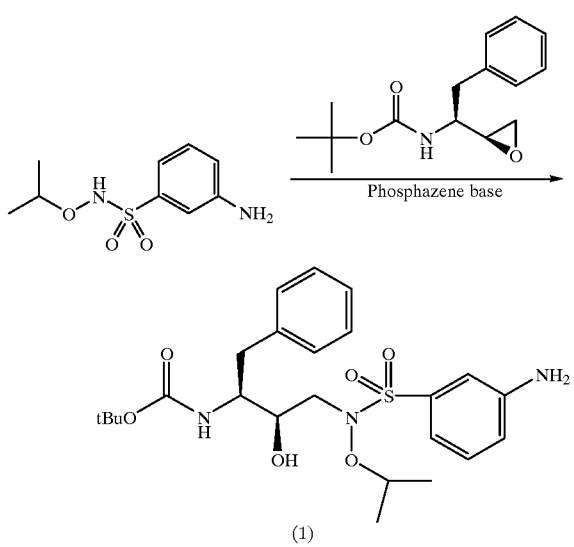

tert-butyl-N-(1S,2R)-3-[[(3-aminophenyl)sulfonyl] (isopropoxy) amino]-1-benzyl-2-hydroxypropylcarbamate. To a solution of 3-amino-N-isopropoxy-1-benzenesulfonamide (2.20 g, 9.56 mmol) and tert-butyl N-(1S)-1-[(2S)oxiran-2-yl]-2-phenylethylcarbamate (2.01 g, 7.65 mmol) in anhydrous THF (10.0 mL) was added phosphazene base P4 t-butyl solution (1.0 M in hexanes, 1.53 mL, 1.53 mmol) with stirring at rt. After 8.0h at rt, the THF was evaporated to give a dark yellow residue that was dissloved in ethyl acetate (200 mT). This solution was washed with 0.50M HCl (3×20.0 mL), sat. NaHCO, (3×20 mL), brine (2×25 mL), dried (MgSO$_4$), filtered, and evaporated to give a yellow foam. The crude product was purified by column chromatography: methylene chloride/ethyl acetate (95/5) to give the product as a light yellow foam (3.61g, 95%). MS: product: M+Na=516 -H NMR (CD$_3$OD) 0.90(m, 15H); 2.50–3.10(m, 4H); 3.60–3.85(m, 2H); 4.70 (m, 1H); 6.90(d, 1H); 7.05(d, 1H); 7.10–7.30(m, 6H).

Example 2

Step 1

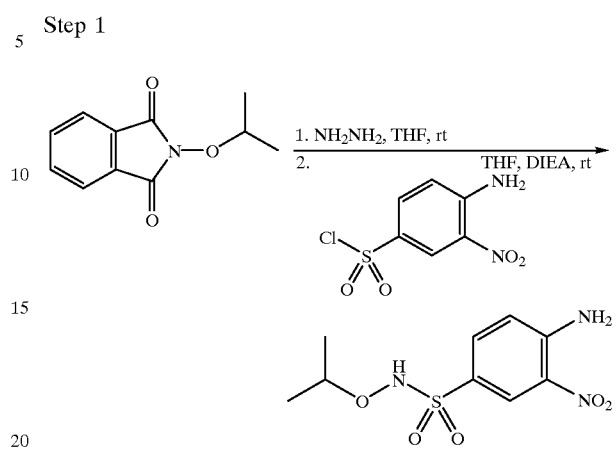

4-amino-N[1]-isopropoxy-3-nitro-1-benzenesulfonamide.

Prepared using the procedure outlined in Example 1. The crude product was purified by column chromatography: 60/40 hexane/ethyl acetate to give the product as a yellow solid (63%). $^1$H NMR (DMSO) 1.05(d, 6H); 4.00(m, 1H); 7.10(d, 1H); 7.65(d, 1H); 8.10(s, 2H); 8.40(s, 1H).

Step 2

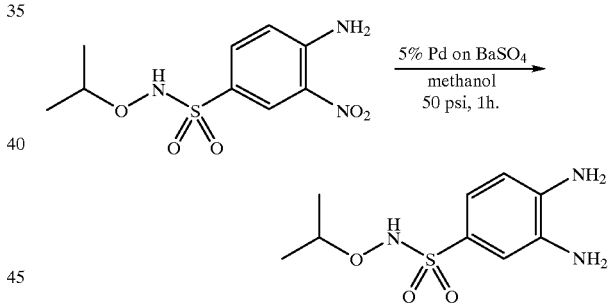

3,4-diamino-N[1]-isopropoxy-1-benzenesulfonamide. Prepared using the procedure outlined in Step 2, Example 1. $^1$H NMR (DMSO) 1.05(d, 6H); 3.95(m, 1H); 4.80(s,2H); 5.30 (s, 2H); 6.50(d, 1H); 6.92(d, 1H); 7.97(s, 1H); 9.50(s, 1H).

Step 3

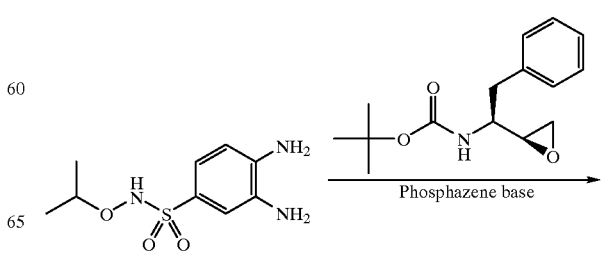

81

-continued

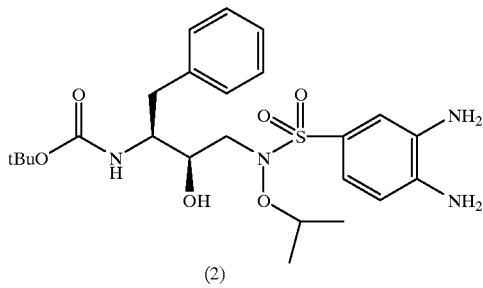

(2)

tert-butyl-N-(1S,2R)-1-benzyl-3-[[(3,4-diaminophenyl)sulfonyl](isopropoxy)amino]-2-hydroxypropylcarbamate. Prepared using the procedure outlined in Step 3, Example 1. The product was purified by column chromatography: to 40/60 hexane/ethyl acetate give the product as a dark orange solid (91%). MS: M+Na=531 $^1$H NMR (CD$_3$OD) 0.90(m, 15H); 2.50–3.10(m, 4H); 3.60–3.85((m, 2H); 4.45(m, 1H); 6.40(d, 1H); 6.70(d, 1H); 7.00–7.30(m, 6H).

Example 3

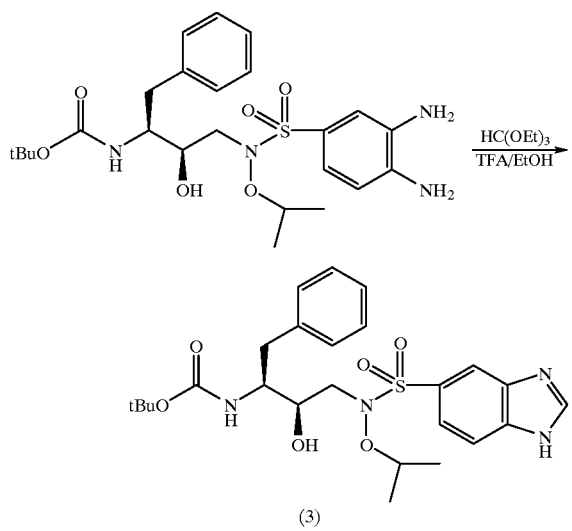

(3)

tert-butyl-N-(1S,2R)-3-[(1H-1,3-benzimidazol-5-ylsulfonyl)(isopropoxy)amino]-1-benzyl-2-hydroxypropylcarbamate. To a solution of tert-butyl N-(1S,2R)-1-benzyl-3-[[(3,4-diaminophenyl)sulfonyl](isopropoxy)amino]-2-hydroxy propylcarbamate (0.70 g, 1.38 mmol) in ethanol(10 mL) was added triethylorthoformate(0.64 mL, 3.86 mmol) and TFA (5.0 µl) with stirring at rt. After 1.0 h., the reaction was neutralized with Aq. sat. NaHCO$_3$ (50 µl ) and evaporated to give an orange residue. The residue was dissolved in ethyl acetate (100 mL) and washed with aq. sat. NaHCO$_3$ (1×20 mL), water (2×20 mL), brine (1×20 mL), dried (MgSO$_4$), filtered, and evaporated to give the crude product as a orange foam. The crude product was purified by column chromatography: 30/70 hexane/ethyl acetate give the product as a white solid (0.60g, 85%%). MS: M+H=519 $^1$H NMR (CD$_3$OD) 1.00–1.40(m, 15H); 2.50–3.10(m, 4H); 3.60–3.85(m, 2H); 4.60(m, 1H); 7.20(m, 5H); 7.80(s, 2H) 8.20(s, 1H); 8.40(s, 1H).

82

Example 4

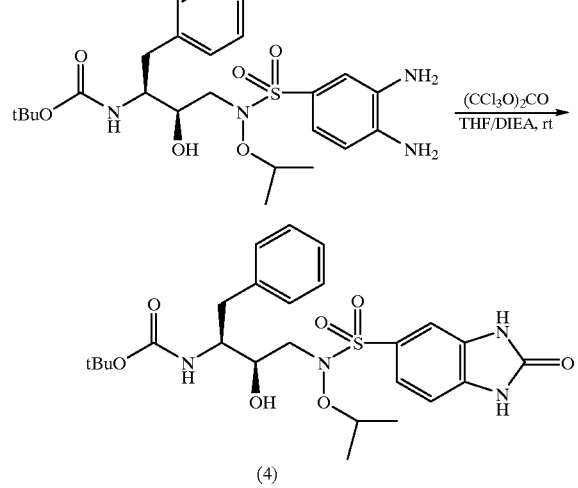

(4)

tert-butyl-N-((1S,2R)-1-benzyl-2-hydroxy-3-isopropoxy[(2-oxo-2, 3-dihydro-1H-1,3-benzimidazol-5-yl)sulfonyl]aminopropyl)carbamate. To a solution of tert-butyl N-(1S, 2R)-1-benzyl-3-[[(3,4-diaminophenyl)sulfonyl](isopropoxy)amino]-2-hydroxypropyl carbamate (0.70 g, 1.38 mmol) and DIEA (0.24 mL, 1.38 mmol) in anhydrous THF (10 mL) was added triphosgene (0.136 g, 0.46 mmol) with stirring at rt. After 0.5h., the THF was removed in vacuo and the residue was dissolved in ethyl acetate(100 mL). This solution was washed with 0.5M HCl (2×25 mL), aq. sat. NaHCO$_3$ (2×25 mL), brine (1×25 mL), dried (MgSO$_4$), filtered and evaporated to give the crude product. The crude product was purified by column chromatography: 30/70 hexane/ethyl acetate give the product as a yellow solid (0.63g, 86%) MS: M+Na=557 H-NMR (CD$_3$OD) 1.00–1.40 (m, 15H); 2.50–3.10(m, 4H); 3.60–3.85(m, 2H); 4.55(m, 1H); 7.20(m, 6H); 7.50(m, 2H).

Example 5

Step 1

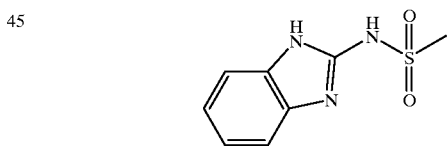

N-methanesulfonyl-2-aminobenzimidazole. 2-aminobenzimidazole (1.0 g, 7.5 mmol) was dissolved in 15 mL of anhydrous CH$_2$Cl$_2$ and 3 mL anhydrous DMF and cooled to ~0° C. Trethylamine(1.6 mL, 1.5 eq.) was added followed by an addition of methanesulfonylchloride (580 µL, 7.5 mmol) over 1 minute. After 1 minute at ~0° C., the reaction was warmed to RT. After 1 hour the reaction was quenched with water, and partitioned between a saturated sodium bicarbonate solution and CH$_2$Cl$_2$. The aqueous layer was extracted with CH$_2$Cl$_2$ and the combined organic layers were washed with water (2 times), brine then dried over NaSO4, filtered and the solvent was removed in vacuo to give 455 mg of N-methanesulfonyl-2-aminobenzimidazole. HPLC shows the material to be 91% pure, (ret. time=3.70). LCMS: obs. M+H@212.1 amu. The material was carried on without purification.

Step 2

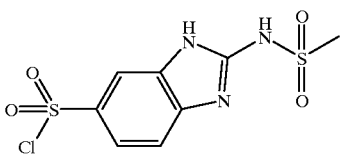

N-methanesulfonyl-5-chlorosulfonyl-2-aminobenzimidazole. To 9.5 mL (20 eq., 142 mmol) of well stirred chlorosulfonic acid at ~25° C. was added N-methanesulfonyl-2-aminobenzimidazole (1.5 g, 7.1 mmol) in small portions over 1C minutes with slight exotherming. The solution was stirred at ~25° C. for 3.5 hours, then was added dropwise to a well stirred mixture of ice and water. The aqueous solution was slowly basified to pH ~7.5 with solid sodium bicarbonate and extracted with EtOAc. A precipitate formed in the organic phase which was filtered off and was washed with H$_2$0 and dried on the filter to yield 1.23 g of N-methanesulfonyl-5-chlorosulfonyl-2-aminobenzimidazole. HPLC, single peak, ret. time=7.61 min. MS: Obs. M +H@ 310.0 amu.

Step 3

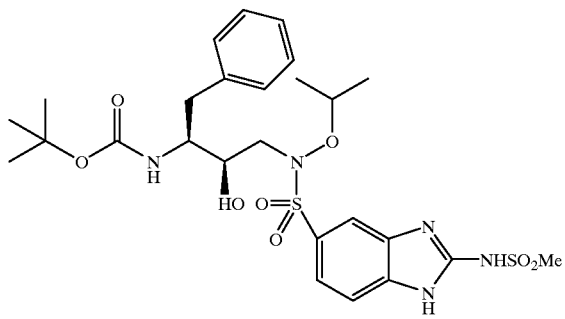

tert-Butyl-N-((1S,2R)-1-benzyl-3-(isopropyloxy)(2-(methylsulfonyl) amino]benzimidazol-5-ylsulfonyl) amino-2-hydroxypropyl)carbamate. tert-Butyl-N-((1S,2R)-1-benzyl-3-(isopropyloxy)amino-2-hydroxypropyl)carbamate (86 mg, 0.25 mmol) was combined with 2-[(methylsulfonyl) amino] benzimidazol-5-ylsulfonyl chloride (77 mg, 0.25 mmol) in anhydrous pyridine (1 ml) with a catalytic amount of N,N-dimethylaminopyridine. The reaction was stirred at room temperature overnight. The solvent was evaporated under vacuum. The crude mixture was diluted in EtOAc and washed with water and brine. Organic phase was dried with MgSO4 and solvent was removed in vacuo. Purification by TLC prep (2% MeOH/CH2Cl2). Recovered 56 mg (37%) of product as a white solid. HPLC showed the material to be 98% pure; Ret. time=9.87 min. $^1$H NMR (CDCl$_3$): 7.12–8.04 (m, 8H), 6.5 (m, 1H), 4.47–4.51 (m, 2H), 3.68 (m, 2H), 3.22 (s, 3H), 2.81–2.88 (m, 3H), 1.75 (m, 2H), 1.22 (s, 9H), 1.16 (d, 6H). MS (ES+): obs. M+H@612.1 amu.

Example 6

Step 1

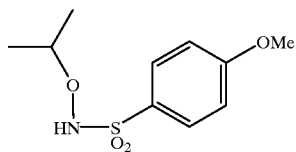

N$^1$-(isopropoxy)-4-methoxy-1-benzenesulfonamide. A vigorously stirred solution of 2-isopropoxy-1H-isoindole-1,3 (2H)-dione [2.50 g, 12.2 mmol, Synth. Comm., 22(10), 1427–1432 (1992)] in 35 mL of tetrahydrofuran under an Argon atmosphere at ambient temperature was treated with anhydrous hydrazine (0.421 mL, 13.41 mmol). After 1.5 hours, 4-methoxybenzenesulphonyl chloride (3.024 g, 14.63 mmol), dichloromethane (20 mL) and N,N-diisopropylethylamine (6.38 mL, 36.6 mmol) was added with continued stirring. After an additional 2 hours at ambient temperature, the reaction mixture was evaporated in vacuo to a residue and partitioned between ethyl acetate and 1N hydrochloric acid. The layers were separated and the aqueous layer was extracted again with ethyl acetate. The combined organic layers were washed with 5% w/v potassium carbonate and brine, dried over anhydrous magnesium sulfate, filtered and evaporated in vacuo to a residue. The crude material was purified on flash grade silica gel eluting with 30% ethyl acetate in hexane. Fractions containing the product were combined, evaporated in vacuo, and dried under high vacuum to provide N-(isopropoxy)-4-methoxy-1-benzenesulfonamide (2.061 g, 69%) as a white solid. H1-NMR (chloroform-D3): 1.22 (d, 6H), 3.92 (s, 3H), 4.27 (m, 1H), 6.70 (s, 1H), 7.05 (d, 2H), 7.90 (d, 2H). MS(ESI): 268 (M+Na).

Step 2

(6)

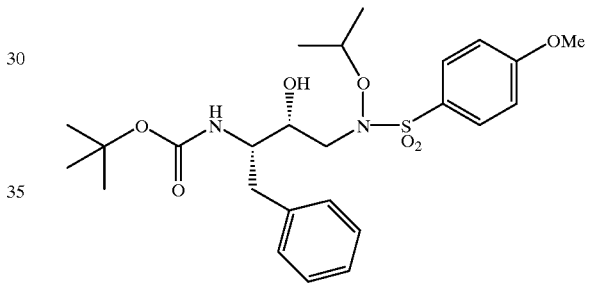

tert-butyl N-((1S,2R)-1-benzyl-3-(cyclopentyloxy)[(4-methoxyphenyl)sulfonyl]amino-2-hydroxypropyl) carbamate. A solution of N-(isopropoxy)-4-methoxy-1-benzenesulfonamide (0.147 g, 0.599 mmol) and tert-butyl N-(1S)-1-[(2S)oxiran-2-yl-2-phenylethylcarbamate (75 mg, 0.285 mmol) in anhydrous tetrahydrofuran (1 mL) under an Argon atmosphere was treated with phosphazene base P<t/4>t-Bu (0.285 mL, 0.285 mmol, 1.0 M in hexane). After stirring for 30 minutes at ambient temperature, the reaction mixture was quenched with several drops of glacial acetic acid and evaporated in vacuo to a residue. The crude product was purified on a preparative TLC plate (20×20, 500 μM) eluting with 35:65 ethyl acetate hexane. The product band was removed, eluted with ethyl acetate, and evaporated in vacuo to a residue. The crude product was purified again on a preparative TLC plate (20×20, 1000 μm) eluting with 4:1 dichloromethane : ethyl acetate. The product band was removed, eluted with ethyl acetate, and evaporated in vacuo. The residue was triturated with water and the resulting slurry was stirred overnight, filtered, and dried under high vacuum to provide tert-butyl N-((1S,2R)-1-benzyl-3-(cyclopentyloxy)[(4-methoxyphenyl) sulfonyl]amino-2-hydroxypropyl)carbamate (87 mg, 60%) as a white solid. HI-NMR (methanol-D4): 1.22 (s, 9H), 1.24 (d, 6H), 2.52 (m, 2H), 3.07 (m, 2H), 3.68 (m, 2H), 3.87 (s, 3H), 4.50 (m, 1H), 7.08 (m, 2H), 7.19 (m, 5H), 7.75 (m, 2H). MS(ESI): 531 (M+Na).

Example 7

Step 1

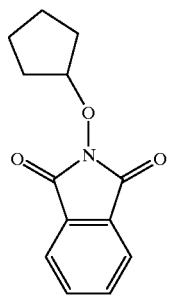

2-(cyclopentyloxy)-1H-isoindole-1,3(2H)-dione. A mixture of N-hydroxypthalimide (10.00 g, 61.3 mmol), cyclopentylbromide (8.21 mL, 76.63 mmol), and 1,8-diazabicyclo)5.4.0]undec-7-ene (13.75 mL, 76.6 mmol) were combined under an Argon atmosphere in dimethylformamide (50 mL). The mixture was heated to 55° C. and stirred vigorously for 1.5 hours. After cooling to ambient temperature, the solvent was removed in vacuo and the residue was partitioned between ethyl acetate and 1N hydrochloric acid. After separating the phases, the aqueous layer was extracted again with ethyl acetate. The combined organic layers were washed with 5% w/v potassium carbonate, saturated aqueous brine, dried over anhydrous magnesium sulfate, filtered and evaporated in vacuo. The residue was triturated with hexane, filtered, and dried under high vacuum to provide 2-(cyclopentyloxy)-1H-isoindole-1,3(2H)-dione (11.37 g, 80%). HL-NMR (chloroform-D3): 1.61 (m, 2H), 1.77 (m, 2H), 1.97 (m, 4H), 4.91 (m, 1H), 7.73 (m, 2H), 7.82 (m, 2H). MS(ESI): 254 (M+Na).

Step 2

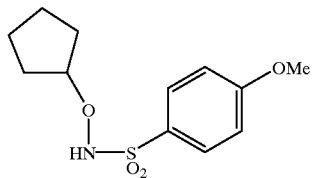

$N^1$-(cyclopentyloxy)-4-methoxy-1-benzenesulfonamide. A mixture of 2-(cyclopentyloxy)-1H-isoindole-1,3(2H)-dione (3.00 g, 12.99 mmol) in anhydrous tetrahydrofuran (15 mL) at ambient temperature under an Argon atmosphere was treated with anhydrous hydrazine (0.448 mL, 14.29 mmol). After stirring vigorously for 1.5 hours, the resulting slurry was filtered and washed with approximately 15 mL of anhydrous tetrahydrofuran. The filtrate was combined with 4-methoxybenzenesulphonyl chloride (2.95 g, 14.29 mmol) and N,N-diisopropylethylamine (2.72 mL, 15.6 mmol). After stirring at ambient temperature for approximately 18 hours, the reaction mixture was evaporated in vacuo to a residue and partitioned between ethyl acetate and 1N hydrochloric acid. The layers were separated and the organic phase was extracted again with ethyl acetate. The combined organic layers were washed with 5% w/v potassium carbonate and brine, dried over anhydrous magnesium sulfate, filtered and evaporated in vacuo to a residue. The crude material was purified on flash grade silica gel eluting with 15:85 ethyl acetate : hexane. Fractions containing the product were combined, evaporated in vacuo, and dried under high vacuum to provide N-(cyclopentyloxy)-4-methoxy-1-benzenesulfonamide (2.771 g, 79%) as an oil. H1-NMR (chloroform-D3): 1.61 (m, 8H), 3.87 (s, 3H), 4.57 (m, 1H), 6.67 (s, 1H), 6.99 (m, 2H), 7.83 (m, 2H). MS(ESI): 294 (M+Na).

Step 3

(7)

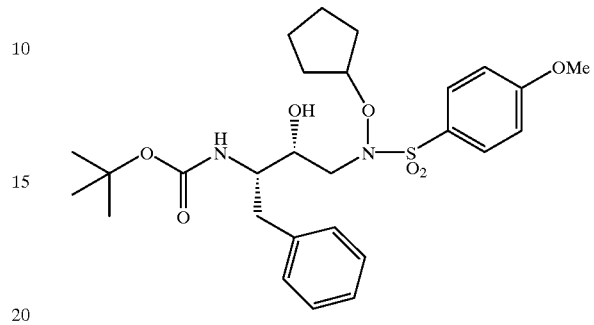

tert-butyl N-((1S,2R)-1-benzyl-3-(cyclopentyloxy)[(4-methoxyphenyl)sulfonyl]amino-2-hydroxypropyl)carbamate. A solution of N-(cyclopentyloxy)-4-methoxy-1-benzenesulfonamide (1.005 g, 3.71 mmol) and tert-butyl N-(1S)-1-[(2S)oxiran-2-yl]-2-phenylethylcarbamate (0.780 g, 2.97 mmol) in anhydrous tetrahydrofuran (5 mL) under an Argon atmosphere was treated with phosphazene base P<t/4>t-Bu (0.593 mL, 0.593 mmol, 1.0 M in hexane). The mixture was stirred at ambient temperature for 2.5 hours and then quenched with several drops of glacial acetic acid. The solution was evaporated in vacuo to a residue and partitioned between ethyl acetate and 1N hydrochloric acid. After separating the phases, the aqueous layer was extracted with ethyl acetate. The combined ethyl acetate layers were washed with brine, dried over anhydrous magnesium sulfate, filtered and evaporated in vacuo. The residue was purified on flash grade silica gel eluting with 9:1 hexane ethyl acetate (0.5 L), 85:15 hexane ethyl acetate (0.5 L), and finally 4:1 hexane ethyl acetate (1.5 L). Fractions containing the product were combined, evaporated in vacuo and dried under high vacuum to provide tert-butyl N-((1S,2R)-1-benzyl-3-(cyclopentyloxy)[(4-methoxyphenyl) sulfonyl]amino-2-hydroxypropyl)carbamate (1.418 g, 89%) as a foam. H1-NMR (chloroform-D3): 1.38 (s, 9H), 1.70 (m, 8H), 2.98 (m, 4H), 3.85 (bm, 2H), 3.92 (s, 3H), 4.61 (bs, 1H), 4.85 (m, 1H), 7.02 (m, 2H), 7.29 (m, 5H), 7.76 (m, 2H) MS (ESI): 535 (MH+)

Example 8

Step 1

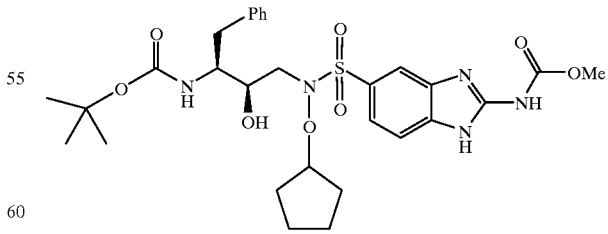

Tert-butyl N-(1S,2R)-1-benzyl-3-[(cyclopentyloxy)(2-[(methoxycarbonyl)amino]-1H-benzimidazol-5-ylsulfonyl)amino]-2-hydroxypropylcarbamate. Tert-butyl N-(1S,2R)-1-benzyl-3-[(cyclopentyloxy)amino]-2-hydroxypropylcarbamate (Step 1, Example 54) (1.73 g, 4.75 mmol), methyl N-[5-(chlorosulfonyl)-1H-benzimidazol-2-yl]carbamate (1.37g, 4.75 mmol), anhydrous diisopropylethylamine (0.83 mL, 4.75 mmol), and N,N-dimethylaminopyridine (170 mg, 1.42 mmol) were combined in anhydrous tetrahydrofuran (15 mL) and anhydrous N,N-dimethylformamide (8 mL) in a 50 mL round bottomed flask under nitrogen. The reaction was stirred for 24 hours and concentrated in vacuo. After the workup described in Step 3, Example 54, the product was isolated as a white foam (2.56 g, 4.14 mmol) and used directly without further purification. $^1$H NMR (d$_6$-DMSO) δ: 7.60–6.64 (m, 9H), 5.11 (d, J=6.1 Hz, 1H), 4.83 (bs, 1H), 3.81 (s, 3H), 3.54–1.42 (m, 14H), 1.15 (s, 9H). MS(ES): 618 (M+1), 616 (M-1).

Step 2

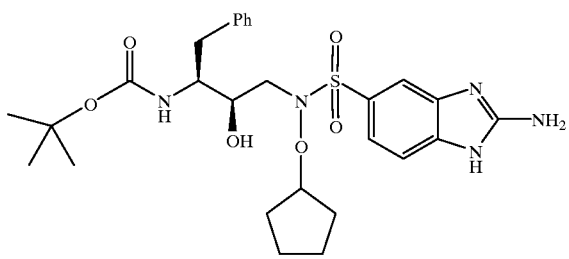

Tert-butyl N-(1S,2R)-1-benzyl-3-[(cyclopentyloxy)(2-amino-1H-benzimidazol-5-ylsulfonyl)amino]-2-hydroxypropylcarbamate. Tert-butyl N-(1S,2R)-1-benzyl-3-[(cyclopentyloxy)(2-[(methoxycarbonyl)amino]-1H-benzimidazol-5-ylsulfonyl)amino]-2-hydroxypropylcarbamate (Step 1, above) (2.52 g, 4.08 mmol) and lithium iodide hydrate (2.60 g, 19.4 mmol) were dissolved in pyridine (15 mL) in a 50 mL round bottomed flask and heated at 100° C. for 8 hours. The reaction was allowed to cool and then concentrated in vacuo. After the workup described in Step 3, Example 54, the product was purified by silica gel flash chromatography using a gradient elution of chloroform: methanol: water (90:10:0 to 10:3:0.5) to yield a beige powder (1.75 g, 3.13 mmol, 77%). $^1$H NMR (d$_6$-DMSO) δ: 7.50–6.64 (m, 9H), 5.07 (d, J=6.0 Hz, 1H), 4.80 (bs, 1H), 3.56–1.40 (m, 16H), 1.18 (s, 9H). MS(ES): 560 (M+i), 558 (M-1).

Step 3

(8)

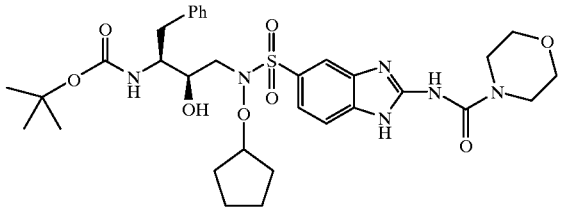

Tert-butyl N-(1S,2R)-1-benzyl-3-[(cyclopentyloxy)(2-[(N-morpholinocarbonyl)-amino]-1H-benzimidazol-5-ylsulfonyl)amino]-2-hydroxypropylcarbamate. Tert-butyl N-(1S,2R)-1-benzyl-3-[(cyclopentyloxy) (2-amino-1H-benzimidazol-5-ylsulfonyl)amino]-2-hydroxypropylcarbamate (Step 2, above) (300 mg, 0.536 mmol), 4-morpholine carbonyl chloride (0.08 mL, 0.643 mmol), and anhydrous diisopropylethylamine (0.11 mL, 0.643 mmol), were combined in anhydrous tetrahydrofuran (8 mL) in a 25 mL round bottomed flask under nitrogen. The reaction was refluxed for 18 hours, allowed to cool, and concentrated in vacuo. After the workup described in Step 3, Example 54, the residue was purified by preparative silica gel TLC using 90:10 chloroform: methanol as an eluent to give the product as a beige solid (70 mg, 0.104 mmol, 20%). $^1$H NMR (d$_6$-DMSO) δ: 7.54–6.65 (m, 8H), 5.11 (d, J=6.0 Hz, 1H), 4.81 (bs, 1H), 3.82–1.40 (m, 23H), 1.17 (s, 9H). MS(ES): 673 (M+1), 671 (M-1).

Example 9

(9)

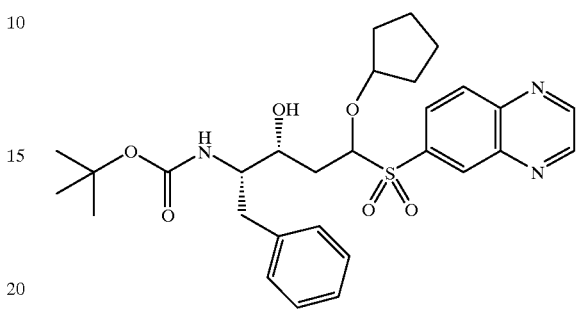

Prepartion of tert-butyl N-[(1S,2R)-1-benzyl-4-(cyclopentyloxy)-2-hydroxy-4-(6-quinoxalinylsulfonyl) butyl]carbamate. A mixture of tert-butyl N-((1S,2R)-1-benzyl-3-(cyclopentyloxy)[(3,4-diaminophenyl)sulfonyl] amino-2-hydroxypropyl)carbamate (Example 10), (750 mg, 1.41 mmol) and 1,5-dioxane-2,3-diol (219 mg, 1.83 mmol) were combined under Argon in absolute ethanol (3 mL) at ambient temperature. After stirring for approximately 11 days, the reaction was evaporated in vacuo and the residue was purified on flash grade silica gel eluting with ethyl acetate : hexane (1:1). Fractions containing the product were combined, evaporated in vacuo and dried under high vacuum to provide tert-butyl N-[(1S,2R)-1-benzyl-4-(cyclopentyloxy)-2-hydroxy-4-(6-quinoxalinylsulfonyl) butyl]carbamate as a yellow foam (696 mg, 89%). An analytical sample was prepared by purification of 75 mg on a preparative TLC plate (20×20 cm, 1000 μM) eluting with 95:5 dichloromethane : methanol. The product band was removed, eluted with 4:1 methylene chloride methanol, filtered, and evaporated in vacuo. The residue was triturated with water and filtered to provide tert-butyl N-[(1S,2R)-1-benzyl-4-(cyclopentyloxy)-2-hydroxy-4-(6-quinoxalinylsulfonyl)butyl]carbamate as a white solid. H1-NMR (dimethylsulfoxide-D6): 1.05 (s, 9H), 1.74 (m, 8H), 2.47 (m, 1H), 2.73 (m, 1H), 3.07 (m, 2H), 3.55 (m, 2H), 4.90 (m, 1H), 5.24 (m, b, 1H), 6.68 (d, 1H), 7.19 (m, 5H), 8.15 (m, 1H), 8.39 (m, 1H), 8.49 (s, 1H), 9.18 (m, 2H). MS(ESI): 579(M+Na).

Example 10

Step 1

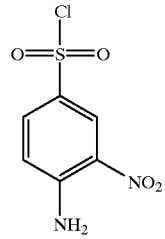

o-nitroaniline-p-sulfonyl chloride. A mixure of o-nitroaniline-p-sulfonic acid sodium salt (25.00 g, 104 mmol) and phosphoryl chloride (75 mL, 804 mmol) under Argon was heated to reflux and vigorously stirred for 4 hours. After cooling to ambient temperature, the reaction mixture was carefully added to a large excess of ice. The resulting slurry was stirred for 15 min., filtered and dried under vacuum to provide o-nitroaniline-p-sulfonyl chloride (21.43 g, 87%) as a yellow solid. H1-NMR (dimethylsulfoxide-D6): 5.8 (b, 2H), 6.97 (d, 1H, J 8.8), 7.57 (m, 1H), 8.18 (d, 1H, J=2.0).

Step 2

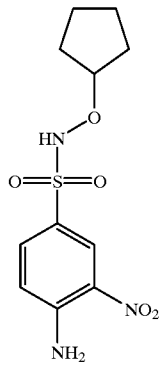

4-amino-N-(cyclopentyloxy)-3-nitrobenzenesulfonamide. A solution of 2-(cyclopentyloxy)-1H-isoindole-1,3(2H)-dione (10.00 g, 43.30 mmol) in anhydrous tetrahydrofuran (100 mL) at ambient temperature under an Argon atmosphere was treated with anhydrous hydrazine (1.49 mL, 47.63 mmol). After stirring vigorously for 2.5 hours, the resulting slurry was filtered and washed with approximately 20 mL of anhydrous tetrahydrofuran. The filtrate was combined with o-nitroaniline-p-sulfonyl chloride (11.26 g, 47.63 mmol) and N,N-diisopropylethylamine (9.05 mL, 51.96 mmol) and stirred under an Argon atmosphere for 16 hrs. at ambient temperature. The reaction mixture was diluted with 1N NaHSO$_4$ and dichloromethane and transferred to a separatory funnel. The organic phase was separated and the aqueous layer was extracted twice with dichloromethane. The combined organic layers were washed with 5% aqueous potassium carbonate, dried over anhydrous magnesium sulfate, filtered through a pad of diatomaceous earth and evaporated in vacuo. The residue was purified on flash grade silica gel eluting with 1:1 ethyl acetate : hexane. Fractions containing the product were combined, evaporated in vacuo to a residue and triturated with hexane. The slurry was filtered and the product was dried under high vacuum to provide 4-amino-N-(cyclopentyloxy)-3-nitrobenzenesulfonamide (8.89 g, 68%) as a yellow solid. H1-NMR (chloroform-D3): 1.57 (m, 4H), 1.74 (m, 4H), 4.61 (m, 1H), 6.52 (b, 2H), 6.73 (s, 1H), 6.90 (d, 1H), 7.79 (m, 1H), 8.70 (d, 1H). MS(ESI): 324(M+Na).

Step 3

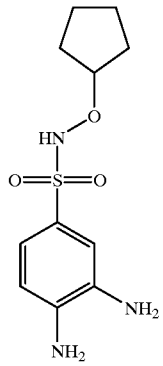

3, 4-diamino-N-(cyclopentyloxy)benzenesulfonamide. A solution of 4-amino-N-(cyclopentyloxy)-3-nitrobenzenesulfonamide (4.50 g, 14.95 mmol) in 1:1 ethyl acetate : ethanol (150 mL) was combined with 5% Pd on barium sulfate and reduced under a hydrogen atmosphere over 72 hours. The reaction mixture was filtered through a pad of diatomaceous earth and evaporated in vacuo to a residue which crystallized on standing. The solid was slurried in hexane, filtered and dried under high vacuum to provide 3,4-diamino-N-(cyclopentyloxy)benzenesulfonamide (4.086 g, 100%) as a light brown solid H1-NMR (dimethylsulfoxide-D6): 1.61 (m, 8H), 4.37 (m, 1H), 4.90 (b, 2H), 5.38 (b, 2H), 6.57 (d, 1H), 6.88 (m, 1H), 6.96 (d, 1H), 9.64 (s, !H). . MS(ESI): 272(M+H).

Step 4

(10)

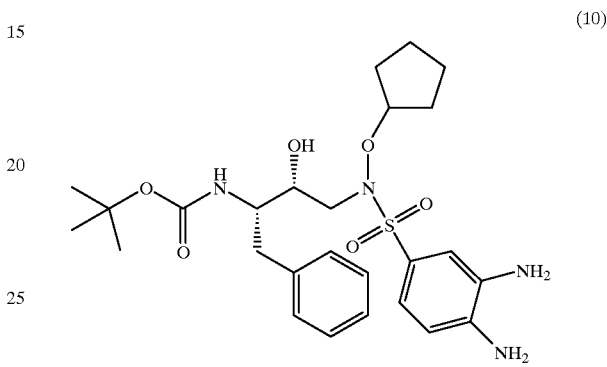

tert-butyl N-((1S,2R)-1-benzyl-3-(cyclopentyloxy)[(3,4-diaminophenyl)sulfonyl]amino-2-hydroxypropyl) carbamate. A solution of 3,4-diamino-N-(cyclopentyloxy) benzenesulfonamide (2.00 g, 7.38 mmol) and tert-butyl N-(1S)-1-[(2S)oxiran-2-yl]-2-phenylethylcarbamate (1.553 g, 5.90 mmol) in anhydrous tetrahydrofuran (10 mL) under an Argon atmosphere was treated with phosphazene base P<t/4>t-Bu (1.2 mL, 1.2 mmol, 1.0 M in hexane). After stirring at ambient temperature for approximately 18 hours, the reaction mixture was quenched with several drops of glacial acetic acid and evaporated in vacuo. The residue was partitioned between ethyl acetate and 1N aqueous sodium hydrogen sulfate. After separating the layers, the organic phase was washed with 5% w/v aqueous potassium carbonate, brine, dried over anhydrous sodium sulfate and evaporated in vacuo to a residue. The crude product was purified on flash grade silica gel eluting with 3:2 ethyl acetate : hexane. Fractions containing the product were combined, evaporated in vacuo and dried under high vacuum to provide tert-butyl N-((1S,2R)-1-benzyl-3-(cyclopentyloxy)[(3,4-diaminophenyl)sulfonyl]amino-2-hydroxypropyl)carbamate (2.553 g, 65%) as a foam. H1-NMR (chloroform-D3): 1.33 (s, 9H), 1.53 (m, 4H), 1.74 (m, 4H), 2.91 (m, 3H), 3.04 (m, 1H), 3.61 (b, 4H), 3.79 (m, 2H), 4.58 (m, 1H), 4.77 (m, 1H), 6.69 (d, 1H), 7.09 (s, 1H), 7.22 (m, 7H). MS(ESI): 535(M+H).

Example 11

Step 1

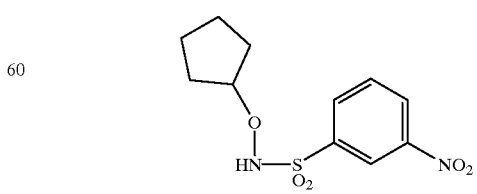

N$^1$-(cyclopentyloxy)-3-nitro-1-benzenesulfonamide. A mixture of 2-(cyclopentyloxy)-1H-isoindole-1,3(2H)-dione (3.00 g, 112.99 mmol) in anhydrous tetrahydrofuran (25 mL) under an Argon atmosphere was treated with anhydrous hydrazine (0.448 mL, 14.29 mmol). After stirring vigorously for 2.5 hours, the resulting slurry was filtered and washed with approximately 15 mL of anhydrous tetrahydrofuran. The filtrate was combined with 3-nitro-1-benzenesulphonyl chloride (3.17 g, 14.29 mmol) and N,N-diisopropylethylamine (2.72 mL, 15.6 mmol). After stirring at ambient temperature for approximately 18 hours, the reaction mixture was evaporated in vacuo to a residue and partitioned between ethyl acetate and 1N hydrochloric acid. The phases were separated and the aqueous layer was extracted twice with ethyl acetate. The combined organic layers were washed with 5% w/v potassium carbonate and brine, dried over anhydrous magnesium sulfate, filtered and evaporated in vacuo to a residue. The crude material was purified on flash grade silica gel eluting with 15:85 ethyl acetate : hexane. Fractions containing the product were combined, evaporated in vacuo, and dried under high vacuum to provide $N^1$-(cyclopentyloxy)-3-nitro-1-benzenesulfonamide (3.224 g, 87%) as a solid. H1-NMR (chloroform-D3): 1.71 (m, 8H), 4.71 (m, 1H), 6.93 (bs, 1H), 7.83 (m, 1H), 8.28 (m, 1H), 8.55 (m, 1H), 8.81 (m, 1H)

Step 2

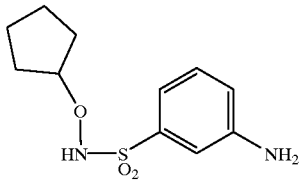

3-amino-$N^1$-(cyclopentyloxy)-1-benzenesulfonamide. A solution of N-(cyclopentyloxy)-3-nitro-1-benzenesulfonamide (2.98 g, 10.41 mmol) in 50 mL of absolute ethanol was combined with 5 wt % Palladium on barium sulfate (300 mg) and reduced under a balloon of hydrogen gas with vigorous agitation for 18 hours. The mixture was filtered, washed with ethanol, and evaporated in vacuo to a residue. The crude product was purified on flash grade silica gel eluting with 4:1 hexane : ethyl acetate. Fractions containing the product were combined, evaporated in vacuo and dried under vacuum to provide 3-amino-N1-(cyclopentyloxy)-1-benzenesulfonamide (2.67 g, 100%) as an oil. Hl-NMR chloroform-D3): 1.62 (m, 8H), 3.92 (bs, 2H), 4.58 (m, 1H), 6.74 (bs, !H), 6.88 (m, 1H), 7.16 (m, 1H), 7.27 (m, 2H). MS(ESI): 257(MH+).

Step 3

(11)

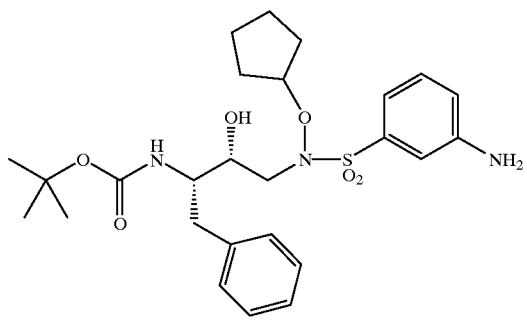

tert-butyl N-(1S,2R)-3-[[(3-aminophenyl)sulfonyl](cyclopentyl oxy)amino]-1-benzyl-2-hydroxypropyl- car-bamate. A solution of 3-amino-$N^1$-(cyclopentyloxy)-1-benzenesulfonamide (2.654 g, 10.36 mmol) and tert-butyl N-(1s)-1-[(2S)oxiran-2-yl]-2-phenylethylcarbamate (2.181 g, 8.29 mmol) in anhydrous tetrahydrofuran (10 mL) under an Argon atmosphere was treated with phosphazene base P<t/4>t-Bu (1.60 mL, 1.60 mmol, 1.0 M in hexane). After stirring at ambient temperature for approximately 18 hours, the reaction mixture was quenched with several drops of glacial acetic acid and evaporated in vacuo. The residue was partitioned between ethyl acetate and 1N $NaHSO_4$. After separating the phases, the aqueous layer was extracted three times with ethyl acetate. The combined organic layers were washed with saturated aqueous brine, dried over anhydrous magnesium sulfate, filtered and evaporated in vacuo to a residue. The crude product was purified on flash grade silica gel eluting with 95:5 methylene chloride : ethyl acetate (2L); 9:1 methylene chloride : ethyl acetate (2L); and finally 1:1 methylene chloride : ethyl acetate. Fractions containing the product were combined, evaporated in vacuo, and dried under high vacuum to provide tert-butyl N-(1S,2R)-3-[[(3-aminophenyl)sulfonyl](cyclopentyl oxy)amino]-1-benzyl-2-hydroxypropylcarbamate (3.328 g, 77%) as a foam. An analytical sample was obtained by purifying 100 mg on two preparative TLC plate (20x20 cm, 1000 WM, silica gel) eluting with 9:1 methylene chloride : methanol. The product bands were removed, eluted with 4:1 methylene chloride : methanol, filtered, and evaporated in vacuo. The residue purified again on a preparative TLC plate (20x20 cm, 1000 WM, silica gel) eluting with 1:1 ethyl acetate : hexane. The product band was removed, eluted with ethyl acetate, filtered, and evaporated in vacuo. The residue was dissolved in diethylether, evaporated in vacuo and dried under high vacuum to provide tert-butyl N-(1S,2R)-3-[[(3-aminophenyl)sulfonyl](cyclopentyloxy)amino]-1-benzyl-2-hydroxypropylcarbamate (54 mg) as a foam. H1-NMR (methanol-D4): 1.24 (s, 9H), 1.71 (m, 8H), 2.55 (m, 1H), 2.90 (bm, 1H), 3.04 (mn, 2H), 3.73 (m, 2H), 4.81 (m, 1H), 6.44 (d, 1H), 6.93 (m, 1H), 7.02 (m, 1H), 7.17 (m, 7H). MS(ESI): 520(MH+).

Example 12

(12)

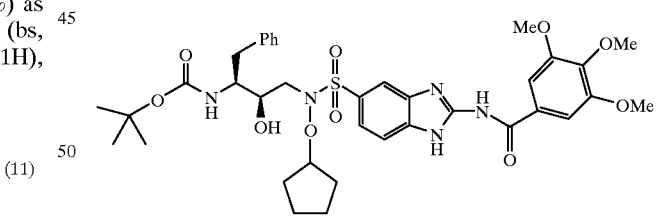

Tert-butyl N-(1S,2R)-1-benzyl-3-[(cyclopentyloxy)(2-[(3,4,5-trimethoxyphenyl-carbonyl)amino]-1H-benzimidazol-5-ylsulfonyl)amino]-2-hydroxypropylcarbamate. Tert-butyl N-(1S,2R)-1-benzyl-3-[(cyclopentyloxy)(2-amino-1H-bbenzimidazol-5-ylsulfonyl)amino]-2-hydroxypropylcarbamate (Step 2, Example 8) (130 mg, 0.232 mmol), 3,4,5-trimethoxybenzoyl chloride (70 mg, 0.302 mmol), and anhydrous pyridine (5 mL) were combined in a 25 mL round bottomed flask under nitrogen. The reaction was stirred for 18 hours and then concentrated in vacuo. After the workup described in Step 3, Example 54, the residue was purified by preparative silica gel TLC using 90:10 chloroform: methanol as an eluent to give the product

Example 13

(13)

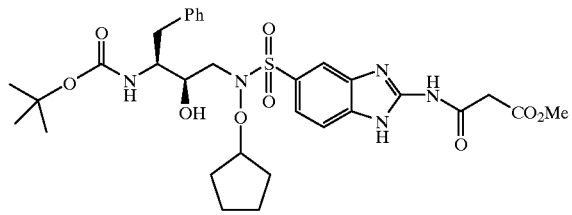

Tert-butyl N-(1S,2R)-1-benzyl-3-[(cyclopentyloxy)(2-[(methyl 3-oxopropionate)amino]-1H-benzimidazol-5-ylsulfonyl)amino]-2-hydroxypropylcarbamate. Tert-butyl N-(1S,2R)-1-benzyl-3-[(cyclopentyloxy)(2-amino-1H-benzimidazol-5-ylsulfonyl)amino]-2-hydroxypropylcarbamate (Step 2, Example 8) (130 mg, 0.232 mmol), methyl malonyl chloride (0.04 mL, 0.348 mmcl), and anhydrous pyrldine (5 mL) were combined in a 25 mL round bottomed flask under nitrogen. The reaction was stirred for 18 hours and then concentrated in vacuo. After the workup described in Step 3, Example 54, the residue was purified by preparative silica gel TLC using 90:10 chloroform: methanol as an eluent to give the product as a pale yellow solid (6 mg, 0.009 mmol). $^1$H NMR ($d_6$-DMSO) δ: 8.62 (d, J=8.5 Hz, 1H), 7.89–6.67 (m, 9H), 5.17 (d, J=6.0 Hz, 1H), 4.85 (bs, 1H), 3.65 (s, 3H), 3.77–1.40 (m, 16H), 1.14 (s, 9H). MS(ES): 660 (M+1), 658 (M−1).

Example 14

(14)

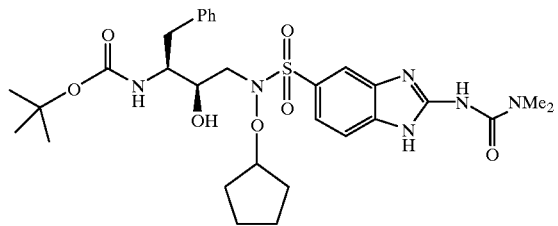

Tert-butyl N-(1S,2R)-1-benzyl-3-[(cyclopentyloxy)(2-[(dimethylamino-carbonyl)amino]-1H-benzimidazol-5-ylsulfonyl)amino]-2-hydroxypropylcarbamate. Tert-butyl N-(1S,2R)-1-benzyl-3-[(cyclopentyloxy)(2-amino-1H-benzimidazol-5-ylsulfonyl)amino]-2-hydroxypropylcarbamate (Step 2, Example 8) (100 mg, 0.179 mmol), dimethyl carbamyl chloride (0.03 mL, 0.286 mmol), and anhydrous pyridine (5 mL) were combined in a 25 mL round bottomed flask under nitrogen. The reaction was stirred for 18 hours and then concentrated in vacuo. After the workup described in Step 3, Example 54, the residue was purified by preparative silica gel TLC using 90:10 chloroform: methanol as an eluent to give the product as a white film (35 mg, 0.056 mmol, 31%). $^1$H NMR (dc-DMSO) δ: 7.53–6.66 (m, 8H), 5.10 (bs, 1H), 4.80 (bs, 1H), 3.56 (bs, 2H), 3.20 (s, 3H), 3.18 (s, 3H), 3.10–1.40 (m, 13H), 1.18 (s, 9H). MS(ES): 631 (M+1), 629.

Example 15

Step 1

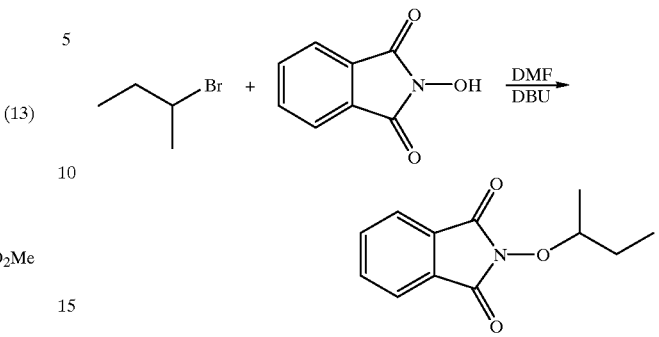

2-(sec-butoxy)-1H-isoindole-1,3(2H)-dione. N-hydroxylphthalimide (18.4 mmol, 3.0 g) was dissolved in anhydrous DMF (20 mL) under nitrogen. To the stirring solution, DBU (1,8-diazabicyclo[5.4.0]undec-7-ene) (27.6 mmol, 4.13 mL) was injected followed by 2-bromobutane (22.1 mmol, 2.41 mL) and the reaction was warmed to 55° C. After stirring for 18 hour, the reaction was cooled to room temperature and concentrated to a red oil. The reaction was partitioned between ethyl acetate and 1N HCl. The organic layer was washed with saturated aqueous sodium bicarbonate solution, distilled water, brine and dried over magnesium sulfate. The solvent was removed under vacuum providing 3.57 g (89%) of a yellow solid. $R_f$: 0.8 (2:1 hexanes/ethyl acetate); H1-NMR (CDCl$_3$): δ7.80 (2H,m), 7.73 (2H,m), 4.31 (1H,m), 1.81 (1H,m), 1.64 (1H,m), 1.32 (3H,d), 1.03 (3H,t).

Step 2

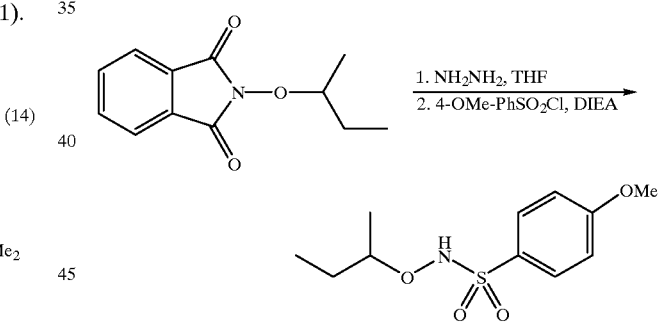

$N^1$-(sec-butoxy)-4-methoxy-1-benzenesulfonamide. O-sec-butoxy-N-hydroxylphthalimide (16.3 mmol, 3.57 g) was combined with hydrazine (17.9 mmol, 0.56 mL) in anhydrous THF (30 mL) under nitrogen. The reaction immediately formed a white suspension and was allowed to stir at room temperature for 5 hours. The suspension was filtered directly into a flask containing 4-methoxybenzenesulfonyl chloride (14.6 mmol, 3.03 g) and diisopropylethylamine (17.6 mmol, 3.1 mL) was added. After stirring at room temperature for 15 hours, the reaction was concentrated to a yellow solid and partitioned between ethyl acetate and 1N HCl. The organic layer was separated and washed with a saturated aqueous solution of sodium bicarbonate and brine, and dried over magnesium sulfate. The product was concentrated to a white solid and purified by silica gel chromatography (5:1 hexanes/ethyl acetate), providing 3.13 g (66%) of a white solid. H1-NMR (CDCl$_3$): δ7.84 (2H,d), 6.98 (2H,d), 6.64 (1H,s), 4.02 (1H,m), 3.86 (3H,s), 1.62–1.55 (1H,m), 1.45–1.38 (1H,m), 1.15 (3H,d), 0.87 (3H,t).

--- as a white film (3 mg, 0.004 mmol). IHNMR ($d_6$-DMSO) δ: 7.56–6.63 (m, 7H), 5.21 (bs, 1H), 4.64 (bs, 1H), 3.86 (s, 6H), 3.76 (s, 3H), 3.40–1.30 (m, 18H), 1.23 (s, 9H). MS(ES): 754 (M+1), 752 (M−1).

Step 3

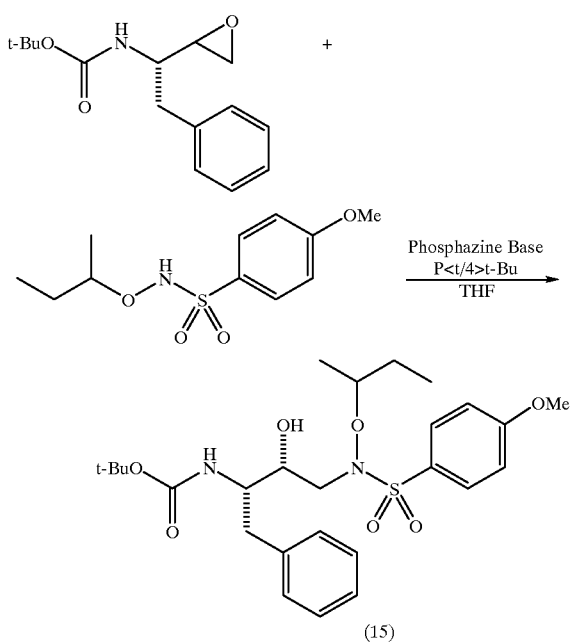

tert-butyl N-((1S,2R)-1-benzyl-3-sec-butoxy[(4-methoxyphenyl)sulfonyl]amino-2-hydroxypropyl) carbamate. N-(sec-butoxy)-4-methoxy-1-benzenesulfonamide (12.1 m=ol, 3.13 g) was combined with tert-butyl N-(1S)-1-[(2S)oxiran-2-yl]-2-phenylethylcarbamate (13.3 mmol, 3.5 g) and THF (25 mL) under nitrogen. Phosphazine base P<t/4>t-Bu (2.4 mmol, 2.4 mL, 1M in hexanes) was injected into the stirring solution. The reaction was allowed to stir for 48 hours at room temperature and was quenched by the addition of a few drops of glacial acetic acid. The reaction product was concentrated to an oil and partitioned between ethyl acetate and 1N HCl. The organic layer was separated and washed with saturated aqueous sodium bicarbonate and brine, dried over magnesium sulfate and concentrated under vacuum to a clear oil. The crude product was purified by silica gel chromatography (2:1 hexanes/ethyl acetate) providing 3.03 g (48%) of a white solid. H1-NMR (CDCl$_3$): 57.12 (2H,d), 7.30–7.19 (6H,m), 6.97 (2H,d), 4.55 (1H,bs), 4.31 (1H,m), 3.86 (3H,s), 3.78 (2H,m), 3.5–2.5 (1H,bm), 2.90 (2H,m), 1.80–1.60 (1H,m), 1.5–1.3 (1H,m), 1.32 (9H,s), 1.21–1.18 (3H,m), 0.93–0.85 (3H,m); MS (ESI): M+Na=545.

Example 16

Step 1

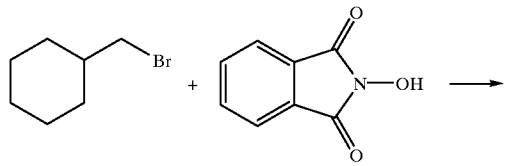

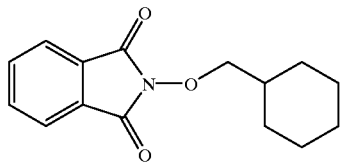

2-(cyclohexylmethoxy)-1H-isoindole-1,3(2H)-dione. N-hydroxylphthalimide (18.4 mmol, 3.0 g) was dissolved in anhydrous DMF (20 mL) under nitrogen. To the stirring solution, DBU (27.6 mmol, 4.13 mL) was injected followed by cyclohexylmethyl bromide (23.0 mmol, 3.21 mL) and the reaction was warmed to 55° C. After stirring for 15 hours, the reaction was cooled to room temperature and concentrated to a red oil. The reaction was partitioned between ethyl acetate and 1N HCl. The organic layer was washed with saturated aqueous sodium bicarbonate solution, brine and dried over magnesium sulfate. The solvent was removed under vacuum, and the crude product was triturated with hexanes providing 3.05 g (64%) of an off-white colored solid. H1-NMR (CDCl$_3$): δ7.80 (2H,m), 7.73 (2H,m), 3.98 (2H,d), 2.03–1.65 20 (5H,m), 1.31–1.03 (6H,m).

Step 2

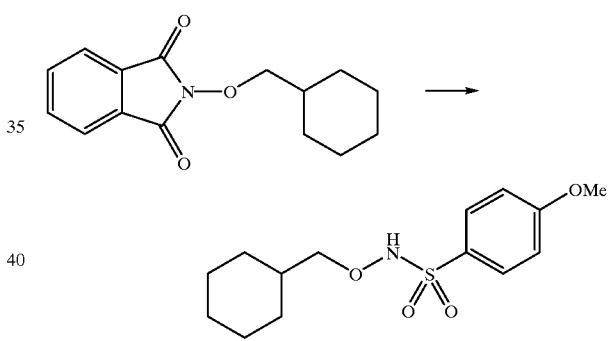

N$^1$-(cyclohexylmethoxy)-4-methoxy-1-benzenesulfonamide. 2-(cyclohexylmethoxy)-1H-isoindole-1,3(2H)-dione (11.8 mmol, 3.05 g) was combined with hydrazine (12.9 mmol, 0.41 mL) in anhydrous THF (25 mL) under nitrogen. The reaction immediately formed a white suspension and was allowed to stir at room temperature for 48 hours. The suspension was filtered directly into a flask containing 4-methoxybenzenesulfonyl chloride (9.5 mmol, 1.97 g) and diisopropylethylamine (11.6 mmol, 2.03 mL) was added. After stirring at room temperature for 18 hours, the reaction was concentrated to a solid residue and partitioned between ethyl acetate and 1N HCl. The organic layer was separated and washed with a saturated aqueous solution of sodium bicarbonate, and brine, and dried over magnesium sulfate. The product was concentrated to a solid and purified by silica gel chromatography (2:1 hexanes/ethyl acetate) providing 2.55g (80%) of a yellow solid. H1-NMR (CDCl$_3$): δ 7.81 (2H,d), 6.97 (2H,d), 6.78 (1H,s), 3.85 (3H,s), 3.75 (2H,d), 1.65–1.55 (6H,m), 1.25–1.07 (3H,m), 0.93–0.85 (2H,m).

Step 3

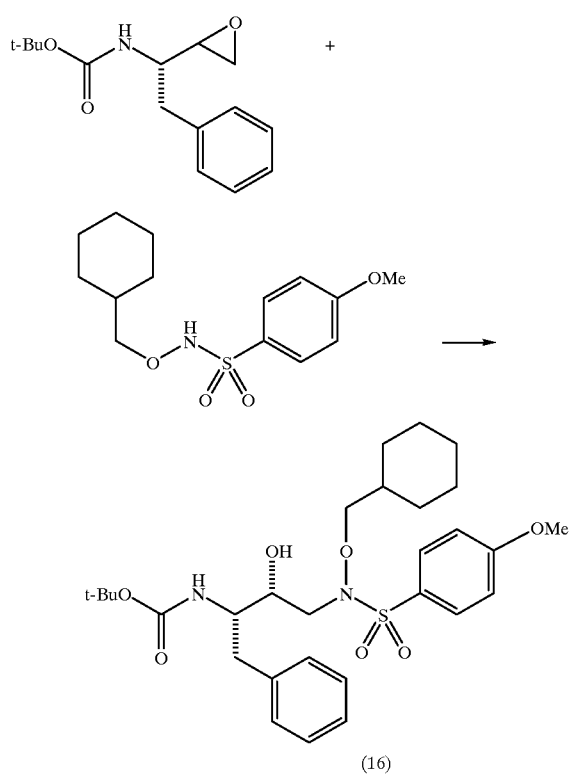

(16)

tert-butyl N-((1S,2R)-1-benzyl-3-(cyclohexylmethoxy)[(4-methoxyphenyl) sulfonyl]amino-2-hydroxypropyl) carbamate. N¹-(cyclohexylmethoxy)-4-methoxy-1-benzenesulfonamide (8.52 mmol, 2.55 g) was combined with tert-butyl N-(1S)-1-[(2S)oxiran-2-yl]-2-phenylethylcarbamate (9.37 mmol, 2.47 g) and THF (16 mL) under nitrogen. Phosphazine base P<t/4>t-Bu (1.7 mmol, 1.7 mL, 1M in hexanes) was injected into the stirring solution. The reaction was allowed to stir for 15 hours at room temperature and was quenched by the addition of a few drops of glacial acetic acid. The reaction product was concentrated to an oil and partitioned between ethyl acetate and 1N HCl. The organic layer was separated and washed with saturated aqueous sodium bicarbonate and brine, dried over magnesium sulfate and concentrated under vacuum to a clear oil. The crude product was purified by silica gel chromatography (2:1 hexanes/ethyl acetate) providing a white solid. H1-NMR (CDCl₃): δ 7.70 (2H,d), 7.28–7.19 (6H,m), 6.97 (2H,d), 4.6 (1H,m), 3.96 (1H,m), 3.87 (3H,s), 3.82 (2H,m), 3.21 (1H,m), 2.99 (1H,m), 2.90 (2H,m), 2.80 (1H,m), 1.65 (6H,m), 1.33 (9H,m), 1.2–1.0 (3H,m), 1.00–0.80 (2H,m); MS (ESI): M+Na=585.

Example 17

Step 1

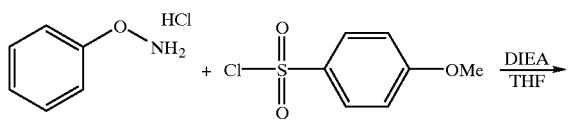

-continued

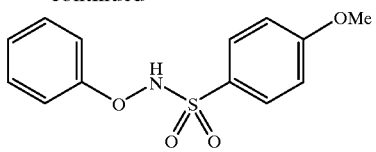

4-methoxy-N¹-phenoxy-1-benzenesulfonamide. O-phenylhydroxylamine hydrochloride (6.9 mmol, 1.0 g), 4-methoxybenzenesulfonyl chloride (6.2 mmol, 1.29 g), diisopropylethylamine (13.1 mmol, 2.28 mL) and andhydrous THF (15 mL) were combined under nitrogen. After stirring for 2 hours at room temperature, a few crystals of 4-dimethylaminopyridine were added and the flask was re-sealed. After another 2 hours, 4 mL of N,N-dimethylformamide was injected and the reaction stirred for an additional 15 hours. The resulting red solution was concentrated to an oil and partitioned between ethyl acetate and 1N HCl. The organic layer was separated and washed with saturated aqueous sodium bicarbonate and brine, dried over magnesium sulfate and concentrated under vacuum. The resulting dark brown residue was purified by silica gel chromatography (3:1 hexanes/ethyl acetate) providing 360 mg (21%) of a redish solid. H1-NMR (CDCl₃): δ7.89 (2H,d), 7.30–7.20 (3H,m), 7.11 (2H,d), 7.02 (1H,s), 7.00 (2H,d), 3.88 (3H,s).

Step 2

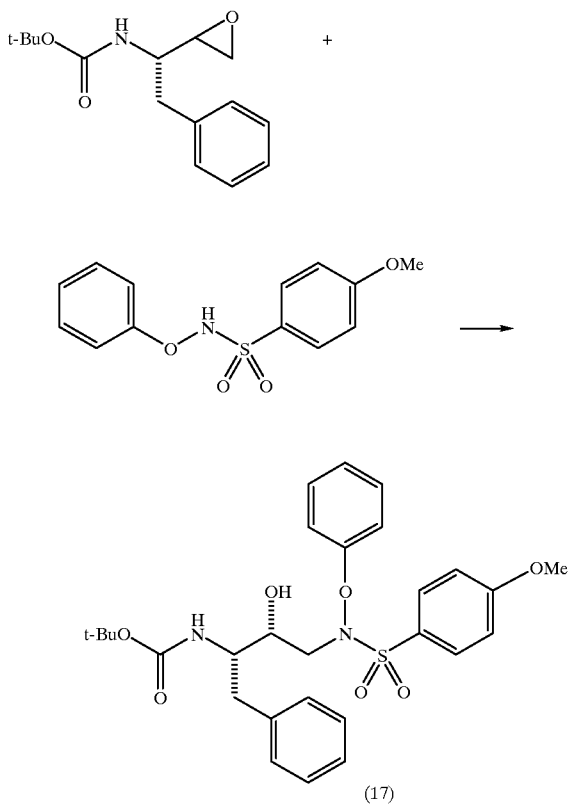

(17)

tert-butyl N-(1S,2R)-1-benzyl-2-hydroxy-3-[[(4-methoxyphenyl)sulfonyl](phenoxy) amino] propylcarbamate. 4-methoxy-N¹-phenoxy-1-benzenesulfonamide (1.3 mmol, 360 mg) was combined with tert-butyl N-(1S)-1-[(2S)oxiran-2-yl]-2-phenylethylcarbamate (1.4 mmol, 373 mg) and THF (3 mL) under nitrogen. Phosphazine base P<t/4>t-Bu (0.26 mmol, 0.26 mL, 1M in hexanes) was injected into the stirring solution. The reaction was allowed to stir for 48 hours at room temperature and was quenched by the addition of a few drops of glacial acetic acid. The reaction product was concentrated to a red oil and partitioned between ethyl acetate and 1N HCl. The organic layer was separated and washed with saturated aqueous sodium bicarbonate and brine, dried over magnesium sulfate and concentrated under vacuum to a red oil. The crude product was purified by silica gel chromatography (2:1 hexanes/ethyl acetate) and crystallization (hexanes/ethyl acetate) providing 300 mg (43%) of red crystals. H1-NMR (CDCl₃): δ7.74 (2H,d), 7.37–7.10 (10H,m), 7.04 (1H,m), 6.98 (2H,d), 4.56 (1H, bs), 3.88 (3H,s), 3.76 (2H, bs), 3.35–3.25 (1H,m), 3.20–2.95 (1H,m), 2.95–2.75 (2H,m), 1.30 (9H,s); MS (ESI): M+Na=565.

Example 18

Step 1

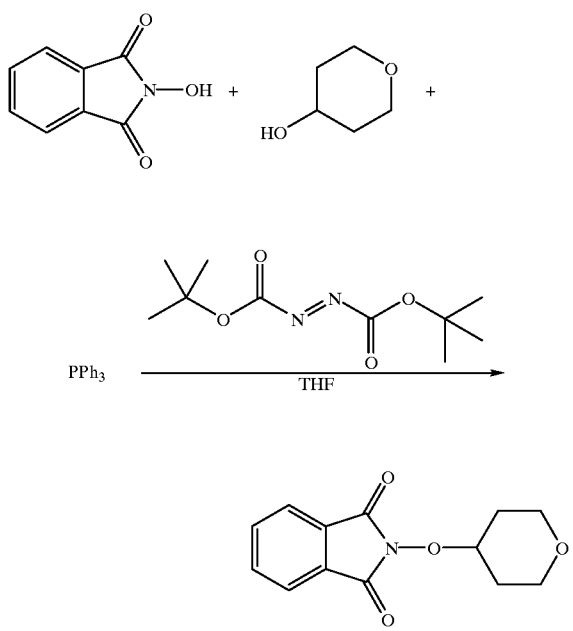

2-(tetrahydro-2H-pyran-4-yloxy)-1H-isoindole-1,3(2H)-dione. A light suspension containing N-hydroxylphthalimide (18.4 mmol, 3.0 g), triphenylphosphine (18.4 mmol, 4.82 g), tetrahydro-4H-pyran-4-ol (18.4 mmol, 1.75 mL) and anhydrous THF (50 mL), were transferred to a flask containing di-tert-butyl azodicarboxylate (20.2 mmol, 4.66 g) under nitrogen. Over 2 hours the reaction stirred at room temperature and changed from a dark orange to yellow in appearance. The solvent was removed under vacuum and replaced with trifluoroacetic acetic acid (10 mL). The reaction was stirred for 30 minutes and the TFA was removed under vacuum. The crude residue was then dissolved in ethyl acetate, washed with a saturated aqueous solution of sodium bicarbonate, 5% aqueous solution of potassium carbonate, brine and dried over magnesium sulfate. The solvent was removed under vacuum and the residual triphenylphosphine oxide was crystallized and filtered using hexanes and ether. The solvent was again removed and the crude solid was purified by silica gel chromatography (2:1 hexanes/ethyl acetate) and recrystallization using methylene chloride and hexanes providing 1.69 g (37%) of a white crystal. R$_f$=0.3 (2:1 hexanes/ethyl acetate); H1-NMR (CDCl₃): δ 7.84–7.82 (2H,m), 7.75–7.73 (2H,m), 4.46–4.40 (1H,m), 4.08–4.02 (2H,m), 3.50–3.44 (2H,m), 2.04–1.98 (2H,m), 1.92–1.84 (2H,m).

Step 2

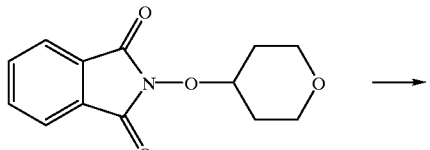

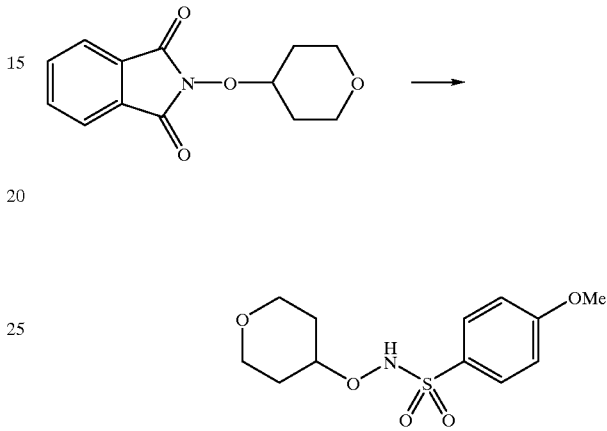

N-(tetrahydro-2H-pyran-4-yloxy)-4-methoxy-1-benzenesulfonamide. 2-(tetrahydro-2H-pyran-4-yloxy)-1H-iscindole-1,3(2H)-dione (6.8 mmol, 1.69 g) was combined with hydrazine (6.8 mmol, 0.22 mL) in anhydrous THF (20 mL) under nitrogen. The reaction immediately formed a white suspension and was allowed to stir at room temperature for 1 hour. The suspension was filtered directly into a flask containing 4-methoxybenzenesulfonyl chloride (6.5 mmol, 1.34 g) and diisopropylethylamine (20.5 mmol, 3.6 mL) was added. After stirring at room temperature for 15 hours, the reaction was refluxed for 4 hours, then stirred at room temperature for 12 days and concentrated to a yellow solid. The resulting solid was partitioned between ethyl acetate and 1N HCl, and the organic layer was separated and washed with a saturated aqueous solution of sodium bicarbonate and brine, and dried over magnesium sulfate. The crude product was concentrated to a white solid and purified by silica gel chromatography (1:1 hexanes/ethyl acetate) and crystallization (hexanes/ethyl acetate) providing 0.554 g (30%) of a white solid. R$_f$=0.4 (1:1 hexanes/ethyl acetate); H1-NMR (CDCl₃): δ7.83 (2H,d), 7.00 (2H,d), 6.72 (1H,s), 4.23–4.11 (1H,m), 3.91–3.81 (2H,m), 3.87 (3H,s), 3.46–3.38 (2H,m), 2.03–1.94 (2H,m), 1.63–1.51 (2H,m).

Step 3

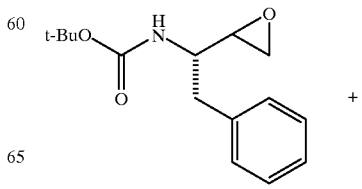

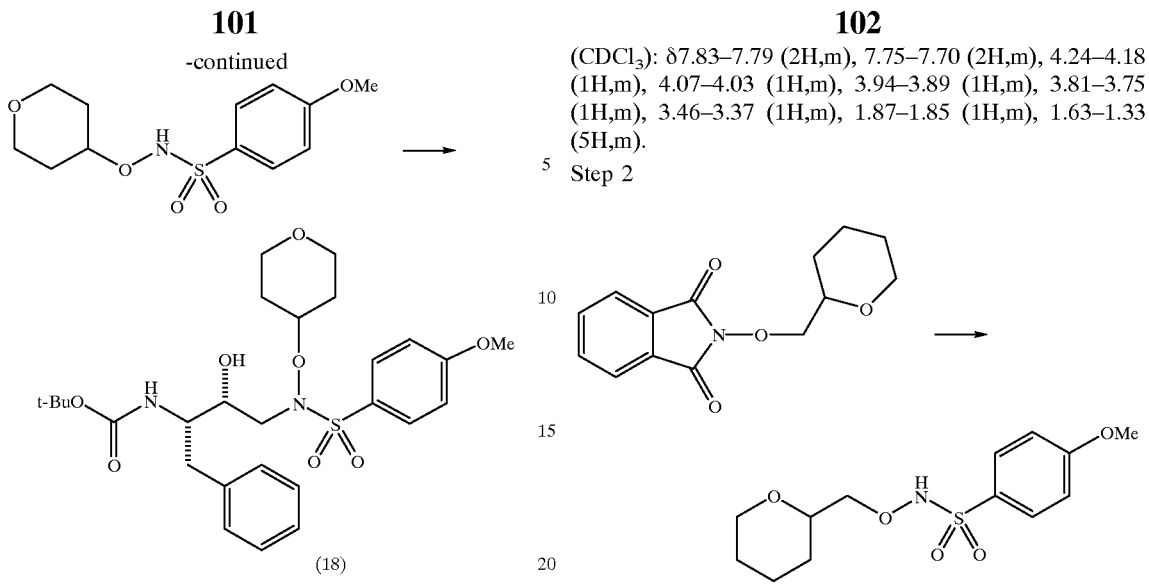

(CDCl$_3$): δ7.83–7.79 (2H,m), 7.75–7.70 (2H,m), 4.24–4.18 (1H,m), 4.07–4.03 (1H,m), 3.94–3.89 (1H,m), 3.81–3.75 (1H,m), 3.46–3.37 (1H,m), 1.87–1.85 (1H,m), 1.63–1.33 (5H,m).

Step 2 tert-butyl N-(1S,2R)-1-benzyl-2-hydroxy-3-[[(4-methoxyphenyl)sulfonyl](tetrahydro-2H-pyran-4-yloxy)amino]propylcarbamate. N-(tetrahydro-2H-pyran-4-yloxy)-4-methoxy-1-benzenesulfonamide (1.93 mmol, 554 mg) was combined with tert-butyl N-(1S)-1-[(2S)oxiran-2-yl]-2-phenylethylcarbamate (1.54 mmol, 406 mg) and THF (5 mL) under nitrogen. Phosphazine base P<t/4>t-Bu (0.31 mmol, 0.31 mL, 1M in hexanes) was injected into the stirring solution. The reaction was allowed to stir for 15 hours at room temperature, quenched by the addition of a few drops of glacial acetic acid and concentrated. The organic layer was separated and washed with 1N NaOH, dried over magnesium sulfate and concentrated under vacuum. The crude product was purified by silica gel chromatography (2:1 hexanes/ethyl acetate) and crystallization (hexanes/ethyl acetate) providing 367 mg (43%) of a white crystal. R$_f$=0.2 (8:1 CH$_2$Cl$_2$/ethyl acetate); H1-NMR (CDCl$_3$): δ7.70 (2H,d), 7.30–7.18 (6H,m), 6.97 (2H,d), 4.60–4.51 (1H,m), 4.44–4.33 (2H,m), 3.97–3.88 (2H,m), 3.86 (3H,s), 3.83–3.71 (2H,m), 3.48–3.34 (2H,m), 3.40–2.60 (1H,bs), 2.95–2.85 (2H,m), 2.07–1.95 (2H,m), 1.56–1.49 (2H,m), 1.32 (9H,s); MS (ESI): M+Na=573.

Example 19
Step 1

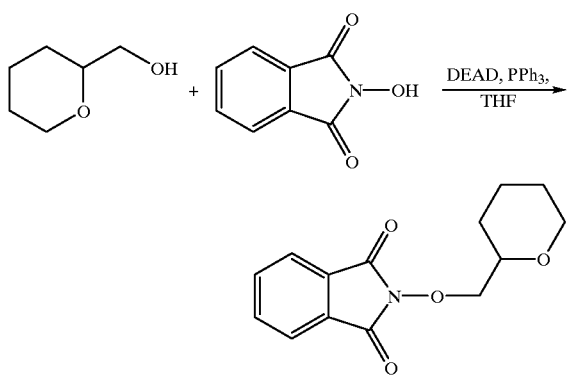

2-(tetrahydro-2H-pyran-2-ylmethoxy)-1H-isoindole-1,3(2H)-dione. This reaction was conducted according to the procedure reported in Grochowski, E; Jurczak, J. Synthesis 1976, 682. R$_f$=0.3 (2:1 hexanes/ethyl acetate); H1-NMR N-(tetrahydro-2H-pyran-2-ylmethoxy)-4-methoxy-1-benzenesulfonamide. 2-(tetrahydro-2H-pyran-2-ylmethoxy)-1H-isoindole-1,3(2H)-dione (6.8 mmol, 1.77 g) was combined with hydrazine (6.8 mmol, 0.21 mL) in anhydrous THF (15 mL) under nitrogen. The reaction immediately formed a white suspension and was allowed to stir at room temperature for 2 hours. The suspension was filtered directly into a flask containing 4-methoxybenzenesulfonyl chloride (6.8 mmol, 1.40 g) and diisopropylethylamine (8.1 mmol, 1.42 mL) was added. After stirring at room temperature for 24 hours, the reaction was concentrated to a yellow solid. The resulting solid was partitioned between ethyl acetate and 1N HCl, and the organic layer was separated and washed with a saturated aqueous solution of sodium bicarbonate and brine, and dried over magnesium sulfate. The crude product was concentrated to a yellow solid and purified by silica gel chromatography (2:1 hexanes/ethyl acetate). The purified product was combined with ether and filtered to remove the residual phthalimide-hydrazine biproduct. The final product was crystallized using hexanes and ethyl acetate to provide 141 mg (7%) of white crystals. R$_f$=0.3 (2:1 hexanes/ethyl acetate); H1-NMR (CDCl$_3$): δ 7.83 (2H,d), 7.05 (1H,s), 6.97 (2H,d), 4.01–3.86 (3H,m), 3.86 (3H,s), 3.63–3.57 (1H,m), 3.42–3.36 (1H,m), 1.88–1.78 (1H,m), 1.59–1.43 (4H,m), 1.3–1.15 (1H,m).

Step 3

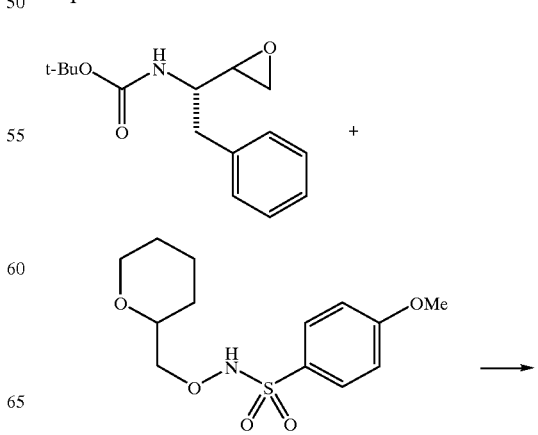

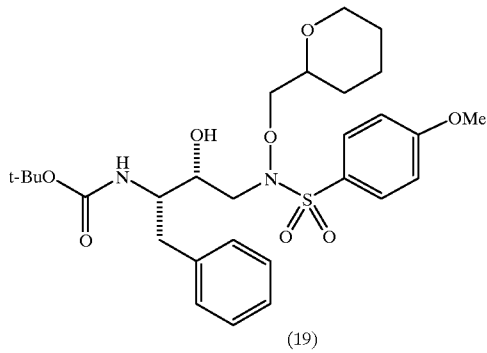

(19)

tert-butyl N-(1S,2R)-1-benzyl-2-hydroxy-3-[[(4-methoxyphenyl)sulfonyl](tetrahydro-2H-pyran-2-ylmethoxy)amino]propylcarbamate. N-(tetrahydro-2H-pyran-2-ylmethoxy)-4-methoxy-1-benzenesulfonamide (0.47 mmol, 141 mg) was combined with tert-butyl N-(1S)-1-[(2S)oxiran-2-yl]-2-phenylethylcarbamate (0.37 mmol, 99 mg) and THF (1 mL) under nitrogen. Phosphazine base P<t/4>t-Bu (0.08 mmol, 0.08 mL, 1M in hexanes) was injected into the stirring solution. The reaction was allowed to stir for 15 hours at room temperature, quenched by the addition of a few drops of glacial acetic acid and concentrated. The crude residue was partitioned between ethyl acetate and 1N HCl, and the organic layer was separated and washed with saturated aqueous sodium bicarbonate solution and brine, and dried over magnesium sulfate. The crude product was purified by silica gel chromatography (2:1 hexanes/ethyl acetate). The purified product was then washed with 1N NaOH to remove remaining sulfonamide starting material that coeluted, brine, and was again dried over magnesium sulfate. The silica gel chromatography was repeated and yielded 130 mg (62%) of a white solid. $R_f$=0.2 (2:1 hexanes/ethyl acetate); H1-NMR (CDCl$_3$): δ 7.68–7.64 (2H,m), 7.28–7.18 (6H,m), 6.96 (2H,d), 4.74–4.60 (1H,m), 4.37–4.18 (1H,m), 4.14–4.06 (1H,m), 4.01–3.93 (2H,m), 3.90–3.75 (2H,m), 3.87 (3H,s), 3.66–3.46 (1H,m), 3.46–3.35 (1H,m), 2.92–2.74 (2H,m), 3.50–2.50 (1H,bs), 1.90–1.81 (1H,m), 1.63–1.42 (4H,m), 1.34 (9H,s), 1.29–1.20 (1H,m); MS (ESI): M=565.

Example 20
Step 1

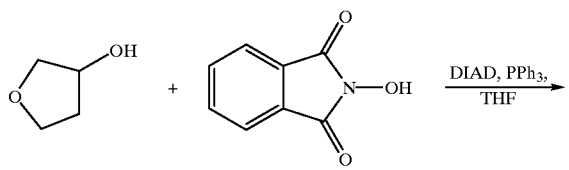

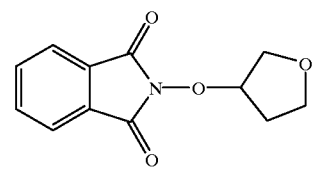

2-(tetrahydro-3-furanyloxy)-1H-isoindole-1,3(2H)-dione. To a light suspension containing N-hydroxylphthalimide (5.7 mmol, 926 mg), triphenylphosphine (5.7 mmol, 1.49 g), tetrahydro-4H-furan-3-ol (5.7 mmol, 0.459 mL) and anhydrous THF (10 mL), diisopropylazodicarboxylate (6.2 mmol, 1.23 mL) was injected under nitrogen atmosphere. The reaction stirred at room temperature for 5 hours and changed from a dark orange to yellow in appearance. The solvent was removed under vacuum, and the resulting residue was purified by silica gel chromatography (2:1 hexanes/ethyl acetate) and crystallization (hexanes/ethyl acetate) providing 373 mg (28%) of white crystals. $R_f$=0.5 (1:1 hexanes/ethyl acetate); H1-NMR (CDCl$_3$): δ 7.85–7.82 (2H, m), 7.77–7.74 (2H,m), 5.05 (1H,m), 4.16–4.09 (2H,m), 3.92–3.87 (2H,m), 2.34–2.28 (1H,m), 2.11–2.03 (1H,m).

Step 2

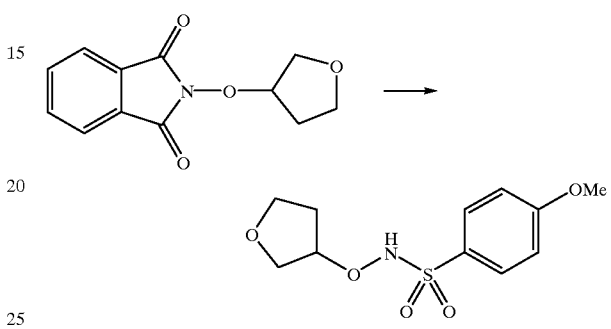

N-(tetrahydro-3-furanyloxy)-4-methoxy-1-benzenesulfonamide. 2-(tetrahydro-3-furanyloxy)-1H-isoindole-1,3(2H)-dione (1.5 mmol, 357 mg) was combined with hydrazine (1.7 mmol, 0.053 mL) in anhydrous THF (3 mL) under nitrogen. The reaction immediately formed a white suspension and was allowed to stir at room temperature for 1 hour. The suspension was filtered directly into a flask containing 4-methoxybenzenesulfonyl chloride (1.5 mmol, 316 mg) and diisopropylethylamine (1.8 mmol, 0.320 mL) was added. After stirring at room temperature for 18 hours, the reaction was concentrated to a solid. The resulting solid was partitioned between ethyl acetate and 1N HCl, and the organic layer was separated and washed with a saturated aqueous solution of sodium bicarbonate and brine, and dried over magnesium sulfate. The crude product was concentrated to a white solid and purified by silica gel chromatography (1:1 hexanes/ethyl acetate). The purified product was then combined with ether and filtered to remove the residual phthalimide-hydrazine biproduct. The filtrate was then crystallized by adding hexanes providing 203 mg (48%) white crystals. $R_f$=0.2 (1:1 hexanes/ethyl acetate); H1-NMR (CDCl$_3$): 67 7.82 (2H,d), 6.99 (2H,d), 6.85 (1H,s), 4.82–4.79 (1H,m), 3.97–3.87 (2H, m), 3.87 (3H,s), 3.83–3.70 (2H,m), 2.12–1.99 (2H,m).

Step 3

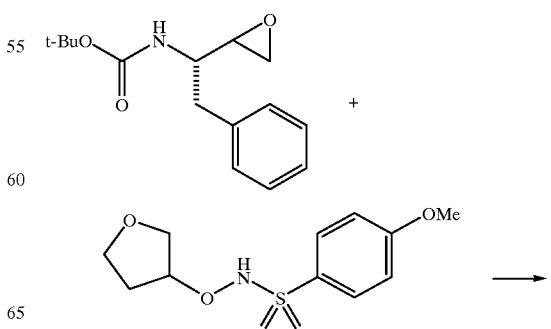

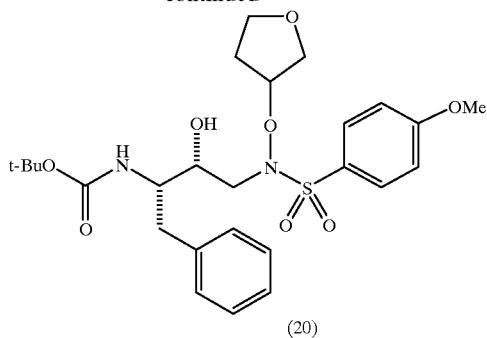

(20)

tert-butyl N-(1S,2R)-1-benzyl-2-hydroxy-3-[[(4-methoxyphenyl) sulfonyl](tetrahydro-3-furanyloxy)amino]propylcarbamate. N-(tetrahydro-3-furanyloxy)-4-methoxy-1-benzenesulfonamide (1.03 mmol, 283 mg) was combined with tert-butyl AT-(1S)-1-[(2S)oxiran-2-yl]-2-phenylethylcarbamate (1.35 mmol, 300 mg) and THF (1 mL) under nitrogen. Phosphazine base P<t/4>t-Bu (0.21 mmol, 0.21 mL, 1M in hexanes) was injected into the stirring solution. The reaction was allowed to stir for 15 hours at room temperature, quenched by the addition of a few drops of glacial acetic acid and concentrated. The crude residue was partitioned between ethyl acetate and 1N HCl, and the organic layer was separated and washed with saturated aqueous sodium bicarbonate solution and brine, and dried over magnesium sulfate. The crude product was purified by silica gel chromatography (2:1 hexanes/ethyl acetate) and reverse phase HPLC (water/acetonitrile) yielding 60 mg (11%) of a white solid. H1-NMR (CDCl$_3$): δ 7.68 (2H,d), 7.32–7.13 (6H,m), 7.01–6.93 (2H,m), 5.17–5.00 (1H,m), 4.66–4.51 (1H,m), 4.34–4.16 (1H,m), 3.87 (3H,s), 3.83–3.68 (5H,m), 3.67–3.57 (1H,m), 2.95–2.78 (2H,m), 2.70 (1H,bs), 2.18–1.97 (2H,m), 1.34 (9H,m); MS (ESI): M+Na=559.

Example 21

Step 1

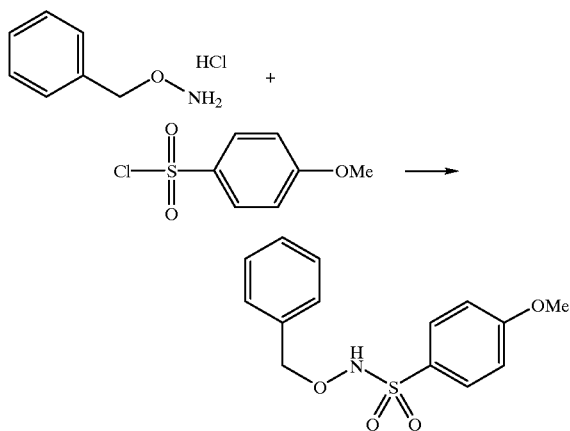

N$^1$-(benzyloxy)-4-methoxy-1-benzenesulfonamide. O-Benzylhydroxylamine hydrochloride (31.3 mmol, 5.0 g), 4-methoxybenzenesulfonyl chloride (34.5 mmol, 7.12 g) and anhydrous THF (50 mL) were combined under nitrogen. The reaction was cooled to 0° C. and dlisopropylethylamine (69.0 mmol, 12.0 mL) was injected. The reaction was allowed to warm to room temperature and continued to stir for 18 hours. An additional 0.25 equivalents of O-Benzylhydroxylamine hydrogen chloride (7.8 mmol, 1.25 g) and 0.75 equivalents of diisopropylethylamine (23.5 mmol, 4.1 mL) were added to encourage complete conversion of the remaining sulfonyl chloride. The reaction stirred for 4 additional hours at room temperature. The reaction solution was concentrated to a solid and partitioned between ethyl acetate and 1N HCl. The organic layer was dried over magnesium sulfate and concentrated under vacuum to yield 9.83 g (76%) of an off-white colored solid. R$_f$: 0.2 (2:1 hexanes/ethyl acetate); H1-NMR (CDCl$_3$): δ 7.84 (2H,d), 7.34 (5H,s) 7.08 (2H,d), 4.92 (2H,s), 3.88 (3H,s).

Step 2

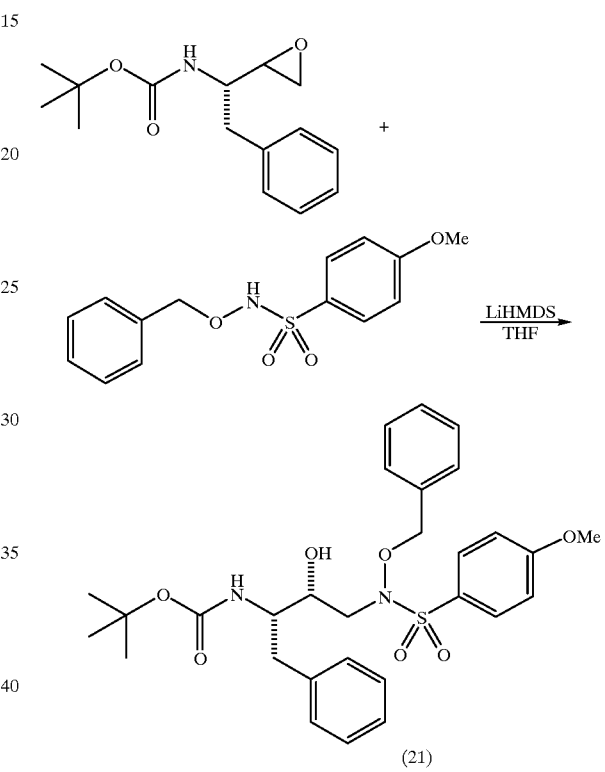

(21)

tert-butyl N-((1S, 2R)-1-benzyl-3-(benzyloxy)[(4-methoxyphenyl) sulfonyl]amino-2-hydroxypropyl) carbamnate. Lithium hexamethyldisilazide (0.6 mmol, 0.6 mL, 1M in THF) was injected into a stirring solution of N$^1$-(benzyloxy)-4-methoxy-1-benzenesulfonamide (3.0 mmol, 1.0 g), tert-butyl N-(1S)-1-[(2S)oxiran-2-yl]-2-phenylethylcarbamate (2.4 mmol, 0.64 g), and anhydrous THF (8 mL). The reaction was allowed to stir for 15 hours at room temperature under nitrogen. The reaction was quenched with a few drops of glacial acetic acid and concentrated to a thick oil. The crude was partitioned between ethyl acetate and 1N HCl, washed with saturated sodium bicarbonate solution and brine, dried over magnesium sulfate and concentrated. The crude product was purified by silica gel chromatography (2:1 hexanes/ethyl acetate) and crystallized from ethyl acetate with hexanes, providing 400 mg (22%) of a white crystal. Rf: 0.4 (2:1 hexanes/ethyl acetate); HL-NMR (CDCl$_3$): δ7.72 (2H,d), 7.4–7.3 (5H,m), 7.3–7.2 (5H,m), 7.19 (1H,d), 6.93 (2H,d), 5.08 (2H,s), 4.40 (1H,m), 3.82 (3H,s), 3.69 (1H,m), 3.53 (1H,bs), 2.98 (1H, bs), 2.83 (2H,m), 2.71 (1H,bs), 1.33 (9H,s); MS (ESI): M+Na=579.

Example 22

Step 1

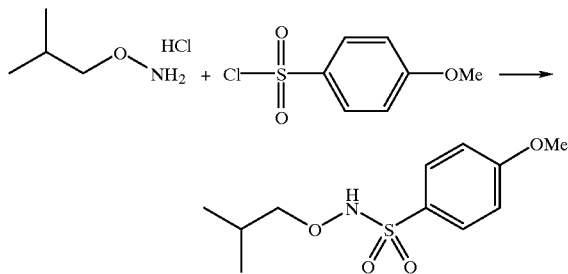

N[1]-isobutoxy-4-methoxy-1-benzenesulfonamide. Isobutoxyamine hydrochloride (7.96 mmol, 1.0 g), 4-methoxybenzenesulfonyl chloride (7.24 mmol, 1.5 g), diisopropylethylamine (18.09 mmol, 3.15 mL) and anhydrous THF (15 mL) were combined under nitrogen. The reaction stirred at room temperature for 15 hours. The reaction solution was concentrated to a white solid and partitioned between ethyl acetate and 1N HCl. The organic layer was separated and washed with saturated aqueous sodium bicarbonate and brine, dried over magnesium sulfate and concentrated under vacuum to yield an off-white colored solid. $R_f$: 0.5 (2:1 hexanes/ethyl acetate); H1-NMR (CDCl$_3$): δ 7.84 (2H,d), 6.99 (2H,d), 6.81 (1H,s), 3.87 (3H,s), 3.74 (2H,d), 1.90 (1H,septet), 0.86 (6H,d).

Step 2

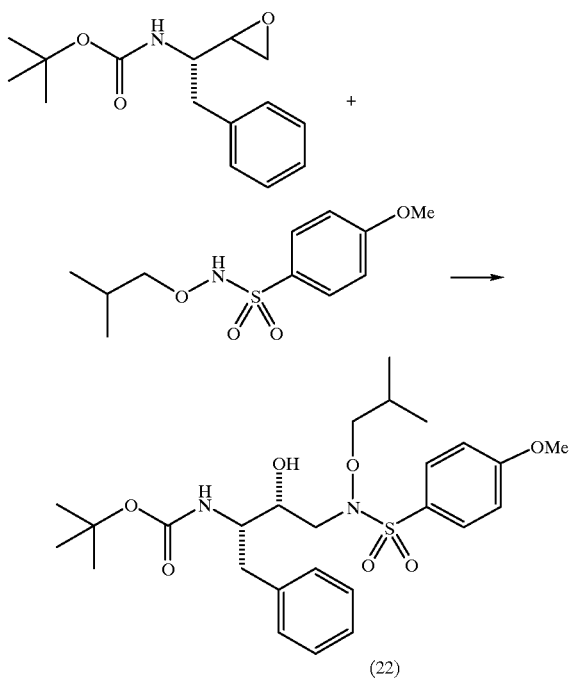

tert-butyl N-((1S, 2R)-1-benzyl-2-hydroxy-3-isobutoxy[(4-methoxyphenyl) sulfonyl]aminopropyl)carbamate. Synthesized under the same conditions as outlined for tert-butyl N-((1S,2R)-1-benzyl-3-(benzyloxy)[(4-methoxyphenyl) sulfonyl] amino-2-hydroxypropyl)carbamate 21. H1-NMR (CDCl$_3$): δ 7.70 (2H,d), 7.30–7.10 (6H,m), 6.96 (2H,d), 4.60 (1H,m), 3.93 (1H,m), 3.86 (3H,s), 3.81 (2H,m), 3.24 (1H, m), 3.01 (1H,m), 2.90 (2H,m), 2.82 (1H,m), 1.82 (1H, septet), 1.32 (9H,s), 0.93–0.81 (6H,m); MS (ESI): M+Na= 545.

Example 23

Step 1

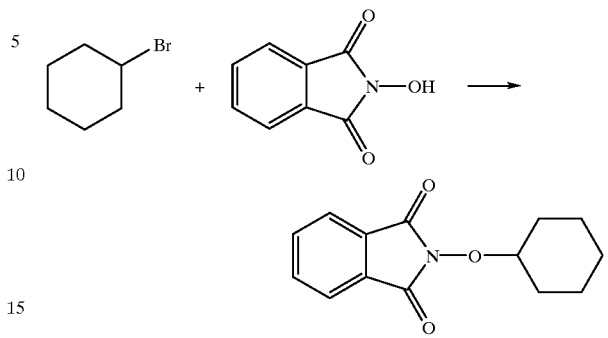

2-(cyclohexyloxy)-1H-isoindole-1,3(2H)-dione. N-hydroxylphthalimide (61.3 mmol, 10.0 g) was dissolved in anhydrous DMF (60 mL) under nitrogen. To the stirring solution, DBU (92.0 mmol, 13.75 mL) was injected followed by cyclohexyl bromide (76.6 irmol, 9.43 mL) and the reaction was warmed to 55° C. After stirring for 15 hours, the reaction was warmed to 80° C. for 5 hours, then cooled to room temperature and concentrated to a red oil. The reaction was partitioned between ethyl acetate and 1N HCl. The organic layer was washed with 1N NaOH, brine and dried over magnesium sulfate. The solvent was removed under vacuum and the crude product was triturated with hexanes providing 2.89 g (19%) of a yellow solid. $R_f$: 0.7 (2:1 hexanes/ethyl acetate); H1-NMR (CDCl$_3$): δ 7.80 (2H, m), 7.73 (2H,m), 4.21 (1H,m), 2.02–1.98 (2H,m), 1.87–1.82 (2H,m), 1.59–1.53 (4H,m), 1.30–1.24 (2H,m).

Step 2

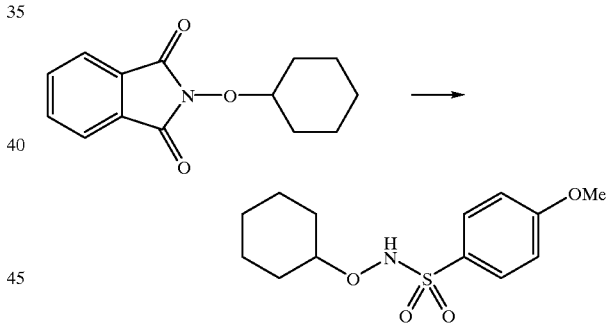

N[1]-(cyclohexyloxy)-4-methoxy-1-benzenesulfonamide. 2-(cyclohexyloxy)-1H-isoindole-1,3(2H)-dione (11.8 mmol, 2.89 g) was combined with hydrazine (13.0 mmol, 0.41 mL) in anhydrous THF (20 mL) under nitrogen. The reaction immediately formed a white suspension and was allowed to stir at room temperature for 18 hours. The suspension was filtered directly into a flask containing 4-methoxybenzenesulfonyl chloride (10.6 mmol, 2.20 g) and diisopropylethylamine (14.2 mmol, 2.47 mL) was added. After stirring at room temperature for 24 hours, the reaction was concentrated to a yellow solid and partitioned between ethyl acetate and 1N HCl. The organic layer was separated and washed with a saturated aqueous solution of sodium bicarbonate, and brine, and dried over magnesium sulfate. The product was concentrated to a yellow solid and purified by silica gel chromatography (1:1 hexanes/ethyl acetate) providing 2.53 g (83%) of a white solid. $R_f$: 0.2 (2:1 hexanes/ethyl acetate); H1-NMR (CDCl$_3$): δ 7.86 (2H,d), 7.00 (2H,d), 6.67 (1H,s), 3.98–3.95 (1H,m), 3.88 (3H,s), 2.00–1.94 (2H,m), 1.75–1.55 (2H,m), 1.35–1.17 (6H,m).

Step 3

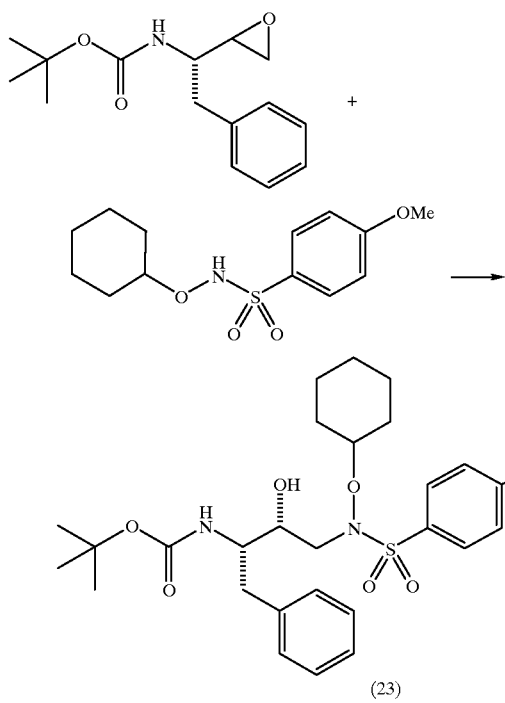

(23)

tert-butyl N-((1S,2R)-1-benzyl-3-(cyclohexyloxy)[(4-methoxyphenyl)sulfonyl]amino-2-hydroxypropyl) carbamate. Synthesized under the same conditions as outlined for tert-butyl N-((1S,2P,)-1-benzyl-3-(benzyloxy)[(4-methoxyphenyl) sulfonyl]amino-2-hydroxypropyl) carbamate. H1-NMR (CDCl₃): 67 7.77 (2H,d), 7.33–7.25 (6H,m), 7.02 (2H,d), 4.60 (1H,m), 4.24 (1H,m), 3.87 (3H,s), 3.84 (3H,m), 3.5–2.5 (1H,m), 2.96 (2H,m), 2.09 (2H,m), 1.77 (2H,m), 1.38 (9H,s), 1.2–1.0 (6H,m); MS (APCI): M+Na=571.

Example 24

(24)

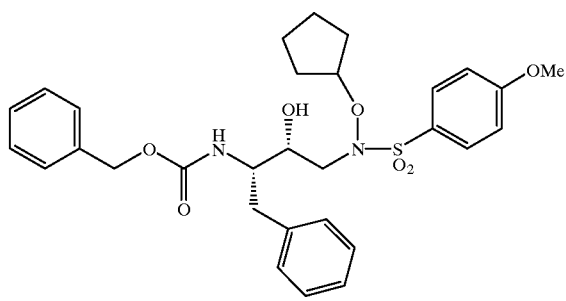

Phenylmethyl N-((1S,2R)-1-benzyl-3-(cyclopentyloxy)[(4-methoxyphenyl) sulfonyl]amino-2-hydroxypropyl) carbamate. To a solution of N¹-[(2R,3S)-3-amino-2-hydroxy-4-phenylbutyl] NT--(cyclopentyloxy)-4-methoxy-1-benzenesulfonamide x trifluoracetic acid (Step 1, Example 48), (50 mg, 0.091 mmol) in approximately 1.5 mnL of dichloromethane under Argon was added benzyichioroformate (15.6 μL, 0.109 mmol) followed by N,N-diisopropylethylamine (47.9 μL, 0.273 mmol). After stirring 18 hours, the reaction mixture was evaporated in vacuo to a residue and purified on a preparative silica gel TLC plate (20×20 cm, 1000 μM) eluting with 95:5 methylene chloride:methanol. The product band was removed, eluted with 4:1 methylene chloride : methanol, filtered, and evaporated in vacuo. The residue was partitioned between dichloromethane and water. The organic layer was separated, dried over anhydrous magnesium sulfate, filtered, and evaporated in vacuo. The residue was lyonhilized from acetonitrile and water to provide phenylmethyl N-((1S,2R)-1-benzyl-3-(cyclopentyloxy)[(4-methoxyphenyl)sulfonyl]amino-2-hydroxypropyl)carbamate (37 mg, 71%). H1-NMR (methanol-D4) 1.71 (m, 8H), 2.59 (m, 1H), 2.93 (m, 2H), 3.10 (m, 1H), 3.81 (m, 2H), 3.83 (s, 3H), 4.86 (m, 3H), 7.06 (m, 2H), 7.21 (m, !OH), 7.73 (m, 2H). MS(ESI): 591(M+Na).

An isomer of Compound 24, with inverted stereochemistry at C-2 was prepared as follows:

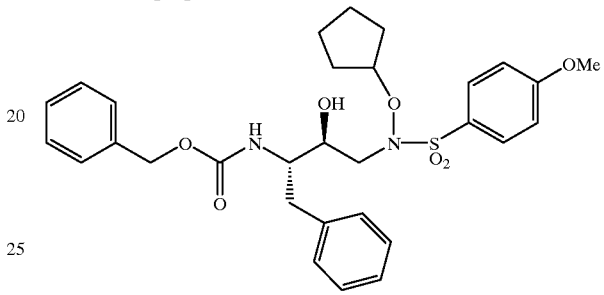

Phenylmethyl N-((1S,2S)-1-benzyl-3-(cyclopentyloxy)[(4-methoxyphenyl)sulfonyl]amino-2-hydroxypropyl) carbamate. A mixture of phenylmethyl N-(1S)-1-[(2S) oxiran-2-yl]-2-phenylethylcarbamate [250 mg, 0.842 mmol, Tetrahedron (1994), 50(21), 6333-46] and N¹-(cyclopentyloxy)-4-methoxy-1-benzenesulfonamide (285 mg, 1.05 mmol) in anhydrous terrahydrofuran (3 mL) under an Argon atmosphere was treated with phosphazene base P<t/4>t-Bu (0.168 mL, 0.168 mmoL, 1.0 M in hexane). The mixture was starred at ambient temperature for approximately 18 hours, quenched with several drops of glacial acetic acid and evaporated in vacuo. The residue was purified on flash grade silica gel eluting with 4:1 hexane : ethyl acetate. Fractions containing the product were combined and evaporated in vacuo. The residue was triturated with hexane and then evaporated in vacuo and dried under high vacuum to provide phenylmethyl N-((1S,2S)-1-benzyl-3-(cyclopentyloxy)[(4-methoxyphenyl)sulfonyllamino-2-hydroxypropyl)carbamate (439 mg, 92%) as a foam. HL-NMR (methanol-D4) 1.66 (m, 8H), 2.94 (m, 4H), 3.83 (m, 2H), 3.92 (s, 3H), 4.59 (m, 1H), 5.10 (m, 2H), 7.10 (m, 2H), 7.29 (m, 10H), 7.69 (m, 2H). MS(ESI): 591(M+Na).

Example 25

(25)

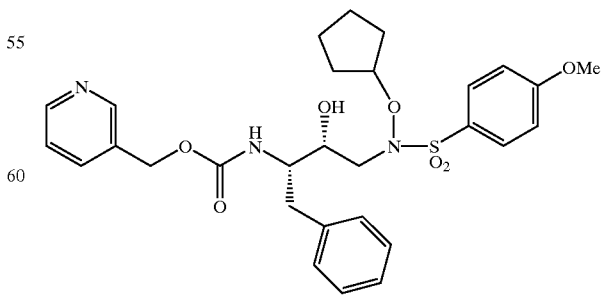

3-pyridylmethyl N-((1S,2R)-1-benzyl-3-(cyclopentyloxy) [(4-methoxyphenyl)sulfonyl]amino-2-hydroxypropyl)

carbamate. Carbonyldiimidazole (13.0 mg, 0.080 mmol) and 3-hydroxymethylpyridine (7.8 Al, 0.080 mmol) were combined under an Argon atmosphere in 2.5 mL of anhydrous ethyl acetate. After stirring for 1.5 hours at ambient temperature, $N^1$[(2R,3S)-3-amino-2-hydroxy-4-phenylbutyl]-$N^1$-(cyclopentyloxy)-4-methoxy-1-benzenesulfonamide x trifluoracetic acid (Step 1, Example 48), (40 mg, 0.073 mmol) was added and the mixture was heated at reflux for 5 hours. Heating was discontinued and the solvent was removed under vacuum. The crude product was purified on a preparative TLC plate (20×20 cm, 1000 μM) eluting with 93:7 methylene chloride : methanol. The product band was removed, eluted with 3:1 methylene chloride : methanol, filtered, and evaporated in vacuo. The residue was dissolved in diethylether, evaporated in vacuo and dried under high vacuum to provide 3-pyridylmethyl N-((1S,2R)-1-benzyl-3-(cyclopentyloxy)[(4-methoxyphenyl)sulfonyl]amino-2-hydroxypropyl) carbamate (18.9 mg, 41%) as a foam. H1-NMR (chloroform-D3): 1.66 (m, 8H), 2.95 (m, SH), 3.86 (s, 3H), 3.87 (m, 2H), 4.77 (m, 1H), 4.98 (m, 3H), 6.97 (d, 2H), 7.20 (m, 6H), 7.54 (m, IH), 7.68 (d, 2H), 8.54 (bm, 2H). MS(ESI): 570(MH+).

Example 26

(26)

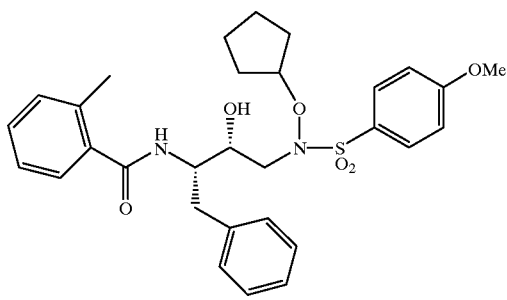

$N^1$-((1S,2R)-1-benzyl-3-(cyclopentyloxy)[(4-methoxyphenyl) sulfonyl]amino-2-hydroxypropyl)-2-methylbenzamide. O-Toluoyl chloride (7.8 uL, 0.0602 mmol) was added to a solution of $N^1$-[(2R,3S)-3-amino-2-hydroxy-4-phenylbutyl]-$N^1$-(cyclopentyloxy)-4-methoxy-1-benzenesulfonamide x trlfluoracetic acid (Step 1, Example 48), (30 mg, 0.055 mmol) and N,N-diisopropylethylamine (23.8 μL, 0.137 mmol) in approximately 1.5 mL of dichloromethane under Argon. After stirring for 18 hours at ambient temperature, the reaction solvent was removed in vacuo and the residue was purified on a preparative TLC plate (20×20 cm, 500 μM) eluting with 96:4 methylene chloride : methanol. The product band was removed, eluted with 4:1 methylene chloride : methanol, filtered, and evaporated in vacuo. The residue was triturated from diethylether and hexane and the solvents were evaporated in vacuo to provide $N^1$-((1S,2R)-1-benzyl-3-(cyclopentyloxy)[(4-methoxyphenyl)sulfonyl]amino-2-hydroxypropyl)-2-methylbenzamide (27 mg, 89%) as a solid. H1-NMR (dimethylsulfoxide-D6): 1.75 (m, 8H), 1.87 (s, 3H), 2.63 (m, 1H), 2.79 (bm, 1H), 3.05 (bm, 1H), 3.21 (bm, 1H), 3.69 (bm, 1H), 3.86 (s, 3H), 4.13 (bm, 1H), 4.86 (bm, 1H), 5.28 (bs, 1H), 6.79 (m, 1H), 7.21 (m, 10H), 7.72 (d, 2H), 8.06 (d, 1H). MS(ESI): 575(M+Na).

Example 27

Step 1:

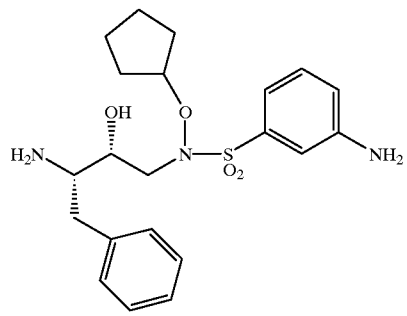

3-amino-$N^1$-[(2R,3S)-3-amino-2-hydroxy-4-phenylbutyl-$N^1$-(cyclopentyloxy)-1-benzenesulfonamide. A mixture of N-(1S,2R)-3-[[(3-aminophenyl)sulfonyl](cyclopentyloxy) amino]-1-benzyl-2-hydroxypropylcarbamate (Step 3, Example 11), (1.500 g, 2.89 mmol) and trifluoroacetic acid (5 mL) was stirred under an Argon atmosphere at ambient temperature for 30 minutes. Trifluoroacetic acid was removed in vacuo and the residue was partitioned between dichloromethane and 1N NaOH. After separating the phases, the aqueous layer was extracted twice with dichloromethane. The combined organic layers were dried over anhydrous sodium sulfate, filtered, evaporated in vacuo and dried under high vacuum to provide 3-amino-$N^1$-[(2R,3S)-3-amino-2-hydroxy-4-phenylbutyl]-$N^1$-(cyclopentyloxy)-1-benzenesulfonamide (1.157 g, 96%) as a foam. H1-NMR (methanol-D4): 1.68 (m, 8H), 2.55 (m, 1H), 2.79 (m, 1H), 2.94 (bm, 1H), 3.12 (m, 2H), 3.77 (m, 1H), 4.76 (m, 1H), 6.96 (m, 1H), 7.05 (m, 1H), 7.16 (m, 4H), 7.27 (m, 3H). MS(ESI): 420(MH+).

Step 2

(27)

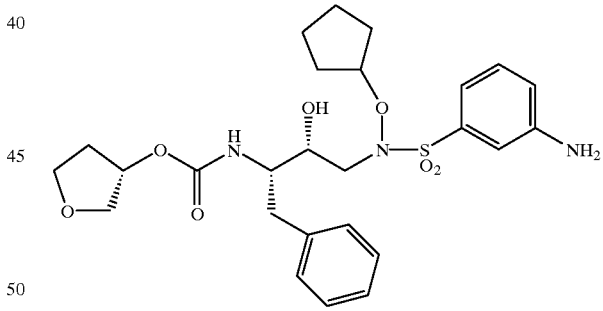

(3S)tetrahydro-3-furanyl N-(1S,2R)-3-[[(3-aminophenyl) sulfonyl](cyclopentyloxy)amino]-1-benzyl-2-hydroxypropylcarbamate. A mixture of 3-amino-$N^1$-[(2R,3S)-3-amino-2-hydroxy-4-phenylbutyl]-N-(cyclopentyloxy)-1-benzenesulfonamide (100 mg, 0.239 mmol), 2,5-dioxo-1-pyrrolidinyl [(3S)tetrahydro-3-furanyl] carbonate (55 mg, 0.239 mmol, W094/05639) and N,N-diisopropylethylamine (41.6 μL, 0.239 mmol) were combined under Argon at ambient temperature in approximately 1.5 mL of acetonitrile. After stirring for approximately 18 hours, the reaction mixture was evaporated in vacuo and purified on two preparative silica gel TLC plates (20×20 cm, 1000 AM) eluting with 95:5 methylene chloride methanol. The product band was removed, eluted with 3:1 methylene chloride : methanol, filtered, evaporated in vacuo and dried under high vacuum to provide (3S)tetrahydro-3-furanyl N-(iS, 2R)-3-[[(3-aminophenyl)sulfonyl](cyclopentyloxy)amino]-1-benzyl-2-hydroxypropylcarbamate (111 mg, 87%) as a foam. H1-NMR (methanol-D4): 1.80 (m, 9H), 2.61 (m, 1H), 3.02 (m, 2H), 3.14 (m, 1H), 3.50 (m, 1H), 3.64 (m, 1H), 3.73 (m, 1H), 3.81 (m, 3H), 4.87 (m, 1H), 5.00 (m, 1H), 6.98 (m, 1H), 7.08 (m, 1H), 7.15 (m, 1H), 7.26 (m, 6H). MS(ESI): 534(MH+)

Example 28

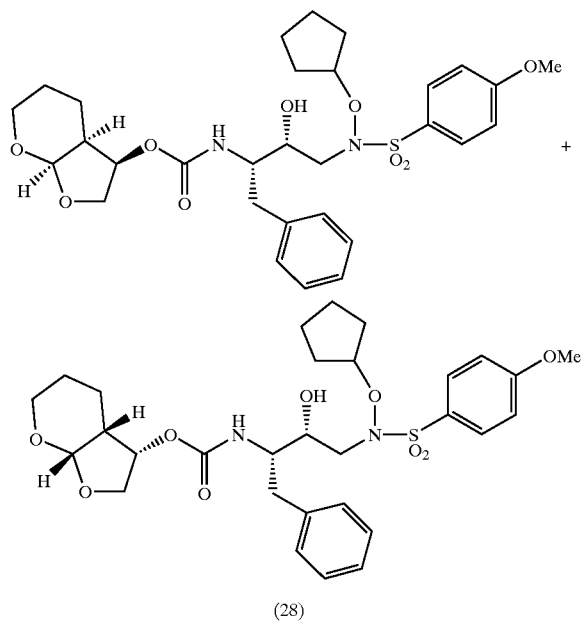

(28)

(3S,3aR,7aS)hexahydro-4H-furo[2,3-b]pyran-3-yl N-((1IS,2R)-1-benzyl-3-(cyclopentyloxy)[(4-methoxyphenyl)sulfonyl]amino-2-hydroxypropyl) carbamate and 3R, 3aS, 7aR) hexahydro-4H-furo[2,3-b]pyran-3-yl N-((1S,2R)-1-benzyl-3-(cyclopentyloxy)[(4-methoxyphenyl) sulfonyl-amino-2-hydroxypropyl)carbamate. A mixture of (3R,3aS,7aR)+(3S,3aR,7aS)hexahydro-4H-furo[2,3-b]pyran-3-yl 4-nitrophenyl) carbonate (68 mg, 0.219 mmol), $N^1$-[(2R,3S)-bz3-amino-2-hydroxy-4-phenylbutyl]-N(-(cyclopentyloxy)[-4-omethoxy-1-benzenesulfonamide x trifluoracetic acid (Step 1, Example 48), (60 mg, 0.109 mmol) and N,N-diisopropylethylamine (66.8 μL, 0.385 mmol) were combined in approximately 1.5 mL of acetonitrile and stirred at ambient temperature under an Argon atmosphere for 18 hours. An additional quantity of carbonate (20 mg, 0.065 mmol) and N,N-diisopropylethylamine (40 μL, 0.224 mmol) was added and the reaction mixture was heated at 60° C. for 1.5 hours. The reaction was cooled and evaporated in vacuo. The residue was dissolved in ethyl acetate and washed three times with 5% w/v potassium carbonate, saturated aqueous brine, dried over anhydrous magnesium sulfate, filtered and evaporated in vacuo to a residue. The crude product was purified on a preparative TLC plate (20×20 cm, 500 μM) eluting with 95:5/methylene chloride:methanol. The product band was removed, eluted with 4:1 methylene chloride : methanol, filtered, and evaporated in vacuo. The residue was dissolved in diethylether, evaporated in vacuo and dried under high vacuum to provide a 1:1 mixture of (3S,3aR,7aS)hexahydro-4H-furo[2,3-b]pyran-3-yl N-((1S,2R)-1-benzyl-3-(cyclopentyloxy)[(4-methoxyphenyl)sulfonyl]amino-2-hydroxypropyl)carbamate and 3R,3aS,7aR)hexahydro-4H-furo[2,3-b]pyran-3-yl N-((1S,2R)-1-benzyl-3-(cyclopentyloxy)[(4-methoxyphenyl)sulfonyl]amino-2-hydroxypropyl) carbamate as a foam (55 mg, 83%). H1-NMR (chloroform-D3): 1.80 (m, 12H), 2.19 (m, 1H), 3.00 (m, 5H), 3.48 (m, 1H), 3.89 (m, 7H), 4.21 (m, 1H), 4.92 (m, 2H), 5.08 (m, 1H), 5.27 (bm, 1H), 7.04 (m, 2H), 7.28 (m, 5H), 7.76 (m, 2H). MS(ESI): 627(M+Na).

Example 29

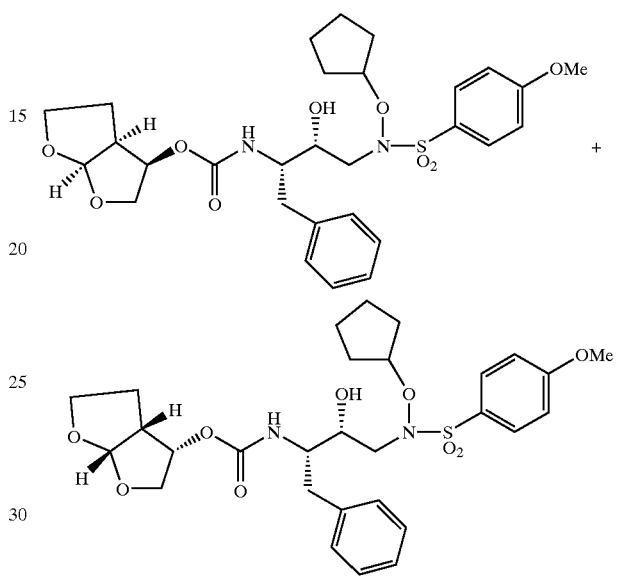

(29)

(3R,3aS,6aR)hexahydrofuro[2,3-b]furan-3-yl N-((1S,2R)-1-benzyl-3-(cyclopentyloxy)[(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(4-methoxyphenyl)sulfonyl]amino-2-hydroxypropyl)carbamate. A mixture of (3R,3aS,6aR) +(3S,3aR,6aS)hexahydrofuro[2,3-b]furan-3-yl (4-nitrophenyl) carbonate (96.5 mg, 0.327 mmol, WO 9721683), $N^1$-[(2R,3S)-3-amino-2-hydroxy-4-phenylbutyl]-$N^1$-(cyclopentyloxy)-4-methoxy-1-benzenesulfonamide x trifluoracetic acid (Step 1, Example 48), (60 mg, 0.109 mmol) and N,N-diisopropylethylamine (85.6 μL, 0.491 mmol) were combined in approximately 1.5 mL of acetonitrile and stirred at ambient temperature under an Argon atmosphere for 18 hours. The reaction mixture was evaporated in vacuo and the residue was purified on a preparative TLC plate (20×20 cm, 500 μM) eluting with 1:1/ethyl acetate:hexane. The product band was removed, eluted with 3:1/methylene chloride:methanol, filtered, and evaporated in vacuo. The residue was dissolved in diethylether, evaporated in vacuo and dried under high vacuum to provide a 1:1 mixture of (3R,3aS,6aR)hexahydrofuro [2,3-b]furan-3-yl N-((1S,2R)-1-benzyl-3-(cyclopentyloxy)[(4-methoxyphenyl)sulfonyl]amino-2-hydroxypropyl)carbamate and (3S,3aR,6aS) hexahydrofuro[2,3-b]furan-3-yl N-((1S,2R)-1-benzyl-3-(cyclopentyloxy)[(4-methoxyphenyl)sulfonyl]amino-2-hydroxypropyl)carbamate (50 mg, 26%) as a foam. H1-NMR (chloroform-D3): 1.68 (m, 10H), 2.95 (m, 6H), 3.64 (m, 2H), 3.88 (s, 3H), 3.93 (m, 4H), 4.82 (m, 2H), 5.01 (bm, 1H), 5.65 (m, 1H), 6.98 (m, 2H), 7.23 (m, 5H), 7.71 (m, 2H). MS(ESI): 613(M+Na).

Example 30

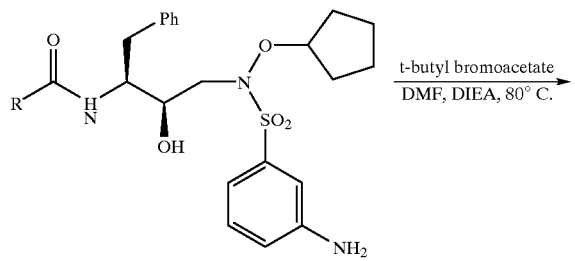

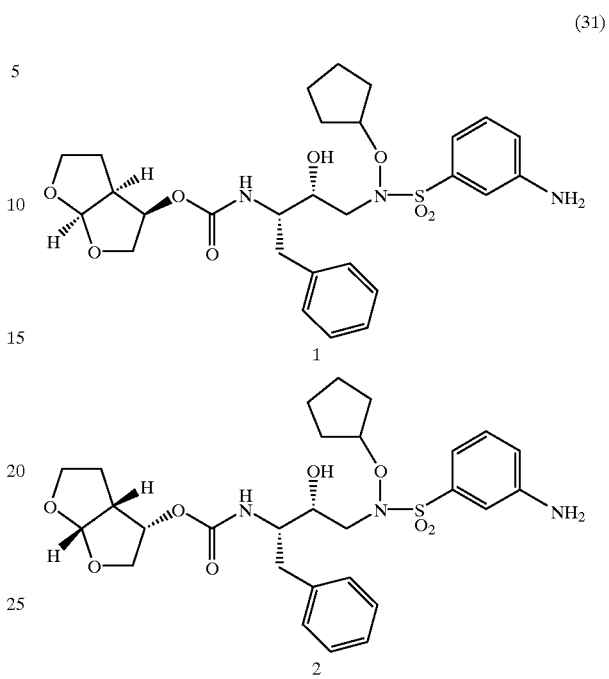

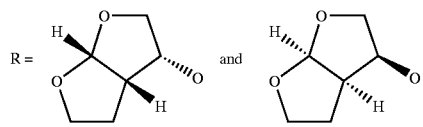

tert-butyl 2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy)amino]sulfonylanilino)acetate and tert-butyl 2-(3-[[(2R,3S)-3-([(3S,3aR,6aS)hexahydrofuro [2,3-b]furan-3-yloxy]carbonylamino)-2-hydroxy-4-phenylbutyl](cyclopentyloxy)amino] sulfonylanilino)acetate A solution of 0.250 g (0.434 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfony]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 0.13 mL (0.87 mmol) of tert-butyl bromoacetate, and 0.15 mL (0.87 mmol) of N,N-diisopropylethylamine in 5 mL of anyhydrous DMF was stirred at 80° C. for 18 hours. The solution was cooled to RT and concentrated in vacuo. The residue was dissolved in dichloromethane. The solution was washed with saturated aqueous brine (3x), dried over anhydrous $MgSO_4$, and concentrated in vacuo. The crude product was purified by flash chromatography (silica gel, 4:6 hexane/EtOAc) to afford 0.28 g (94%) of the desired product as a light yellow foam. H1-NMR (DMSO-$d_6$): 7.31–7.07 (7H), 6.93–6.80 (3H), 6.61 (1H), 5.47 (1H), 5.19 (1H), 4.83–4.64 (2H), 3.81–3.40 (7H), 3.06–2.60 (5H), 2.53-2.27 (1H), 1.95–1.16 (19H). LCMS(ESI): 690 (M+H).

Example 31

(3R,3aS,6aR)hexahydrofuro[2,3-b]furan-3-yl N-(1S,2R)-3-[[(3-aminophenyl)sulfonyl](cyclopentyloxy)amino]-1-benzyl-2-hydroxypropylcarbamate (1) and (3S,3aR,6aS) hexahydrofuro[2,3-b]furan-3-yl N-(1S,2R)-3-[[(3-aminophenyl)sulfonyl](cyclopentyloxy)amino]-1-benzyl-2-hydroxypropylcarbamate (2) as a white lyophile. A mixture of (3R,3aS,6aR)+(3S,3aR,6aS) hexahydrofuro[2,3-b]furan-3-yl (4-nitrophenyl) carbonate (211 mg, 0.716 mmol), 3-amino-$N^1$[(2R,3S)-3-amino-2-hydroxy-4-phenylbutyl]-$N^1$-(cyclopentyloxy)-1-benzenesulfonamide (Step 1, Example 27), (100 mg, 0.239 mmol), and N,N-diisopropylethylamine (166.4 AL, 0.955 mmol) were combined in approximately 3 mL of acetonitrile and stirred at ambient temperature under an Argon atmosphere for approximately 18 hours. The reaction mixture was evaporated in vacuo and purified on two preparative silica TLC plates (20×20 cm, 1000 $\mu$M) eluting with 93:7/methylene chloride:methanol. The product band was removed, eluted with 4:1/methylene chloride:methanol, filtered, and evaporated in vacuo. The residue was partitioned between 1N NaOH and dichloromethane. The layers were separated and the aqueous layer was extracted with dichloromethane. The combined organic layers were dried over anhydrous magnesium sulfate, filtered and evaporated in vacuo to a foam. The mixture of diastereomers were separated by supercritical fluid chromatography [Chiralpak AD (2 cm, Chiral Technologies), 21 Mpa; 11.3 mL/min methanol+0.1% triethylamine; 45 g/min $CO_2$; 40° C.]. The fraction containing the diastereomer possessing a shorter retention time was evaporated in vacuo to a residue and then purified again by preparative TLC as above. The product was lyophilized from acetonitrile and water to provide (3R,3aS,6aR) hexahydrofuro[2,3-b]furan-3-yl N-(1S,2R)-3-[[(3-aminophenyl)sulfonyl](cyclopentyloxy)amino]-1-benzyl-2- hydroxypropylcarbamate (1) as a white lyophile (18 mg, 13%). The fraction containing the diastereomer possessing a longer retention time was evaporated in vacuo to a residue and then purified again by preparative TLC as above. The product was lyophilized from acetonitrile and water to provide (3S,3aR,6aS)hexahydrofuro[2,3-b]furan-3-yl N-(1S,2R)-3-[r(3-aminophenyl)sulfonyl](cyclopentyloxy)amino]-1-benzyl-2-hydroxypropylcarbamate (2) as a white lyophile (18 mg, 13%).

1 H1-NMR (methanol-D4) 1.62 (m, 10H), 2.52 (m, 1H), 2.88 (m, 2H), 3.10 (m, 2H), 3.62 (m, 2H), 3.76 (m, 3H), 3.87 (m, 1H), 4.81 (m, 1H), 4.90 (m, 1H), 5.55 (d, 1H), 6.93 (m, 1H), 7.02 (m, 1H), 7.08 (m, 1H), 7.14 (m, 1H), 7.21 (m, 5H). MS(ESI): 598(M+Na).

2 H1-NMR (methanol-D4): 1.73 (m, 10H), 2.57 (m, 1H), 2.93 (m, 2H), 3.09 (m, 2H), 3.46 (m, 1H), 3.79 (m, 5H), 4.84 (m, 2H), 5.57 (d, 1H), 6.92 (m, 1H), 7.02 (m, 1H), 7.09 (m, 1H), 7.20 (m, 6H). MS(ESI): 598(M+Na).

Example 32

Step 1

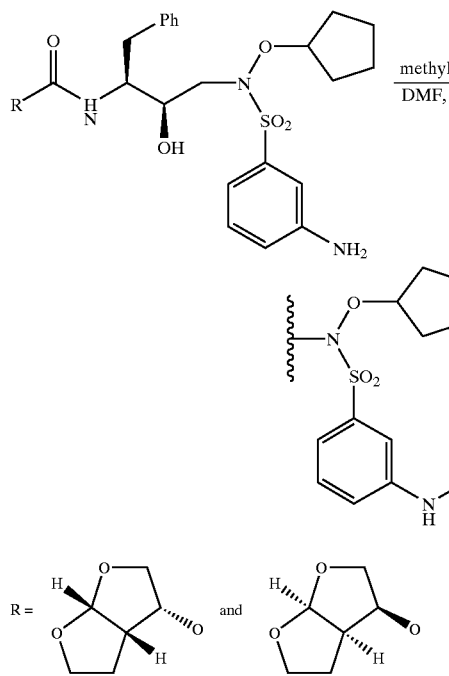

methyl 2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy)amino]sulfonylanilino)acetate and methyl 2-(3-[[(2R,3S)-3-([(3S,3aR,6aS)hexahydrofuro[2,3-b]furan-3-yloxy]carbonylamino)-2-hydroxy-4-phenylbutyl](cyclopentyloxy)amino]sulfonylanilino)acetate. A solution of 0.500 g (0.869 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 0.250 mL (2.61 mmol) of methyl bromoacetate, and 0.450 mL (2.61 mmol) of N,N-diisopropylethylamine in 5 mL of anhydrous DMF was stirred at 80° C. for 18 hours. The solution was cooled to RT and concentrated in vacuo. The residue was dissolved in ethyl acetate. The solution was washed with saturated aqueous brine (3x), dried over anhydrous MgSO$_4$, and concentrated in vacuo. The crude product was purified by flash chromatography (silica gel, 97:3 CH$_2$Cl$_2$/MeOH) to afford 0.50 g (89%) of the desired product as a light yellow foam. H1-NMR (DMSO-d$_6$): 7.38–7.08 (7H), 7.01–6.85 (3H), 6.71 (1H), 5.52 (1H), 5.21 (1H), 4.88–4.70 (2H), 3.99 (2H), 3.88–3.46 (8H), 3.13–2.64 (5H), 2.57–2.35 (1H), 2.01–1.17 (10H). LCMS(ESI): 648 (M+H).

Step 2

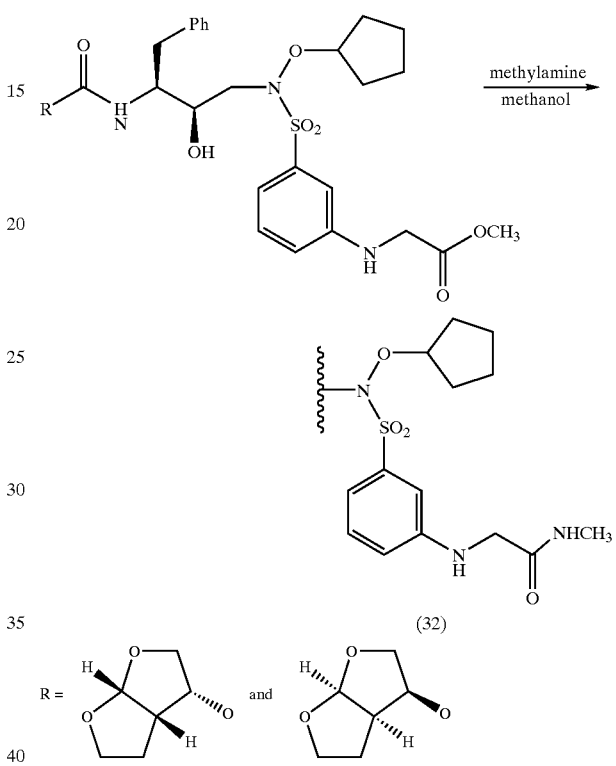

(3R,3aS,6aR)hexahydrofuro[2,3-b]furan-3-yl N-((1S,2R)-1-benzyl-3-(cyclopentyloxy)[(3-[2-(methylamino)-2-oxoethyl]aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-[2-(methylamino)-2-oxoethyl]aminophenyl)sulfonyl]amino-2-hydroxypropyl)carbamate. A solution of 50.0 mg (0.0770 mmol) of a 1:1 mixture of methyl 2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy)amino]sulfonylanilino)acetate and methyl 2-(3-[[(2R,3S)-3-([(3S,3aR,6aS)hexahydrofuro[2,3-b]furan-3-yloxy]carbonyl amino)-2-hydroxy-4-phenylbutyl](cyclopentyloxy)amino]sulfonylanilino)acetate in 5 mL of 2M methylamine in MeOH was stirred at RT in a sealed tube. After 4 hours the solution was concentrated in vacuo and the residue subjected to flash chromatography (silica gel, 97:3 EtOAc/MeCH) to afford 38 mg (76%) of the desired product as a white foam. H1-NMR (CDCl$_3$) 7.53–7.00 (11H), 6.80–6.59 (1H), 6.68 (1H), 5.50–5.18 (1H), 5.06 (1H), 4.85 (1H), 4.09–3.60 (7H), 3.28–2.78 (8H), 2.00–1.47 (10H). MS(ESI): 647 (M+H), 669 (M+Na).

Example 33

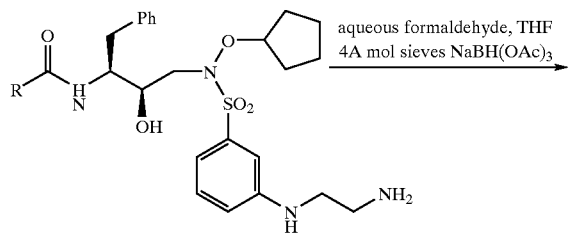

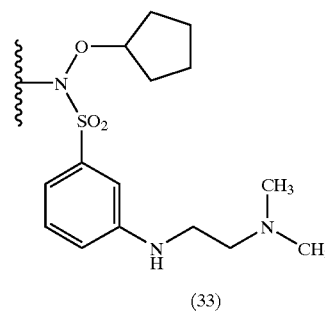

(33)

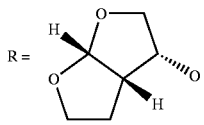 and 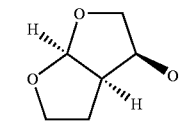

(3R,3aS,6aR)hexahydrofuro[2,3-b]furan-3-yl N-((1S,2R)-1-benzyl-3-(cyclopentyloxy)[(3-[2-(dimethylamino)ethyl]aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-[2-(dimethylamino)ethyl]aminophenyl)sulfonyl]amino-2-hydroxypropyl)carbamate.

A solution of 65.0 mg (0.110 mmol) of a 1:1 mixture of (3R,3aS,6aR)hexahydrofuro[2,3-b]furan-3-yl N-(1S,2R)-3-[(3-[(2-aminoethyl)amino]phenylsulfonyl)(cyclopentyloxy)aminol-1-benzyl-2-hydroxypropylcarbamate and (3S,3aR,6aS)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate (see example 83), 0.050 mL (0.55 mmol) of 37% aqueous formaldehyde, and 0.117 g (0.550 mmol) of NaBH(OAc)₃ was treated with 0.150 g of powdered 4A molecular sieves and the mixture was stirred at RT. After stirring at RT for 18 hours, tlc (silica gel, 9:1 CH₂Cl₂/MeOH) indicated complete loss of starting material at $R_f$=0.05 and two new components at $R_f$=0.31 and 0.63. The reaction mixture was filtered and the filtrate concentrated to dryness. The residue was dissolved in CH₂Cl₂. The solution was washed with saturated aqueous NaHCO₃ (3x), dried over MgSO₄, and concentrated in vacuo. The crude product was subjected to flash chromatography (silica gel, 95:5 to 90:10 CH₂Cl₂/MeOH) to afford 14 mg (20%) of the Rf=0.31 product as a white foam. H1-NMR (CDCl₃): 7.37–7.11 (8H), 7.10–6.90 (2H), 6.85 (1H), 5.62 (1H), 5.18–4.89 (2H), 4.79 (1H), 4.00–3.49 (5H), 3.32–2.60 (10H), 2.38 (6H), 1.94–1.40 (10H). LCMS(ESI): 647 (M+H).

Example 34

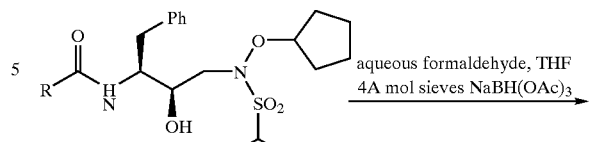

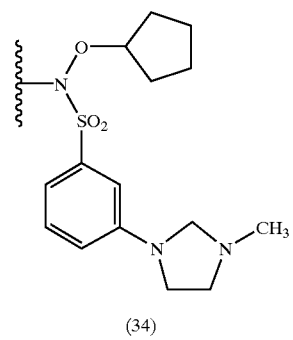

(34)

R = (same structures as above) and (3R,3aS,6aR)hexahydrofuro[2,3-b]furan-3-yl N-[(1S,2R)-1-benzyl-3-((cyclopentyloxy)[3-(3-methyl-1-imidazolidinyl)phenyl]sulfonylamino)-2-hydroxypropyl]carbamate and (3S,3aR,6aS)hexahydrofuro[2,3-b]furan-3-yl N-[(1S,2R)-1-benzyl-3-((cyclopentyloxy)[3-(3-methyl-1-imidazolidinyl)phenyl]sulfonylamino)-2-hydroxypropyl]carbamate A solution of 65.0 mg (0.110 mmol) of a 1:1 mixture of (3R,3aS,6aR)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate and (3S,3aR,6aS)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate (see example 83), 0.050 mL (0.55 mmol) of 37% aqueous formaldehyde, and 0.117 g (0.550 mmol) of NaBH(OAc)₃ was treated with 0.150 g of powdered 4A molecular sieves and the mixture stirred at RT. After stirring at RT for 18 hours, tlc (silica gel, 9:1 CH₂Cl₂/MeOH) indicated complete loss of starting material at R.=0.05 and two new components at R,=0.31 and 0.63. The reaction mixture was filtered and the filtrate concentrated to dryness. The residue was dissolved in CH₂C₁₂. The solution was washed with saturated aqueous NaHCO₃ (3x), dried over MgSO₄, and concentrated in vacuo. The crude product was subjected to flash chromatography (silica gel, 95:5 to 90:10 CH₂Cl₂/MeOH) to afford 20 mg (28%) of the $R_f$=0.63 product as a white foam. H1-NMR (CDCl₃): 7.40–7.01 ;(8H), 6.88 (1H), 6.70 (1H), 5.62 (1H), 5.06–4.73 (3H), 4.21–3.39 (7H), 3.23–2.62 (10H), 2.52 (3H), 1.93–1.20 (10H). LCMS (ESI): 645 (M+H).

Example 35

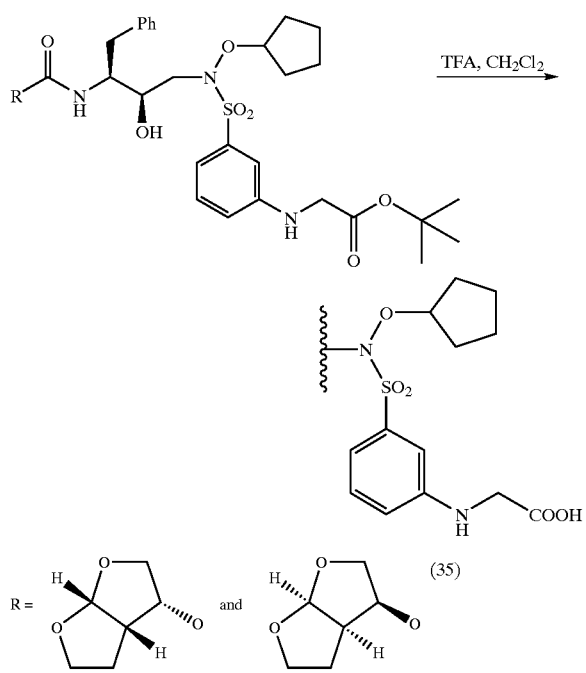

(35)

2-2-(3-[[(2R,3S)-3-([(3R,3aS,6aR)hexahydrofuro[2,3-b]furan-3-yloxy)carbonylamino)-hydroxy-4-phenylbutyl](cyclopentyloxy)amino]sulfonylanilino)acetic acid and 2-2-(3-[[(2R,3S)-3-([(3S,3aR,6aS)hexahydrofuro[2,3-b]furan-3-yloxy]carbonylamino)-hydroxy-4-phenylbutyl](cyclopentyloxy)amino]sulfonylanilino)acetic acid.

A solution of 0.218 g (0.316 mmol) of a 1:1 mixture of tert-butyl 2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy)amino]sulfonylanilino)acetate and tert-butyl 2-(3-[[(2R,3S)-3-([(3S,3aR,6aS)hexahydrofuro[2,3-b]furan-3-yloxy]carbonylamino)-2-hydroxy-4-phenylbutyl](cyclopentyloxy)amino]sulfonylanilino)acetate (see example 30) in 5 mL of CH$_2$Cl$_2$ was treated with 6 mL of trifluoroacetic acid. After stirring at RT for 2 hours tlc (silica gel, hexane/EtOAc) indicated complete loss of starting material and the formation of a new more polar product. The solution was concentrated in vacuo. The residue was dissolved in a minimum volume of CH$_2$Cl$_2$ and the solution added dropwise to rapidly stirred 4:1 hexane/ether. An off-white solid precipitated which was collected by filtration and dried in vacuo. yield=0.183 g (92%). H1-NMR (DMSO-d$_6$): 7.25–7.05 (7H), 6.87 (3H), 6.53 (1H), 5.46 (1H), 5.16 (1H), 4.82–4.65 (2H), 3.83–3.23 (7H), 3.08–2.60 (5H), 2.38 (1H), 1.91–1.04 (1OH). MS(ESI): 634 (M+H), 656 (M+Na).

Example 36

Step 1

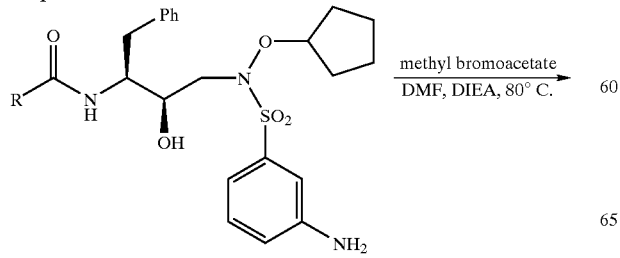

methyl bromoacetate
DMF, DIEA, 80° C.

-continued

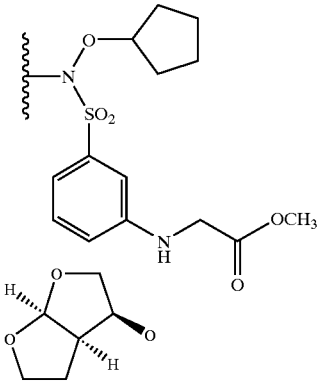

methyl 2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy)amino]sulfonylanilino)acetate and methyl 2-(3-[[(2R,3S)-3-([(3S,3aR,6aS)hexahydrofuro[2,3-b]furan-3-yloxy]carbonylamino)-2-hydroxy-4-phenylbutyl](cyclopentyloxy)amino]sulfonylanilino)acetate A solution of 0.500 g (0.869 mmol) of a 1:1 mixture of (3R,3aS,6aR) hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 0.250 mL (2.61 mmol) of methyl bromoacetate, and 0.450 mL (2.61 mmol) of N,N-diisopropylethylamine in 5 mL of anyhydrous DMF was stirred at 80° C. for 18 hours. The solution was cooled to RT and concentrated in vacuo. The residue was dissolved in ethyl acetate. The solution was washed with saturated aqueous brine (3x), dried over anhydrous MgSO$_4$, and concentrated in vacuo. The crude product was purified by flash chromatography (silica gel, 97:3 CH$_2$Cl$_2$/MeOH) to afford 0.50 g (89%) of the desired product as a light yellow foam. H1-NMR (DMSO-d$_6$): 7.38–7.08 (7H), 7.01–6.85 (3H), 6.71 (1H), 5.52 (1H), 5.21 (1H), 4.88–4.70 (2H), 3.99 (2H), 3.88–3.46 (8H), 3.13–2.64 (5H), 2.57–2.35 (IH), 2.01–1.17 (1OH). LCMS(ESI): 648 (M+H).

Step 2

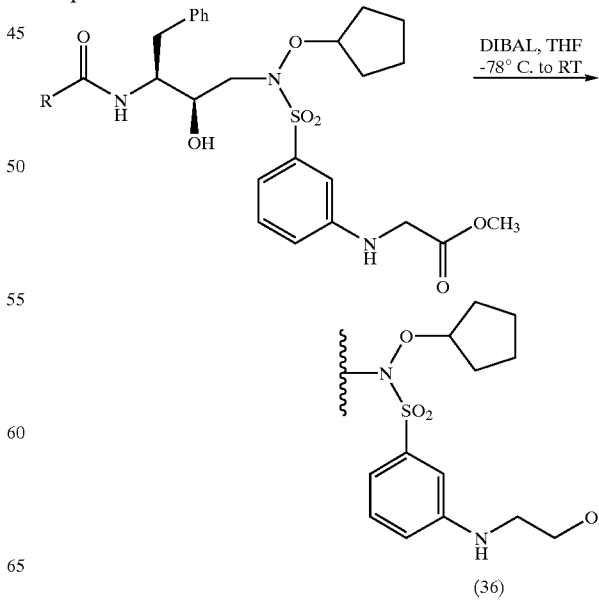

DIBAL, THF
-78° C. to RT (36)

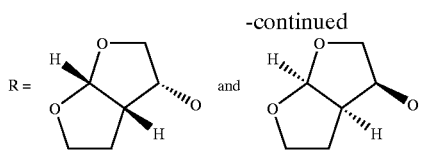

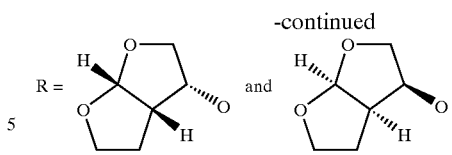

(3R,3aS, 6aR)hexahydrofuro[2,3-b]furan-3-yl N-(1S,2R)-1-benzyl-3-[(cyclopentyloxy)(3-[(2-hydroxyethyl)amino]phenylsulfonyl)amino]-2-hydroxypropylcarbamate and (3S, 3aR,6aS)hexahydrofuro[2,3-b]furan-3-yl N-(1S,2R)-1-benzyl-3-[(cyclopentyloxy)(3-[(2-hydroxyethyl)amino]phenylsulfonyl)amino]-2-hydroxypropylcarbamate. A solution of 0.100 g (0.154 mmol) of a 1:1 mixture of methyl 2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy) amino]sulfonylanilino) acetate and methyl 2-(3-[[(2R,3S)-3-([(3S,3aR,6aS)hexahydrofuro[2,3-b]furan-3-yloxy]carbonyl amino)-2-hydroxy-4-phenylbutyl](cyclopentyloxy)amino]sulfonylanilino)acetate in 10 mL of anhydrous THF at −78° C. was treated with 0.23 mL (0.34 mmol) of 1.5 M diisobutylaluminum hydride in toluene by dropwise addition. The solution was allowed to warm to RT. The reaction progress was monitored by tlc (silica gel, hexane/EtOAc). Two additional 0.30 mL aliquots of DIBAL solution were added at 1 hour intervals (cooling the reaction vessel to −78° C. each time) to induce complete loss of starting material. After 2 additional hours the reaction mixture was mixed with 25 mL of saturated potassium sodium tartrate and stirred vigorously for 30 minutes. The mixture was diluted with water and extracted with CH$_2$Cl$_2$ (3x). The combined extracts were washed with water (3x), dried over anhydrous MgSO$_4$, and concentrated in vacuo. The residue was purified by flash chromatography (silica gel, 99:1 EtOAc/MeOH) to afford 25 mg (26%) of the desired product as a white foam. H1-NMR (CDCl$_3$): 7.40–7.03 (1OH), 6.92 (1H), 5.62 (1H), 5.13–4.88 (2H), 4.81 (1H), 3.96–3.44 (8H), 3.32 (2H), 3.22–2.59 (6H), 1.90–1.20 (1OH). LCMS(ESI): 620 (M+H).

Example 37

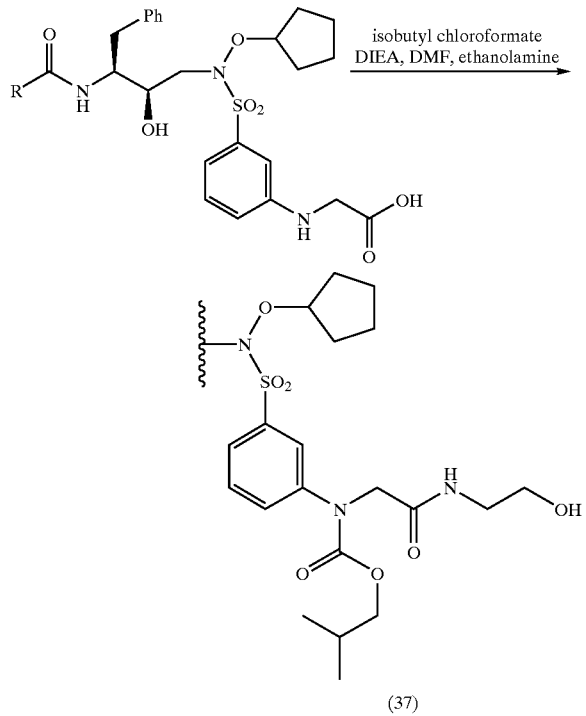

(37)

(3R,3aS,6aR)hexahydrofuro[2,3-b]furan-3-y1 N-(1S,2R)-1-benzyl-3-[(cyclopentyloxy) (3-[2-[(2-hydroxyethyl)amino]-2-oxoethyl (isobutoxycarbonyl) amino]phenylsulfonyl) amino]-2-hydroxypropylcarbamate and (3S, 3aR, 6aS) hexahydrofuro [2,3-b]furan-3-yl N-(1S,2R)-1-benzyl-3-[(cyclopentyloxy) (3-[2-[(2-hydroxyethyl)amino]-2-oxoethyl(isobutoxycarbonyl)amino]phenylsulfonyl)amino]-2-hydroxypropylcarbamate.

A solution of 60.0 mg (0.0947 mmol) of a 1:1 mixture of 2-2-(3-[[(2R,3S)-3-([(3R,3aS,6aR)hexahydrofuro[2,3-b]furan-3-yloxy]carbonylamino)-hydroxy-4-phenylbutyl](cyclopentyloxy) amino]sulfonylanilino)acetic acid and 2-2-(3-[[(2R,3S)-3-([(3S,3aR,6aS)hexahydrofuro[2,3-b]furan-3-yloxy]carbonyl amino)-hydroxy-4-phenylbutyl](cyclopentyloxy)amino] sulfonylanilino)acetic acid (see example 35) in 3 mL of anhydrous DMF at 0° C. was treated with 0.033 mL (0.19 mmol) of N,N-diisopropylethylamine followed by 0.025 mL (0.19 mmol) of isobutyl chloroformate. After stirring at 0° C. for 15 minutes the reaction was treated with 3 drops (excess) of ethanolamine. After warming to RT and stirring for 18 hours the solution was concentrated to dryness. The residue was purified by flash chromatography (silica gel, 93:7 CH$_2$Cl$_2$/MeOH) to afford 66 mg (90%) of the desired compound as a white foam. H1-NMR (DMSO-d$_6$): 8.05 (1H), 7.80 (1H), 7.69 (1H), 7.63–7.50 (2H), 7.24–7.02 (5H), 6.96 (1H), 5.47 (1H), 5.21 (1H), 4.80–4.67 (2H), 4.63 (1H), 4.56 (1H), 4.20 (2H), 3.82–3.20 (8H), 3.10 (2H), 3.05–2.35 (8H), 1.88–1.10 (11H), 0.90–0.72 (6H). LCMS (ESI): 777 (M+H).

Example 38

Step 1

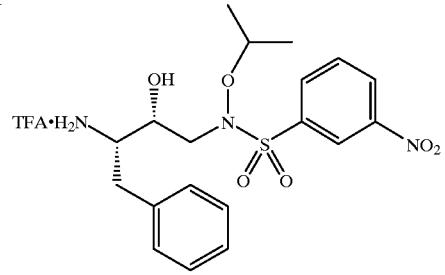

(1S,2R)-1-benzyl-3-(isopropyloxy)[(3-nitrophenyl)sulfonyl]amino-2-hydroxypropylamine •trifluoroacetic salt. tert-Butyl-N-((1S,2R)-1-benzyl-3-(isopropyloxy)[(3-nitrophenyl) sulfonyl]amino-2-hydroxypropyl)carbamate (1.37 g, 2.62 mmol) was dissolved in CH2Cl2 (50 ml). Trifluoroacetic acid (10 mL) was added at 0° C. with stirring and the reaction was stirred 2h at room temperature. The solvent was removed by evaporation and was keeped under vacuum. The product was used without purification.

Step 2

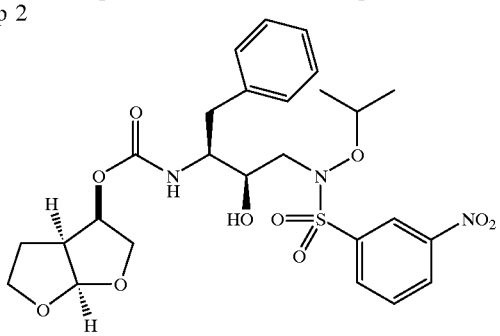

(3R,3aS,6aR)Hexahydrofuro[2,3b]furan-3-yl-N-(1S,2R)-1-benzyl-3-[(isopropyloxy)[(3-nitrophenyl)sulfonyl]amino-2-hydroxypropylcarbamate. (iS,2R)-1-benzyl-3-(isopropyloxy)[(3-nitrophenyl)sulfonyl]amino-2-hydroxypropylamine-trifluoroacetlc salt (305 mg, 0.57 mmol) was combined with (3R,3aS,6aR)Hexahydrofuro[2,3b]furan-3-yl (4-nitrophenyl) carbonate (184 mg, 0.62 mmol) in anhydrous CH3CN (8 ml) under a N2 atmosphere. Triethylamine (400 µL, 2.8 mmol) was added and the reaction was stirred at 50° C. for 16 hours. Reaction mixture was diluted in EtOAc and washed with water and brine. The organic phase was dried with MgSO4 and solvent was removed in vacuo. Purification by flash chromatography (30% EtOAc/Hex). Recovered 204 mg (62%) of the product as a white foam. HPLC showed the material to be 98% pure; Ret. time=10.10 min. $^1$H NMR (CDCl$_3$): 8.60 (s, 1H), 8.46 (m, 1H), 8.02 (m, 1H), 7.72 (m, 1H), 7.10–7.23 (m, 5H), 5.58 (m, 1H), 4.97 (m, 1H), 4.80 (m, 1H), 4.94 (m, 1H), 4.50–4.55 (m, 1H), 3.77–3.96 (m, 4H), 3.59–3.64 (m, 2H), 2.70–2.97 (m, 5H), 1.60 (m, 1H), 1.45 (m, 1H), 1.21 (m, 6H). MS (ES+): Obs M+H@580.1 amu.
Step 3

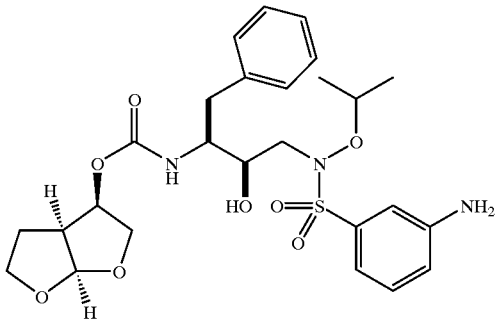

(3R,3aS,6aR)Hexahydrofuro[2,3b]furan-3-yl-N-(1S,2R)-1-benzyl-3-[(isopropyloxy)[(3-aminophenyl)sulfonyl]amino-2-hydroxypropylcarbamate.
(3R,3aS,6aR)Hexahydrofuro[2,3b]furan-3-yl-N-(1S,2R)-1-benzyl-3-[(isopropyloxy)[(3-nitrophenyl)sulfonyl]amino-2-hydroxypropylcarbamate (100 mg, 0.17 mmol) was added in 10 mL of NH3 (2N) in MeOH. To this solution was added 100 mg of 10% Pd/C. The hydrogenetion was performed under 30 psi of hydrogen over 30 minutes. The catalyst was removed by filtration throught a pad of celite. The solvant was removed in vacuo. Recovered 91 mg (96%) of the product as a white foam. HPLC showed the material to be 98% pure; Ret. time=9.12 min. $^1$H NMR (CDCl$_3$): 7.09–7.24 (m, 9H), 7.00 (s, 1H), 6.84 (m, 1H), 5.58 (d, 1H), 4.97 (m, 1H), 4.78 (m, 1H), 4.44–4.48 (m, 1H), 3.77–3.91 (m, 5H), 3.64 (m, 2H), 2.71–3.10 (m, 6H), 1.44–1.62 (2x m, 2H), 1.17 (d, 6H). MS (ES+): Obs M+H@550.2 amu.

Example 39

(39)

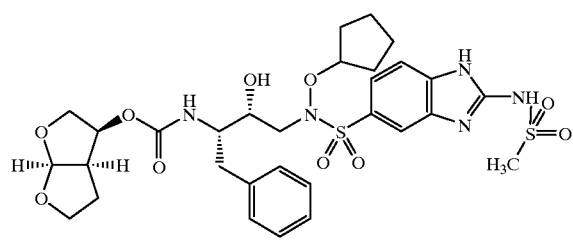

(3S,3aR,6aS)Hexahydrofuro[2,3-b]furan-3-yl-N-((1S,2R)-1-benzyl-3-(cyclopentyloxy) (2-[(methylsulfonyl)amino] benzimidazol-5-ylsulfonyl)amino-2-hydroxypropyl) carbamate. (3S,3aR,6aS) Hexahydrofuro[2,3-b]furan-3-yl-N-((1S,2R)-1-benzyl-3-(cyclopentyloxy)amino-2-hydroxypropyl)carbamate (0.050 g, 0.1 mmol) was combined with 2-[(methylsulfonyl)amino]benzimidazol-5-ylsulfonyl chloride (0.055 g, 0.2 mmol) in anhydrous DMF (1 ml) under a N2 atmosphere. The resulting solution was chilled to 0° C. and diisopropylethylethyl amine (0.062 ml, 0.4 mmol) was added. The reaction was allowed to warm to room temperature and stirred for 24 hours. Reaction mixture was diluted in EtOAc and washed with sat. NaHCO3, 0.5N KHSO4 and brine. Organic phase was dried with MgSO4 and solvent was removed in vacuo. Purification by preparative TLC (5% MeOH/EtOAc). Recovered 0.051 g (62%) of the product as a white foam. R$_f$=0.42 (5% MeOH/EtOAc). $^1$H NMR (CDCl$_3$) 8.09 (1H,s), 7.76 (1H,d), 7.39 (1H,d), 7.32–7.12 (5H,m), 6.54–6.40 (2H,m), 5.67 (1H,d), 5.10–4.92 (2H,m), 4.85 (1H,m), 4.00–3.83 (3H,m), 3.82–3.70 (2H,m), 3.62–3.51 (1H,m), 3.38 (1H,m), 3.31 (3H,s), 3.10 (1H,m), 3.04–2.80 (4H,m), 1.92–1.70 (6H,m), 1.69–1.44 (4H,m). LRMS (M+H)$^+$694.1.

Example 40

(40)

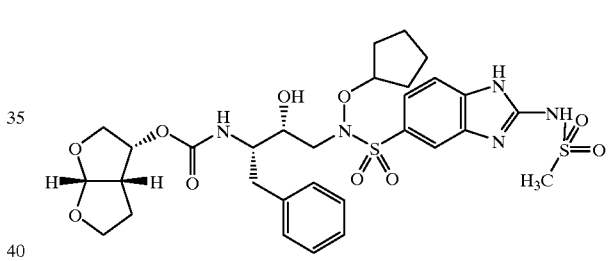

(3R,3aS,6aR)Hexahydrofuro[2,3-b]furan-3-yl-N-((1S,2R)-1-benzyl-3-(cyclopentyloxy)(2-[(methylsulfonyl)amino] benzimidazol-5-ylsulfonyl)amino-2-hydroxypropyl) carbamate. (3R,3aS,6aR)Hexahydrofuro[2,3-b]furan-3-yl-N-((1S,2R)-1-benzyl-3-(cyclopentyloxy)amino-2-hydroxypropyl)carbamate (Step 2, Example 54), (0.065 g, 0.2 mmol) was combined with 2-[(methylsulfonyl)amino] benzimidazol-5-ylsulfonyl chloride (0.071 g, 0.2 mmol) in anhydrous DMF (2 ml) under a N2 atmosphere. The resulting solution was chilled to 0° C. and diisopropylethylethyl amine (0.080 ml, 0.5 mmol) was added. The reaction was allowed to warm to room temperature and stirred for 24 hours. Reaction mixture was diluted in EtOAc and washed with sat. NaHCO3, 0.5N KHSO4 and brine. Organic phase was dried with MgSO4 and solvent was removed in vacuo. Purification by preparative TLC (5% MeOH/EtOAc). Recovered 0.051 g (62%) of the product as a white foam. Rf=0.53 (5% MeOH/EtOAc). $^1$H NMR (CDCl$_3$) 8.09 (1H, s), 7.69 (1H,d), 7.43 (1H,d), 7.32–7.08 (5H,m), 6.31–6.18 (2H,m), 5.71–5.59 (2H,m), 5.10–4.92 (2H,m), 4.85 (1H,m), 4.00–3.83 (3H,m), 3.82–3.70 (2H,m), 3.62–3.51 (1H,m), 3.38 (1H,m), 3.31 (3H,s), 3.10 (1H,m), 3.04–2.80 (4H,m), 1.92–1.70 (6H,m), 1.69–1.44 (4H,m). LRMS (M+H)$^+$694.0.

Example 41

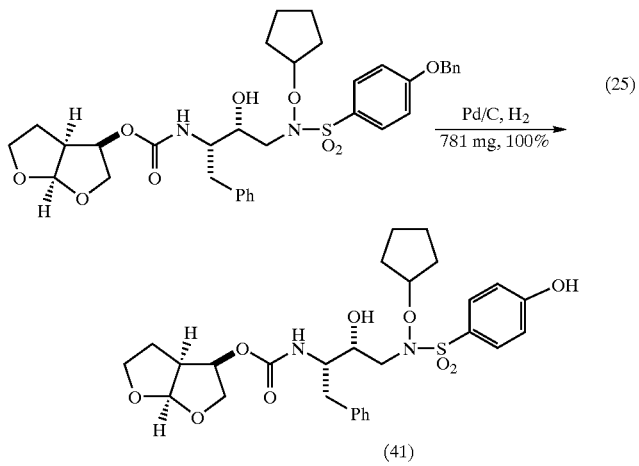

(3R,3aS,6aR)hexahydrofuro[2,3-b]furan-3-yl N-((1S,2R)-1-benzyl-3-(cyclopentyloxy)[(4-hydroxyphenyl)sulfonyl]amino-2-hydroxypropyl)carbamate. (3R,3aS,6aR) hexahydrofuro[2,3-b]furan-3-ylN-(1S,2R)-1-benzyl-3-[[4-(benzyloxy)phenyl]sulfonyl(cyclopentyloxy) amino]-2-hydroxypropylcarbamate (Example 95), (1.4 mmol, 903 mg) was stirred vigorously with 10% palladium on carbon (200 mg), glacial acetic acid (2.8 mmol, 0.156 mL) and ethyl acetate (1 mL) under hydrogen for 20 hours at room temperature. The reaction was filtered and the filtrate concentrated to produce 781 mg (>99%) of a white solid. $R_f$=0.2 (1:1 hexanes/ethyl acetate); Hl-NMR (CDCl$_3$): δ7.66 (2H, d), 7.30–7.12 (6H,m), 6.93 (2H,d), 5.78 (1H,bs), 5.66 (1H, s), 4.98 (1H,m), 4.81–4.70 (2 H,m), 3.98–3.80 (4H,m), 3.80–3.54 (3H,m), 3.15–2.53 (6H,m), 1.85–1.65 (4H,m), 1.65–1.35 (4H,m); M.S. (ESI) M+H=577.

Example 42

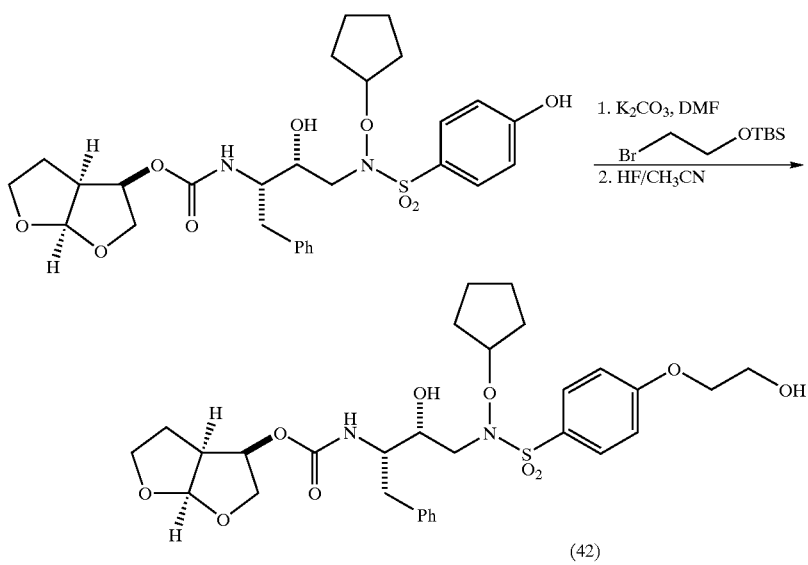

(3R,3aS,6aR)hexahydrofuro[2,3-b]furan-3-yl N-[(1S,2R)-1-benzyl-3-((cyclopentyloxy)[4-(2-hydroxyethoxy)phenyl]sulfonylamino)-2-hydroxypropyl]carbamate. (3R,3aS,6aR) hexahydrofuro[2,3-b]furan-3-yl N-((1S,2R)-1-benzyl-3-(cyclopentyloxy)[(4-hydroxyphenyl)sulfonyllamino-2-hydroxypropyl)carbamate (Example 41), (0.13 mmol, 75 mg), (2-bromoethoxy)(tert-butyl)dimethylsilane (0.16 mmol, 37 mg), potassium carbonate (0.40 mmol, 54 mg), and anhydrous DMF (0.5 mL) were stirred at room temperature for 20 hours under nitrogen. The reaction was warmed to 50° C. for 2 additional hours. The reaction was concentrated under vacuum, dissolved in ethyl acetate, washed with distilled water and brine, and dried over magnesium sulfate. The crude material was concentrated under vacuum and the resulting clear oil was purified by silica gel flash chromatography (2:1 hexanes/ethyl acetate) to yield 60 mg (63%) of a clear oil. The resulting silyl ether was then stirred in a 3:1 (CH$_3$CN/HF(49%)) solution for 1 hour and quenched with a saturated aqueous solution of sodium bicarbonate. The reaction was concentrated under vacuum, dissolved in ethyl acetate, washed with distilled water and brine, and dried over magnesium sulfate. The desired alcohol was crystallized from an ether/hexanes solution yielding 20 mg (39%) of white powdery crystals. $R_f$=0.1 (1:1 hexanes/ethyl acetate); H1-NMR (CDCl$_3$): δ7.72 (2H, d), 7.30–7.12 (6H,m), 7.01 (2H,d), 5.64 (1H,s), 4.98 (1H,m), 4.85–4.70 (2H,m), 4.18–4.11 (2H,m), 4.04–3.76 (7H,m), 3.73–3.55 (2H,m), 3.10 (1H,bs), 3.04–2.55 (5H,m), 2.10 (1H, m), 1.86–1.68 (4H,m), 1.68–1.44 (4H,m); MS (ESI): M+H=621.

Example 43

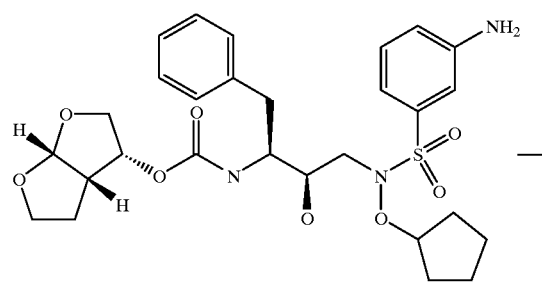

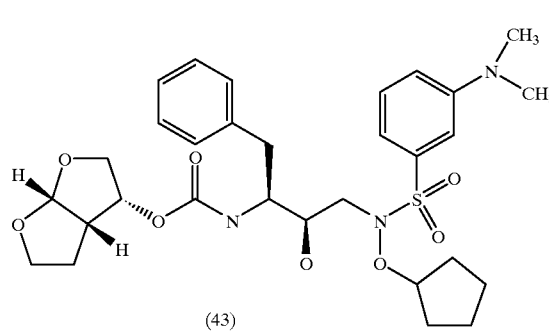

(43)

(3R,3aS,6aR)hexahydrofuro[2,3-b]furan-3-yl N-(1S,2R)-3-[[(3-N,N-dimethylaminophenyl)sulfonyl](cyclopentyloxy)amino]-1-benzyl-2-hydroxypropylcarbamate. A mixture of 58mg (0.1 mMol) of (3R,3aS,6aR)hexahydrofuro[2,3-b]furan-3-yl N-(S,2R)-3-[[(3-aminophenyl)sulfonyl](cyclopentyloxy)amino]-1-benzyl-2-hydroxypropylcarbamate (Example 77) and 0.25 mL of 37% formaldehyde in 25 mL ethanol was treated with ca.10 mg of 5% palladium on carbon and hydrogenated at 5OPSI for 20 minutes. The mixture was filtered, evaporated and purified on a 2 inch plug of silica gel (5% methanol-dichloromethane) to give the desired product as a white foam (30mg). 1H-NMR (CDCl$_3$): 1.5–1.9 (13H), 2.8 (4H), 2.97 (6H), 3.18 (1H), 3.64 (2H), 3.9 (4H), 4.75–4.95 (4H), 4.99 (1H), 5.62 (1H), 6.95 (1H), 7.0–7.4 (8H). MS: (LC-MS): 604 (MH+).

Example 44

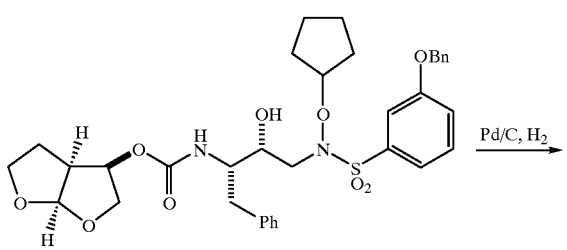

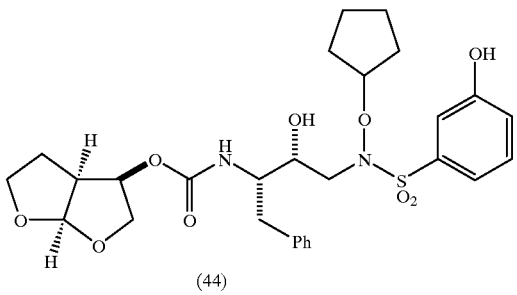

(44)

(3R,3aS,6aR)hexahydrofuro[2,3-b]furan-3-yl N-((1S,2R)-1-benzyl-3-(cyclopentyloxy)[(3-hydroxyphenyl)sulfonyl]amino-2-hydroxypropyl)carbamate. This compound was formed (from Example 96) under the same conditions used for (3R,3aS,6aR)hexahydrofuro[2,3-b]furan-3-yl N-((1S,2R)-1-benzyl-3-(cyclopentyloxy)[(4-hydroxyphenyl)sulfonyl]amino-2-hydroxypropyl)carbamate (Example 41). R$_f$=0.2 (1:1 hexanes/ethyl acetate); H1-NMR (CDCl$_3$): δ7.43–7.35 (2H,m), 7.30–7.10 (8H,m), 6.63 (1H,bs), 5.70 (1H,s), 5.11–4.95 (2H,m), 4.79 (1H,m), 4.03–3.64 (7H,m), 3.16–2.79 (6H,m), 1.88–1.69 (4H,m), 1.69–1.43 (4H,m); MS (ESI): M+Na=599.

Example 45

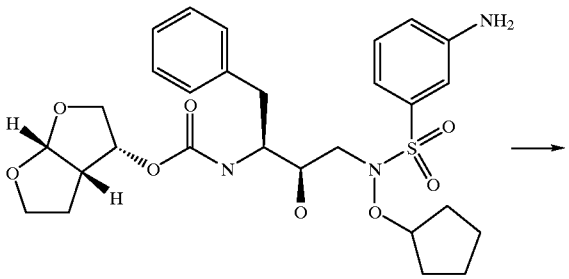

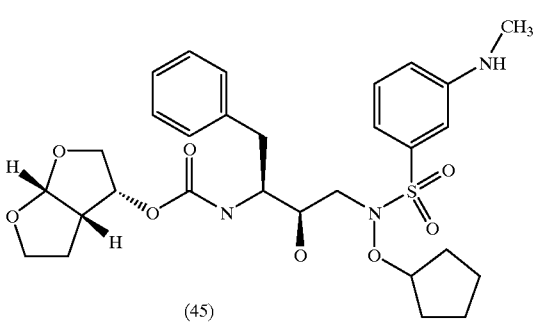

(45)

(3R,3aS,6aR)hexahydrofuro[2,3-blfuran-3-yl N-(1S,2R)-3-[((3-N-methylaminophenyl)sulfonyl](cyclopentyloxy)amino]-1-benzyl-2-hydroxypropylcarbamate. A mixture of 40mg (0.069 mMol) of (3R,3aS,6aR)hexahydrofuro[2,3-b]furan-3-yl N-(1S,2R)-3-[[(3-aminophenyl)sulfonyl](cyclopentyloxy)amino]-1-benzyl-2-hydroxypropylcarbamate (Example Example 77), 0.0048 mL (0.077 mMol) of iodomethane and 0.014 mL (0.1 mMol) of triethylamine in 1 mL of dimethyl formamide was heated to B00C for 12h.

The volatiles were removed in vacuo and the residue was purified by semi-prep C-18 HPLC to give the desired mono-amine as a white solid (8 mg). 1H-NMR (CDCl$_3$) :1.5–1.9 (13H), 2.75 (1H), 2.8–3.0 (3H), 2.99 (3H), 3.15 (1H), 3.7 (1H), 3.9 (5H), 4.8 (1H), 5.0 (1H), 5.5 (1H), 7.0–7.4 (7H), 7.5 (2H). MS (LC-MS): 590 (MH+).

Alternatively this material can also be obtained according to the following method: In a dried flask was introduced 1 eq. of (3R,3aS,6aR) Hexahydrofuro[2,3b]furan-3-yl-N-(1S, 2R)-1-benzyl-3-[(cyclopentyloxy)[(3-(N-(methyl-tert-Butoxycarbonyl))phenyl) sulfonyl]amino-2-hydroxy propylcarbamate (21.5 mg, 0.031 mmol) in 2 mL dichloromethane. To this solution was added 1 mL of trifluoroacetic acid. The reaction was continued at room temperature for 45 min. The solvent was evaporated in vacuo to an oil. The crude material was purified on flash grade silica gel eluting with 50% ethyl acetate in hexane. Fractions containing the product were combined, evaporated in vacuo and dried under high vacuum to provide (3R,3aS, 6aR)Hexahydrofuro[2,3b]furan-3-yl-N-(1S,2R)-1-benzyl-3-[(cyclopentyloxy)[(3-N-methylphenyl) sulfonyl]amino-2-hydroxypropyl carbamate (17.1 mg, 93%). HPLC showed the material to be 98% pure; Ret. time=11.0 min. H$^1$-NMR (CDCl$_3$): 7.12–7.35 (m, 9H), 5.60 (m, 1H), 4.75–5.10 (m, 3H), 3.70–3.91 (m, 6H), 3.54 (m, 2H), 3.29 (m, 1H), 2.84–3.09 (m, 7H), 1.18–1.98 (m, 9H) and LCMS (ES+), M+H=590.2.

Example 46

Step 1

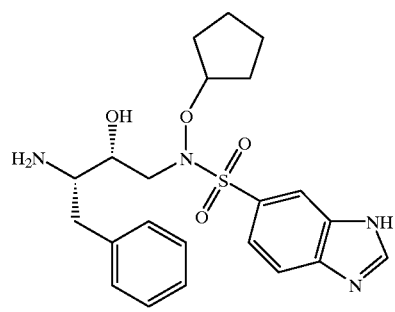

N-[(2R,3S)-3-amino-2-hydroxy-4-phenylbutyl]-N-(cyclopentyloxy)-1H-benzimidazole-6-sulfonamide. A mixture of tert-butyl N-(1S, 2R)-3-[(1H-benzimidazol-6-ylsulfonyl)(cyclopentyloxy)amino]-1-benzyl-2-hydroxypropylcarbamate (Example 82), (0.500 g, 0.919 mmol) and trifluoroacetic acid (5mL) was stirred under an Argon atmosphere at ambient temperature for approximately one hour. The reaction was evaporated in vacuo and the residue was partitioned between 1N aqueous sodium hydroxide and dichloromethane. After separating the layers, the aqueous phase was diluted with saturated aqueous brine and extracted three times with dichloromethane followed by two extractions with ethyl acetate. The organic layers were combined, dried over anhydrous sodium sulfate, filtered, evaporated in vacuo and dried under high vacuum to provide N-[(2R,3S)-3-amino-2-hydroxy-4-phenylbutyl]-N-(cyclopentyloxy)-1H-benzimidazole-6-sulfonamide (0.423 g, 104%). H1-NMR (chloroform-D3): 1.60 (m, 4H), 1.84 (m, 4H), 2.52 (m, 4H), 2.90 (m, 1H), 3.03 (m, 1H), 3.27(m, 2H), 3.86 (m, 1H), 4.90 (m, 1H), 7.25(m, 6H), 7.81(m, 2H), 8027(m, 2H). MS(ESI): 445(M+H).

Step 2

(46)

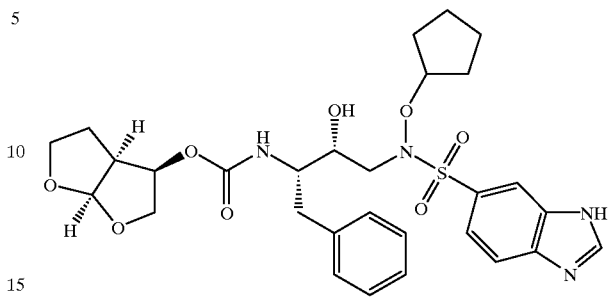

(3R,3aS,6aR)hexahydrofuro[2,3-b]furan-3-yl N-(1S,2R)-3-[(1H-benzimidazol-6-ylsulfonyl)(cyclopentyloxy)amino]-1-benzyl-2-hydroxypropylcarbamate. A mixture of (2R,3aS, 6aR)hexahydrofuro[2,3-b]furan-2-yl 4-nitrophenyl carbonate (38.3 mg, 0.124 mmol) and imidazole (15 mg, 0.222 mmol) were heated under Argon in approximately 2 mL of acetonitrile for 1.5 hrs. To this mixture was then added (N-[(2R,3S)-3-amino-2-hydroxy-4-phenylbutyl]-N-(cyclopentyloxy)-1H-benzimidazole-6-sulfonamide (50 mg, 0.113 mmol) and N,N-diisopropylethylamine (58.9 AL, 0.338 mol). After heating at reflux for an additional 6 hrs., the reaction was cooled and evaporated in vacuo. The residue was dissolved in ethyl acetate, washed three times with 5% aqueous potassium carbonate, washed with brine, dried over anhydrous sodium sulfated, filtered and evaporated in vacuo. The residue was purified on a preparative TLC plate (20×20 cm, 1000 pM) eluting with 95:5 methylene chloride:methanol. The plate was allowed to dry through evaporation and then eluted again with 93:7 chloroform::methanol. The product band was removed, eluted with 4:1 methylene chloride:methanol, filtered, and evaporated in vacuo. The residue was lyophilized from acetonitrile : water to provide (3R,3aS,6aR)hexahydrofuro[2,3-b]furan-3-yl N-(1S, 2R)-3-[(1H-benzimidazol-6-ylsulfonyl)(cyclopentyloxy)amino]-1-benzyl-2-hydroxypropylcarbamate (25 mg, 37%). HL-NMR (dimethylsulfoxide-D6): 1.05 (m, 1H), 1.27 (m, 1H), 1.58 (m, BH), 2.33(m, 1H), 2.64 (m, 2H), 2.96 (m, 2H), 3.45 (m, 4H), 3.62 (m, 2H), 4.72 (m, 2H), 5.16 (m, 1H), 5.42 (d, 1H), 7.10 (m, 6H), 7.51 (m, 1H), 7.72 (m, 1H), 7.93 (m, 1H); 8.44 (s, 1H), 13.0 (b, 1H). MS(ESI): 601(M+H).

Example 47

(47)

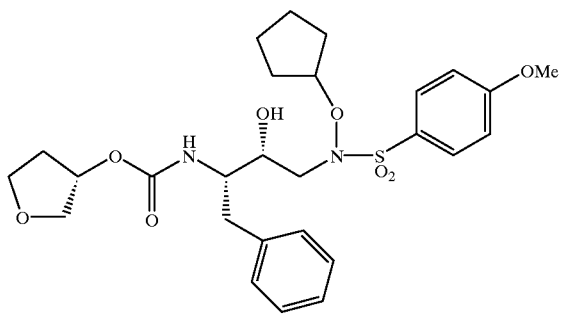

3S)tetrahydro-3-furanyl N-((1S,2R)-1-benzyl-3-(cyclopentyloxy)[(4-methoxyphenyl)sulfonyl]amino-2- hydroxypropyl)carbamate. A mixture of 2,5-dioxo-1-pyrrolidinyl [(3S)tetrahydro-3-furanyl]carbonate (13.8 mg, 0.0602 mmol, W094/05639), $N^1$-[(2R,3S)-3-amino-2-hydroxy-4-phenylbutyl]-$N^1$-(cyclopentyloxy)-4-methoxy-1-benzenesulfonamide x trifluoracetic acid (Step 1, Example 48), (30 mg, 0.0547 mmol), and N,N-diisopropylethylamine (23.8 AL, 0.137 mmol) were combined at ambient temperature under an Argon atmosphere. After stirring for 18 hours, the reaction mixture was evaporated in vacuo to a residue and purified on a preparative silica gel TLC plate (20x20 cm, 500 WM) eluting with 96:4 chloroform : methanol. The product band was removed, eluted with 3:1 methylene chloride methanol, filtered, evaporated in vacuo and dried under high vacuum to provide (3S)tetrahydro-3-furanyl N-((1S,2R) -1-benzyl-3-(cyclopentyloxy)[(4-methoxyphenyl)sulfonyl]amino-2-hydroxypropyl) carbamate (26 mg, 87%) as a foam. H1-NMR (chloroform-D3): 1.73 (m, 9H), 2.14 (m, 1H), 2.92 (m, 5H), 3.77 (m, 6H), 3.87 (s, 3H), 4.79 (bm, 2H), 5.10 (bs, 1H), 6.97 (d, 2H), 7.23 (m, 5H), 7.70 (d, 2H). MS(ESI): 571 (M+Na).

Example 48

Step 1

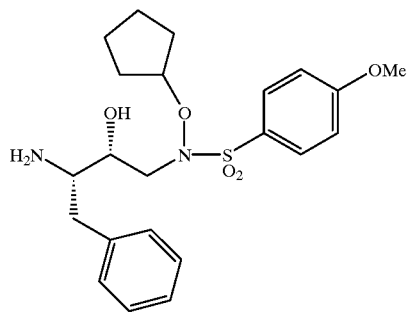

$N^1$-[(2R,3S)-3-amino-2-hydroxy-4-phenylbutyl]-$N^1$-(cyclopentyloxy)-4-methoxy-1-benzenesulfonamide. trifluoracetic acid. Tert-butyl N-((1S, 2R)-1-benzyl-3-(cyclopentyloxy)[(4-methoxyphenyl) sulfonyl]amino-2-hydroxypropyl)carbamate (0.693 g, 1.29 mmol) was combined with trifluoroacetic acid (5 mL) under an Argon atmosphere at ambient temperature. After stirring for 20 minutes, the reaction mixture was evaporated in vacuo. The residue was dissolved several times in dichloromethane and evaporated to remove excess trifluoroacetic acid. The crude product was triturated with hexane and then evaporated and dried under high vacuum to provide the trifluoracetic acid salt of N-[(2R,3S)-3-amino-2-hydroxy-4-phenylbutyl]-$N^1$-(cyclopentyloxy)-4-methoxy-1-benzenesulfonamide (0.769g, 108%). H1-NMR (chloroform-D3 +NaOD): 1.58 (m, 4H), 1.78 (m, 4H), 2.45 (m, 1H), 2.85 (m, 1H), 2.96 (m, 1H), 3.15 (m, 1H), 3.22 (m, 1H), 3.77 (m, 1H), 3.88 (s, 3H), 4.78 (m, 1H), 7.00 (m, 2H), 7.23 (m, 5H), 7.78 (m, 2H). MS(ESI): 435 (MH+).

Step 2

(48)

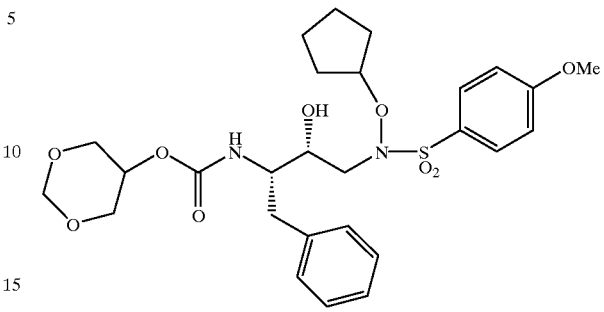

1,3-dioxan-5-yl N-((1S,2R)-1-benzyl-3-(cyclopentyloxy)[(4-methoxyphenyl)sulfonyl]amino-2-hydroxypropyl) carbamate. A mixture of 1,3-dioxan-5-yl (4-nitrophenyl) carbonate [16.2 mg, 0.0602 mmol, Application: WO 96-US5473), $N^1$-(2R,3S)-3-amino-2-hydroxy-4-phenylbutyl]-$N^1$-(cyclopentyloxy)-4-methoxy-1-benzenesulfonamide-trifluoracetic acid (30 mg, 0.0547 mmol], and N,N-diisopropylethylamine (23.8 µL, 0.137 mmol) were combined in approximately 1.5 mL acetonitrile at ambient temperature under an Argon atmosphere. After stirring for 18 hours, the reaction mixture was evaporated if vacuo to a residue and purified on a preparative silica gel TLC plate (20x20 cm, 500 pM) eluting with 96:4 chloroform : methanol. The product band was removed, eluted with 3:1 methylene chloride : methanol, filtered, and evaporated in vacuo. The residue was dissolved in diethylether, evaporated in vacuo and dried under high vacuum to provide 1,3-dioxan-5-yl N-((l5,2R)-1-benzyl-3-(cyclopentyloxy)[(4-methoxyphenyl)sulfonyl]amino-2-hydroxypropyl) carbamate (20.6 mg, 67%) as a foam. H1-NMR (chloroform-D3): 1.66 (m, 8H), 2.94 (m, 5H), 3.87 (mn, 8H), 4.48 (bs, 1H), 4.76 (m, 2H), 4.94 (m, 2H), 6.97 (m, 2H), 7.24 (m, 5H), 7.69 (m, 2H). MS(ESI): 587 (M+Na).

Example 49

(49)

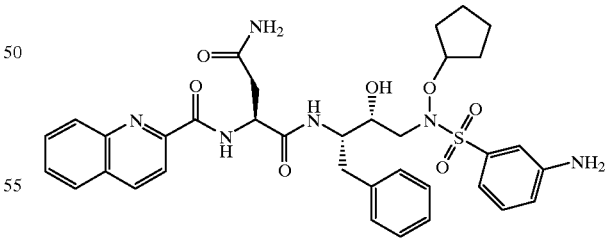

(2S)-$N^1$-(1S,2R)-3-[[(3-aminophenyl)sulfonyl](cyclopentyloxy)amino]-1-benzyl-2-hydroxypropyl-2-[(2-quinolinyl carbonyl)amino]butanediamide. A mixture of 3-amino-$N^1$-[(2R,3S)-3-amino-2-hydroxy-4-phenylbutyl]-$N^1$-(cyclopentyloxy)-1-benzenesulfonamide (Step 1, Example 27), (60 mg, 0.143), 1-(3-dimethylaminopropyl)-3-ethylcarbodiimide hydrochloride (29 mg, 0.15 mmol), N-hydroxybenzotriazole (20 mg, 5 mmol), and (2S)-4- amino-4-oxo-2-[(2-quinolinylcarbonyl, amino]butanoic acid hydrochloride (49 mg, 0.15 mmol, Eur. Pat. Appl. EP 432694) was combined under an Argon atmosphere at ambient temperature in anhydrous dimethylformamide (2 mL). After addition of N,N- diisopropylethylamine (76 AL, 0.437 mmol), the mixture was stirred for 16 hours. The reaction solvent was removed in vacuo and the residue was dissolved in ethyl acetate. The solution was transferred to a separatory funnel and washed twice with 1N sodium hydrogen sulfate. The combined aqueous layers were extracted with ethyl acetate. The combined organic layers were washed with 5% aqueous potassium carbonate and brine, dried over anhydrous sodium sulfate, filtered and evaporated in vacuo. The residue was purified on a preparative TLC plate (20×20 cm, 1000 μM) eluting with 95:5 methylene chloride : methanol.

The product band was removed, eluted with 3:1 methylene chloride : methanol, filtered, and evaporated in vacuo. The residue was purified again on a preparative TLC plate (20×20 cm, 500 μM) eluting with 95:5 methylene chloride : methanol.

The product band was removed, eluted with 3:1 methylene chloride: methanol, filtered, and evaporated in vacuo. The residue was lyophilized from acetonitrile : water to provide (2S)-$N^1$-(1S,2R)-3-[[(3-aminophenyl)sulfonyl] (cyclopentyloxy) amino]-1-benzyl-2-hydroxypropyl-2-[(2-quinolinylcarbonyl) amino]butanediamide (32 mg, 33%) as a white lyophile. H1-NMR (chloroform-D3): 1.57 (m, 8H), 2.57 (m, 1H), 2.82 (m, 4H), 3.09 (m, 1H), 3.35 (b, 1H), 3.73 (b, 1H), 4.18 (m, 3H), 4.74 15 (m, 1H), 4.87 (m, 1H), 5.47 (b, 1H), 5.86 (b, 1H), 7.00 (m, 10H), 7.56 (m, 1H), 7.73 (m, 1H), 7.81 (d, 1H), 8.11 (m, 2H), 8.24 (d, 1H), 9.15 (d, 1H). MS(ESI): 689(M+H).

Example 50

(50)

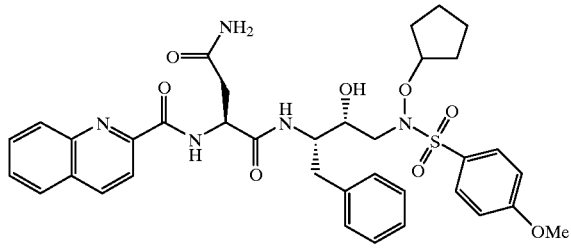

(2S)-$N^1$-((1S,2R)-1-benzyl-3-(cyclopentyloxy)[(4-methoxyphenyl)sulfonyl]amino-2-hydroxypropyl)-2-[(2-quinolinylcarbonyl)amino]butanediamide. A mixture of $N^1$-[(2R,3S)-3-amino-2-hydroxy-4-phenylbutyl]-$N^1$-(cyclopentyloxy)-4-methoxy-1-benzenesulfonamide (Step 1, Example 48), (73 mg, 0.168), 1-(3-dimethylaminopropyl)-3-ethylcarbodiimide hydrochloride (34 mg, 0.18 mmol), N-hydroxybenzotriazole (24 mg, 0.18 mmol), and (2S)-4-amino-4-oxo-2-[(2-quinolinylcarbonyl) amino]butanoic acid hydrochloride (57 mg, 0.18 mmol, Eur. Pat. Appl. EP 432694) was combined under an Argon atmosphere at ambient temperature in anhydrous dLmethylformamide (2 mL). After addition of N,N- diisopropylethylamine (896 μL, 0.513 mmol), the mixture was stirred for 16 hours. The reaction solvent was removed in vacuo and the residue was dissolved in ethyl acetate. The solution was transferred to a separatory funnel and washed twice with 1N sodium hydrogen sulfate. The combined aqueous layers were extracted with ethyl acetate. The combined organic layers were washed with 5% aqueous potassium carbonate and brine, dried over anhydrous magnesium sulfate, filtered and evaporated in vacuo. The residue was purified on a preparative TLC plate (20×20 cm, 1000 μM) eluting with 97:3 chloroform : methanol. The product band was removed, eluted with 3:1 methylene chloride methanol, filtered, and evaporated in vacuo. The residue was triturated with hexane and diethyl ether. The slurry was evaporated in vacuo to a residue and dried under high vacuum to provide (2S)-$N^1$-((1S,2R)-1-benzyl-3-(cyclopentyloxy)[(4-methoxyphenyl)sulfonyl]amino-2-hydroxypropyl)-2-[(2-quinolinylcarbonyl)amino]butanediamide (49 mg, 41%) as a white solid. HL-NMR (chloroform-D3): 1.52 (m, 4H), 1.75 (m, 4H), 2.82 (m, 5H), 3.10 (m, 1H), 3.82 (b, 1H), 3.84 (s, 3H), 3.91 m, 1H), 4.29 (m, 1H), 4.78 (m, 1H), 4.95 (m, 1H), 5.76 (b, 1H), 6.22 (b, 1H), 7.00 (m, 5H), 7.12 (d, 2H), 7.22 (d, 1H), 7.60 (m, 1H). 7.75 (m, 3H), 7.83 (d, IH), 8.14 (m, 2H), 8.25 (d, 1H), 9.15 (d, 1H). MS(ESI): 704(M+H).

Example 51

Step 1

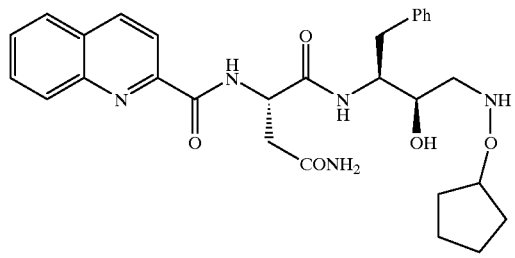

(2S)-4-Amino-4-oxo-2-[(2-quinolinylcarbonyl)amino] butanamido N-(1S,2R)-1-benzyl-3-[(cyclopentyloxy) amino]-2-hydroxypropylcarbamate. Tert-butyl N-(1S,2R)-1-benzyl-3-[(cyclopentyloxy)amino]-2-hydroxypropylcarbamate (412 mg, 1.13 mmol) was dissolved in dichloromethane (8 mL) in a 25 mL round bottomed flask under nitrogen and trifluoroacetic acid (4 mL) was added slowly. After the solution was stirred for 4 hours, TLC indicated loss of starting material. After the workup described in Step 2, Example 54, the residue was dissolved in anhydrous DMF (5 mL) followed by (2S)-4-amino-4-oxo-2-[(2-quinolinylcarbonyl) amino]butanoic acid hydrochloride (320 mg, 1.13 mmol), anhydrous diisopropylethylamine (0.4 mL, 2.26 mmol), 1-(3-dimethyl-aminopropyl)-3-ethylcarbodiimide hydrochloride (220 mg, 1.13 mmol), and 1-hydroxy-benzotriazole (150 mg, 1.13 mmol). The reaction was stirred for 18 h and concentrated in vacuo. Ethyl acetate (15 mL) and 1N HCl (15 mL) were added and the layers were separated. The aqueous layer was adjusted with solid sodium carbonate to pH 9 and then extracted with ethyl acetate (25 mL). The organic layer was dried over sodium sulfate, filtered, and concentrated in vacuo. Preparative silica gel TLC of the residue using 90:10 chloroform: methanol as eluent yielded the product as a white solid (91 mg, 0.171 mmol, 15%). MS(ES): 534 (M+1), 532 (M−1).

Step 2

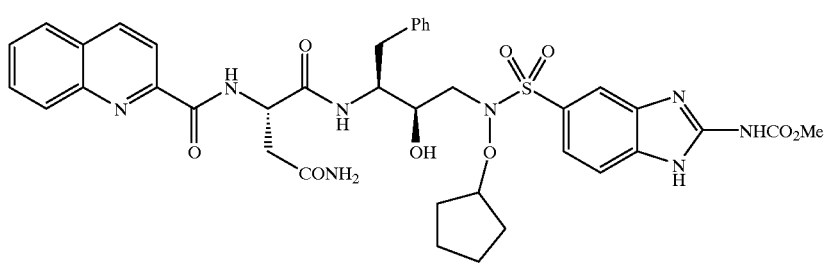

(51)

(2S)-4-Amino-4-oxo-2-[(2-quinolinylcarbonyl)amino]butanamido N-(1S,2R)-1-benzyl-3-[(cyclopentyloxy)(2-{(methoxycarbonyl)amino]-1H-benzimidazol-5-ylsulfonyl)amino]-2-hydroxypropylcarbamate. (2S)-4-Amino-4-oxo-2-[(2-quinolinylcarbonyl)amino]butanamido N-(1S,2R)-1-benzyl-3-[(cyclopentyloxy)-amino]-2-hydroxypropylcarbamate (Step 1, above), (44 mg, 0.0825 mmcl), methyl N-[5-(chlorosulfonyl)-1H-benzimidazol-2-yl]carbamate (24 mg, 0.0825 mmol), and anhydrous diisopropylethylamine (0.05 mL, 0.280 mmol) were combined in anhydrous tetrahydrofuran (3 mL) in a 25 mL round bottomed flask under nitrogen. The reaction was stirred for 24 hours and concentrated in vacuo. Ethyl acetate (30 mL) and water (10 mL) were added and the layers were separated. The organic layer was washed with brine (10 mL), dried over anhydrous sodium sulfate, filtered, and concentrated in vacuo. The residue was purified by preparative silica gel TLC using 90:10 chloroform: methanol as an eluent to provide the desired product as a white solid (11 mg, 0.014 mmol, 17%). $^1$HNMR (d$_6$-DMSO) δ: 8.86 (d, J=8.4 Hz, 1H), 8.62 (d, J=8.4 Hz, 1H), 8.22–6.94 (m, 12H), 5.19 (d, J=6.2 Hz, 1H), 4.77–4.72 (m, 2H), 4.02–1.35 (m, 17H), 3.80 (s, 3H). MS(ES): 787 (M+1), 785 (M-1).

Example 52

(52)

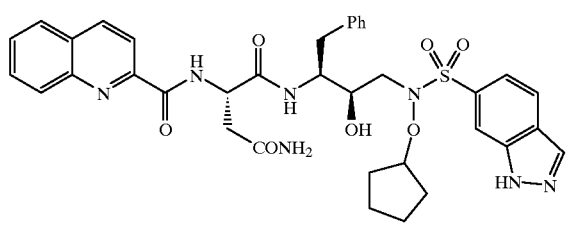

(2S)-4-Amino-4-oxo-2-[(2-quinolinylcarbonyl)amino]butanamido N-(1S,2R)-1-benzyl-3-[(cyclopentyloxy)(1H-indazol-6-ylsulfonyl)amino]-2-hydroxypropylcarbamate. (2S)-4-Amino-4-oxo-2-[(2-quinolinylcarbonyl)-amino]butanamido N-(1S,2R)-1-benzyl-3-[(cyclopentyloxy)-aminol-2-hydroxypropylcarbamate (Step 1, Example 51), (44 mg, 0.0825 mmol), 1-trityl-1H-indazole-6-sulfonyl chloride (38 mg, 0.0825 mmol), and anhydrous diisopropylethylamine (0.05 mL, 0.280 mmol) were combined in anhydrous tetrahydrofuran (3 mL) in a 25 mL round bottomed flask under nitrogen. The reaction was stirred for 24 hours and concentrated in vacuc. Ethyl acetate (30 mL) and water (10 mL) were added and the layers were separated. The organic layer was washed with brine (10 mL), dried over anhydrous sodium sulfate, filtered, and concentrated in vacuc. The compound was deprotected as described in Example 57 and purified by preparative silica gel TLC using 90:10 chloroform: methanol as an eluent to provide the desired product as a white film (9 mg, 0.013 mmol, 15%). $^1$HNMR (d$_6$-DMSO) 6:8.84 (d, J=8.5 Hz, 1H), 8.61 (d, J=8.5 Hz, 1H), 8.31–6.95 (m, 13H), 5.24 (d, J=6.6 Hz, 1H), 4.81–4.72 (m, 2H), 3.97 (bs, 1H), 3.68 (bs, 1H), 3.40–1.20 (m, 15H). MS(ES): 714 (M+1), 712 (M-1).

Example 53

Step 1

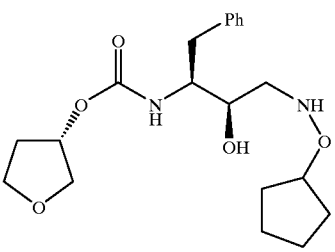

(3S)Tetrahydro-3-furanyl N-(1S,2R)-1-benzyl-3-[(cyclopentyloxy)amino]-2-hydroxypropylcarbamate. Tert-butyl N-(1S,2R)-1-benzyl-3-[(cyclopentyloxy)amino]-2-hydroxypropylcarbamate [Example 54] (1.05 g, 2.88 mmol) was dissolved in dichloromethane (12 mL) in a 50 mL round bottomed flask under nitrogen and trifluoroacetic acid (8 mL) was added slowly. After the solution was stirred for 4 hours, TLC indicated loss of starting material. After the workup described in Step 2, Example 54, the residue was dissolved in anhydrous acetonitrile (15 mL), followed by 1-([(3S)tetrahydro-3-furanyloxy]-carbonyloxy)dihydro-1H-pyrrole-2,5-dione (660 mg, 2.88 mmol), anhydrous diisopropylethylamine (0.50 mL, 2.88 mmol), and N,N-dimethylaminopyridine (105 mg, 0.86 mmol). The reaction was heated at 50° C. for 2 hours, allowed to cool, and concentrated in vacuo. After the workup described in Step 2, Example 54, the residue was purified by flush chromatography over a bed of silica gel using a gradient elution of hexane: ethyl acetate (1:2 to 1:5) to give the desired product as a white foam (440 mg, 1.16 mmol, 40%). MS(ES): 379 (M+1).

Step 2

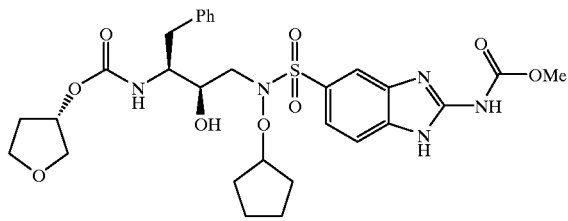
(53)

(3S)Tetrahydro-3-furanyl N-(1S,2R)-1-benzyl-3-[(cyclopentyloxy)(2-[(methoxycarbonyl)amino]-1H-benzimidazol-5-ylsulfonyl)amino]-2-hydroxypropylcarbamate.

(3S)Tetrahydro-3-furanyl N-(1S,2R)-1-benzyl-3-[(cyclopentyloxy)amino]-2-hydroxypropylcarbamate (120 mg, 0.317 mmol), methyl N-[5-(chlorosulfonyl)-1H-benzimidazol-2-yl]carbamate (100 mg, 0.345 mmol), anhydrous diisopropylethylamine (0.06 mL, 0.345 mmol), and N,N-dimethylaminopyridine (12 mg, 0.09 mmol) were combined in anhydrous tetrahydrofuran (6 mL) and anhydrous N,N-dimethylformamide (3 mL) in a 25 mL round bottomed flask under nitrogen. The reaction was stirred for 24 hours and concentrated in vacuo. After the workup described in Step 3, Example 54, the residue was purified by preparative silica gel TLC using 90:10 chloroform: methanol as an eluent to provide the desired product as a colorless glass (43 mg, 0.068 mmol, 21%). $^1$HNMR ($d_6$-DMSO) δ: 7.96–7.08 (m, 10H), 5.19 (d, J=6.7 Hz, 1H), 4.96–4.82 (m, 3H), 3.81 (s, 3H), 3.75–3.40 (m, 6H), 3.09–2.40 (m, 4H), 2.09–1.35 (m, 8H). MS(ES): 632 (M+1), 630 (M-1).

Example 54

Step 1

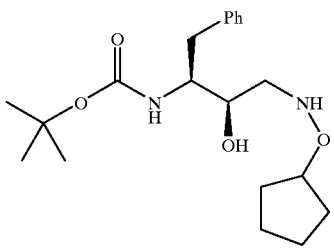

Tert-butyl N-(1S,2R)-1-benzyl-3-[(cyclopentyloxy)amino]-2-hydroxypropylcarbamate. To a solution of 2-(cyclopentyloxy)-1H-isoindole-1,3(2H)-dione (11.3 g, 48.9 mmol) in anhydrous tetrahydrofuran (60 mL) in a 200 mL round bottomed flask under nitrogen was added anhydrous hydrazine (1.6 g, 48.9 mmol) dropwise via syringe. The resulting thick white slurry was vigorously stirred for 2.5 hours and then filtered through a fritted funnel. The cake was washed with tetrahydrofuran (2×20 mL) and the combined filtrates were placed in a 300 mL round bottomed flask under nitrogen and equipped with a condenser. Tert-butyl N-(1S)-1-[(2S)oxiranyl]-2-phenylethylcarbamate (7.50 g, 28.5 mmol) was added along with anhydrous lithium triflate (6.20 g, 39.7 mmol) and the reaction was heated at reflux for 24 hours. The reaction was allowed to cool and was concentrated in vacuo to a viscous oil. Diethyl ether (150 mL) and water (50 mL) were added and the layers were separated. The ethereal layer was dried over anhydrous sodium sulfate, filtered, and concentrated in vacuo. Flush chromatography over a bed of silica gel using a gradient elution of hexane: ethyl acetate (4:1 to 2:1) gave the desired product as a white solid (8.90 g, 24.4 mmol, 86% based upon starting epoxide). $^1$HNMR (CDCl$_3$) δ: 7.32–7.19 (m, 5H), 5.90 (bs, 1H), 4.59 (d, J=8.1 Hz, 1H), 4.24–4.20 (m, 1H), 3.90–3.58 (m, 3H), 3.16–2.83 (m, 4H), 1.69–1.35 (m, 16H) MS(ES): 365 (M+1), 265 (M-BOC).

Step 2

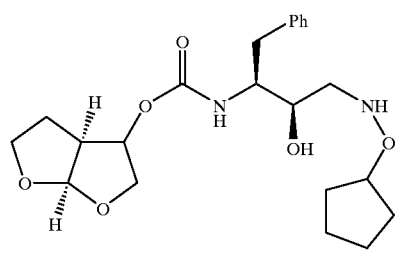

(3aS,6aR)Hexahydrofuro[2,3-b]furan-3-yl N-(1S,2R)-1-benzyl-3-[(cyclopentyloxy)amino]-2-hydroxypropylcarbamate. Tert-butyl N-(1S,2R)-1-benzyl-3-[(cyclopentyloxy)amino]-2-hydroxy-propylcarbamate (step 1 above), (1.50 g, 4.12 mmol) was dissolved in dichloromethane (15 mL) in a 50 mL round bottomed flask under nitrogen and trifluoroacetic acid (10 mL) was added slowly. After the solution was stirred for 3 hours, TLC indicated loss of starting material. The reaction was concentrated in vacuo and ethyl acetate (30 mL) was added. A 10% solution of aqueous sodium carbonate was added portionwise until the pH was adjusted to 9. The layers were separated and the organic layer was extracted with 1N HCl (20 mL). The aqueous layer was then neutralized with solid sodium carbonate until the pH was 9. The resulting white precipitate was dissolved by the addition of ethyl acetate (100 mL) and the layers were separated. The aqueous layer was extracted with ethyl acetate (25 mL) and the combined organic layers were dried over anhydrous sodium sulfate, filtered, and concentrated in vacuo to a sticky white solid. Anhydrous acetonitrile (20 mL) was added, followed by racemic (3aS, 6aR)hexahydrofuro[2,3-b]furan-3-yl 4-nitrophenyl carbonate (1.21 g, 4.12 mmol), anhydrous diisopropylethylamine (0.72 mL, 4.12 mmol), and N,N-dimethylaminopyridine (150 mg, 1.23 mmol). The reaction was heated at 50° C. for 2 hours, allowed to cool, and concentrated in vacuo. Diethyl ether (50 mL) and 5% sodium carbonate (20 mL) were added and the layers were separated. The organic layer was washed with water (20 mL), brine (15 mL), dried over anhydrous sodium sulfate, filtered, and concentrated in vacuo. Flush chromatography over a bed of silica gel using a gradient elution of hexane: ethyl acetate (1:1 to 1:4) gave the desired product as a pale yellow foam (1.41 g, 33.5 mol, 81%). $^1$HNMR ($d_6$-DMSO): δ 7.29–7.13 (m, 5H), 6.18 (bs, 1H), 5.58–5.52 (m, 1H), 4.96–4.82 (m, 2H), 4.14 (bs, 1H), 3.88–3.34 (m, 6H), 3.04–2.53 (m, 6H), 1.92–1.30 (m, 9H). MS (ES): 421 (M+1), 419 (M-1).

Step 3

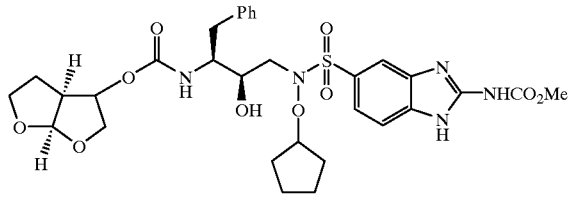
(54)

(3aS,6aR)Hexahydrofuro[2,3-b]furan-3-yl N-(1S,2R)-1-benzyl-3-[(cyclopentyloxy)(2-[(methoxycarbonyl)amino]-1H-benzimidazol-5-ylsulfonyl)amino]-2-hydroxypropylcarbamate. (3aS,6aR)Hexahydrofuro[2,3-b]furan-3-yl N-(1S,2R)-1-benzyl-3-[(cyclopentyloxy)amino]-2-hydroxypropylcarbamate (100 mg, 0.238 mmol), methyl N-[5-(chlorosulfonyl)-1H-benzimidazol-2-yl]carbamate (70 mg, 0.238 mmol), anhydrous diisopropylethylamine (0.04 mL, 0.238 mmol), and N,N-dimethylamino-pyridine (9 mg, 0.07 mmol) were combined in anhydrous tetrahydrofuran (5 mL) and anhydrous N,N-dimethylformamide (3 mL) in a 25 mL round bottomed flask under nitrogen. The reaction was stirred for 24 hours and concentrated in vacuo. Ethyl acetate (30 mL) and 0.5 N HCl (10 mL) were added and the layers were separated. The organic layer was washed with brine (10 mL), dried over anhydrous sodium sulfate, filtered, and concentrated in vacuo. Preparative silica gel TLC using 90:10 chloroform: methanol as an eluent provided the product as a white foam (83 mg, 0.123 mmol, 52%). $^1$HNMR ($d_6$-DMSO) δ: 7.60–7.15 (m, 10H), 5.51–5.46 (m, 1H), 5.21 (bd, J=5.9 Hz, 1H), 4.82–4.69 (m, 2H), 3.81 (s, 3H), 3.78–3.57 (m, 8H), 3.19–2.42 (m, 4H), 2.02–1.30 (m, 8H). MS(ES): 674 (M+1), 672 (M-1).

Example 55

Step 1

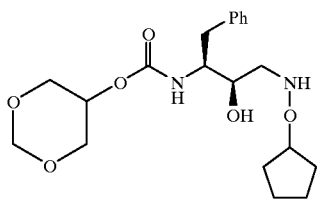

1,3-Dioxan-5-yl N-(1S,2R)-1-benzyl-3-[(cyclopentyloxy)amino]-2-hydroxypropylcarbamate. Tert-butyl N-(1S,2R)-1-benzyl-3-[(cyclopentyloxy)amino]-2-hydroxypropylcarbamate (1.38 g, 3.79 mmol) was dissolved in dichloromethane (15 mL) in a 50 mL round bottomed flask under nitrogen and trifluoroacetic acid (8 mL) was added slowly. After the solution was stirred for 4 hours, TLC Indicated loss of starting material. After the workup described in Step 2, Example 54, the residue was dissolved in anhydrous acetonitrile (20 mL), followed by 1,3-dioxan-5-yl 4-nitrophenyl carbonate (1.02 g, 3.79 mmol), anhydrous diisopropylethylamine (0.65 mL, 3.8 mmol), and N,N-dimethylaminopyridine (140 mg, 1.14 mmol). The reaction was heated at 50° C. for 2 hours, allowed to cool, and concentrated in vacua. After the workup described in Step 2, Example 54, the residue was purified by flush chromatography over a bed of silica gel using a gradient elution of hexane: ethyl acetate (1:2 to 1:4) to give the desired product as a white foam (600 mg, 1.52 mmol, 40%). $^1$HNMR ($d_6$-DMSO) δ: 7.30–7.17 (m, 5H), 6.15 (bs, 1H), 4.91–4.67 (m, 3H), 4.35–3.50 (m, 4H), 3.11–2.52 (m, 8H), 1.68–1.36 (m, 8H). MS(ES): 395 (M+1).

Step 2

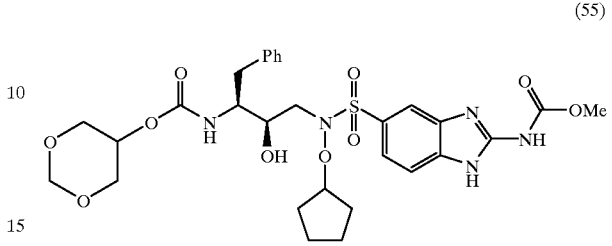
(55)

1,3-Dioxan-5-yl N-(1S,2R)-1-benzyl-3-[(cyclopentyloxy)(2-{(methoxycarbonyl)amino]-1H-benzimidazol-5-ylsulfonyl)amino]-2-hydroxypropylcarbamate. 1,3-Dioxan-5-yl N-(1S,2R)-1-benzyl-3-[(cyclopentyloxy)-amino]-2-hydroxypropylcarbamate (Step 1, above), (100 mg, 0.254 mmol), methyl N-[5-(chlorosulfonyl)-1H-benzimidazol-2-yl]carbamate (73 mg, 0.254 mmol), anhydrous duisopropylethyl-amine (0.05 mL, 0.254 mmol), and N,N-dimethylaminopyridine (9 mg, 0.08 mmol) were combined in anhydrous tetrahydrofuran (5 mL) and anhydrous N,N-dimethylformamide (2 mL) in a 25 mL round bottomed flask under nitrogen. The reaction was stirred for 24 hours and concentrated in vacua. After the workup described in Step 3, Example 54, the residue was purified by preparative silica gel TLC using 93:7 chloroform: methanol as an eluent to provide the desired product as a colorless glass (40 mg, 0.0618 mmol, 24%). $^1$HNMR ($d_6$-DMSO) δ: 7.96–7.16 (m, 10H), 5.17 (d, J=6.4 Hz, 1H), 4.82–4.65 (m, 3H), 4.26 (bs, 1H), 3.81 (s, 3H), 3.78–3.49 (m, 5H), 3.05–2.40 (m, 4H), 2.05–1.40 (m, 8H). MS(ES): 648 (M+1), 646 (M-1).

Example 56

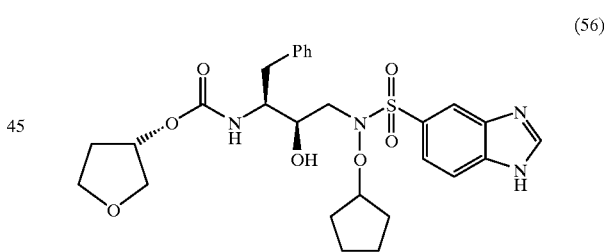
(56)

(3S)Tetrahydro-3-furanyl N-(1S,2R)-1-benzyl-3-[(cyclopentyloxy)(1H-indazol-5-ylsulfonyl)amino]-2-hydroxypropylcarbamate. (3S)Tetrahydro-3-furanyl N-(iS, 2R)-1-benzyl-3-[(cyclopentyloxy)amino]-2-hydroxypropylcarbamate (Step 1, Example 53), (90 mg, 0.238 mmol), 1-trityl-1H-indazole-5-sulfonyl chloride (110 mg, 0.238 mmol), anhydrous diisopropylethylamlne (0.04 mL, 0.238 mmol), and N,N-dimethylaminopyridine (9 mg, 0.07 mmol) were combined in anhydrous tetrahydrofuran (4 mL) in a 25 mL round bottomed flask under nitrogen. The reaction was stirred for 24 hours and concentrated in vacuo. After the workup described in Step 3, Example 54, the residue was purified by preparative silica gel TLC using 1:1 hexane: ethyl acetate as an eluent to give the tritylated product as a colorless film. The compound was deprotected as described in Example 57 and purified by preparative silica gel TLC using 3:1 ethyl acetate: hexane as an eluent to provide the desired product as a colorless film (6 mg, 0.01 mmol, 5%). (no HNMR data available). MS(ES): 559 (M+1), 557 (M-1).

Example 57

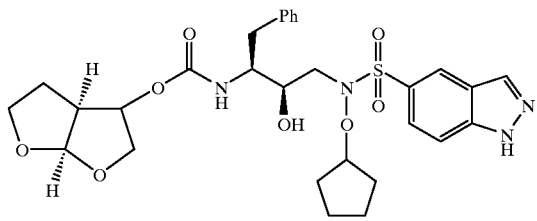

(57)

(3aS,6aR)Hexahydrofuro[2,3-b]furan-3-yl N-(1S,2R)-1-benzyl-3-[(cyclopentyloxy)(1H-indazol-5-ylsulfonyl)amino]-2-hydroxypropylcarbamate. (3aS,6aR)Hexahydrofuro[2,3-b]furan-3-yl N-(1S,2R)-1-benzyl-3-[(cyclopentyloxy)-amino]-2-hydroxy propylcarbamate (100 mg, 0.238 mmol) (Step 2, Example 54), 1-trityl-1H-indazole-5-sulfonyl chloride (110 mg, 0.238 mmol), anhydrous diisopropylethylamine (0.04 mL, 0.238 mmol), and N,N-dimethylaminopyridine (9 mg, 0.07 mmol) were combined in anhydrous tetrahydrofuran (5 mL) in a 25 mL round bottomed flask under nitrogen. The reaction was stirred for 24 hours and concentrated in vacuo. After the workup described in Step 3, Example 54, the residue was purified by preparative silica gel TLC using 1:1 hexane: ethyl acetate as an eluent to give the tritylated product as a colorless film (80 mg, 0.095 mmol, 40%). The trityl protecting group was removed by dissolving the compound in dichloromethane (3 mL) and adding trifluoroacetic acid (1 mL). After 2.5 hours of stirring, the reaction was concentrated in vacuc. Ethyl acetate (15 mL) and 10% aqueous sodium carbonate (5 mL) were added and the layers separated. The organic layer was dried over anhydrous sodium sulfate, filtered, and concentrated in vacuo. The residue was purified by preparative silica gel TLC using 3:1 ethyl acetate: hexane as an eluent to provide the desired product as a white solid (30 mg, 0.05 mmol, 53%). 1HNMR (d$_6$-DMSO) δ: 8.39–8.30 (m, 2H), 7.81–7.67 (m, 2H), 7.25–7.17 (m, 5H), 5.51–5.46 (m, 1H), 5.25 (d, J=6.3 Hz, 1H), 4.83–4.62 (m, 2H), 4.14–4.12 (m, 4H), 3.72–1.26 (m, 18H). MS(ES): 601 (M+1), 599 (M-1)

Example 58

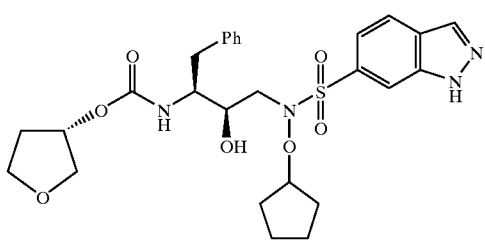

(58)

(3S)Tetrahydro-3-furanyl N-(1S,2R)-1-benzyl-3-[(cyclopentyloxy)(1H-indazol-6-ylsulfonyl)amino]-2-hydroxypropylcarbamate. (3S)Tetrahydro-3-furanyl N-(1S,2R)-1-benzyl-3-[(cyclopentyloxy)amino]-2-hydroxypropylcarbamate (Step 1, Example 53), (120 mg, 0.317 mmol), 1-trityl-1H-4Indazole-6-sulfonyl chloride (146 mg, 0.317 mmol), anhydrous diisopropylethylamine (0.06 mL, 0.317 mmol), and N,N-dimethylaminopyridine (12 mg, 0.1 mmol) were combined in anhydrous tetrahydrofuran (5 mL) in a 25 mL round bottomed flask under nitrogen. The reaction was stirred for 24 hours and concentrated in vacuo. After the workup described in Step 3, Example 54, the residue was purified by preparative silica gel TLC using 1:1 hexane: ethyl acetate as an eluent to give the tritylated product as a colorless film (100 mg, 0.125 mmol). The compound was deprotected as described in Example 57 and purified by preparative silica gel TLC using 3:1 ethyl acetate: hexane as an eluent to provide the desired product as a colorless glass (30 mg, 0.0537 mmol, 43%). $^1$HNMR (d$_6$-DMSO) δ: 8.33 (bs, 1H), 8.07–8.00 (m, 2H), 7.49–7.41 (m, 1H), 7.26–7.08 (m, 5H), 5.32–4.78 (m, 4H), 3.81–1.25 (m, 20H). MS(ES): 559 (M+1), 557 (M-1).

Example 59

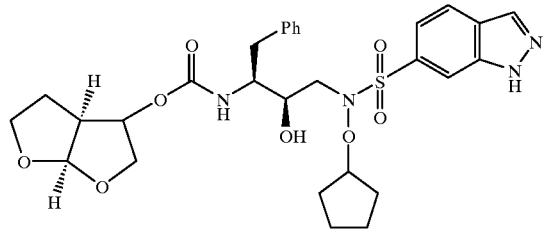

(59)

(3aS,6aR)Hexahydro[2,3-b]furan-3-yl N-(1S,2R)-1-benzyl-3-[(cyclopentyloxy)(1H-indazol-6-ylsulfonyl)amino]-2-hydroxypropylcarbamate. (3aS,6aR)Hexahydrofuro[2,3-b]furan-3-yl N-(1S,2R)-1-benzyl-3-[(cyclopentyloxy)-amino]-2-hydroxypropylcarbamate (Step 2, Example 54), (100 mg, 0.238 mmol), 1-trityl-1H-indazole-6-sulfonyl chloride (110 mg, 0.238 mmol), anhydrous diisopropylethylamine (0.04 mL, 0.238 mmol), and N,N-dimethylaminopyridine (9 mg, 0.07 mmol) were combined in anhydrous tetrahydrofuran (5 mL) in a 25 mL round bottomed flask under nitrogen. The reaction was stirred for 24 hours and concentrated in vacuc. After the workup described in Step 3, Example 54, the residue was purified by preparative silica gel TLC using 1:1 hexane: ethyl acetate as an eluent to give the tritylated product as a colorless film (117 mg, 0.139 mmol, 58%). The compound was deprotected as described in Example 57 and purified by preparative silica gel TLC using 3:1 ethyl acetate: hexane as an eluent to provide the desired product as a colorless film (60 mg, 0.100 mmcl, 72%). $^1$HNMR (d$_6$-DMSO) δ: 8.33 (bs, 1H), 8.08–7.99 (m, 2H), 7.50–7.45 (m, 1H), 7.23–7.15 (m, 5H), 5.51–5.45 (m, 1H), 5.26 (bd, J=5.9 Hz, 1H), 4.85–4.66 (m, 2H), 3.77–1.14 (m, 22H). MS(ES): 601 (M+1), 599 (M-1).

Example 60

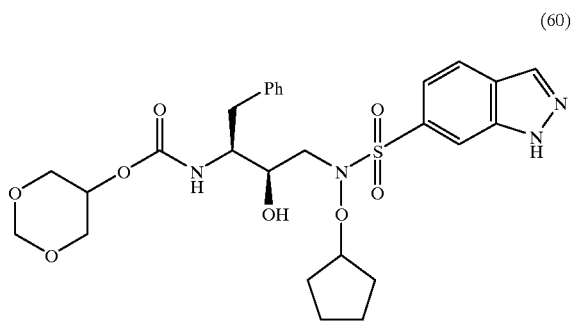

(60)

1,3-Dioxan-5-yl N-(1S,2R)-1-benzyl-3-[(cyclopentyloxy)(1H-indazol-6-ylsulfonyl)amino]-2-hydroxypropylcarbamate. 1,3-Dioxan-5-yl N-(1S,2R)-1-benzyl-3-[(cyclopentyloxy)amino]-2-hydroxypropylcarbamate (Step 1, Example 55), (100 mg, 0.254 nimol), 1-trityl-1H-indazole-6-sulfonyl chloride (117 mg, 0.254 mmol), anhydrous diisopropylethylamine (0.05 mL, 0.254 mmol), and N,N-dimethylaminopyridine (9 mg, 0.08 mmol) were combined in anhydrous tetrahydrofuran (5 mL) in a 25 mL round bottomed flask under nitrogen. The reaction was stirred for 24 hours and concentrated in vacuo. After the workup described in Step 3, Example 54, the residue was purified by preparative silica gel TLC using 1:1 hexane: ethyl acetate as an eluent to give the tritylated product as a beige foam. The compound was deprotected as described in Example 57 and purified by preparative silica gel TLC using 3:1 ethyl acetate: hexane as an eluent to provide the desired product as a colorless glass (53 mg, 0.0922 mmol, 36%). ¹HNMR (d₆-DMSO) δ: 8.32 (bs, 1H), 8.06–8.00 (m, 2H), 7.49–7.46 (m, 1H), 7.33–7.16 (m, 5H), 5.22 (d, J=6.5 Hz, 1H), 4.85–4.66 (m, 3H), 4.23–3.00 (m, 12H), 2.01–1.43 (m, 8H). MS(ES): 575 (M+1), 573 (M−1).

Example 61

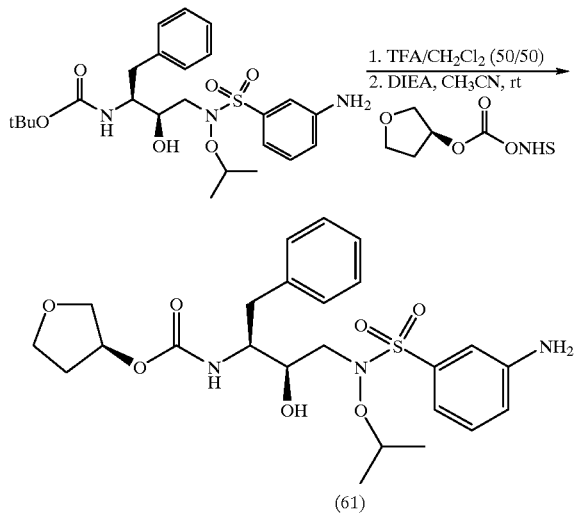

(61)

(3S)tetrahydro-3-furanyl N-(1S,2R)-3-[[(3-aminophenyl)sulfonyl](isopropoxy)amino]-1-benzyl-2-hydroxypropylcarbamate. tert-Butyl N-(1S,2R)-3-[[(3-aminophenyl)sulfonyl](isopropoxy)amino]-1-benzyl-2-hydroxypropylcarbamate (0.50 g, 1.01 mmol) was dissolved in TFA/CH₂Cl₂(50/50, 5.0 mL) at rt. After 0.5h., the TFA/CH₂Cl₂ was removed in vacuo and the reside was partitioned between CH₂Cl₂(100 mL) and 1.0N NaOH (50 mL). The organic layer was washed with water (1 x 25 mL), brine (1 x 25 mL), dried (MgSO₄), filtered, and evaporated to give the free base. To a solution of the free base in CH₃CN(10 mL) was added DIEA (0.175 mL, 1.01 mmol) and 2,5-dioxo-1-pyrrolidinyl [(3S)tetrahydro-3-furanyl]carbonate (0.213 g, 0.93 mmol) respectively with stirring at rt. After 1.0 h., the reaction mixture was evaporated and the crude residue purified by column chromatography: 40/60 hexane/ethyl acetate to give the product as a white solid (0.320g, 63%). MS: M+NA=530. H NMR (CD₃OD) 1.25(m, 6H); 1.80(m, 1H); 2.05(m, 1H); 2.40–3.10(m, 4H); 3.45(d, 1H); 3.75(m, 1H); 3.70–3.90(m, 5H); 4.50(m, 1H); 4.95(m, 1H); 6.90(d, 1H); 7.05(d, 1H); 7.10–7.35(m, 7H).

Example 62

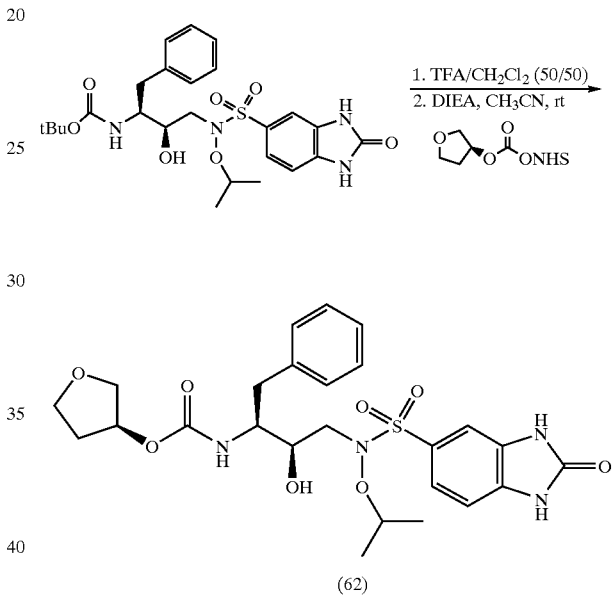

(62)

(3S)tetrahydro-3-furanyl N-((1S,2R)-1-benzyl-2-hydroxy-3-isopropoxy[(2-oxo-2,3-dihydro-1H-1,3-benzimidazol-5-yl)sulfonyl]aminopropyl)carbamate. Prepared using the procedure outlined in Example 61. The product was purified by column chromatography: 97/3 CH₂Cl₂/MeOH and isolated as a white solid (40%). MS: M+H=549 ¹H NMR (CD₃OD) 1.25 (m, 6H); 1.60 (mn, 1H); 1.95(m, 1H); 2.40–3.10(m, 4H); 3.40(d, 1H); 3.70–3.90(m, 5H); 4.55(m, 1H); 4.90(m, 1H); 7.20(m, 5H); δ 7.80(m, 2H) 8.20(s, 1H); 8.40(s,1H) 7.20(m, 6H); 7.50((m, 2H).

Example 63

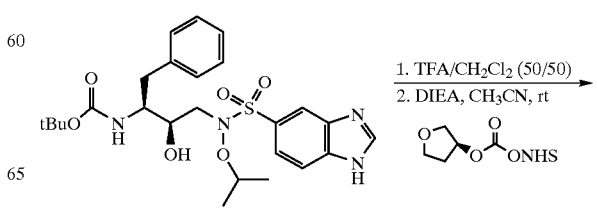

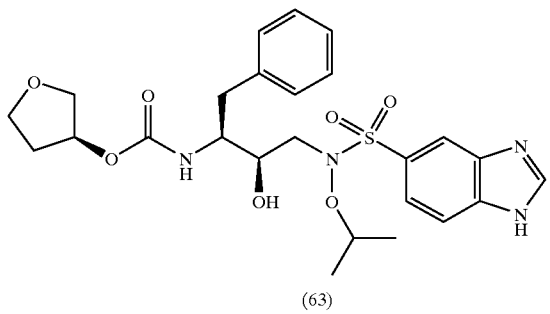

(63)

(3S)tetrahydro-3-furanyl N-(1S,2R)-3-[(1H-1,3-benzimidazol-5-ylsulfonyl)(isopropoxy)amino]-1-benzyl-2-hydroxypropylcarbamate. Prepared using the procedure outlined in Example 6. The product was purified by column chromatography: 97/3 CH$_2$Cl$_2$/MeOH and isolated as white solid (31%). MS: M+H=533 H NMR (CD$_3$OD) 1.25(m, 6H); 1.60(m, 1H); 1.95(m, 1H); 2.40–3.10(m, 4H); 3.40(d, 1H); 3.70–3.90(m, 5H); 4.55(m, 1H); 4.90(m, 1H); 7.20(m, 5H); 7.80(rr, 2H) 8.20(s, 1H); 8.40(s,1H).

Example 64

(3S)tetrahydro-3-furanyl N-((1S,2R)-1-benzyl-3-(cyclohexyloxy)[(4-methoxyphenyl) sulfonyl]amino-2-hydroxypropyl)carbamate. tert-butyl N-((1S,2R)-1-benzyl-3-(cyclohexyloxy)[(4-methoxyphenyl)sulfonyl]amino-2-hydroxypropyl)carbamate (0.09 mmol, 50 mg) was dissolved in a 1:1 solution of CH$_2$Cl$_2$/TFA (1 mL) and allowed to stir at room temperature for 1 hour. The solution was then extracted into ethyl acetate, washed with saturated sodium bicarbonate solution and brine, dried over magnesium sulfate, and concentrated to a clear oil. The resulting oil was then dissolved in THF (1 mL) and combined with 2,5-dioxo-1-pyrrolidinyl [(3S)tetrahydro-3-furanyl] carbonate (0.05 mmol, 13 mg) DIEA (0.08 mmol, 14 gL) and allowed to stir for 15 hours. The reaction was neutralized by the addition of acetic acid and partitioned between water and ethyl acetate. The organic layer was washed with saturated sodium bicarbonate and brine, and dried over magnesium sulfate. The crude product was concentrated to a white solid and purified by silica gel chromatography (1:1 hexanes/ethyl acetate), providing 19 mg (37%) of a white solid. H$_1$-NMR (CDCl$_3$): δ7.70 (2H,d), 7.29–7.17 (6H,m), 6.97 (2H,d), 5.1 (1H,s), 4.76 (1H,d), 4.17 (1H,m), 3.86 (3H,s), 3.87–3.70 (6H,m), 3.68–3.60 (1H,m), 3.06 (1H,bs), 2.89 (2H,m), 2.02 (3H,m), 1.89 (1H,m), 1.71 (2H,m), 1.28–1.08 (6H,m); MS (ESI): M+Na=585.

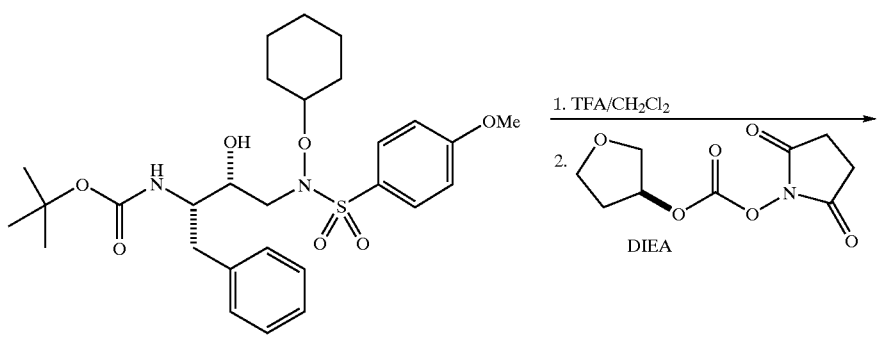

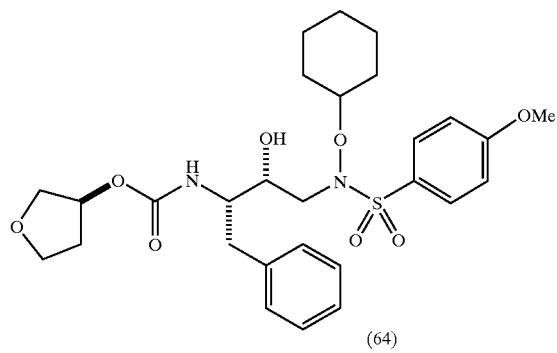

(64)

Example 65

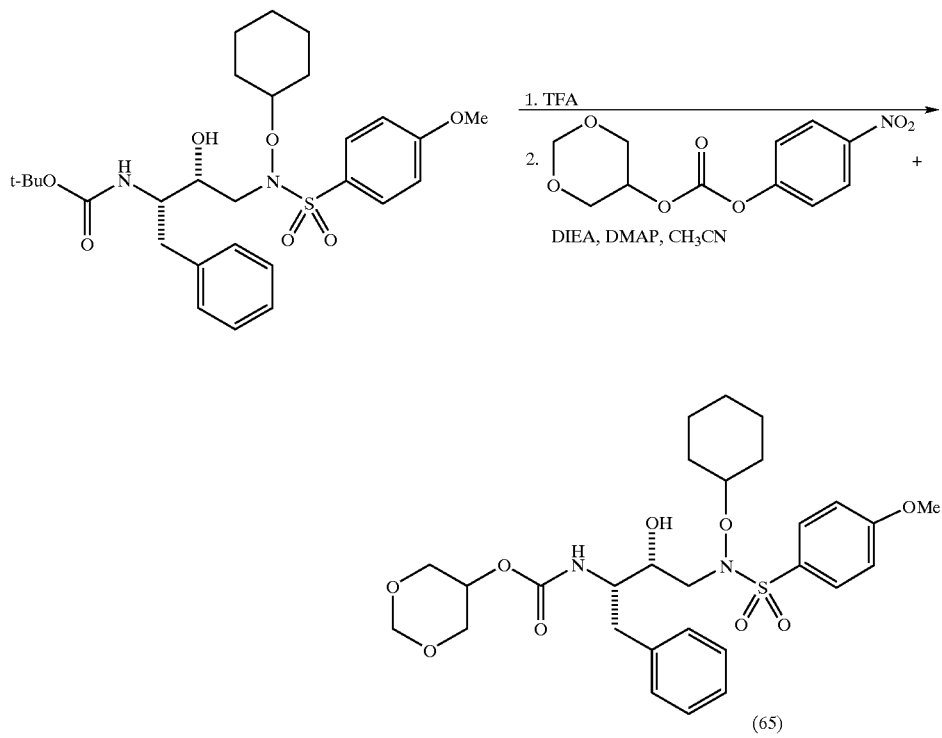

1,3-dioxan-5-yl N-((1S,2R)-1-benzyl-3-(cyclohexyloxy)[(4-methoxyphenyl)sulfonyl]amino-2-hydroxypropyl)carbamate. tert-butyl N-((1S,2R)-1-benzyl-3-(cyclohexyloxy)[(4-methoxyphenyl)sulfonyl]amino-2-hydroxypropyl)carbamate (0.09 mmol, 50 mg) was stirred in 1 mL trifluoroacetic acid (TFA) at room temperature for 5 hours. The TFA was removed under vacuum, and the resulting residue was dissolved in ethyl acetate, washed with 5% aq. potassium carbonate solution, brine, dried over magnesium sulfate, and concentrated to a residue. The resulting free amine, 1,3-dioxan-5-yl 4-nitrophenyl carbonate (0.09 mmol, 25 mg), diisopropylethylamine (0.14 mmol, 0.024 mL), a crystal of N,N-dlmethylaminopyridine, 4 A molecular sieves and acetonitrile (0.5 mL) were combined and stirred at room 'temperature for 20 hours. The reaction solution was concentrated to a residue, dissolved in ethyl acetate, washed with 1N HCl, 5% aq. potassium carbonate solution, brine, dried over magnesium sulfate, and concentrated under vacuum. The crude residue was purified by silica gel chromatography (2:1 hexanes/ethyl acetate) and crystallization from ether and hexanes to yield 10 mg (19%) of white solid. $R_f$=0.2 (2:1 hexanes/ethyl acetate); H1-NMR (CDCl$_3$): δ 7.69 (2H,d), 7.29–7.18 (6H,m), 6.96 (2H,d), 5.01–4.93 (1H, m), 4.93–4.85 (1H,m), 4.74–4.70 (1H,m), 4.51–4.45 (1H,m), 4.22–4.11 (1H,m), 3.95–3.72 (7H,m), 3.86 (3H,s), 3.00–2.80 (3H,m), 2.10–1.97 (2H,m), 1.79–1.67 (2H,m), 1.61–1.53 (2H,m), 1.38–1.02 (6H,m); MS (ESI): M+H=580.

Example 66

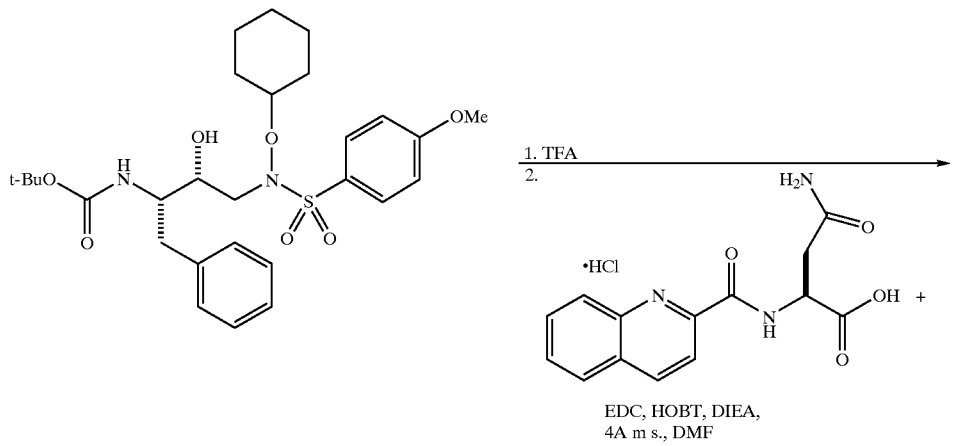

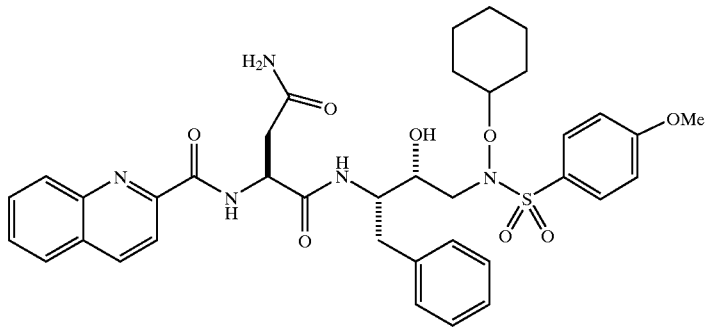

(66)

(2S)-N[1]-((1S,2R)-1-benzyl-3-(cyclohexyloxy)[(4-methoxyphenyl)sulfonyl]amino-2-hydroxypropyl)-2-[(2-quinolinylcarbonyl)amino]butanediamide. tert-butyl N-((1S,2R)-1-benzyl-3-(cyclohexyloxy)[(4-methoxyphenyl)sulfonyl]amino-2-hydroxypropyl)carbamate (0.18 mmol, 100 mg) was stirred in 1 mL trifluoroacetic acid (TFA) at room temperature for 1 hour. The TFA was removed under vacuum, and the resulting residue was dissolved in ethyl acetate, washed with 5% aq. potassium carbonate solution, brine, dried over magnesium sulfate, and concentrated to a residue. The resulting free amine, (2S)-4-amino-4-oxo-2-[(2-quinolinylcarbonyl)amino]butanoic acid hydrochloride (0.18 mmol, 56 mg), 1-hydroxybenzotriazole hydrate (0.18 mmol, 25 mg), N-(3-Dimethylaminopropyl)-N'-ethylcarbodiimide hydrochloride (0.20 mmol, 38 mg), diisopropylethylamine (0.91 mmol, 0.157 mL) and anhydrous N,N-dimethylformamide (0.5 mL) were combined at room temperature and stirred for 15 hours. The crude reaction mixture was concentrated to a residue, dissolved in ethyl acetate, washed with 1N HCl, 5% aq. potassium carbonate solution, brine and dried over magnesium sulfate. The solution was concentrated to a residue, purified by silica gel chromatography (ethyl acetate), and lyophylized providing a fluffy white solid. H-1-NMR (CDCl$_3$): δ 9.19–9.17 (1H,m), 8.32–8.30 (1H,m), 8.23–8.16 (2H,m), 7.89–7.87 (1H,m), 7.79–7.76 (3H,m), 7.65–7.61 (1H,m), 7.13–7.11 (2H,m), 7.05–6.94 (6H,m), 5.73–5.64 (1H,m), 5.41–5.33 (1H,m), 4.96–4.85 (1H,m), 4.28–4.08 2H,m), 3.89–3.74 (1H,m), 3.86 (3H,s), 3.25 (1H, bs), 2.95–2.79 (5H,m), 2.65–2.60 (1H,m), 2.04 (2H,bs), 1.70 (2H,bs), 1.57–1.41 (1H,m), 1.30–1.10 (5H,m); MS (ESI): M+H=719.

Example 67
Step 1

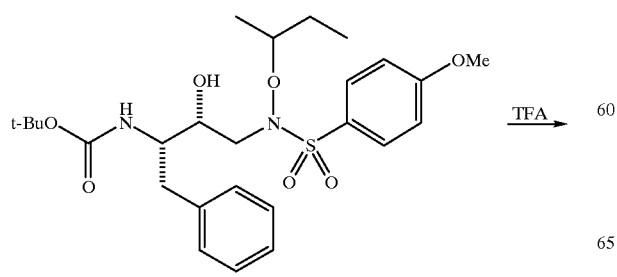

-continued

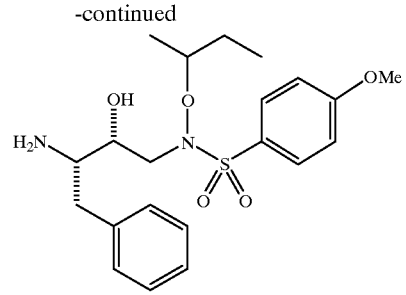

N-[(2R,3S)-3-amino-2-hydroxy-4-phenylbutyl]-N-(sec-butoxy)-4-methoxybenzene-sulfonamide. tert-butyl N-((iS,2R)-1-benzyl-3-sec-butoxy[(4-methoxyphenyl)sulfonyl]amino-2-hydroxy-propyl)carbamate (1.9 mmol, 1 g) was stirred in neat trifluoroacetic acid (TFA) at room temperature for 1 hour. The TFA was removed under vacuum, and the resulting residue was dissolved in ethyl acetate, washed with 5% aq. potassium carbonate solution, brine and dried over magnesium sulfate. The dried solution was concentrated under vacuum and stored as a sticky white solid. H1-NMR (CDCl$_3$): δ 7.81 (2H,d), 7.28–7.16 (5H,m), 7.01 (2H,d), 4.31 (2H,bs), 4.01–3.90 (1H,bs), 3.88 (3H,s), 3.5–2.5 (1H,bs), 3.33 (2H,bs), 2.89 (2H,bs), 2.63 (2H,bs), 1.71 (1H,bs), 1.43–1.40 (1H,m), 1.27–1.19 (3H,m), 0.98–0.85 (3H,m); MS (ESI): M+H=423.

Step 2

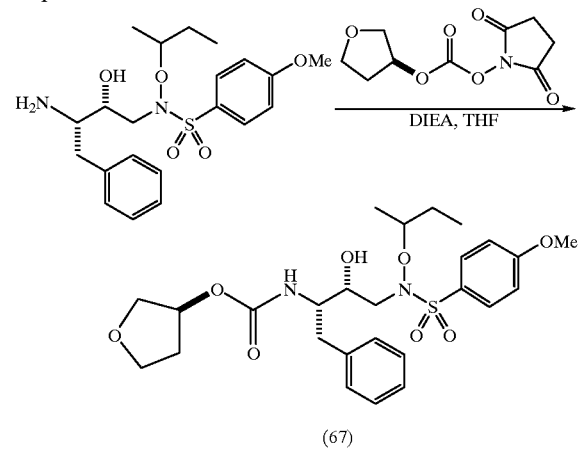

(67)

(3S)tetrahydro-3-furanyl N-((1S,2R)-1-benzyl-3-sec-butoxy[(4-methoxyphenyl)sulf-onyl]amino-2-hydroxypropyl)carbamate. N-[(2R,3S)-3-amino-2-hydroxy-4-phenylbutyl]-N-(sec-butoxy)-4-methoxybenzenesulfonamide (0.12 mmol, 50 mg), 1-([(3S)tetrahydro-3-furanyloxy] carbonyloxy)dihydro-1H-pyrrole-2,5-dione (0.12 mmol, 29 mg), diisopropylethylamine (0.18 mmol, 0.031 mL) and anhydrous THF (1 mL) were combined and stirred at room temperature for 20 hours. The reaction product was concentrated to a residue, purified directly by silica gel chromatography (2:1 hexanes/ethyl acetate) and crystallized from diethyl ether providing 40 mg (63%) of a white crystal. H1-NMR (CDCl$_3$): δ7.74–7.70 (2H,m), 7.30–7.17 (6H,m), 7.00–6.96 (2H,m), 5.11 (1H,bs), 4.75 (1H,bs), 4.31–4.30 (1H,m), 3.87 (3H,s), 3.87–3.75 (6H,m), 3.65–3.60 (1H,m), 3.21–2.64 (1H,bs), 2.89 (2H,bs), 2.15–2.01 (1H,m), 1.95–1.78 (1H,m), 1.78–1.58 (1H,m), 1.47–1.32 (1H,m), 1.24–1.13 (3H,m), 0.94–0.84 (3H,m); MS (ESI): M+Na=560.

Example 68 hexahydrofuro[2,3-b]furan-2-yl 4-nitrophenyl carbonate (0.12 mmol, 35 mg), diisopropylethylamine (0.18 mmol, 0.031 mL) and acetonitrile (1 mL). The reaction was allowed to stir at room temperature for 15 hours, then heated to reflux for a minute and cooled to room temperature. The reaction was concentrated to a yellow oil, dissolved in ethyl acetate, washed with 1N HCl, saturated aq. sodium bicarbonate solution, brine and dried over magnesium sulfate. The crude product was purified by silica gel chromatgraphy (1:1 hexanes/ethyl acetate) and crystallization from an ether/hexanes solution to yield 30 mg (43%) of white crystals. R$_f$=0.2 (1:1 hexanes/ethyl acetate); H1-NMR (CDCl$_3$): δ7.74–7.71 (2H,m), 7.28–7.14 (6H,m), 7.00–6.97 (2H,m), 5.63–5.62 (1H,m), 5.05–4.93 (1H,m), 4.87–4.75 (1H,m), 4.36–4.23 (1H,m), 3.98–3.76 (4H,m), 3.87 (3H,s), 3.68 (2H,m), 3.10 (1H,bs), 3.08–2.70 (6H,m),1.77–1.57 (1H,m),

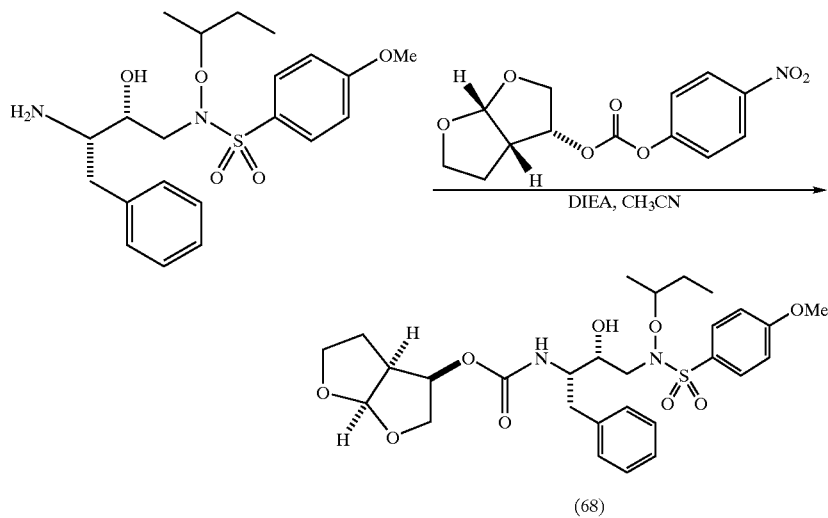

(68)

(3R,3aS,6aR)hexahydrofuro[2,3-b]furan-3-yl N-((1S,2R)-1-benzyl-3-sec-butoxy[(4-methoxyphenyl)sulfonyl]amino-2-hydroxypropyl)carbamate. N-[(2R, 3S)-3-amino-2-hydroxy-4-phenylbutyl]-N-(sec-butoxy)-4-methoxybenzenesulfon-amide (step 1, Example 67) (0.12 mmol, 50 mg) was combined with (2R,3aS,6aR)

1.50–1.32 (1H,m), 1.23–1.18 (3H,m), 0.93–0.86 (3H,m); MS (ESI): M+Na=601.

Example 69

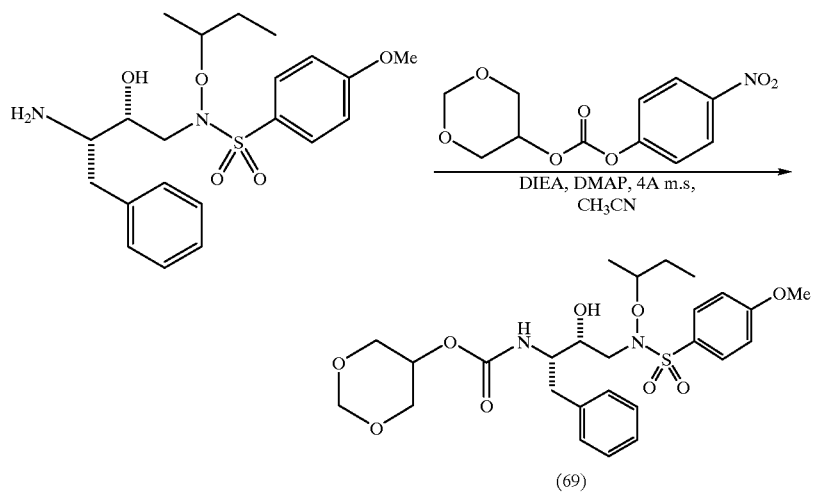

(69)

1,3-dioxan-5-yl N-((1S,2R)-1-benzyl-3-sec-butoxy[(4-methoxyphenyl)sulfonyl]amino-2-hydroxypropyl)carbamate. N-[(2R,3S)-3-amino-2-hydroxy-4-phenylbutyl]-N-(sec-butoxy)-4-methoxybenzenesulfon-amide (Step 1, Example 67) (0.09 mmol, 38 mg), 1,3-dioxan-5-yl 4-nitrophenyl carbonate (0.09 mmol, 24 mg), diisopropylethylamine (0.13 mmol, 0.024 mL), 4 A molecular sieves, a crystal of N,N-dimethylaminopyridine and aceLonitrile (1 mL) were combined and allowed to stir for 20 hours at room temperature. The reaction was then concentrated to a residue, dissolved in ethyl acetate, washed with 1N HCl, 5% aq. potassium carbonate solution, brine, and dried over magnesium sulfate. The reaction was purified directly by crystallization from a solution of de diethyl ether and hexanes to yield 30 mg (60%) of white crystals. $R_f$=0.7 (1:1 hexanes/ethyl acetate); H1-NMR (CDCl$_3$): δ 7.72–7.69 (2H,m), 7.29–7.18 (6H,m), 6.98–6.95 (2H,m), 5.03–4.93 (1H,m), 4.93–4.87 (1H,m), 4.76–4.69 (1H,m), 4.53–4.44 (1H,m), 4.38–4.25 (1H,m), 3.95–3.72 (7H,m), 3.86 (3H,s), 3.24–2.62 (3H,m), 1.76–1.60 (1H,m), 1.47–1.29 (1H,m), 1.22–1.16 (3H,m), 0.94–0.83 (3H,m); MS (ESI): M+H=553.

Example 70

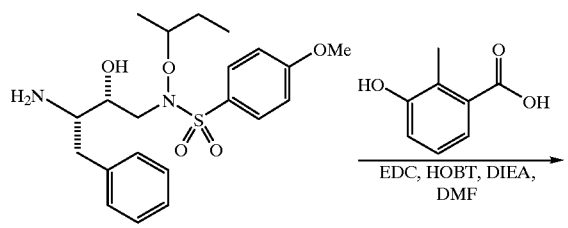

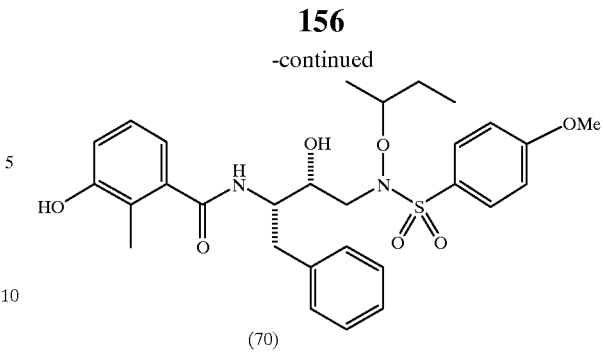

(70)

N-(sec-butoxy)-N-[(2R,3S)-2-hydroxy-3-(3-hydroxy-2-methylanilino)-4-phenylbutyl]-4-methoxybenzenesulfon-amide.
N-[(2R,3S)-3-amino-2-hydroxy-4-phenylbutyl]-N-(sec-butoxy)-4-methoxybenzenesulfon-amide (Step 1, Example 67)(0.12 mmol, 50 mg), 3-hydroxy-2-methylbenzoic acid (0.12 mmol, 18 mg), 1-hydroxybenzotriazole hydrate (0.12 mmol, 16 mg), N-(3-Dimethylaminopropyl)-N'-ethylcarbodiimide hydrochloride (0.13 mmol, 25 mg), diisopropylethylamine (0.14 mmol, 0.025 mL) and anhydrous N,N-dimethylformamide (0.5 mL) were combined at room temperature and stirred for 18 hours. The crude reaction mixture was concentrated to a residue, dissolved in ethyl acetate, washed with 1N HCl, 5% aq. potassium carbonate solution, brine and dried over magnesium sulfate. The solution was concentrated to a residue, purified by RPHPLC (water/acetonitrile) and lyophilized providing 20 mg (30%) of a white solid. H1-NMR (CDCl$_3$): δ 7.76–7.73 (2H,m), 7.32–7.23 (5H,m), 7.00–6.97 (3H,m), 6.78–6.76 (1H,m), 6.56–6.53 (1H,m), 5.90 (1H,bs), 4.42–4.27 (2H,m), 4.09–3.95 (1H,m), 3.87 (3H,s), 3.25–2.27 (5H,m), 2.05–1.95 (3H,m), 1.77–1.58 (1H,m), 1.55–1.22 (1H,m), 1.24–1.20 (3H,m), 0.93–0.86 (3H,m); MS (ESI): M+H=557.

Example 71

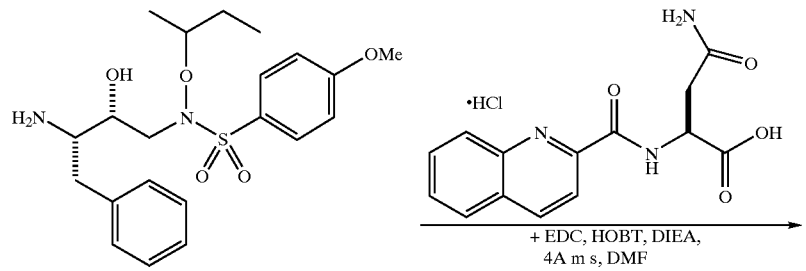

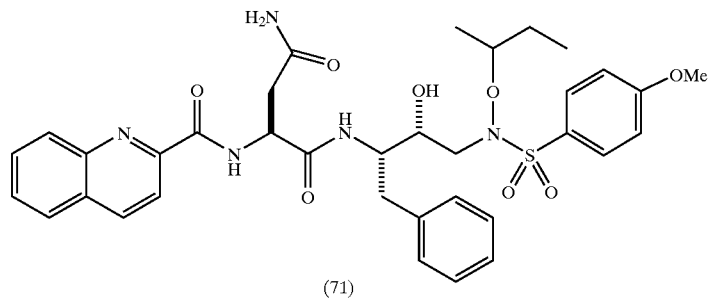

(71)

(2S)-N¹-(1S,2R)-1-benzyl-3-sec-butoxy[(4-methoxyphenyl)sulfonyl]amino-2-hydroxypropyl)-2-[(2-quinolinylcarbonyl)amino]butanediamide. N-[(2R,3S)-3-amino-2-hydroxy-4-phenylbutyl]-N-(sec-butoxy)-4-methoxybenzenesulfon-amide (Step 1, Example 67) (0.114 mmol, 48 mg), (2S)-4-amino-4-oxo-2-[(2-quinolinylcarbonyl)amino]butanoic acid hydrochloride (0.136 mmol, 42 mg), 1-hydroxybenzotriazole hydrate (0.136 mmol, 19 mg), N-(3-Dimethylaminopropyl)-N'-ethylcarbodiimide hydrochloride (0.148 mmol, 28 mg), diisopropylethylamine (5.68 mmol, 0.990 mL) and anhydrous N,N-dimethylformamide (0.5 mL) were combined at room temperature and stirred for 15 hours. The crude reaction mixture was concentrated to a residue, dissolved in ethyl acetate, washed with 1N HCl, 5% aq. potassium carbonate solution, brine and dried over magnesium sulfate. The solution was concentrated to a residue, purified by silica gel chromatography (1:1 hexanes/ethyl acetate) and crystallization from ether and hexanes, providing 20 mg (25%) of a pink solid. H1-NMR (CDCl$_3$): δ9.20–9.18 (1H,m), 8.32–8.30 (1H,m), 8.22–8.16 (2H,m), 7.89–7.87 (1H,m), 7.80–7.76 (3H,m), 7.65–7.61 (1H,m), 7.14–7.11 (2H,m), 7.05–6.97 (6H,m), 5.76–5.64 (1H,bs), 5.49–5.26 (1H,m), 4.94–4.86 (1H,m), 4.36–4.14 (2H,m), 3.99–3.80 (1H,m), 3.86 (3H,s), 3.14 (1H,bs), 2.98–2.71 (5H,m), 2.71–2.59 (1H,m), 1.80–1.52 (1H,m), 1.48–1.30 (1H,m), 1.22–1.14 (3H,m), 0.94–0.80 (3H,m); MS (ESI): M+H=692.

Example 72

(3S)tetrahydro-3-furanyl N-(1S,2R)-1-benzyl-2-hydroxy-3-[[(4-methoxyphenyl)sulfonyl](tetrahydro-2H-pyran-4-yloxy)amino]propylcarbamate, tert-butyl N-(iS,2R)-1-benzyl-2-hydroxy-3-[[(4-methoxyphenyl)sulfonyl](tetrahydro-2H-pyran-4-yloxy)amino]propylcarbamate, (Example 18), (0.09 mmol, 50 mg) was stirred in 1 mL trifluoroacetic acid (TFA) at room temperature for 1 hour. The TFA was removed under vacuum, and the resulting residue was dissolved in ethyl acetate, washed with 1N HCl, 5% aq. potassium carbonate solution, brine, and dried over magnesium sulfate. The resulting free amine, 1-([(3S)tetrahydro-3-furanyloxy]carbonyloxy)dihydro-1H-pyrrole-2,5-dione (0.09 mmol, 22 mg), diusopropylethylamine (0.14 mmol, 0.024 mL) and acetonitrile (0.5 mL) were combined and stirred at room temperature for 30 minutes. The reaction product was concentrated to a residue, dissolved in ethyl acetate, washed with 1N HCl, 5% aq. potassium carbonate solution, brine, and dried over magnesium sulfate. The crude solution was concentrated, and the purified reaction product crystallized out of diethyl ether providing 28 mg (55%) of a white crystal. R$_f$=0.1 (1:1 hexanes/ethyl acetate); H1-NMR (CDCl$_3$): δ 7.70 (2H,d), 7.32–7.15 (6H,m), 6.98 (2H,d), 5.11 (1H,bs), 4.81–4.71 (1H,m), 4.44–4.35 (1H,m), 3.97–3.70 (8H,m), 3.87 (3H,s), 3.65 (1H,m), 3.52–3.33 (2H,m), 3.25–2.5 (1H,bs), 2.93–2.88 (2H,m), 2.12–1.95 (3H,m), 1.93–1.80 (1H,m), 1.57–1.41 (2H,m); MS (ESI): M+H=565.

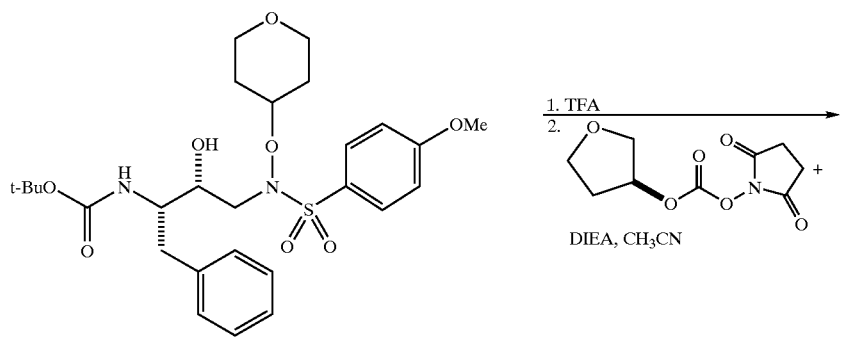

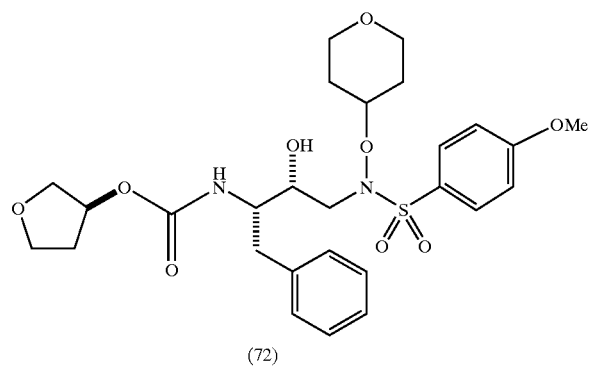

(72)

Example 73

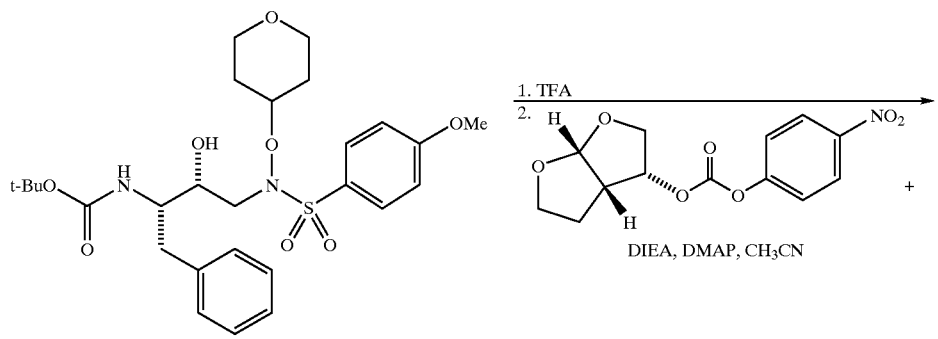

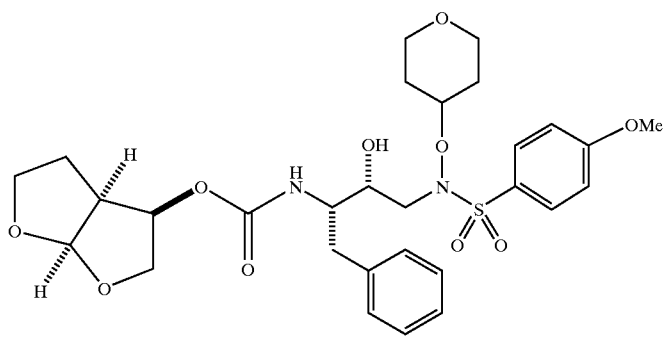

(73)

(3R,3aS,6aR)hexahydrofuro[2,3-b]furan-3-yl N-(1S,2R)-1-benzyl-2-hydroxy-3-[[(4-methoxyphenyl)sulfonyl](tetrahydro-2H-pyran-4-yloxy)amino]propylcarbamate Lert-butyl N-(1S,2R)-1-benzyl-2-hydroxy-3-[[(4-methoxyphenyl)sulfonyl](tetrahydro-2H-pyran-4-yloxy)amino]propylcarbamate (Example 18), (0.09 mmol, 50 mg) was stirred in 1 mL trifluoroacetic acid (TFA) at room temperature for 1 hour. The TFA was removed under vacuum, and the resulting residue was dissolved in ethyl acetate, washed with 5% aq. potassium carbonate solution, brine, dried over magnesium sulfate, and concentrated to a residue. The resulting free amine, (2R,3aS,6aR) hexahydrofuro[2,3-b]furan-2-yl 4-nitrophenyl carbonate (0.09 mmol, 27 mg), diisopropylethylamine (0.14 mmol, 0.024 mL), a crystal of N,N-dimethylaminopyridine, 4 A molecular sieves and acetonitrile (0.5 mL) were combined and stirred at room temperature for 15 hours. The reaction solution was concentrated to a residue, dissolved in ethyl acetate, washed with 1N HCl, 5% aq. potassium carbonate solution, brine, dried over magnesium sulfate, and concentrated under vacuum. The crude residue was purified by silica gel chromatography (1:1 hexanes/ethyl acetate) and crystallization from ether and hexanes to yield 20 mg (36%) of white crystals. $R_f$=0.2 (1:1 hexanes/ethyl acetate); H1-NMR (CDCl$_3$): δ7.71 (2H,d), 7.31–7.12 (6H,m), 6.99 (2H,d), 5.65–5.61 (1H,m), 5.05–4.95 (1H,m), 4.90–4.72 (1H,m), 4.49–4.34 (1H,m), 4.00–3.76 (7H,m), 3.88 (3H,s), 3.71–3.60 10 (2H,m), 3.48–3.35 (2H,m), 3.40–2.40 (1H,bs), 3.28–2.61 (5H,m), 3.04–2.71 (2H,m), 2.09–1.97 (2H,m); MS (ESI): M+H=607.

Example 74

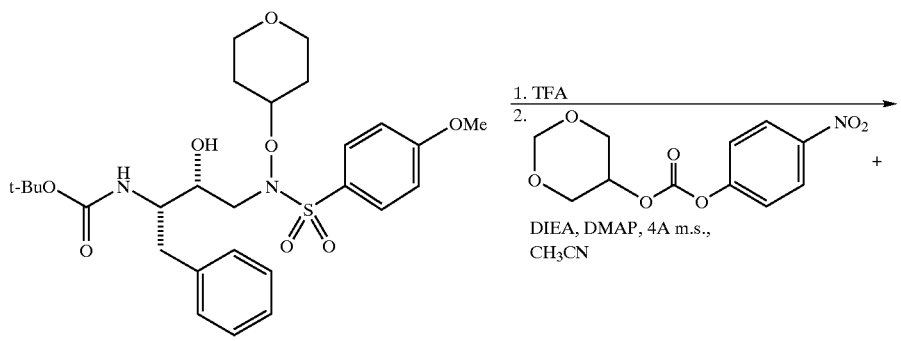

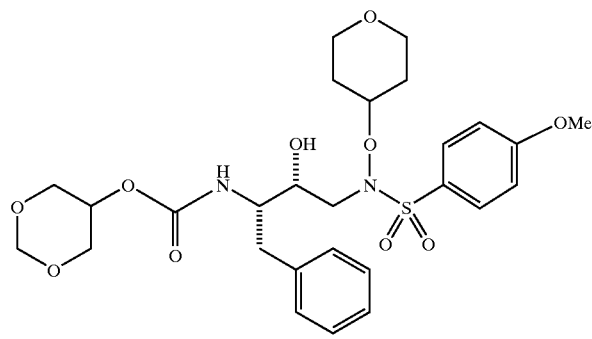

(74)

1,3-dioxan-5-yl N-(1S,2R)-1-benzyl-2-hydroxy-3-[[(4-2C methoxyphenyl)sulfonyl](tetrahydro-2H-pyran-4-yloxy) amino]propylcarbamate. tert-butyl N-(1S,2R)-1-benzyl-2-hydroxy-3-[[(4-methoxyphenyl)sulfonyl](tetrahydro-2H-pyran-4-yloxy)amino]propylcarbamate (Example 18), (0.09 mmol, 50 mg) was stirred in 1 mL trifluoroacetic acid (TFA) at room temperature for 5 hours. The TFA was removed under vacuum, and the resulting residue was dissolved in ethyl acetate, washed with 5% aq. potassium carbonate solution, brine, dried over magnesium sulfate, and concentrated to a residue. The resulting free amine, 1,3-dioxan-5-yl 4-nitrophenyl carbonate (0.08 mmol, 22 mg), diisopropylethylamine (0.14 mmol, 0.024 mL), a crystal of N,N-dimethylaminopyridine, 4 A molecular sieves and acetonitrile (0.5 mL) were combined and stirred at room temperature for 20 hours. The reaction solution was concentrated to a residue, dissolved in ethyl acetate, washed with 1N HCl, 5% aq. potassium carbonate solution, brine, dried over magnesium sulfate, and concentrated under vacuum. The crude residue was purified by silica gel chromatography (1:1 hexanes/ethyl acetate) and crystallization from ether and hexanes to yield 3 mg (6%) of white crystals. $R_f$=0.2 (1:1 hexanes/ethyl acetate); H1-NMR (CDCl$_3$): δ7.69 (2H,d), 7.32–7.17 (6H,m), 6.98 (2H,d), 5.02–4.94 (1H,m), 4.94–4.87 (1H,m), 4.76–4.69 (1H,m), 4.53–4.45 (1H,m), 4.45–4.34 (1H,m), 4.00–3.70 (9H,m), 3.87 (3H,s), 3.49–3.30 (2H,m), 3.10 (1H,bs), 3.47–3.35 (2H,m), 2.99–2.78 (2H,m), 2.07–1.95 (2H,m); MS (ESI): M+H=581.

Example 75

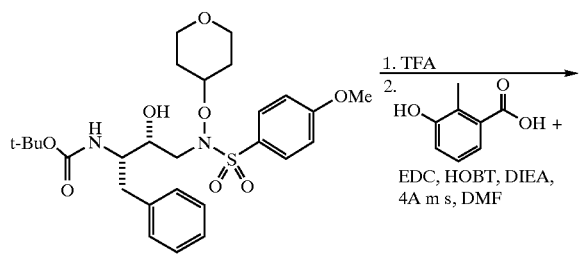

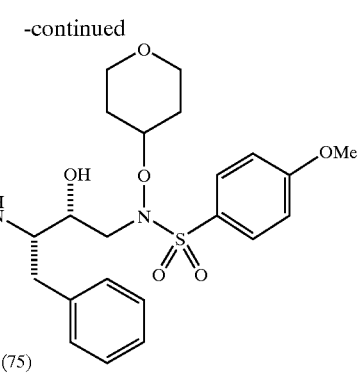

(75)

N-(1S,2R)-1-benzyl-2-hydroxy-3-[[(4-methoxyphenyl) sulfonyl] (tetrahydro-2H-pyran-4-yloxy)amino]propyl-3-hydroxy-2-methylbenzamide. tert-butyl N-(1S,2R)-1-benzyl-2-hydroxy-3-[[(4-methoxyphenyl)sulfonyl] (tetrahydro-2H-pyran-4-yloxy)amino]propylcarbamate (Example 18), (0.10 mmol, 54 mg) was stirred in 1 mL trifluoroacetic acid (TFA) at room temperature for 5 hours. The TFA was removed under vacuum, and the resulting residue was dissolved in ethyl acetate, washed with 5% aq. potassium carbonate solution, brine, dried over magnesium sulfate, and concentrated to a residue. The resulting free amine, 3-hydroxy-2-methylbenzoic acid (0.10 mmol, 15 mg), 1-hydroxybenzotriazole hydrate (0.10 mmol, 14 mg), N-(3-Dimethylaminopropyl)-N'-ethylcarbodiimide hydrochloride (0.11 mmol, 21 mg), diisopropylethylamine (0.15 mmol, 0.026 mL) and anhydrous N,N-dimethylformamide (0.5 mL) were combined at room temperature and stirred for 20 hours. The crude reaction mixture was concentrated to a residue, dissolved in ethyl acetate, washed with 1N HCl, 5% aq. potassium carbonate solution, brine and dried over magnesium sulfate. The solution was concentrated to a residue, and purified by crystallization from ether and hexanes providing 21 mg (37%) of a white solid. R=0.2 (1:1 hexanes/ethyl acetate); H1-NMR (CDCl$_3$): δ7.73 (2H,d), 7.33–7.17 (5H,m), 7.02–6.94 (3H,m), 6.77 (1H,d), 6.53 (1H,d), 5.84–5.76 (!H,m), 4.49–4.28 (2H,m), 3.99–3.89 (3H,m), 3.87 (3H,s), 3.47–3.35 (2H,m), 3.50–2.50 (1H,bs), 3.14–3.04 (2H,m), 3.00–2.88 (2H,m), 2.08–1.88 (2H,m), 2.01 (3H,s), 1.7–1.3 (2H,m); MS (ESI): M+H=585.

Example 76

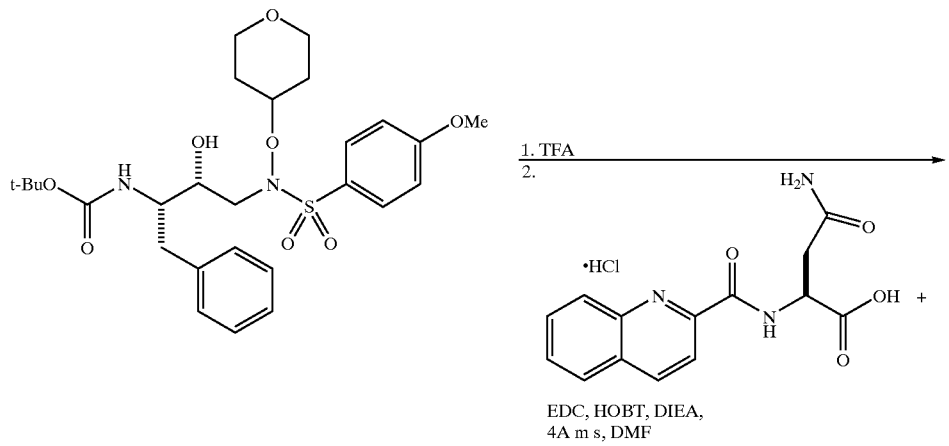

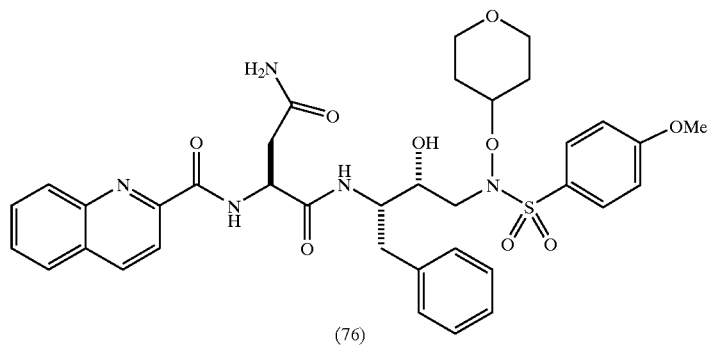

(2S)-N¹-(1S,2R)-1-benzyl-2-hydroxy-3-[[(4-methoxyphenyl)sulfonyl](tetrahydro-2H-pyran-4-yloxy)aminolpropyl-2-[(2-quinolinyl carbonyl)amino]butanediamide. tert-butyl N-(1S,2R)-1-benzyl-2-hydroxy-3-[[(4-methoxyphenyl)sulfonyl](tetrahydro-2H-pyran-4-yloxy)amino]propylcarbamate (Example 18), (0.09 mmol, 50 mg) was stirred in 1 mL trifluoroacetic acid (TFA) at room temperature for 5 hours. The TFA was removed under vacuum, and the resulting residue was dissolved in ethyl acetate, washed with 5% aq. potassium carbonate solution, brine, dried over magnesium sulfate, and concentrated to a residue. The resulting free amine, (2S)-4-amino-4-oxo-2-[(2-quinolinylcarbonyl)amino]butanoic acid hydrochloride (0.09 mmol, 28 mg), 1-hydroxybenzotriazole hydrate (0.09 mmol, 13 mg), N-(3-Dimethylaminopropyl)-N'-ethylcarbodiimide hydrochloride (0.10 mmol, 19 mg), diisopropylethylamine (0.27 mmol, 0.047 mL) and anhydrous N,N-dimethylformamide (0.5 mL) were combined at room temperature and stirred for 20 hours. The crude reaction mixture was concentrated to a residue, dissolved in ethyl acetate, washed with 1N HCl, 5% aq. potassium carbonate solution, brine and dried over magnesium sulfate. The solution was concentrated to a residue, purified by silica gel chromatography (20:1 ethyl acetate/methanol) and crystallization from ether and hexanes, providing 6 mg (8%) of a pink solid. H1-NMR (CDCl₃): δ9.18 (1H,d), 8.31 (1H,d), 8.24–8.13 (2H,m), 7.88 (1H,d), 7.80–7.74 (3H,m), 7.66–7.60 (1H,m), 7.15–7.08 (2H,m), 7.08–6.93 (6H,m), 5.74 (1H,bs), 5.46 (1H,bs), 4.94–4.85 (1H,m), 4.44–4.35 (1H,m), 4.27–4.18 (1H,m), 3.96–3.80 (3H,m), 3.88 (3H,s), 3.47–3.34 (2H,m), 3.14 (1H,bs), 2.98–2.76 (5H,m), 2.72–2.60 (1H,m), 2.09–1.95 (2H,bs), 1.65–1.39 (2H,m); MS (ESI): M+H=720.

Example 77

(77)

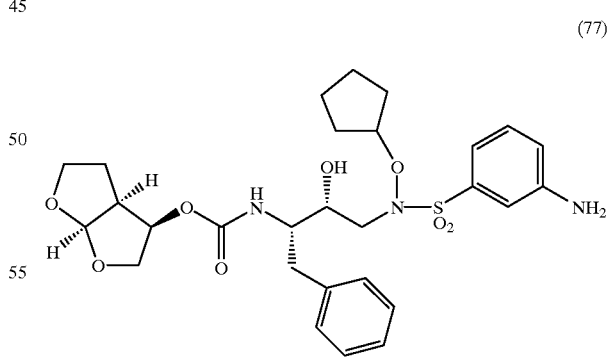

(3R,3aS,6aR)hexahydrofuro[2,3-b]furan-3-yl N-(1S,2R)-3-[[(3-aminophenyl)sulfonyl](cyclopentyloxy)amino]-1-benzyl-2-hydroxypropylcarbamate. This material was obtained from the corresponding m-nitro precursor (Example 100, Step 1) via hydrogenation. The material was identical to isomer 1 of Example 31.

Example 78

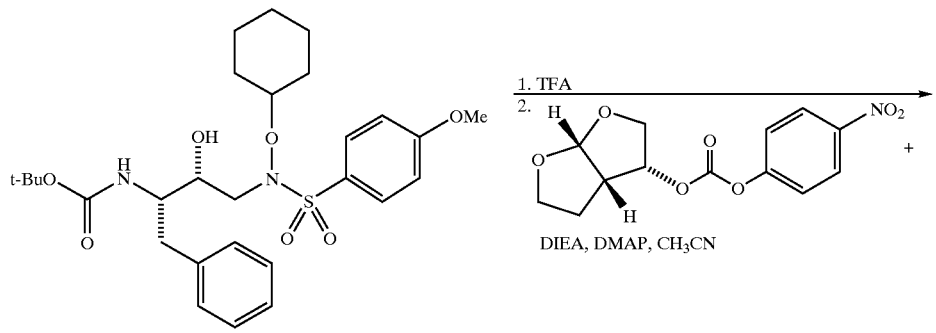

(3R,3aS,6aR)hexahydrofuro [2,3-b]furan-3-yl N-((S,2R)-1-benzyl-3-(cyclohexyloxy)[(4-methoxyphenyl) sulfonyl]] amino-2-hydroxypropyl)carbamate. tert-butyl N-((1S,2R)-1-benzyl-3-(cyclohexyloxy)[(4-methoxyphenyl) sulfonyllamino-2-hydroxypropyl)carbamate (0.09 mmol, SO mg) was stirred in 1 mL trifluoroacetic acid (TFA) at room temperature for 5 hours. The TFA was removed under vacuum, and the resulting residue was dissolved in ethyl acetate, washed with 5% aq. potassium carbonate solution, brine, dried over magnesium sulfate, and concentrated to a residue. The resulting free amine, (2R,3aS,6aR) hexahydrofuro[2,3-b]furan-2-yl 4-nitrophenyl carbonate (0.09 mmol, 27 mg), diisopropylethylamine (0.13 mmol, 0.018 mL), a crystal of N,N-dimethylaminopyridine, 4 A molecular sieves and acetonitrile (0.5 mL) were combined and stirred at room temperature for 3 days. The reaction solution was concentrated to a residue, dissolved in ethyl acetate, washed with 1N HCl, 5% aq. potassium carbonate solution, brine, dried over magnesium sulfate, and concentrated under vacuum. The crude residue was purified by crystallization from ether to yield 15 mg (27%) of white crystals. H1-NMR (CDCl$_3$) δ 7.71 (2H,d), 7.28–7.16 (6H, m), 6.97 (2H,d), 5.63–5.61 (1H,m), 5.00–4.98 (1H,m), 4.87–4.77 (1H,m), 4.24–4.11 (1H,m), 3.98–3.79 (4H,m), 3.87 (3H,s), 3.72–3.61 (2H,m), 3.05 (1H,bs), 3.05–2.72 (6H,m), 2.10–1.98 (2H,m), 1.78–1.68 (2H,m), 1.37–1.04 (6H,m); MS (ESI): M+H=605.

Example 79

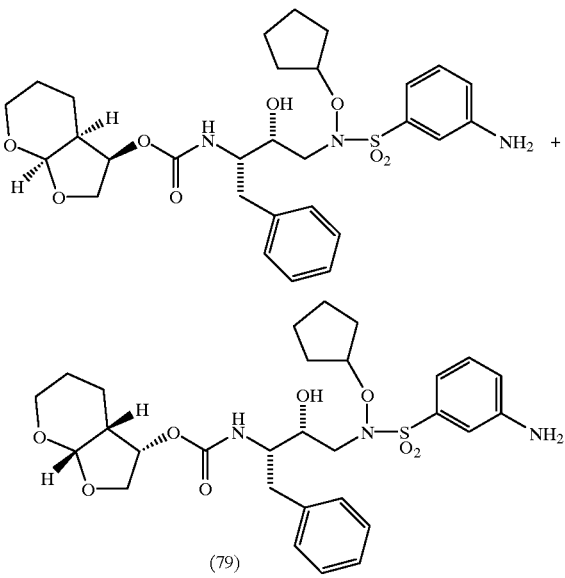

(3S,3aR,7aS)hexahydro-4H-furo[2,3-b]pyran-3-yl N-(1S,2R)-3-[[(3-aminophenyl)sulfonyl](cyclopentyloxy)amino]-1-benzyl-2-hydroxypropylcarbamate+(3R,3aS,7aR)

hexahydro-4H-furo[2,3-b]pyran-3-yl N-(1S,2R)-3-[[(3-aminophenyl)sulfonyl](cyclopentyloxy)amino]-1-benzyl-2-hydroxypropylcarbamate. A mixture of (3R,3aS,7aR)+(3S,3aR,7aS)hexahydro-4H-furo[2,3-b]pyran-3-yl (4-nitrophenyl) carbonate (332 mg, 1.074 mmol, WO 9633187), 3-amino-N-[(2R, 3S)-3-amino-2-hydroxy-4-phenylbutyl]-N-(cyclopentyloxy)-1-benzenesulfonamide (Step 1, Example 27), (150 mg, 0.358 mmol) and N,N-diisopropylethylamine (249 µL, 1.432 mmol) were combined in approximately 3 mL of acetonitrile and stirred at ambient temperature under an Argon atmosphere for 18 hours. The reaction solvent was removed in vacuo and the residue was partitioned between dichloromethane and 1N NaOH. After separating the layers, the aqueous phase was extracted with dichloromethane. The combined organic layers were combined, dried over anhydrous magnesium sulfated, filtered and evaporated in vacuc. The residue was purified on three preparative silica gel TLC plates (20×20 cm, 1000 µM) eluting with 65:35 ethyl acetate hexane. The product band was removed, eluted with 4:1 methylene chloride : methanol, filtered, and evaporated in vacuo. The residue was dissolved in dichloromethane, dried over anhydrous magnesium sulfate, filtered, evaporated in vacuc, and dried under high vacuum to provide a 1:1 mixture of (3S,3aR,7aS)hexahydro-4H-furo[2,3-b]pyran-3-yl N-(1S,2R)-3-[[(3-aminophenyl)sulfonyl](cyclopentyloxy)amino]-1-benzyl-2-hydroxypropylcarbamate and (3R,3aS,7aR) hexahydro-4H-furo[2,3-b]pyran-3-yl N-(1S,2R)-3-[[(3-aminophenyl)sulfonyl](cyclopentyloxy)amino]-1-benzyl-2-hydroxypropylcarbamate (146 mg, 69%) as a foam. H1-NMR (methanol-D4) 1.14 (m, 1H), 1.78 (m, 11H), 2.56 (m, 1H), 3.05 (m, 3H), 3.41 (m, 1H), 3.76 (m, 5H), 4.06 (m, 1H), 4.84 (m, 1H), 4.96 (m, 1H), 5.06 (m, 1H), 6.93 (m, 1H), 7.02 (m, 1H), 7.09 (m, 1H), 7.14 (m, 1H), 7.22 (m, 5H). MS(ESI): 612(M+Na).

Example 80

Step 1

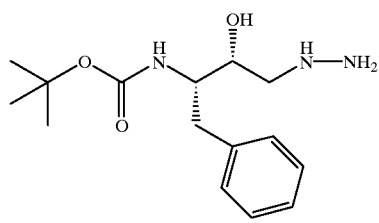

tert-butyl N-[(1S,2R)-1-benzyl-3-hydrazino-2-hydroxypropyl]carbamate. A mixture of tert-butyl N-(1S)-1-[(2S)oxiran-2-yl]-2-phenylethylcarbamate (2.50 g, 9.51 mmol) and anhydrous hydrazine (3.00 mL, 95.0 mmol) in 15 mL of isopropanol was heated at reflux under an Argon atmosphere for 18 hours. The reaction solvent was removed in vacuo and the residue was triturated with diethylether, filtered and dried under high vacuum to provide tert-butyl N-[(1S,2R)-1-benzyl-3-hydrazino-2-hydroxypropyl] carbamate (1.766 g, 63%) as a white solid. H1-NMR (chloroform-D3) 1.35 (d, 9H), 1.67 (b, 4H), 2.89 (m, 4H), 3.91 (m, 3H), 4.63 (m, 1H), 7.25 (m, 5H). MS (ESI): 318(M+Na).

Step 2

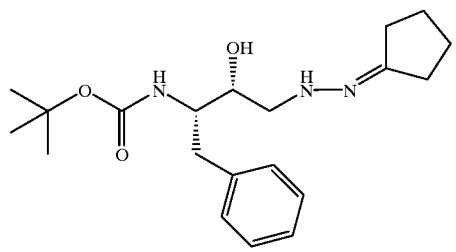

tert-butyl N-[(1S,2R)-1-benzyl-3-(2-cyclopentylidenhydrazino)-2-hydroxypropyl]carbamate.

A solution of tert-butyl N-[(1S,2R)-1-benzyl-3-hydrazino-2-hydroxypropyl]carbamate (500 mg, 1.695 mmol) in 5 mL of isopropanol under Argon was treated with cyclopentanone (180 µL, 2.034 mmol). After stirring for approximately 18 hours, the reaction solvent was removed in vacuo and the residue was triturated with diethylether. The slurry was filtered and the solid was dried under high vacuum to provide tert-butyl N-[(1S,2R)-1-benzyl-3-(2-cyclopentylidenhydrazino)-2-hydroxypropyl]carbamate (85 mg, 14%) as a white solid. H1-NMR (chloroform-D3) 1.34 (s, 9H), 1.54 (b, 2H), 1.73 (m, 2H), 1.83 (m, 2H), 2.22 (m, 2H), 2.35 (m, 2H), 2.90 (m, 1H), 3.02 (m, 1H), 3.14 (m, 1H), 3.38 (m, 1H), 3.64 (bm, 1H), 3.84 (bm, 1H), 4.52 (m, 1H), 7.25 (m, 5H). MS(APCI): 361(M+Na).

Step 3

(80)

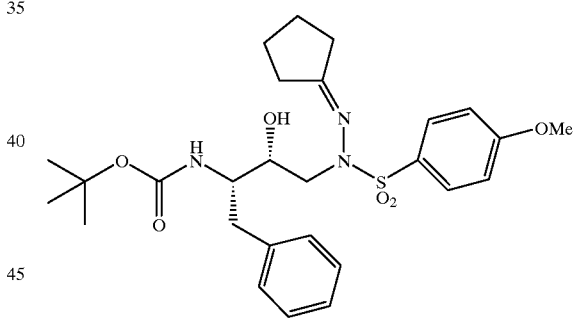

tert-butyl N-((1S,2R)-1-benzyl-3-2-cyclopentyliden-1-[(4-methoxyphenyl)sulfonyl]hydrazino-2-hydroxypropyl) carbamate.

A solution of tert-butyl AT-[(1S,2R)-1-benzyl-3-(2-cyclopentylidenhydrazino)-2-hydroxypropyl]carbamate (76 mg, 0.210 mmol) in 2 mL of dichloromethane at ambient temperature under Argon was treated with 4-methoxyphenylsulphonylchloride (46 mg, 0.221 mmol) and N,N-diisopropylethylamine (38.5 µL, 0.221 mmol) and allowed to stir at ambient temperature over approximately 18 hours. The reaction solvent was removed in vacuc and the residue was purified on flash grade silica gel eluting with 2:3 ethyl acetate:hexane. Fractions containing the product were combined, evaporated in vacuo to a residue and triturated with hexane and diethyl ether. The solvents were removed in vacuo and the residual solid was dried under high vacuum to provide tert-butyl N-((1S,2R)-1-benzyl-3-2-cyclopentyliden-1-[(4-methoxyphenyl)sulfonyl]hydrazino- 2-hydroxypropyl)carbamate (26 mg, 23%) as a solid. H1-NMR (chloroform-D3): 1.34 (m, 9H), 1.62 (m, 4H), 1.83 (m, 2H), 2.42 (m, 1H), 2.87 (m, 3H), 3.12 (m, 1H), 3.58 (m, 1H), 3.83 (m, 5H), 4.32 (m, 1H), 4.57 (b, 1H), 6.97 (m, 2H), 7.20 (m, 5H), 7.69 (m, 2H). MS(APCI): 554(M+Na).

Example 81

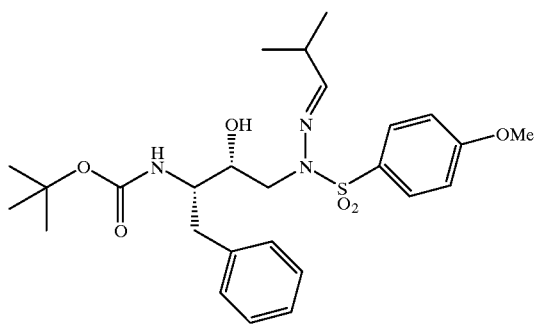

(81)

tert-butyl N-((1S,2R)-1-benzyl-2-hydroxy-3-1-[(4-methoxyphenyl)sulfonyl]-2-[(Z)-2-methylpropylidene]hydrazinopropyl)carbamate. A solution of tert-butyl N-[(1S,2R)-1-benzyl-3-hydrazino-2-hydroxypropyl]carbamate (Step 1, Example 80), (100 mg, 0.339 mmol) in approximately 2 mL of dichloromethane under Argon was treated with isobutyraldehyde (46.2 μL, 0.508 mmol). After stirring at ambient temperature for 20 minutes, 4-methoxyphenylsulphonylchloride (77 mg, 0.372 mmol) and N,N-diisopropylethylamine (88.6 μL, 0.508 mmol) were added and the reaction was maintained for an additional 18 hours. The reaction mixture was evaporated in vacuo and purified on flash grade silica gel eluting with 3:7 ethyl acetate hexane. Fractions containing the product were combined, evaporated in vacuo, and crystallized from ethyl acetate and hexane. The slurry was filtered, washed with hexane, and dried under high vacuum to provide tert-butyl N-((1S,2R)-1-benzyl-2-hydroxy-3-1-[(4-methoxyphenyl)sulfonyl]-2-[(Z)-2-methylpropylidene]hydrazinopropyl)carbamate (34 mg, 19%) as a solid. H1-NMR (chloroform-D3): 1.00 (m, 6H), 1.44 (s, 9H), 1.77 (m, 1H), 2.57 (m, 1H), 2.94 (m, 3H), 3.54 (m, 1H), 3.93 (s, 3H), 3.94 (m, 2H), 4.35 (m, 1H), 7.02 (m, 2H), 7.17 (m, 2H), 7.31 (m, 4H), 7.81 (m, 2H). MS(ESI): 542(M+Na).

Example 82

(82)

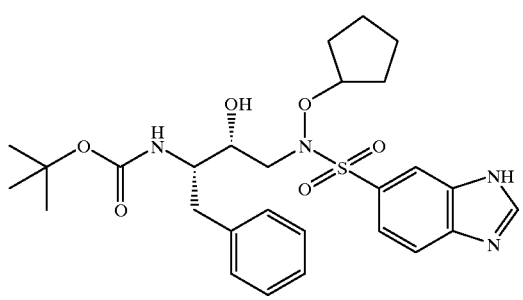

tert-butyl N-(1S,2R)-3-[(1H-benzimidazol-6-ylsulfonyl)(cyclopentyloxy)amino]-1-benzyl-2-hydroxypropylcarbamate. A solution of tert-butyl N-((1S,2R)-1-benzyl-3-(cyclopentyloxy)[(3,4-diaminophenyl)sulfonyl]amino-2-hydroxypropyl)carbamate (Step 4, Example 10), (0.600 g, 1.12 mmol) in absolute ethanol (15 mL) was treated with triethylorthoformate (280 μL, 1.69 mmol) followed by trifluoroacetic acid (15 μL, 0.19 mmol). After stirring at ambient temperature under an Argon atmosphere for 1.5 hrs., the reaction mixture was quenched with several drops of 5% w/v aqueous potassium carbonate and evaporated in vacuo. The residue was purified on flash grade silica gel sequentially eluting with 4:1 ethyl acetate : hexane (0.5 L); ethyl acetate (0.5 L); and 95:5 ethyl acetate : methanol (0.5 L). Fractions containing the product were combined, evaporated in vacuo to a residue and dried under high vacuum to provide tert-butyl N-(1S,2R)-3-[(1H-benzimidazol-6-ylsulfonyl)(cyclopentyloxy)amino]-1-benzyl-2-hydroxypropylcarbamate (0.570 g, 93%). H1-NMR (dimethylsulfoxide-D6): 1.14 (s, 9H), 1.72 (m, 8H), 2.47 (m, 1H), 2.70 (m, 1H), 2.99 (m, 2H), 3.55 (m, 2H), 4.85 (m, 1H), 5.14 (m, 1H), 6.67 (d, 1H), 7.20 (m, 6H), 7.61 (d, 1H), 7.81 (d, 1H), 8.04 (s, 1H), 8.52 (s, 1H). MS(ESI): 545(M+H).

Example 83

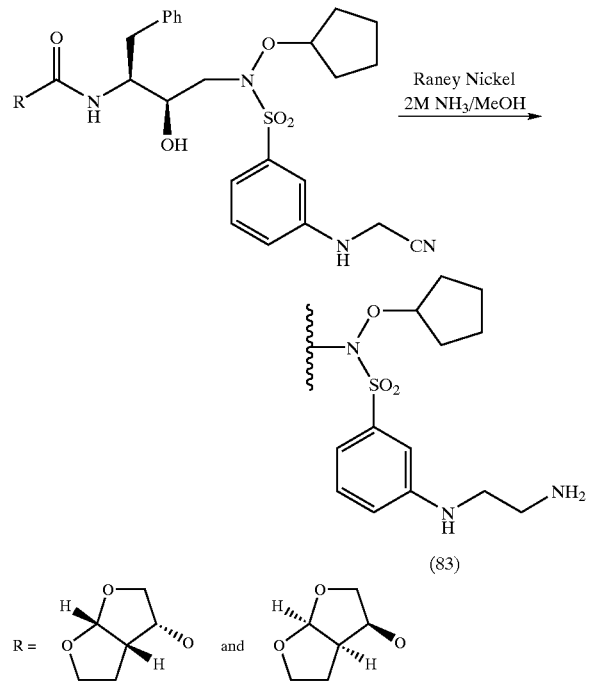

(83)

(3R,3aS,6aR)hexahydrofuro[2,3-b]furan-3-yl N-(1S,2R)-3-[(3-[(2-aminoethyl)amino]phenylsulfonyl)(cyclopentyloxy)aminol-1-benzyl-2-hydroxypropylcarbamate and (3S,3aR,6aS)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate. A solution of 25 mg (0.041 mmol) of a 1:1 mixture of (3R,3aS, 6aR) hexahydrofuro[2,3-b]furan-3-yl N-(1S,2R)-1-benzyl-3-[(3-[(cyanomethyl)aamino]phenylsulfonyl) (cyclopentyloxy) amino]-2-hydroxypropylcarbamate and (3S,3aR,6aS) hexahydrofuro[2,3-b]furan-3-yl N-(iS,2R)-1-benzyl-3-[(3-[(cyanomethyl)amino]phenylsulfonyl) (cyclopentyloxy) amino]-2-hydroxypropylcarbamate (see example 86) in 8 mL of 2M NH$_3$/MeOH in a Parr bottle was treated with approximately 20 mg of Raney nickel. The resulting mixture was subjected to hydrogenation at 30 psi for 1 hour. The vessel was purged, catalyst removed by filtration through celite and the filtrate concentrated in vacuo. The residue was dissolved in a minimum volume of $CH_2Cl_2$ and the solution added dropwise to rapidly stirred 1:1 ether/hexane. A white solid precipitated which was collected by filtration and dried in vacuo. yield=16 mg (64%). 1H-NMR (DMSO-$d_6$): 7.32–7.03 (7H), 6.95–6.78 (3H), 6.20 (1H), 5.45 (1H), 5.19 (1H), 4.82–4.65 (2H), 3.81–3.40 (7H), 3.18–2.60 (9H), 2.39 (1H), 1.93–1.04 (10H). MS(ESI): 619(M+H).

Example 84

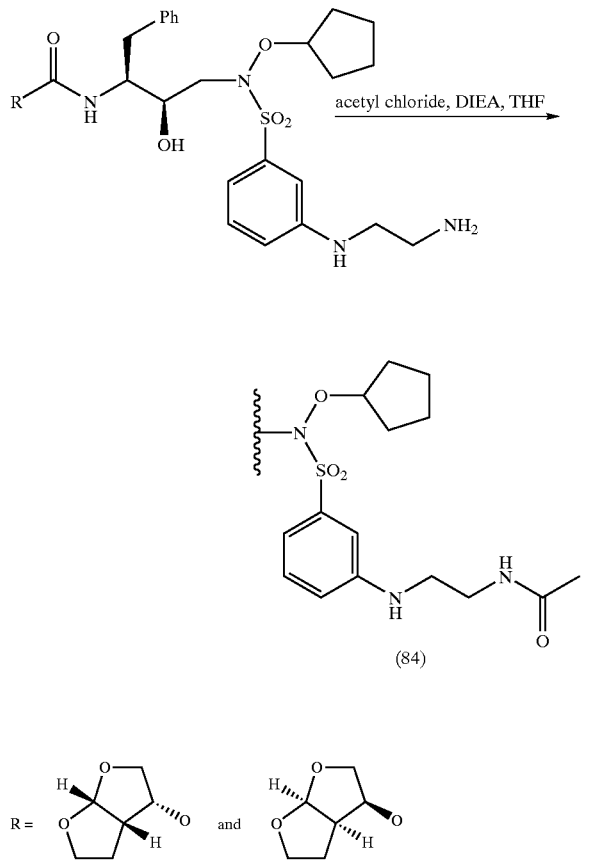

(84)

(3R,3aS,6aR)hexahydrofuro[2,3-b]furan-3-yl N-(1S,2R)-3-[[(3-[2-(acetylamino)ethyl]aminophenyl)sulfonyl] (cyclopentyloxy) amino]-1-benzyl-2-hydroxypropylcarbamate and (3S,3aR,6aS)hexahydrofuro[2,3-b]furan-3-yl N-(1S,2R)-3-[[(3-[2-(acetylamino)ethyl] aminophenyl)sulfonyl](cyclopentyloxy) amino]-1-benzyl-2-hydroxypropylcarbamate. A solution of 33 mg (0.053 mmol) of a 1:1 mixture of (3R,3aS,6aR)hexahydrofuro[2,3-b]furan-3-yl N-(1S,2R)-3-[(3-[(2-aminoethyl)amino] phenylsulfonyl)(cyclopentyloxy)amino]-1-benzyl-2-hydroxypropylcarbamate and (3S,3aR,6aS)hexahydrofuro[2,3-b]furan-3-yl N-(1S,2R)-3-[(3-[(2-aminoethyl)amino] phenylsulfonyl)(cyclopentyloxy)amino]-1-benzyl-2-hydroxypropylcarbamate in 3 mL of anhydrous THF at 0° C. was treated with 0.010 mL (0.058 mmol) of N,N-diisopropylethylamine followed by 0.004 mL (0.06 mmol) of acetyl chloride. The resulting solution was allowed to warm to RT with stirring. After 18 hours the solution was concentrated in vacuo and the residue subjected to flash chromatography (silica gel, 95:5 $CH_2Cl_2$/2M $NH_3$ in MeOH) to afford 30 mg (86%) of the desired product as a white foam. 1H-NMR (CDCl$_3$): 7.71–7.00 (10H), 6.90 (1H), 6.40–6.02 (1H), 5.62 (1H), 5.32 (1H), 4.99 (1H), 4.80 (1H), 4.02–3.40 (7H), 3.38–2.60 (8H), 2.20–1.40 (13H). LCMS (ESI): 661(M+H)

Example 85

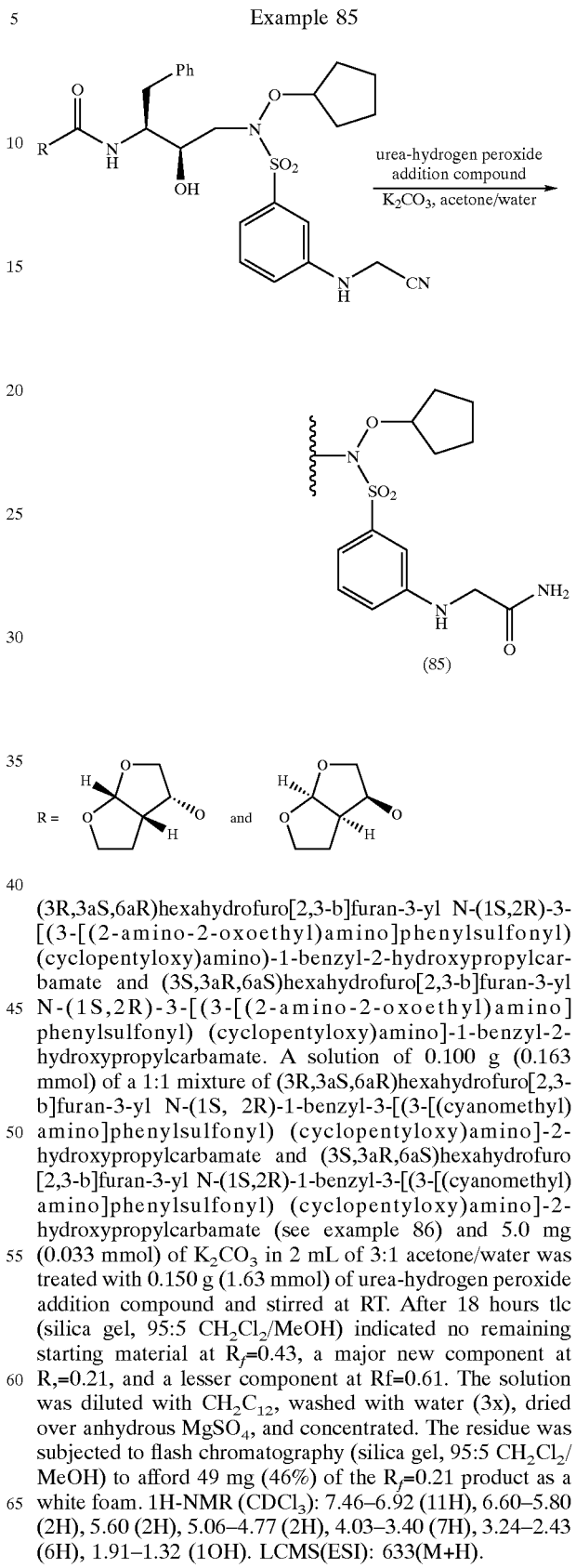

(85)

(3R,3aS,6aR)hexahydrofuro[2,3-b]furan-3-yl N-(1S,2R)-3-[(3-[(2-amino-2-oxoethyl)amino]phenylsulfonyl) (cyclopentyloxy)amino)-1-benzyl-2-hydroxypropylcarbamate and (3S,3aR,6aS)hexahydrofuro[2,3-b]furan-3-yl N-(1S,2R)-3-[(3-[(2-amino-2-oxoethyl)amino] phenylsulfonyl) (cyclopentyloxy)amino]-1-benzyl-2-hydroxypropylcarbamate. A solution of 0.100 g (0.163 mmol) of a 1:1 mixture of (3R,3aS,6aR)hexahydrofuro[2,3-b]furan-3-yl N-(1S, 2R)-1-benzyl-3-[(3-[(cyanomethyl) amino]phenylsulfonyl) (cyclopentyloxy)amino]-2-hydroxypropylcarbamate and (3S,3aR,6aS)hexahydrofuro [2,3-b]furan-3-yl N-(1S,2R)-1-benzyl-3-[(3-[(cyanomethyl) amino]phenylsulfonyl) (cyclopentyloxy)amino]-2-hydroxypropylcarbamate (see example 86) and 5.0 mg (0.033 mmol) of $K_2CO_3$ in 2 mL of 3:1 acetone/water was treated with 0.150 g (1.63 mmol) of urea-hydrogen peroxide addition compound and stirred at RT. After 18 hours tlc (silica gel, 95:5 $CH_2Cl_2$/MeOH) indicated no remaining starting material at $R_f$=0.43, a major new component at $R_f$=0.21, and a lesser component at Rf=0.61. The solution was diluted with $CH_2Cl_2$, washed with water (3x), dried over anhydrous $MgSO_4$, and concentrated. The residue was subjected to flash chromatography (silica gel, 95:5 $CH_2Cl_2$/MeOH) to afford 49 mg (46%) of the $R_f$=0.21 product as a white foam. 1H-NMR (CDCl$_3$): 7.46–6.92 (11H), 6.60–5.80 (2H), 5.60 (2H), 5.06–4.77 (2H), 4.03–3.40 (7H), 3.24–2.43 (6H), 1.91–1.32 (10H). LCMS(ESI): 633(M+H).

Example 86

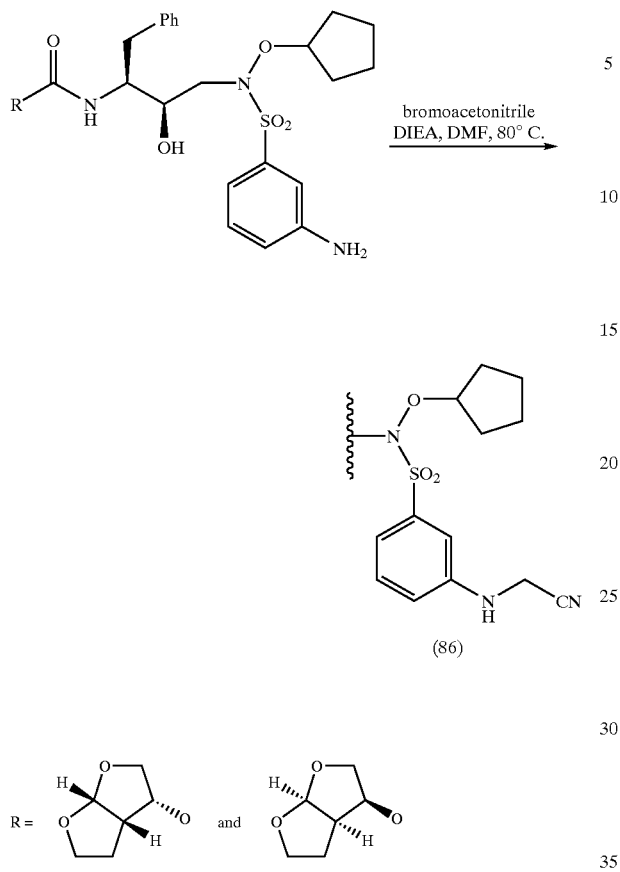

(3R,3aS,6aR)hexahydrofuro[2,3-b]furan-3-yl N-(1S,2R)-1-benzyl-3-[(3-[(cyanomethyl)amino]phenylsulfonyl)(cyclopentyloxy)amino]-2-hydroxypropylcarbamate and (3S,3aR,6aS)hexahydrofuro[2,3-b]furan-3-yl N-(1S,2R)-1-benzyl-3-[(3-[(cyanomethyl)amino]phenylsulfonyl)(cyclopentyloxy)amino]-2-hydroxypropylcarbamate A solution of 0.200 g (0.347 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 0.050 mL (0.70 mmol) of bromoacetonitrile, and 0.12 mL (0.70 mmol) of N,N-diisopropylethylamine in 5 mL of anhydrous DMF was heated to 80OC with stirring in a sealed tube. After 21 hours the solution was cooled to RT and concentrated in vacuo. The residue was dissolve in $CH_2Cl_2$. The resulting solution was washed with aqueous brine (3x), dried over anhydrous $MgSO_4$, and concentrated to dryness. The crude product was purified by flash chromatography (silica gel, 95:5 $CH_2Cl_2$/MeOH) to afford 145 mg (67%) of the desired product as a tan solid. 1H-NMR (DMSO-$d_6$): 7.41 (1H), 7.28–6.99 (9H), 6.83 (1H), 5.46 (1H), 5.20 (1H), 4.82–4.63 (2H), 4.30 (2H), 3.80–3.40 (5H), 3.04–2.60 (5H), 2.40 (1H), 1.98–1.10 (10H). MS(ESI): 615(M+H).

Example 87

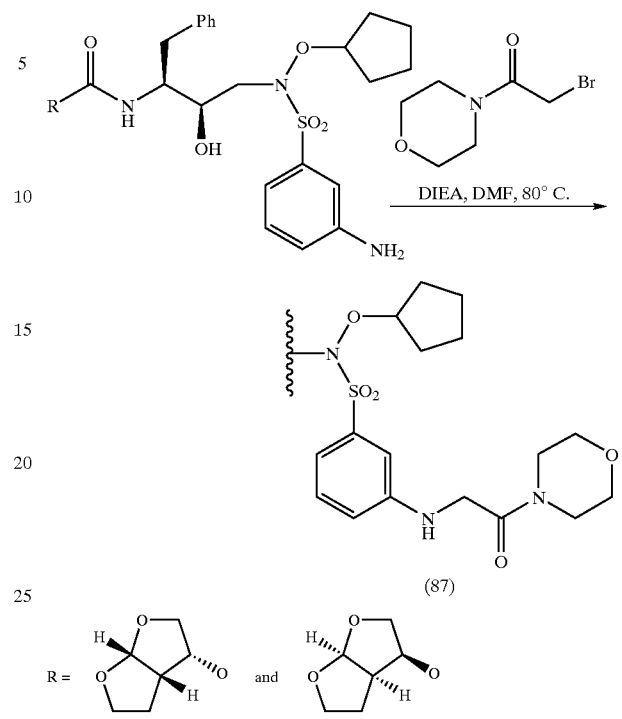

(3R,3aS,6aR)hexahydrofuro[2,3-b]furan-3-yl N-(1S,2R)-1-benzyl-3-[(cyclopentyloxy)(3-[(2-morpholino-2-oxoethyl)amino)phenylsulfonyl)amino]-2-hydroxypropylcarbamate and (3S,3aR,6aS)hexahydrofuro[2,3-b]furan-3-yl N-(1S,2R)-1-benzyl-3-[(cyclopentyloxy)(3-[(2-morpholino-2-oxoethyl)amino]phenylsulfonyl)amino]-2-hydroxypropylcarbamate. A solution of 0.100 g (0.174 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 54.0 mg (0.261 mmol) of N-(bromoacetyl)morpholine, and 0.050 mL (0.26 mmol) of N,N-diisopropylethylamine in 4 mL of anhydrous DMF was heated to 80° C. with stirring in a sealed tube. After 4.5 hours the solution was cooled to RT and was treated with an additional 54.0 mg of N-(bromoacetyl)morpholine, and 0.050 mL (0.26 mmol) of N,N-diisopropylethylamine. The solution was heated at 80° C. for an additional 18 hours, cooled to RT, and concentrated in vacuo. The crude product was purified by flash chromatography (silica gel, EtOAc) to give a viscous yellow oil. This material was dissolved in a minimum volume of $CH_2Cl_2$ and the solution was added to rapidly stirred 1:1 ether/hexane. A white solid precipitated which was collected by filtration and dried in vacuo. yield=54 mg (44%). 1H-NMR (DMSO-$d_6$): 7.31–7.06 (7H), 7.03–6.83 (3H), 6.26 (1H), 5.45 (1H), 5.18 (1H), 4.71 (2H), 3.92 (2H), 3.79–3.22 (13H), 3.08–2.60 (5H), 2.39 (1H), 1.95–1.04 (10H). LCMS(ESI): 703(M+H).

Example 88

Step 1

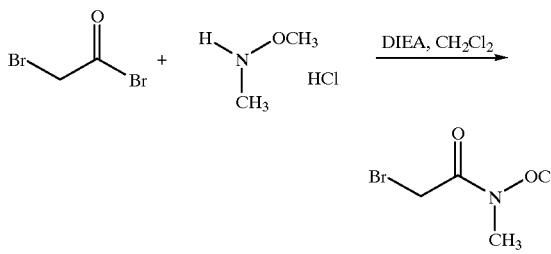

N-methoxy-N-methylbromoacetamide A solution of 4.5 mL (51.3 mmol) of bromoacetylbromide and 5.00 g (51.3 mmol) of N,O-dimethylhydroxylamine hydrochloride in 80 mL of anhydrous $CH_2Cl_2$ at 0° C. was treated with a solution of 18.7 mL (108 mmol) of N,N-diusopropylethylamine in 40 mL of $CH_2C_{12}$ via addition funnel over 10 minutes. A dark brown solution resulted which was allowed to warm to RT. After 18 hours the solution was washed with 5% aqueous citric acid (3x), saturated aqueous $NaHCO_3$ (3x), dried over $MgSO_4$, and concentrated to give a dark brown oil. This material was subjected to flash chromatography (8:2 to 6:4 hexane/EtOAc) to afford 2.97 g (32%) of the desired product as a yellow-brown liquid. 1H-NMR ($CDCl_3$): 4.22 (2H), 3.72 (3H), 3.20 (3H).

Step 2

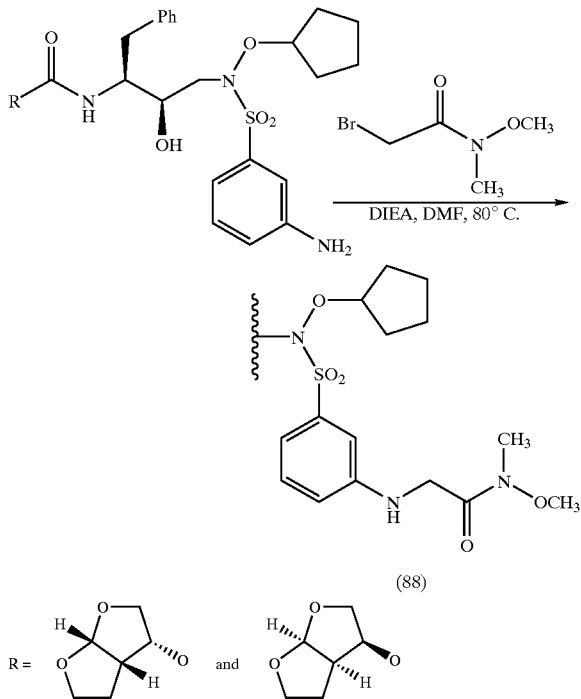

(3R,3aS,6aR)hexahydrofuro[2,3-b]furan-3-yl N-[(1S,2R)-1-benzyl-3-((cyclopentyloxy)[3-(2-[methoxy(methyl)amino]-2-oxoethylamino)phenyl]sulfonylamino)-2-hydroxypropyl]carbamate and (3S,3aR, 6aS) hexahydrofuro [2,3-b]furan-3-yl N-[(1S,2R)-1-benzyl-3-((cyclopentyloxy) [3-(2-[methoxy(methyl)amino]-2-oxoethylamino)phenyl] sulfonylamino)-2-hydroxypropyl]carbamate. A solution of 0.100 g (0.174 mmol) of a 1:1 mixture of (3R,3aS,6aR) hexahydrofuro[2,3-b]furan-3-yl N-((1S, 2R)-1-benzyl-3-(cyclopentyloxy)[(3-aminophenyl)sulfonyl]amino-2-hydroxypropyl)carbamate and (3S,3aR,6aS)hexahydrofuro [2,3-b]furan-3-yl N-((1S,2R)-1-benzyl-3-(cyclopentyloxy) [(3-aminophenyl)sulfonyl]amino-2-hydroxypropyl) carbamate (see example 31), 40.0 mg (0.210 mmol) of N-methoxy-N-methylbromoacetamide, and 0.040 mL (0.21 mmol) of N,N-diisopropylethylamine in 3 mL of anhydrous DMF was heated to 80° C. with stirring in a sealed tube. After 24 hours the solution was cooled to RT and was treated with an additional 20.0 mg of N-methoxy-N-methylbromoacetamide and 0.020 mL of N,N-diisopropylethylamine. The solution was again warmed to 80° C. After an additional 18 hours the solution was cooled to RT and was concentrated in vacuo. The residue was dissolved in $CH_2Cl_2$. The solution was washed with saturated aqueous brine (3x), dried over $MgSO_4$, and concentrated to dryness. The crude product was purified by flash chromatography (silica gel, 85:15 hexane/EtOAc) to afford 40 mg (34%) of the desired product as a white foam. 1H-NMR ($CDCl_3$): 7.40–6.84 (11H), 5.62(1H), 5.18–4.87 (2H), 4.81(1H), 4.05 (2H), 3.99–3.53 (8H), 3.26–2.70 (9H), 1.92–1.41 (10H). LCMS(ESI): 677(M+H).

Example 89

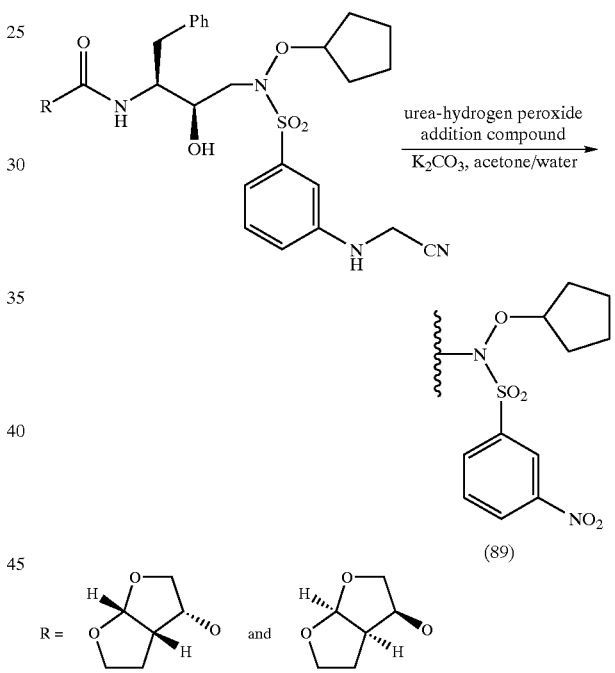

(3R,3aS,6aR)hexahydrofuro[2,3-b]furan-3-yl N-((1S,2R)-1-benzyl-3-(cyclopentyloxy)[(3-nitrophenyl)sulfonyl] amino-2-hydroxypropyl)carbamate and (3S,3aR,6aS) hexahydrofuro[2,3-b]furan-3-yl N-((1S,2R)-1-benzyl-3-(cyclopentyloxy)[(3-nitrophenyl)sulfonyl]amino-2-hydroxypropyl)carbamate A solution of 0.100 g (0.163 mmol) of a 1:1 mixture of (3R, 3aS, 6aR) hexahydrofuro [2,3-b]furan-3-yl N-(iS,2R)-1-benzyl-3-[(3-[(cyanomethyl) amino]phenylsulfonyl)(cyclo pentyloxy)amino]-2-hydroxypropylcarbamate and (3S,3aR,6aS)hexahydrofuro [2,3-b]furan-3-yl N-(1S,2R)-1-benzyl-3-[(3-[(cyanomethyl) aminolphenylsulfonyl) (cyclopentyloxy)amino]-2-hydroxypropylcarbamate (see example 86) and 5.0 mg (0.033 mmol) of $K_2CO_3$ in 2 mL of 3:1 acetone/water was treated with 0.150 g (1.63 mmol) of urea-hydrogen peroxide addition compound and was stirred at RT. After 18 hours tic (silica gel, 95:5 $CH_2Cl_2$/MeOH) indicated no remaining starting material at $R_f$=0.43, a major new component at Rf=0.21, and a lesser component at $R_f$=0.61. The solution was diluted with $CH_2Cl_2$, washed with water (3x), dried over anhydrous $MgSO_4$, and concentrated. The residue was subjected to flash chromatography (silica gel, 95:5 $CH_2Cl_2$/MeOH) to afford 15 mg (15%) of the $R_f$=0.61 product as a white foam. 1H-NMR ($CDCl_3$): 8.62 (1H), 8.51 (1H), 8.06 (1H), 7.75 (1H), 7.31–7.14 (6H), 5.65 (1H), 5.08–4.78 (3H), 3.98–3.57 (5H), 3.22–2.60 (6H), 1.95–1.40 (10H). LCMS (ESI): 606 (M+H)

Example 90

Step 1

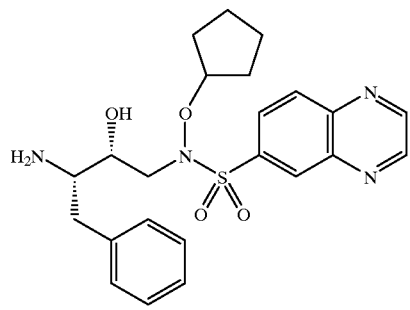

(3R,4S)-4-amino-i-(cyclopentyloxy)-5-phenyl-i-(6-quinoxalinyl sulfonyl)-3-pentanol. A mixture of tert-butyl N-[(1S,2R)-1-benzyl-4-(cyclopentyloxy)-2-hydroxy-4-(6-quinoxalinylsulfonyl)butyl]carbamate (563 mg, 1.01 mmol) and trifluoroacetic acid (5 mL) was stirred under an Argon atmosphere for 0.5 hrs. The acid was removed in vacuo and the residue was partitioned between dichloromethane and 1N sodium hydroxide. The organic layer was separated and the aqueous layer was extracted again with dichloromethane. The combined organic layers were dried over anhydrous sodium sulfate, filtered and evaporated in vacuo. The crude product was purified on flash grade silica gel eluting with dichloromethane : methanol (98:2). Fractions containing the product were combined and evaporated in vacuo and dried under high vacuum to provide (3R,4S)-4-amino-1-(cyclopentyloxy)-5-phenyl-1-(6-quinoxalinylsulfonyl)-3-pentanol as a foam (379 mg, 82%). H1-NMR (chloroform-D3): 1.66 (m, 11H), 2.51 (m, 1H), 2.86 (m, 1H), 3.07 (m, 1H), 3.23 (m, 1H), 3.32 (m, 1H), 3.84 (m, 1H), 4.90 (m, 1H), 7.20 (m, 5H), 8.16 (m, 1H), 8.28 (d, 1H), 8.70 (m, 1H), 8.99 (m, 2H<. MS(ESI): 457(M+H).

Step 2

(90)

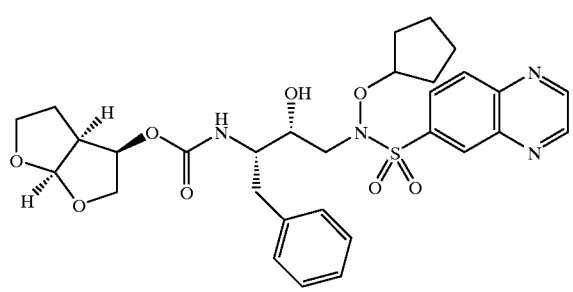

(3R,3aS,6aR)hexahydrofuro[2,3-b]furan-3-yl N-[(1S,2R)-1-benzyl-4-(cyclopentyloxy)-2-hydroxy-4-(6-quinoxalinylsulfonyl)butyl]carbamate. A mixture of (3R, 4S)-4-amino-i-(cyclopentyloxy)-5-phenyl-i-(6-quinoxalinylsulfonyl)-3-pentanol (50 mg, 0.110 mmoL), (2R,3aS,6aR)hexahydrofuro[2,3-b]furan-2-yl 4-nitrophenyl carbonate (37.3 mg, 0.121 mmol), and N,N-diisopropylethylamine (47.8 AL, 0.274 mmol) were combined under an Argon atmosphere in approximately 1.5 mL of acetonitrile. After stirring at ambient temperature for 16 hours, the solvent was removed in vacuo and the residue was dissolved in ethyl acetate and washed three times with 5% w/v aqueous potassium carbonate. The combined aqueous layers were back-extracted with ethyl acetate. The combined organic layers were washed with brine, dried over anhydrous magnesium sulfate, filtered and evaporated in vacuo. The crude product was purified on a preparative TLC plate (20×20 cm, 1000 μM) eluting with 95:5 dichloromethane : methanol. The product band was removed, eluted with 3:1 methylene chloride:methanol, filtered, and evaporated in vacuo. The residual solid was dried under high vacuum to provide (3R,3aS,6aR)hexahydrofuro[2,3-b]furan-3-yl N-[(1S,2R)-1-benzyl-4-(cyclopentyloxy)-2-hydroxy-4-(6-quinoxalinylsulfonyl)butyl]carbamate (53 mg, 79%). H1-NMR (chloroform-D3): 1.58 (m, 6H), 1.81 (m, 4H), 2.80 (m, 1H), 2.95 (m, 4H), 3.17 (m, 1H), 3.65 (m, 2H), 3.88 (m, 4H), 4.85 (m, 2H), 4.98 (m, 1H), 5.62 (d, 1H), 7.21 (m, 5H), 8.08 (m, 1H), 8.26 (d, 1H), 8.63 (m, 1H), 9.00 (m, 1H). MS(ESI): 613(M+H).

Example 91

(91)

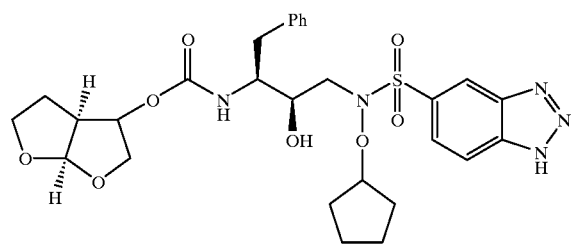

(3aS,6aR)Hexahydrofuro[2,3-b]furan-3-yl N-(1S,2R)-1-benzyl-3-[(cyclopentyloxy)(benzotriazole-5-ylsulfonyl)amino]-2-hydroxypropylcarbamate. (3aS,6aR)Hexahydrofuro[2,3-b]furan-3-yl N-(1S,2R)-1-benzyl-3-[(cyclopentyloxy)-amino]-2-hydroxypropylcarbamate (280 mg, 0.666 mmol) (Step 2, Example 54), benzotrizole-5-sulfonyl chloride (140 mg, 0.666 mmol), and anhydrous diisopropylethylamine (0.04 mL, 0.238 mmol) were combined in anhydrous tetrahydrofuran (5 mL) in a 25 mL round bottomed flask under nitrogen. The reaction was stirred for 24 hours and concentrated in vacuo. After the workup described in Step 3, Example 54, the residue was purified by preparative silica gel TLC using 90:10 chloroform: methanol as an eluent to give the product as a white foam (70 mg, 0.116 mmol, 17%). $^1$HNMR ($d_6$-DMSO) δ: 8.42 (bs, 1H), 8.16 (bs, 1H), 7.84 (bs, 1H), 7.26–7.15 (m, 5H), 5.51–5.47 (m, 1H), 5.31–5.28 (m, 1H), 4.85–4.70 (m, 2H), 4.12 (m, 1H), 3.79–1.15 (m, 21H). MS(ES): 602 (M+1), 600 (M−1).

Example 92

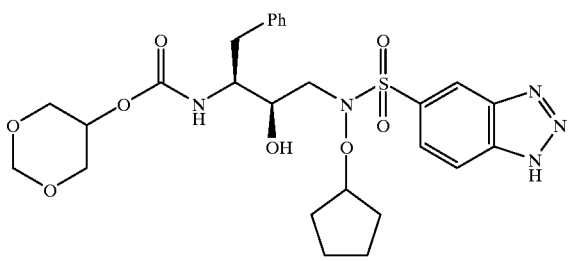

(92)

1,3-Dioxan-5-yl N-(1S,2R)-1-benzyl-3-[(cyclopentyloxy) (benzotriazole-5-ylsulfonyl)amino]-2-hydroxypropylcarbamate. 1,3-Dioxan-5-yl N-(1S,2R)-1-benzyl-3-[(cyclopentyloxy)amino]-2-hydroxypropylcarbamate (Step 1, Example 55), (130 mg, 0.330 mmol), benzotriazole-5-sulfonyl chloride (72 mg, 0.330 mmol), and anhydrous diisopropylethylamine (0.06 mL, 0.330 mmol), were combined in anhydrous tetrahydrofuran (5 mL) in a 25 mL round bottomed flask under nitrogen. The reaction was stirred for 24 hours and concentrated in vacuo. After the workup described in Step 3, Example 54, the residue was purified by preparative silica gel TLC using 90:10 chloroform: methanol as an eluent to give the product as a white film (56 mg, 0.0973 mmol, 30%). $^1$HNMR (d$_6$-DMSO) δ: 8.43 (bs, 1H), 8.14 (m, 1H), 7.83 (m, 1H), 7.27–7.15 (m, 5H), 4.86–4.66 (m, 3H), 4.23–3.02 (m, 13H), 1.93–1.40 (m, 8H). MS(ES): 576 (M+1), 574 (M−1).

Example 93

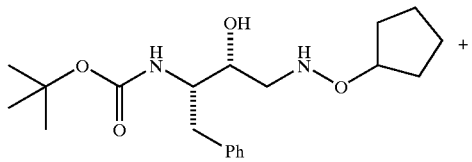

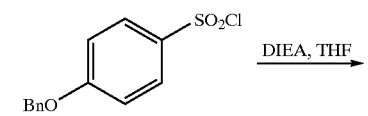

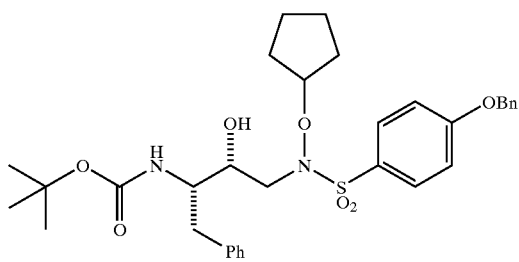

(93)

tert-butyl N-(1S,2R)-1-benzyl-3-[[4-(benzyloxy)phenyl]sulfonyl(cyclopentyloxy) amino]-2-hydroxypropylcarbamate.

tert-butyl N-(1S,2R)-1-benzyl-3-[(cyclopentyloxy)amino]-2-hydroxypropylcarbamate (3.5 mmol, 807 mg), 3-phenoxybenzenesulfonyl chloride (3.5 mmol, 1.0 g), and diisopropylethylamine (5.3 mmol, 0.924 mL) were dissolved in anhydrous THF (10 mL), and the solution was stirred at room temperature under nitrogen for 72 hours. The reaction was concentrated to a white solid under vacuum, dissolved in ethyl acetate, washed with 1N HCl, 1N NaOH, brine, dried over magnesium sulfate and concentrated. The crude product was purified by silica gel chromatography (2:1 hexanes/ethyl acetate) and yielded 1.08 g (50%) of a white solid. Note: The 3-phenoxybenzenesulfonyl chloride was prepared from 4-bromophenylbenzylether (Corrie, J.; Papageorgiou, G. *J. Chem. Soc.*, *Perkin Trans.* 1 1996, 1583). R$_f$=0.3 (5:1 hexanes/ethyl acetate); H$_1$-NMR (CDCl$_3$): δ 7.69 (2H,d), 7.41–7.28 (5H,m), 7.27–7.19 (6H, m), 7.03 (2H,d), 5.11 (2H,s), 4.79 (1H,m), 4.56 (1H,m), 3.79 (2H,bs), 3.31 (1H,bs), 3.02 (1H,m), 2.91 (2H,m), 2.79 (1H,m), 1.85–1.67 (4H,m), 1.67–1.43 (4H,m), 1.32 (9H,s).

Example 94

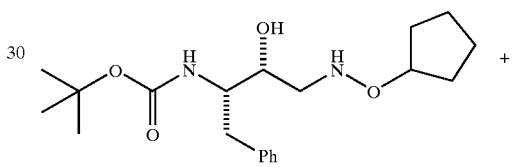

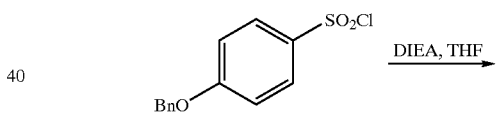

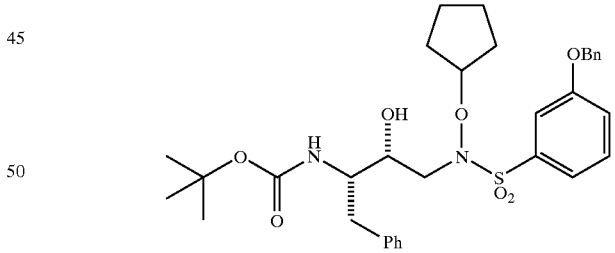

(94)

tert-butyl N-(1S,2R)-1-benzyl-3-[[3-(benzyloxy)phenyl] sulfonyl (cyclopentyloxy) amino]-2-hydroxypropylcarbamate. This compound was prepared under the same conditions described for the tert-butyl N-(1S,2R)-1-benzyl-3-[[4-(benzyloxy)phenyl]sulfonyl (cyclopentyloxy)amino]-2-hydroxypropylcarbamate. R=0.3 (5:1 hexanes/ethyl acetate); H1-NMR (CDCl$_3$): δ 7.44–7.30 (8H,m), 7.29–7.16 (7H,m), 5.08 (2H,s), 4.79 (1H,m), 4.53 (1H,m), 3.78 (2H, bs), 3.34 (1H,bs), 3.06 (1H,m), 2.91 (2H,m), 1.85–1.66 (4H,m), 1.66–1.43 (4H,m), 1.32 (9H,s).

Example 95

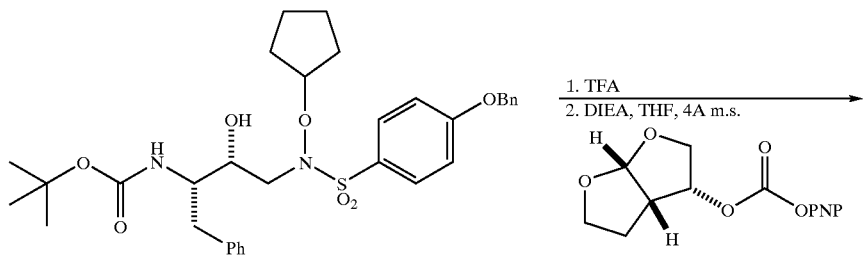

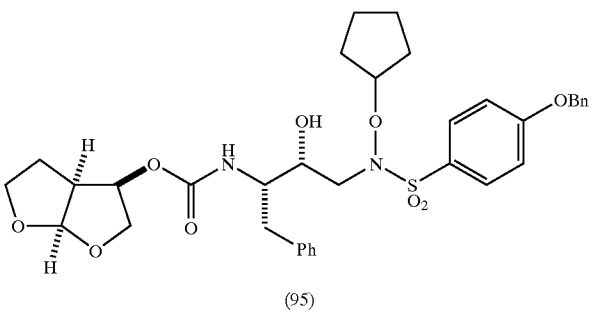

(95)

(3R,3aS,6aR)hexahydrofuro[2,3-b]furan-3-yl N-(1S,2R)-1-benzyl-3-[[4-(benzyloxy)phenyl]sulfonyl(cyclopentyloxy)amino]-2-hydroxypropylcarbamate. This compound was prepared (from Example 93) under the conditions described for (3R,3aS,6aR)hexahydrofuro[2,3-b]furan-3-yl N-((1S,2R)-1-benzyl-3-(cyclohexyloxy)[(4-methoxyphenyl)sulfonyl]amino-2-hydroxypropyl)carbamate. $R_f$=0.2 (2:1 hexanes/ethyl acetate); H1-NMR (CDCl$_3$): δ7.70 (2H,d), 7.44–7.31 (5H,m), 7.29–7.11 (6H,m), 7.05 (2H,d), 5.63 (1H,s), 5.11 (2H,s), 5.00 (1H,m), 4.88–4.74 (2H,m), 3.96–3.78 (4H,m), 3.67 (2H,m), 3.08 (1H,bs), 3.05–2.94 (2H,m), 2.90 (2H,m), 2.81 (2H,m), 1.87–1.68 (4H,m), 1.68–1.44 (4H,m).

(3R,3aS,6aR)hexahydrofuro[2,3-b]furan-3-yl N-(1S,2R)-1-benzyl-3-[[3-(benzyloxy)phenylsulfonyl(cyclopentyloxy)amino]-2-hydroxypropylcarbamate. This compound was prepared under the conditions (from Example 94) described for (3R,3aS,6aR)hexahydrofuro[2,3-b]furan-3-yl N-(1S,2R)-1-benzyl-3-(cyclohexyloxy)[(4-methoxyphenyl)sulfonyl]amino-2-hydroxypropyl)carbamate. $R_f$=0.2 (2:1 hexanes/ethyl acetate); H1-NMR (CDCl$_3$): δ 7.48–7.30 (8H,m), 7.30–7.11 (7H,m), 5.59 (1H,s), 5.09 (2H,s), 4.97 (1H,m), 4.78 (2H,m), 3.95–3.77 (4H,m), 3.71–3.57 (2H,m), 3.12 (1H,bs), 3.05–2.90 (3H,m), 2.90–2.72 (3H,m), 1.88–1.67 (4H,m), 1.67–1.42 (4H,m).

Example 96

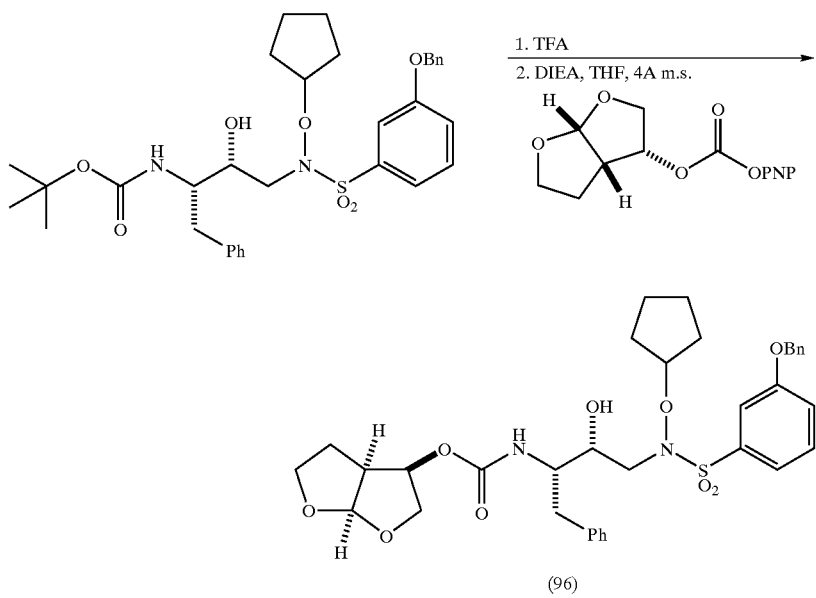

(96)

Example 97

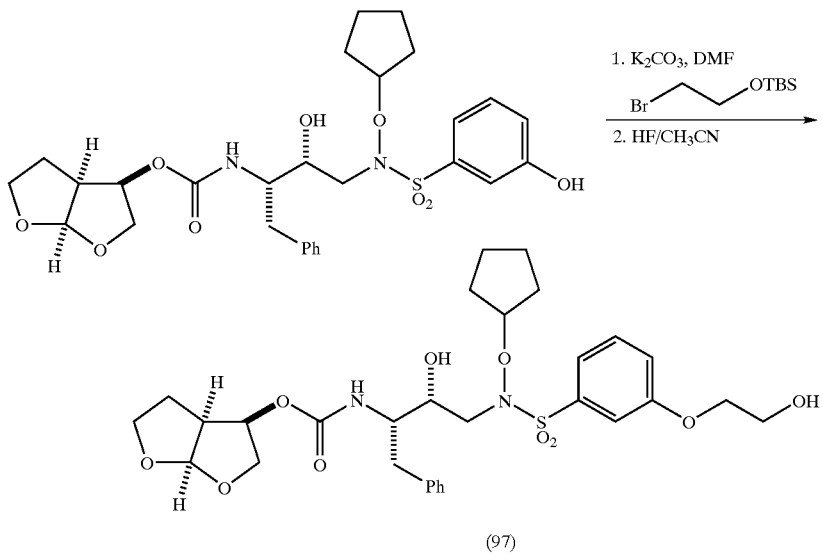

(3R,3aS,6aR)hexahydrofuro[2,3-b]furan-3-yl N-[(1S,2R)-1-benzyl-3-((cyclopentyloxy)[3-(2-hydroxyethoxy) phenyl] sulfonylamino)-2-hydroxypropyl]carbamate. This compound was synthesized (from Example 44) under the same conditions as Example 42 (3R,3aS,6aR)hexahydrofuro [2,3-b]furan-3-yl N-[(1S,2R)-1-benzyl-3-((cyclopentyloxy)[4-(2-hydroxyethoxy)phenyl]sulfonylamino)-2-hydroxypropyl] carbamate. $R_f$=0.1 (1:1 hexanes/ethyl acetate); H1-NMR (CDCl$_3$): δ7.47–7.14 (10H,m), 5.63 (1H, s), 5.00 (1H,m), 4.88–4.70 (2H,m), 4.12 (2H,m), 3.98 (2H, m), 3.94–3.72 (5H,m), 3.72–3.51 (2H,m), 3.14 (1H,bs), 3.07–2.69 (5H,m), 2.20 (1H,bs), 1.89–1.69 (4H,m), 1.69–1.42 (4H,m); MS (ESI): M+H=621.

Example 98 solution of (3R,3aS,6aR)hexahydrofuro[2,3-b]furan-3-yl N-((1S,2R)-1-benzyl-3-(cyclopentyloxy)[(4-hydroxyphenyl)sulfonyl]amino-2-hydroxypropyl) carbamate (Example 41), (0.13 mmol, 75 mg), triphenylphosphine (0.16 mmol, 43 mg), 4-(2-hydroxyethyl) morpholine (0.16 mmol, 0.020 mL), and anhydrous THF (0.5 mL) stirring under nitrogen, diethylazodicarboxylate (0.17 mmol, 0.027 mL) was injected. The reaction stirred for 3 hours at room temperature and was then concentrated to a viscous oil under vacuum. The crude was purified directly by silica gel flash chromatography (1:1 hexanes/ethyl acetate) resulting in 50 mg (56%) of a white solid. $R_f$=0.15 (ethyl acetate); H1-NMR (CDCl$_3$): δ 7.70 (2H,d), 7.30–7.10 (6H,m), 6.99 (2H,d), 5.63 (1H,s), 5.00 (1H,m), 4.86–4.73

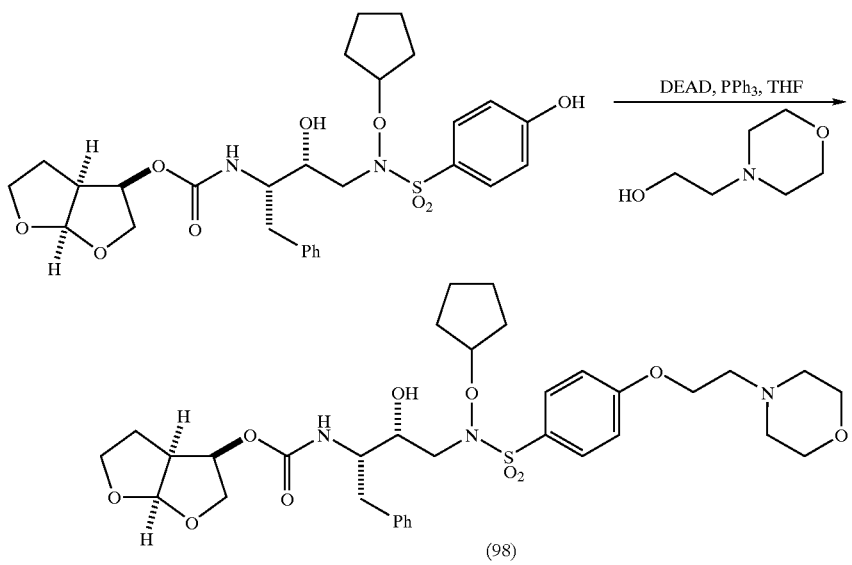

(3R,3aS,6aR)hexahydrofuro[2,3-b]furan-3-yl N-[(1S,2R)-1-benzyl-3-((cyclopentyloxy)[4-(2-morpholinoethoxy) phenyl] sulfonylamino)-2-hydroxypropyl]carbamate. To a (2H,m), 4.16 (2H,m), 3.97–3.79 (4H,m), 3.78–3.58 (6H,m), 3.15–2.69 (9H,m), 2.57 (4H,m), 1.88–1.66 (4H,m), 1.66–1.43 (4H,m); MS (ESI): M+H=690.

Example 99

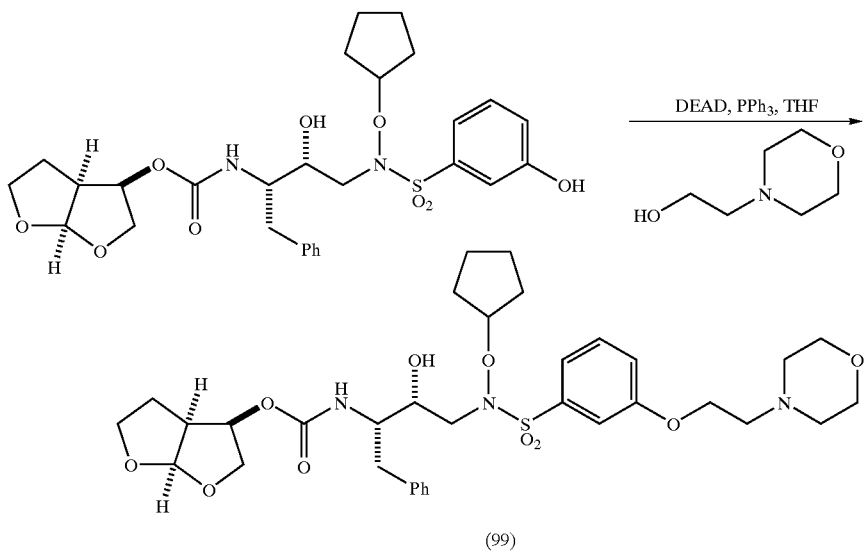

(99)

(3R,3aS,6aR)hexahydrofuro[2,3-b]furan-3-yl N-[(1S,2R)-1-benzyl-3-((cyclopentyloxy)[3-(2-morpholinoethoxy)phenyl]sulfonylamino)-2-hydroxypropyl]carbamate. This compound was prepared from Example 44 under the same conditions used for the preparation of Example 98 (3R,3aS,6aR)hexahydrofuro[2,3-b]furan-3-yl N-[(1S,2R)-1-benzyl-3-((cyclopentyloxy)[4-(2-morpholinoethoxy) phenyl] sulfonylamino)-2-hydroxypropyl]carbamate. $R_f$=0.15 (ethyl acetate); H1-NMR (CDCl$_3$): δ7.44–7.14 (10H,m), 5.62 (1H, s), 5.00 (1H,m), 4.79 (2H,m), 4.16 (2H,m), 3.98–3.60 (10H, m), 3.12 (1H,bs), 3.02–2.71 (8H,m), 2.58 (4H,m), 1.90–1.72 (4H,m), 1.72–1.42 (4H,m); MS (ESI): M+H=690.

Example 100

Phosphate ester of (3R,3aS,6aR)hexahydrofuro[2,3-b]furan-3-yl N-(1S,2R)-3-[[(3-aminophenyl)sulfonyl](cyclopentyloxy) amino]-1-benzyl-2-hydroxypropylcarbamate.

Step 1

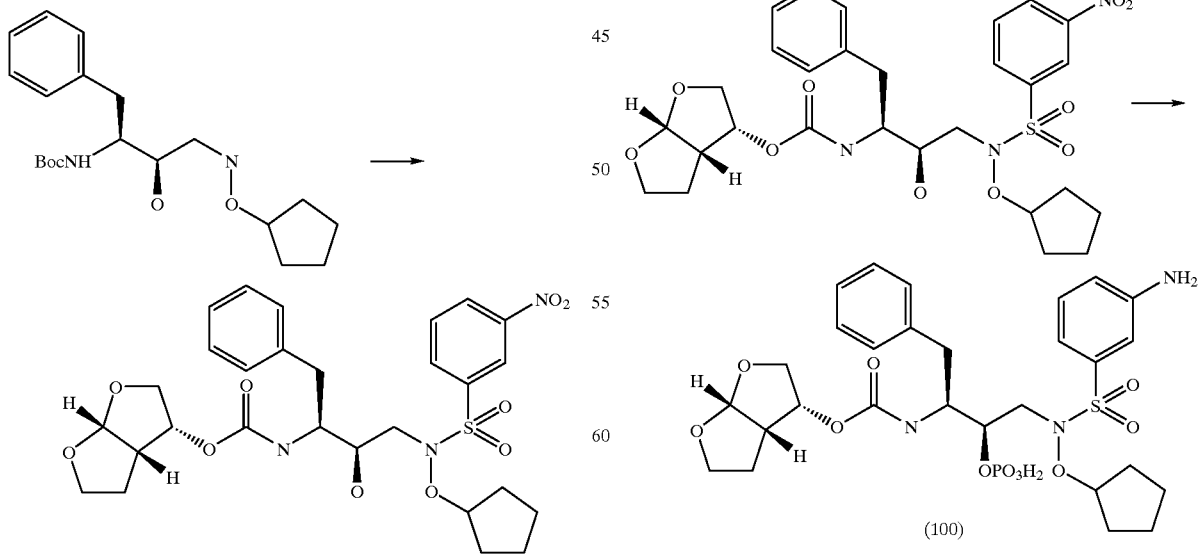

A solution of 0.792g (2.18 mmol) of tert-butyl N-(1S,2R)-1-benzyl-3-[(cyclopentyloxy)aamino]-2-hydroxypropyl-carbamate (Example 54), 0.445g (2.4 mmol) of m-nitrobenzenesulfonyl chloride and 0.35 mL (2.5 mmol) of triethylamine in 10 mL of tetrahydrofuran was stirred at rt for 12 h, diluted with ethyl acetate and exracted with 1N HCl and saturated sodium bicarbonate. Purification on silica gel afforded the desired sulfonamide which was treated with 50 mL of 1:1 trifluoroacetic acid/ dichloromethane for 1 h at rt. Evaporation of the volatiles and partitioning between ethyl acetate and 1N sodium hydroxide, afforded the free base which was treated with 0.885g (3 mmol) of (3R,3aS,6aR)-hexahydrofuro[2,3-b]furan-3-yl (4-nitrophenyl) carbonate, 10 mg of dimethylamino pyridine, and 0.7 mL of triethylamine in 20 mL of tetrahydrofuran for 12 h at rt. The resulting mixture was loaded onto a bed of silica gel and eluted with 50% to 100% ethylacetate-hexanes) to give the desired compound (750 mg) as a white foam.

Step 2

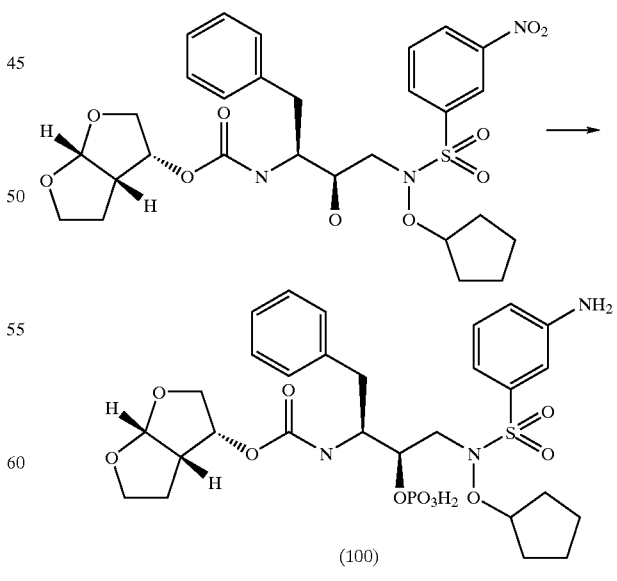

(100)

A solution of 60.5 mg (0.1 mmol) of the material obtained in Step 1 above, 0.042 mL (0.125 mmol) of diisopropylamino-dibenzylphosphite and 9 mg (0.13 mmol) of tetrazole in 2 mL of dichloromethane was stirred for 3 h at rt and then loaded onto a bed of silica gel and eluted with 30% ethylacetate-hexane to give the intermediate phosphite which was re-dissolved in 3 mL of acetonitrile and treated with 48.3 mg (0.15 mmol) of iodosobenzene diacetate. The mixture was stirred at rt for 1 h and then loaded on a plug of silica gel and eluted with 80% ethylacetate-hexane. The resulting phosphate ester was obtained as a white foam (48 mg), which was re-dissolved in 50 ml methanol and treated with ca. 50 mg of 5% palladium on carbon. The mixture was hydrogenated at 55PSI for 8h, filtered and evaporated. Purification on C-18 semi-preparative HPLC gave the desired phosphate (6 mg) as a white fluffy solid. 1H-NMR (methanol-d4): 1.4–2.0 (14H), 2.65 (1H), 2.9 (1H), 3.2 (2H), 3.55 (1H), 3.6–4.0 (4H), 4.4 (1H), 4.65 (1H), 4.8 (2H), 5.6 (1H), 7.2–7.6 (9H). 31P-NMR: 1.1 ppm. MS (LC-MS): 656 (MH+).

Example 101

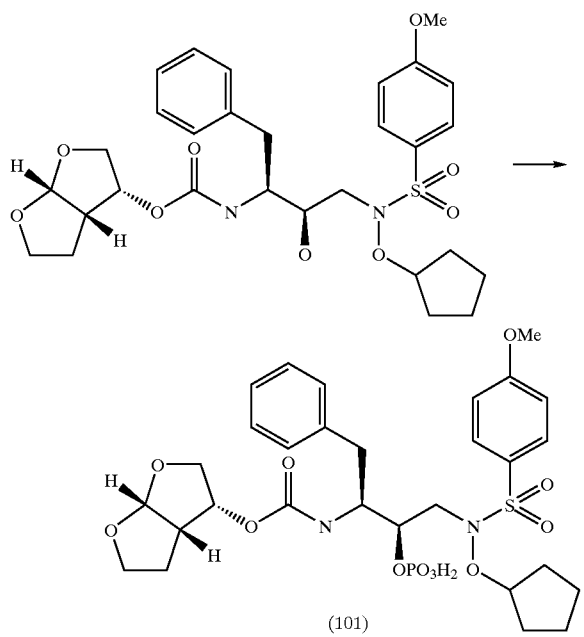

(101)

Phosphate ester of (3R,3aS,6aR)hexahydrofuro[2,3-b]furan-3-yl N-((1S,2R)-1-benzyl-3-(cyclopentyloxy)[(4-methoxyphenyl) sulfonyl]amino-2-hydroxypropyl)carbamate. A solution of 0.6 g (1 mmol) of (3R,3aS,6aR) hexahydrofuro[2,3-b]furan-3-yl N-((1S,2R)-1-benzyl-3-(cyclopentyloxy)[(4-methoxyphenyl)sulfonyl]amino-2-hydroxypropyl)carbamate (Example 102), 0.42 mL (1.25 mmol) of diisopropylamino-dibenzylphosphite and 0.09g (1.25 mmol) of tetrazole in 10 mL of dichloromethane was stirred at rt for 12h. The mixture was loaded onto a plug of silica gel and eluted with 40% ethylacetate-hexane to give the desired phosphite. 250 mg of the material so obtained were dissolved in 15 mL of acetonitrile and treated with 0.19 g (0.6 mmol) of iodosobenzene diacetate. After 2h at rt, the mixture was diluted with ethyl acetate and extracted with 1N HCl and 1N NaOH. The volatiles were removed and the residue was chromatographed on silica gel to give 220 mg of the protected phosphate as a white foam. 100 mg of the so obtained material was dissolved in 20 mL of methanol and trated with ca. 20 mg of 5% palladium on carbon. Hydrogenation at 50 PSI for 1h and filtration gave the desired acid which was dissolved in 2M methanolic ammonia and re-evaporated. The ammoinum salt was isolated as a white solid (65mg). 1H-NMR (methanol-D4):1.5–2.2 (14H), 2.7 (1H), 2.9 (3H), 3.15 (1H), 3.4–4 (5H), 3.97 (3H), 4.2–4.7 (2H), 4.9 (2H), 5.6 (1H), 7.2 (3H), 7.3 (4H), 7.85 (2H). 31P-NMR: 0.08ppm MS (LC-MS): 671 (MH+).

Example 102

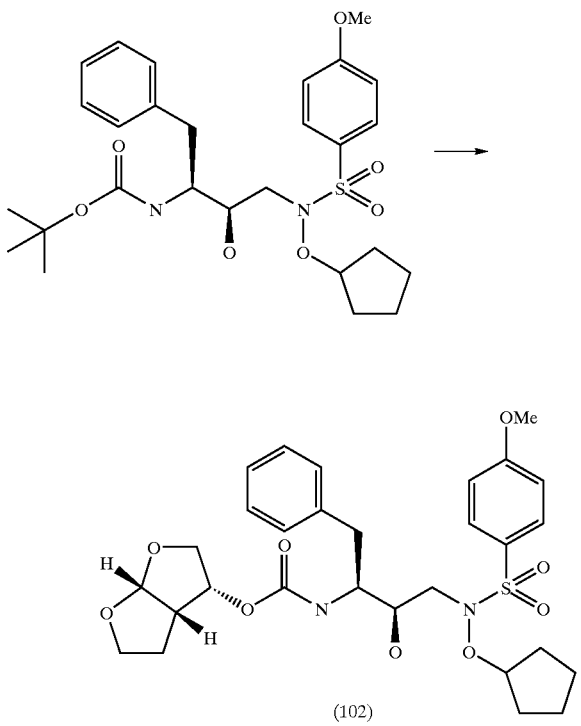

(102)

(3R,3aS,6aR)hexahydrofuro[2,3-b]furan-3-yl N-((1S,2R)-1-benzyl-3-(cyclopentyloxy)[(4-methoxyphenyl)sulfonyl]amino-2-hydroxypropyl)carbamate. This compound was obtained in analogous manner to Example 29, using the appropriate optically pure activated carbonate. 1H-NMR (CDCl$_3$): 1.4–1.9 (12H), 2.75 (2H), 2.9 (1H), 3.1 (2H), 3.65 (2H), 3.9 (6H), 4.75 (2H), 5.00 (1H), 5.62 (1H), 7.0 (2H), 7.15 (5H), 7.75 (2H)

Example 103
Prepared as outlined for Example 86, using chiral starting materials.

Example 104

(104)

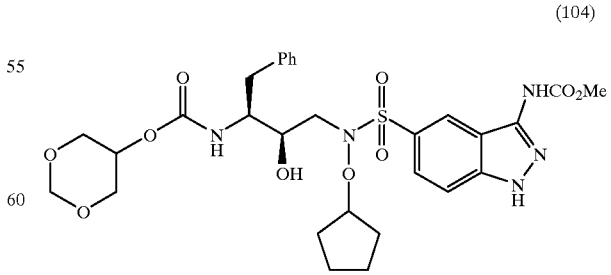

1,3-Dioxan-5-yl-N-(1S,2R)-1-benzyl-3-[(cyclopentyloxy)(3-(carbomethoxyamino)-indazole-5-ylsulfonyl)amino]-2-hydroxypropylcarbamate. 1,3-Dioxan-5-yl N-(1S,2R)-1- benzyl-3-[(cyclopentyloxy)(1-carbomethoxy-3-(carbomethoxyamino) indazole-5-ylsulfonyl)amino]-2-hydroxypropylcarbamate (Example 120), (40 mg, 0.057 mmol) and lithium iodide (23 mg, 0.17 mmol) were dissolved in pyridine (3 mL) in a 10 mL round bottomed flask and heated at 95OC for 2 hours. The reaction was allowed to cool and then concentrated in vacuo. The product was purified by preparative silica gel TLC using 90:10 chloroform: methanol as an eluent to yield a beige solid (35 mg, 0.054 mmol, 95%). $^1$HNMR (d$_6$-DMSO) δ: 13.12 (s, 1H), 10.26 (s, 1H), 8.42 (s, 1H), 7.62 (m, 2H), 7.25–7.09 (m, 6H), 5.12 (d, J=6.2 Hz, 1H), 4.76–4.18 (m, 5H), 3.76–2.91 (m, 9H), 3.66 (s, 3H), 1.90–1.40 (m, 8H). MS(ES): 648 (M+1), 646 (M−1).

Example 105

(105)

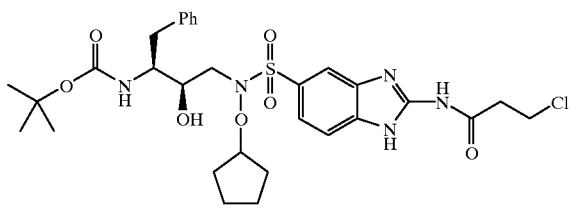

Tert-butyl N-(1S,2R)-1-benzyl-3-[(cyclopentyloxy)(2-[(3-chloropropionyl)amino]-1H-benzimidazol-5-ylsulfonyl)amino]-2-hydroxypropylcarbamate. Tert-butyl N-(1S,2R)-1-benzyl-3-[(cyclopentyloxy)(2-amino-1H-benzimidazol-5-ylsulfonyl)amino]-2-hydroxypropylcarbamate (Step 2, Example 8) (65 mg, 0.116 mmol), 3-chloropropionyl chloride (0.01 mL, 0.116 mmol), and 4,4-dimethylaminopyridine were combined in anhydrous THF (5 mL) in a 25 mL round bottomed flask under nitrogen. The reaction was stirred for 18 hours and then concentrated in vacuo. After the workup described in Step 3, Example 54, the residue was purified by preparative silica gel TLC using 10:3:0.5 chloroform: methanol: water as an eluent to give the product as a white solid (17 mg, 0.026 mmol, 22%). $^1$HNMR (d$_6$-DMSO) δ: 7.55–6.62 (m, 8H), 5.08 (bs, 1H), 4.62 (bs, 1H), 4.15 (bs, 1H), 3.57 (m, 2H), 3.10–1.40 (m, 16H), 1.18 (s, 9H). MS(ES): 650, 652 (M+1).

Example 106

Prepared as outlined in Example 8, Step 2.

Example 107

Tert-butyl N-(1S,2R)-1-benzyl-3-[(cyclopentyloxy)(2-amino-1-methyl-1H-benzimidazol-5-ylsulfonyl)amino]-2-hydroxypropylcarbamate and Tert-butyl N-(1S,2R)-1-benzyl-3-[(cyclopentyloxy)(2-amino-3-methyl-1H-benzimidazol-5-ylsulfonyl)amino]-2-hydroxypropylcarbamate. Tert-butyl N-(1S,2R)-1-benzyl-3-[(cyclopentyloxy)(2-amino-1H-benzimidazol-5-ylsulfonyl)amino]-2-hydroxypropyl-carbamate (Step 2, Example 8) (120 mg, 0.214 mmol), methyl iodide (0.03 mL, 0.429 mmol), and anhydrous diisopropylethylamine (0.07 mL, 0.429 mmol) were combined in anhydrous THF (5 mL) in a 25 mL round bottomed flask under nitrogen. The reaction was heated at reflux for 18 hours and then concentrated in vacuo. After the workup described in Step 3, Example 54, the residue was purified by preparative silica gel TLC using 90:10 chloroform: methanol as an eluent to give the product as mixture of two compounds methylated at the 1- and 3-positions of the imidazole ring (76 mg, 0.133 mmol, 62%). LC-MS: 574 (M+1), 572 (M-1)

Example 108

(108)

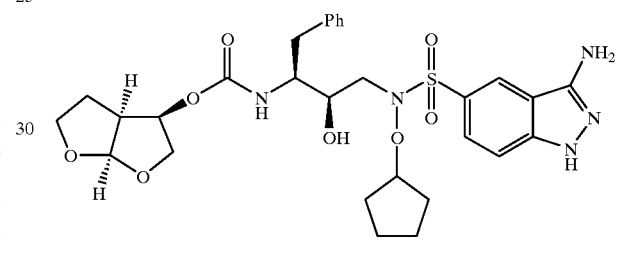

(3R,3aS,6aR)Hexahydrofuro[2,3-b]furan-3-yl N-(1S,2R)-1-benzyl-3-[(cyclopentyloxy)(3-aminoindazole-5-ylsulfonyl)amino]-2-hydroxypropylcarbamate. (3R,3aS,6aR)Hexahydrofuro[2,3-b]furan-3-yl N-(1S,2R)-1-benzyl-3-[(cyclopentyloxy)(1-carbomethoxy-3-aminoindazole-5-ylsulfonyl)amino]-2-hydroxypropylcarbamate (100 mg, 0.148 mmol) and lithium iodide hydrate (50 mg, 0.37 mmol) were dissolved in pyridine (3 mL) in a 10 mL round bottomed flask and heated at 75° C. for 5 hours. The reaction was allowed to cool and then concentrated in vacuo. The product was purified by preparative silica gel TLC using 90:10 chloroform: methanol as an eluent to yield a glass (76 mg, 0.124 mmol, 84%). $^1$HNMR (d$_6$-DMSO): 12.05 (s, 1H), 8.35 (m, 1H), 7.56–7.14 (m, 7H), 5.86 (bs, 2H), 5.50 (d, J=5.2 Hz, 1H) 5.22 (d, J=6.5 Hz, 1H), 4.85–4.79 (m, 2H), 3.78–1.14 (m, 22H). MS(ES): 616 (M+1), 614 (M−1).

(107)

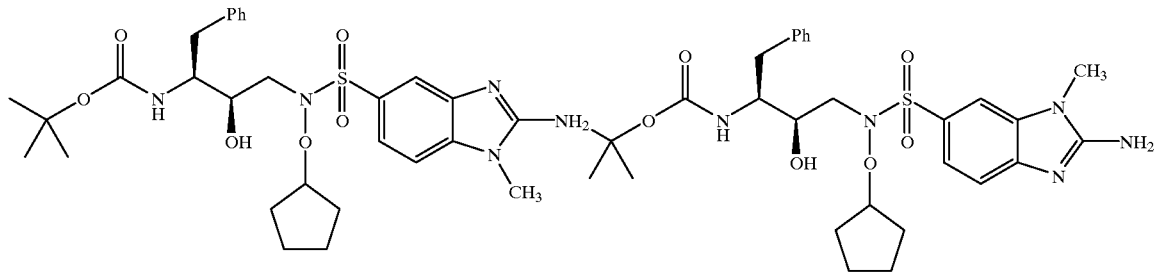

Example 109

Step 1

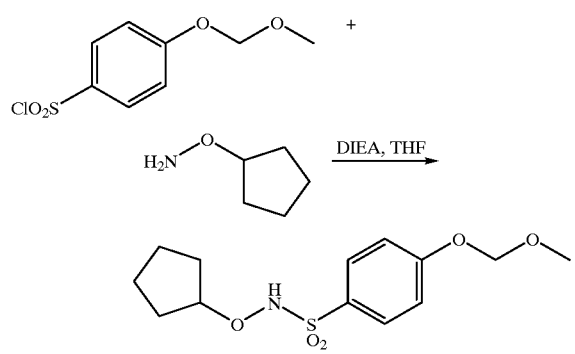

N¹-(cyclopentyloxy)-4-(methoxymethoxy)-1-benzenesulfonamide The 4-methoxymethoxybenzenesulfonyl chloride (2.4 mmol, 568 mg) was prepared from methylmethoxy-protected 4-bromophenol (Corrie, J.; Papageorgiou, G. J. Chem. Soc., Perkin Trans. 1 1996, 1583) and was combined with cyclopentyl hydroxylamine (2.4 mmol, 243 mg) in the presence of diisopropylethylamine (3.6 mmol, 0.628 mL), and anhydrous THF. The reaction stirred under nitrogen for 36 hours at room temperature and was concentrated under vacuum. The resulting oil was diluted in ethyl acetate, washed with 1N HCl, 5% potassium carbonate, brine and was dried over magnesium sulfate. The crude product was concentrated under vacuum and purified by silica gel chromatography (5:1 hex/ethyl acetate) followed by crystallization from ether/hexanes. The reaction produced 173 mg (24%) of white crystals. $R_f$=0.15 (1:1 hexanes/ethyl acetate); H1-NMR (CDCl₃): δ7.82 (2H,d), 7.12 (2H,d), 6.67 (1H,s), 5.23 (2H,s), 4.58 (1H,m), 3.47 (3H,s), 1.84–1.64 (4H,m), 1.64–1.43 (4H,m).

Step 2

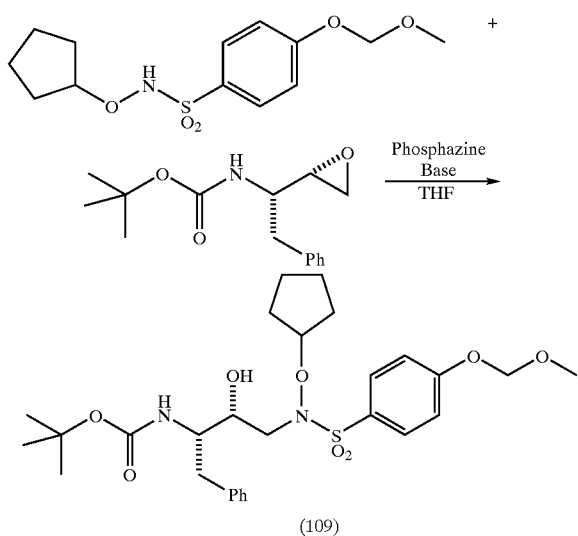

tert-butyl N-((1S,2R)-1-benzyl-3-(cyclopentyloxy)[(4-methoxymethoxyphenyl)sulfonyl]amino-2-hydroxypropyl)carbamate. N-(cyclopentyloxy)-4-methoxymethoxy-1-benzenesulfonamide (0.57 mmol, 173 mg) was combined with tert-butyl N-(1S)-1-[(2S)oxiran-2-yl]-2-phenylethylcarbamate (0.46 mmol, 121 mg) and anhydrous THF (1 mL) under nitrogen. Phosphazine base P<t/4>t-Bu (0.09 mmol, 0.092 mL, 1 M in hexanes) was injected into the stirring solution. The reaction was allowed to stir for 4 hours at room temperature and was quenched by the addition of a few drops of glacial acetic acid. The reaction product was concentrated to an oil and partitioned between ethyl acetate and 1N HCl. The organic layer was separated and washed with 1 N NaOH and brine, dried over magnesium sulfate and concentrated under vacuum to a clear oil. The crude product was purified by silica gel chromatography (5:1 hexanes/ethyl acetate) and crystallization from ether/hexanes providing 110 mg (43%) of a white crystal. $R_f$=0.5 (2:1 hexanes/ethyl acetate); H1-NMR (CDCl₃): 7.69 (2H,d), 7.31–7.16 (6H,m), 7.11 (2H,d), 5.21 (2H,s), 4.83–4.75 (1H,m), 4.61–4.51 (1H,m), 3.85–3.70 (2H,m), 3.47 (3H,s), 3.12–2.95 (1H,m), 2.95–2.87 (2H,m), 2.87–2.68 (1H,m), 1.86–1.66 (4H,m), 1.66–1.43 (4H,m), 1.33 (9H,s); MS (ESI): M+H=565.

Example 110

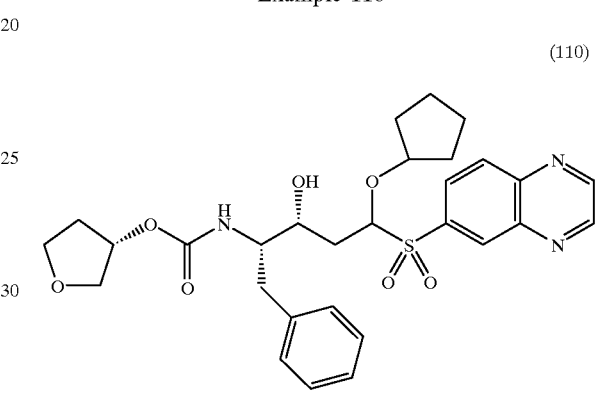

(3S) tetrahydro-3-furanyl N-[(1S, 2R)-1-benzyl-4-(cyclopentyloxy)-2-hydroxy-4-(6-quinoxalinylsulfonyl)butyl]carbamate. A mixture of (3R,4S)-4-amino-1-(cyclopentyloxy)-5-phenyl-1-(6-quinoxalinylsulfonyl)-3-pentanol (50 mg, 0.110 mmoL), 2,5-dioxo-1-pyrrolidinyl [(3S)tetrahydro-3-furanyl]carbonate (28 mg, 0.121 mmol, WO 94/05639) and N,N-diisopropylethylamine (47.8 uL, 0.274 mmol) were combined under Argon at ambient temperature in approximately 1.5 mL of acetonitrile. After stirring for approximately 16 hours at ambient temperature, the reaction mixture was evaporated in vacuo and partitioned between ethyl acetate and aqueous potassium carbonate (5% w/v). The layers were separated and the aqueous layer-was back extracted with ethyl acetate. The combined organic layers were washed twice with 1N sodium hydrogen sulfate. The acid layers were combined and back extracted with ethyl acetate. The combined organic layers were washed with brine, dried over anhydrous magnesium sulfate, filtered and evaporated in vacuo. The residue was purified on a preparative TLC plate (20×20 cm, 1000 μM) eluting with 93:7 dichloromethane:methanol. The product band was removed, eluted with 3:1 methylene chloride: methanol, filtered, and evaporated if vacuo. The residue was crystallized with several drops of methanol. The residual solid was dried under high vacuum to provide (3S)tetrahydro-3-furanyl N-[(1S,2R)-1-benzyl-4-(cyclopentyloxy)-2-hydroxy-4-,(6-quinoxalinyl sulfonyl)butyl]carbamate (54 mg, 86%) as a white solid. H1-NMR (chloroform-D3): 1.61 (m, 5H), 1.86 (m, 4H), 2.09 (m, 1H), 2.97 (m, 3H), 3.20 (m, 2H), 3.80 (m, 6H), 4.83 (m, 1H), 4.93 (m, 1H), 5.14 (m, 1H), 7.28 (m, 5H), 8.13 (m, 1H), 8.31 (d, 1H), 8.69 (d, 1H), 9.05 (s, 2H). MS(ESI): 571(M+H).

Example 111

Step 1

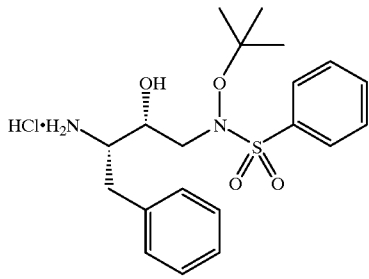

(1S,2R)-1-benzyl-3-(tert-butyloxy)[(phenyl)sulfonyl]amino-2-hydroxypropylamine hydrochloride. tert-Butyl-N-((1S,2R)-1-benzyl-3-(tert-butyloxy)[(phenyl)sulfonyl]amino-2-hydroxypropyl)carbamate (Example 112, Step 2), (0.060 g, 0.12 mmol) was dissolved in EtOAc (50 ml). Dry hydrochloric acid gas was bubbled through the stirred solution 15 minutes at −10° C. The reaction was warmed to ambient temperature, solvent removed in vacuo and the resulting crude residue used directly in the next reaction.

Step 2

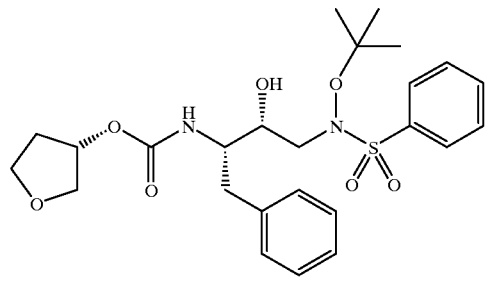

(111)

(3S) Tetrahydro-3-furanyl-N-(1S,2R)-1-benzyl-3-(tert butyloxy)[(phenyl)sulfonyl]amino-2-hydroxypropyl- carbamate. (1S,2R)-1-benzyl-3-(tert-butyloxy)[(phenyl)sulfonyl]amino-2-hydroxypropylamine hydrochloride(0.12 mmol) was combined with dilsopropylethylamine (0.064 ml, 0.37 mmol) in CH$_2$C$_{12}$ (10 ml). To the reaction was added 2,5-dioxo-1-pyrrolidinyl [(3S) tetrahydro-3-furanyl] carbonate (0.042g, 0.18 mmol) with stirring. After 3 h at ambient temperature, the reaction mixture was concentrated in vacuo, taken up in EtOAc, washed with sat. aq. NaHCO$_3$, and brine. The organic phase was dried over MgSO$_4$, filtered and solvent removed in vacuo. Purification by preparative TLC (1:1 EtOAc/Hex). Recovered 0.044 g (67%) of the product as a white foam. Rf=0.38 (1:1 EtOAc/Hex), LRMS (M+H)$^+$507.3.

Example 112

Step 1

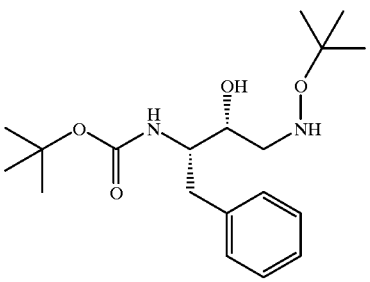

tert-Butyl-N-((1S,2R)-1-benzyl-3-(tert-butyloxy)amino-2-hydroxypropyl)carbamate. tert-Butyl-N-((1S)-1-[(2S) oxiranyl]-2-phenylethylcarbamate (0.155 g, 0.59 mmol) and O-(tert-butyl)hydroxylamine hydrochloride (0.089 g, 0.71 mmol) were heated with diisopropylethylamine (0.154 ml, 0.88 mmol) in isopropanol (2 ml) in a sealed tube at 60° C. for 5 days. The reaction mixture was concentrated in vacuo, taken up in EtOAc, washed with sat. aq. NaHCO$_3$, and brine. The organic phase was dried over MgSO$_4$, filtered and solvent removed in vacuo. Purication by column chromatography (1% MeOH in CH$_2$C$_{12}$) gave 100 mg of a white solid which was used directly in the next reaction.

Step 2

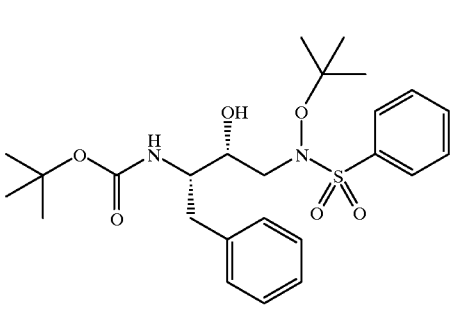

(112)

tert-Butyl-N-((1S,2R)-1-benzyl-3-(tert-butyloxy)[(phenyl) sulfonyl]amino-2-hydroxypropyl)carbamate. tert-Butyl-N-((1S, 2R)-1-benzyl-3-(tert-butyloxy) amino-2-hydroxypropyl)carbamate (0.100 g, 0.28 mmol) was combined with diisopropylethylamine (0.075 ml, 0.43 mmol) in CH$_2$C$_{12}$ (10 ml). Benzenesulfonyl chloride (0.060 g, 0.34 mmol) was added and the reaction was stirred at room temperature overnight. Reaction mixture was concentrated in vacuo, taken up in EtOAc, washed with sat. aq. NaHCO3, and brine. The organic phase was dried over MgSO$_4$, filtered and solvent removed in vacuo. Purication by preparative TLC (1:1/EtOAc/Hex). Recovered 0.064 g (46%) of the product as a white foam. R$_f$=0.78 (1:1/EtOAc/Hex), LRMS (M+H)$^+$493.4.

Example 113

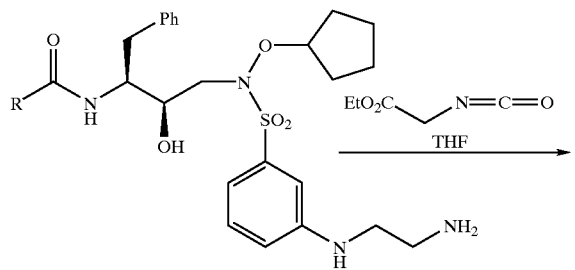

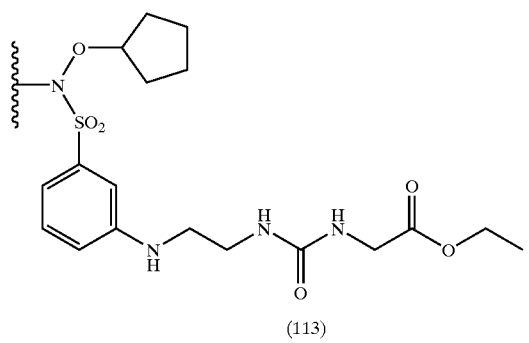

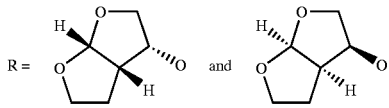

Ethyl 2-[([2-(3-[[(2R,3S)-3-([(3R,3aS,6aR)hexahydrofuro(2,3-b]furan-3-yloxy]carbonylamino)-2-hydroxy-4-phenylbutyl](cyclopentyloxy)amino]sulfonylanilino)ethyl]amin ocarbonyl)amino]acetate and ethyl 2-[([2-(3-[[(2R,3S)-3-([[(3S,3aR,6aS)hexahydrofuro[2,3-b]furan-3-yloxy]carbonylamino)-2-hydroxy-4 phenylbutyl](cyclopentyloxy)amino]sulfonylanilino)ethyl]aminocarbonyl)amino]acetate.

A solution of 50 mg (0.081 mmol) of a 1:1 mixture of (3R,3aS,6aR)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate and (3S,3aR,6aS) hexahydrofuro[2,3-b]furan-3-yl AT-(1S,2R)-3-[(3-[,(2-aminoethyl)amino]phenylsulfonyl)(cyclopentyloxy)amino]-1-benzyl-2-hydroxypropylcarbamate (Example 83) in 1.5 mL of anhydrous THF was treated with 0.010 mL (0.085 mmol) of ethyl isocyanatoacetate. The resulting solution was stirred at RT. After 18 hours the solution was concentrated in vacua and the residue subjected to flash chromatography (silica gel, 95:5/CH$_2$Cl$_2$/2M NH$_3$ in MeOH) to afford 56 mg (92%) of the desired product as a white foam. 1H-NMR (CDCl$_3$): 7.60–7.06 (13H), 6.00–4.80 (4H), 4.34–2.62 (19H), 2.10–1.43 (!OH), 1.32 (3H). LCMS(ESI): 748 (M+H).

Example 114

(114)

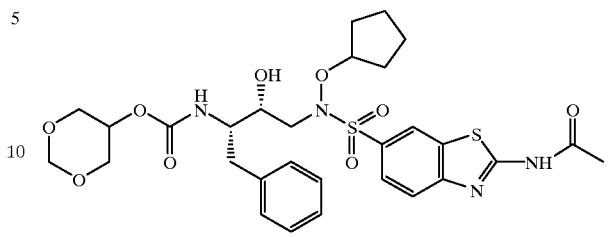

1,3-Dioxane-5-yl N-(1S,2R)-1-benzyl-3-[(cyclopentyloxy)(2-acetamido)]-benzothiazol-6-ylsulfonyl) amino]-2-hydroxypropylcarbamate. To 21 mg (0.034 mmol) of 1,3-Dioxane-5-yl N-(1S,2R)-1-benzyl-3-[(cyclopentyloxy)(2-amino) ]-benzothiazol-6-ylsultonyl) amino]-2-hydroxypropylcarbamate, (Example 125, Step 3), dissolved in 1 mL of dichloromethane and cooled to approximately. 0° C., was added 5.3 µL (1.2 eq.) at chlorotrimethylsilane. The reaction was warmed to 25° C. and stirred for 45 minutes. Triethylamine (12 µL, 2.5 eq.) was added followed by 100 Al (1.2eq.) of a dilute solution of (24 µl acetyl chloride in 1 mL CH$_2$Cl$_2$). The reaction was stirred at 25° C. for 3 hours. 105 µL (3.0 eq.) of 1.0 M tetrabutylammonium fluoride was added and the reaction stirred for 1 hour. The solvent was removed in vacuo and the residue was purified by preparative chromatography to give 8 mg of carbamate, 114. HPLC showed the material to be over 80% pure. Ret. time=10.48 min. LC/MS, M+H=649.1.

Example 115

(115)

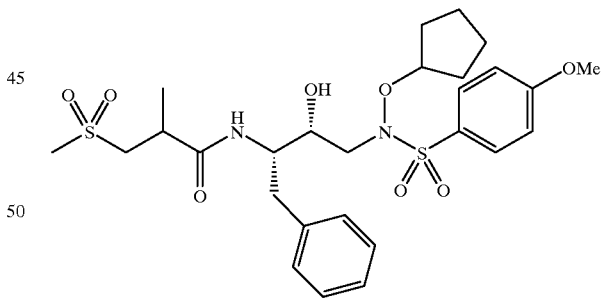

1N-(3-Methylsulfonylisobutyryl)-(1S,2R)-1-benzyl-3-(cyclopentyloxy)[4-methoxyphenylsulfonyl]amino-2-hydroxypropylamine. (1S,2R)-1-benzyl-3-(cyclopentyloxy)[(4-methoxyphenyl)sulfonyl]amino-2-hydroxypropylamine trifluoroacetic acid salt (0.012 g, 0.03 mmol) was combined with 3-methylsulfonylisobutyric acid (0.005 g, 0.03 mmol) and 1-hydroxybenzotriazole hydrate (0.004 g, 0.03 mmol) in anhydrous DMF (1 ml). Triethylamine (0.010 ml, 0.05 mmol) was added followed by 1-(3-dimethylaminopropyl)-3-ethylcarbodiimide hydrochloride (0.009 g, 0.03 mmol). Reaction was stirred at room temperature for 2 hours. Reactiom mixture was diluted in EtOAc and washed with sat. NaHCO3, 0.5N KHSO$_4$ and brine. Organic phase was dried with MgSO$_4$ and the solvent was removed in vacuo. Purification by preparative TLC (3:1/EtOAc/Hex). Recovered 0.010 g (70%) of the product as a colorless residue. R$_f$=0.44 (3:1 EtOAc/Hex). $^1$H NMR (CDCl$_3$) 8.78 (1H,d), 7.38–7.17 (5H,m), 7.05–6.98 (2H,m), 6.09 (0.5H,d), 5.98 (0.5H,d), 5.80 (1H,m), 4.32 (0.5H,m), 4.20 (0.5H,m), 4.02 (0.5H,m), 3.90 (3H,s), 3.60 (0.5H,m), 3.49 (1H,m), 3.12–2.96 (2H,m), 2.95–2.70 (4H,m), 1.90–1.70 (4H,m), 1.69–1.50 (4H,m), 1.20 (1.5H,d), 1.00 (1.5H,d). LRMS (M+H)$^+$583.0.

Example 116

Step 1

(3S,3aS,6aR)hexahydrofuro[2,3b]furan-3-p-nitrobenzoyl ester (A) and (3R,3aR,6aS)hexahydrofuro[2,3b]furan-3-p-nitrobenzoyl ester (B)

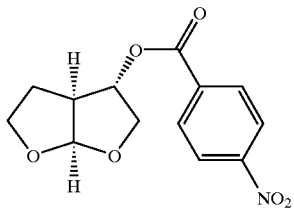

(A)

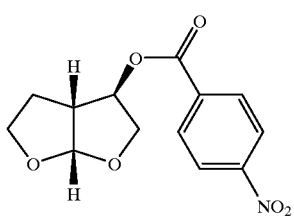

(B)

In a dried flask was introduced 1 eq. of (3S,3aS,6aR)-3-Hydroxyhexahydrofuro[2,3b]furan (200 mg, 1.54 mmol) in 10 mL of dried THF. To this solution was introduced 1.1 eq. of PPh$_3$ (443 mg, 1.69 mmol) and 1.1 eq. of p-nitrobenzoic acid (282 mg, 1.69 mmol). The solution was cooled to 0° C. and then 1.2 eq of diethyl azodicarboxylate (290 uL, 1.84 mmol) was added dropwise. The reaction was continued at room temperature for 24 h. The solvent was evaporated in vacuo to an oil which was solubilized in dichloromethane washed with 1N hydrochloric acid, saturated sodium bicarbonate and brine. The organic layer was dried over anhydrous magnesium sulfate, filtered and evaporated in vacuo to a residue. The crude material was purified on flash grade silica gel eluting with 20–50% ethyl acetate in hexane. Fractions containing the product were combined, evaporated in vacuo and dried under high vacuum to provide (3S,3aS,6aR)Hexahydrofuro [2,3b]furan-3-p-nitrobenzoyl ester (914 mg, 98%). HPLC showed the material to be 98% pure;

Ret. time=9.88 min. $^1$H NMR (CDCl$_3$): 8.14–8.24 (dd, 4H), 5.88 (d, 1H), 5.29 (s, 1H), 4.07–4.17 (m, 2H), 3.83–3.93 (m, 2H), 2.97 (m, 1H), 2.19–2.28 (m, 1H), 1.86–1.98 (m, 1H).

Step 2

(3S,3aS,6aR)-3-Hydroxyhexahydrofuro[2,3b]furan (C) and (3R,3aR,6aS)-3-Hydroxyhexahydrofuro[2,3b]furan (D)

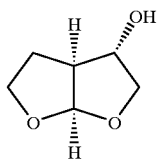

(C)

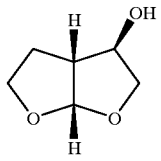

(D)

In a flask was introduced 1 eq. of (3R3aR,6aS) Hexahydrofuro [2,3b]furan-3-p-nitrobenzoyl ester (1.34 g, 4.82 mmol) in 20 mL of methanol. To this solution was introduced at room temperature 1 eq. of lithium hydroxide (202 mg, 4.82 mmol).

After 45 min the solvent was evaporated in vacuo to an oil who was purified on flash grade silica gel eluting with 50–100% ethyl acetate in hexane. Fractions containing the product were combined, evaporated in vacuo and dried under high vacuum to provide (3R,3aR,6aS)-3-Hydroxyhexahydrofuro [2,3b]furan (401 mg, 80%). $^1$H NMR (CDCl$_3$): 5.82 (s 1H), 4.15 (s, 1H), 3.74–3.94 (m, 4H), 2.72–2.76 (m, 1H), 2.06–2.14 (m, 1H), 1.99 (s, 1H), 1.60–1.66 (m, 1H).

Step 3

(3S,3aS,6aR)Hexahydrofuro[2,3b]furan-3-yl (4-nitrophenyl) carbonate (E) and (3R,3aR,6aS) hexahydrofuro[2,3b]furan-3-yl (4-nitrophenyl) carbonate (F)

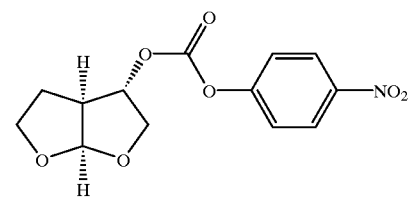

(E)

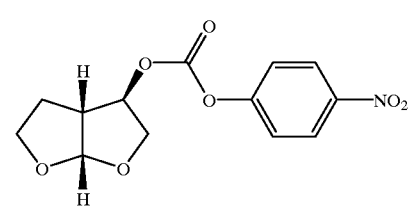

(F)

In a dried flask was introduced 1 eq. of (3S,3aS,6aR)-3-Hydroxy hexahydrofuro[2,3b]furan (210 mg, 1.61 mmol) in 5 mL of dried dichloromethane. To this solution was introduced 1 eq. of p-nitrobenzylchloroformate (325 mg, 1.61 mmol) and 1 eq. of N-methylmorpholine (177 µL, 1.61 mmol). The reaction was continued at room temperature for 24 h. The precipitate was filtered off and the solvent was evaporated in vacuo to an oil. The crude material was purified on flash grade silica gel eluting with 50% ethyl acetate in hexane. Fractions containing the product were combined, evaporated in vacuo and dried under high vacuum to provide (3S, 3aS,6aR)Hexahydrofuro[2,3b]furan-3-yl (4-nitrophenyl) carbonate (350 mg, 99%). HPLC showed the material to be 99% pure; Ret. time=8.8 min. $^1$H NMR (CDCl$_3$): 7.28–8.25 (dd, 4H), 5.88 (d, 1H), 5.05 (s, 1H), 4.04–4.15 (m, 2H), 3.80–3.91 (m, 2H), 2.97–3.01 (m, 1H), 2.18–2.26 (m, 1H), 1.77–1.83 (m, 1H). Step 4:

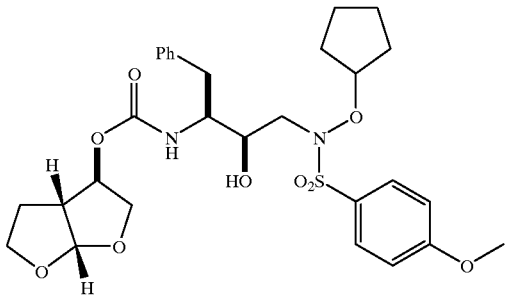

(116)

(3R,3aR,6aS)hexahydrofuro[2,3b]furan-3-yl-N-(1S,2R)-1-benzyl-3-[(cyclopentyloxy)[(4-methoxyphenyl)sulfonyl]amino-2-hydroxypropylcarbamate. In a dried flask was introduced 1 eq. of N$^1$-[(2R,3S)-3-amino-2-hydroxy-4-phenylbutyl]-N$^1$-(cyclopentyloxy)-4-methoxy-1-benzenesulfonamide trifluoroacetic acid (40.9 mg, 0.083 mmol) in 1 mL of N,N-dimethylformamide. To this solution was added 1.1 eq. of (3R,3aR,6aS)hexahydrofuro [2,3b]furan-3-yl-(4-nitrophenyl) carbonate (27 mg, 0.091 mmol) and 5 eq. of triethylamine (58 μL, 0.4 mmol). The reaction was continued at room temperature for 4 days. The reaction mixture was solubilized in ethyl acetate washed with water and brine. The organic layer was dried over anhydrous magnesium sulfate, filtered and evaporated in vacuo to a residue. The crude material was purified on a preparative TLC plate (20×20 cm, 1 mm) eluting with 50% ethyl acetate in hexane. The product band was removed, eluted (4:1/dichloromethane:methanol), filtered and evaporated in vacuo and dried under high vacuum to provide (3S,3aS,6aR) Hexahydrofuro [2,3b]furan-3-yl N-((1S,2R)-1-benzyl-3-(cyclopentyloxy)[(4-methoxyphenyl)sulfonyl]amino-2-hydroxypropyl)carbamate (19.5 mg, 40%). HPLC showed the material to be 96% pure; Ret. time=11.88 min. $^1$H NMR (CDCl$_3$): 7.65 (d, 2H), 7.13–7.24 (m, 5H), 6.92 (d, 2H), 5.71 (m, 1H), 4.73–4.82 (m, 3H), 3.71–3.91 (m, 7H), 2.68–3.03 (m, 7 H), 2.12 (m, 1H), 1.48–1.74 (m, 10H) and MS (ES+), M+H=591.0.

Example 117
(3S,3aS,6aR)hexahydrofuro[2,3b]furan-3-yl-N-(1s,2R)-1-benzyl-3-[(cyclopentyloxy)[(4-methoxyphenyl)sulfonyl]amino-2-hydroxypropylcarbamate

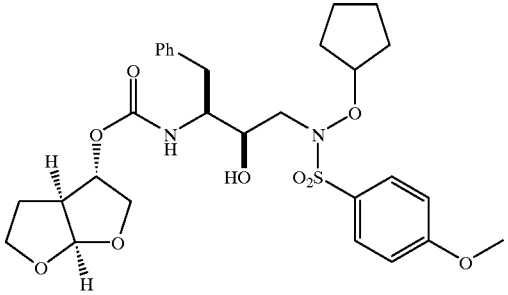

(117)

In a dried flask was introduced 1 eq. of N$^1$-[(2R,3S)-3-amino-2-hydroxy-4-phenylbutyl]-N$^1$-(cyclopentyloxy)-4-methoxy-1-benzenesulfonamide-trifluoroacetic acid (40.2 mg, 0.081 mmol) in 1 mL of N,N-dimehylformamide. To this solution was added 1.1 eq. of (3S,3aS,6aR) hexahydrofuro [2,3b]furan-3-yl (4-nitrophenyl) carbonate (26 mg, 0.089 mmol) and 5 eq. of triethylamine (56 μL, 0.4 mmol). The reaction was continued at room temperature for 4 days. The reaction mixture was solubilized in ethyl acetate washed with water and brine. The organic layer was dried over anhydrous magnesium sulfate, filtered and evaporated in vacuo to a residue. The crude material was purified on a preparative TLC plate (20×20 cm, 1 mm) eluting with 50% ethyl acetate in hexane. The product band was removed, eluted (4:1/dichloromethane:methanol), filtered and evaporated in vacuo and dried under high vacuum to provide (3S,3aS,6aR)Hexahydrofuro [2,3b]furan-3-yl N-((1S,2R)-1-benzyl-3-(cyclopentyloxy)[(4-methoxyphenyl)sulfonyl]amino-2-hydroxypropyl)carbamate (18.4 mg, 38%). HPLC showed the material to be 96% pure; Ret. time=11.8 min. $^1$H NMR (CDCl$_3$): 7.65 (d, 2H), 7.13–7.24 (m, 5H), 6.92 (d, 2H), 5.71 (m, 1H), 4.73–4.82 (m, 3H), 3.71–3.91 (m, 7H), 2.68–3.03 (m, 7 H), 2.12 (m, 1H), 1.48–1.74 (m, 10H) and MS (ES+), M+H=591.0.

Example 119

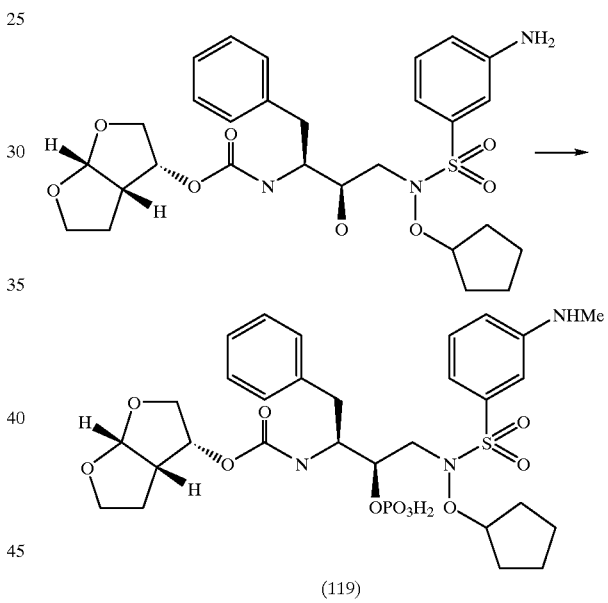

(119)

Phosphate ester of (3R,3aS,6aR)hexahydrofuro[2,3-b]furan-3-yl N-(1S,2R)-3-[[(3-N-methylaminophenyl)sulfonyl](cyclopentyloxy)amino)-1-benzyl-2-hydroxypropylcarbamate.

A solution of 0.145g (0.25 mmol) of (3R,3aS,6aR) hexahydrofuro[2,3-b]furan-3-yl N-(1S,2R)-3-[[(3-N-aminophenyl)sulfonyl](cyclopentyloxy)amino]-1-benzyl-2-hydroxypropylcarbamate (Example 77), 0.042 mL (0.3 mmol) of triethylamine and 0.081 g (0.3 mmol) of 2,4-dinitrobenzenesulfonyl chloride in 2 mL of tetrahydrofuran was treated with 0.2 mL of pyridine and 0.03 g of 4-N,N-dimethylamino pyridine and stirred at rt overnight. The mixture was diluted with ethylacetate and extracted with 1N HCl and saturated sodium bicarbonate. Chromatography on silica gel (1:1 ethyl acetate-hexanes) gave 75mg of a yellow foam which was dissolved in 1 mL of dimethylformamide and treated with 0.03 mL of iodomethane and 0.06 mL of triethylamine. The resulting mixture was heated to 70° C. for 10h and then evaporated. Chromatography on silicagel (40% ethylacetate-hexanes) gave a white foam which was dissolved in 1 mL of acetonitrile and 1 mL of dichloromethane. This solution was treated with 0.06 mL of dibenzyldiisopropyl phosphoramidite and 0.02g of tetrazole. The resulting solution was stirred at rt for 0.5 h and evaporated. Chromatography on silicagel (40% ethylacetate-hexanes) gave a colorless oil which was dissolved in 1 mL of acetonitrile and 1 mL of dichloromethane and treated with 0.2g of iodosobenzene diacetate. After two hours at rt, the volatiles were removed and the residue was re-dissolved in dichloromethane. The solution was treated with 1.5 mL of n-propylamine for 15 minutes and then evaporated. Chromatography on silicagel (60% ethylacetate-hexanes) gave a yellow oil which was dissolved in 20 mL of 2M ammonia in methanol and treated with 5 mg of 5% palladium on carbon. The mixture was hydrogenated for 1 h at 50 PSI, filtered and evaportated to give 15 mg of a white powdery solid. 1H NMR (CD$_3$CN):1.5–1.9 (13H), 2.75 (1H), 2.8–3.0 (3H), 2.90(3H), 3.15 (1H), 3.7 (1H), 3.9 (5H), 4.8 (1H), 5.0 (1H), 5.5 (1H), 7.0–7.4 (7H), 7.5 (2H). $^{31}$p NMR (CD$_3$CN): 2.1 ppm). LC-MS: 671 (MH+).

Example 120

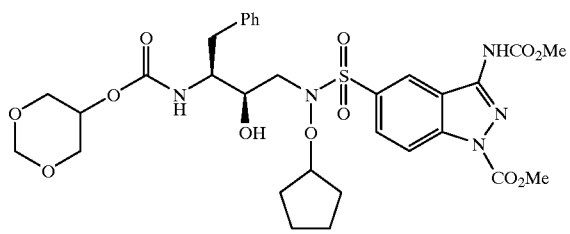

1,3-Dioxan-5-yl N-(1S,2R)-1-benzyl-3-[(cyclopentyloxy)(1-carbomethoxy-3-(carbomethoxyamino)indazole-5-ylsulfonyl)amino]-2-hydroxypropylcarbamate. 1,3-Dioxan-5-yl N-(1S,2R)-1-benzyl-3-[(cyclopentyloxy)amino]-2-hydroxypropylcarbamate (Step 1, Example 55), (130 mg, 0.330 mmol), 1-carbomethoxy-3-(carbomethoxyamino)indazole-5-sulfonyl chloride (110 mg, 0.330 mmol), and anhydrous diisopropylethylamine (0.06 mL, 0.330 mmol), were combined in anhydrous tetrahydrofuran (5 mL) in a 25 mL round bottomed flask under nitrogen. The reaction was stirred for 24 hours and concentrated in vacuo. After the workup described in Step 3, Example 54, the residue was purified by preparative silica gel TLC using 3:1/ethyl acetate:hexane as an eluent to give the product as a oil (91 mg, 0.129 mmol, 39%). $^1$HNMR (d$_6$-DMSO): 10.99 (s, 1H), 8.73 (s, 1H), 8.35 (d, J=8.9 Hz, 1H), 7.95 (d, J=8.9 Hz, 1H), 7.27–7.16 (m, 5H), 5.24 (d, J=6.5 Hz, 1H), 4.85–4.63 (m, 3H), 4.06 (s, 3H), 3.80–3.00 (m, 11H), 3.76 (s, 3H), 1.97–1.40 (m, 8H). MS(ES): 706 (M+1), 704 (M-1).

Example 121

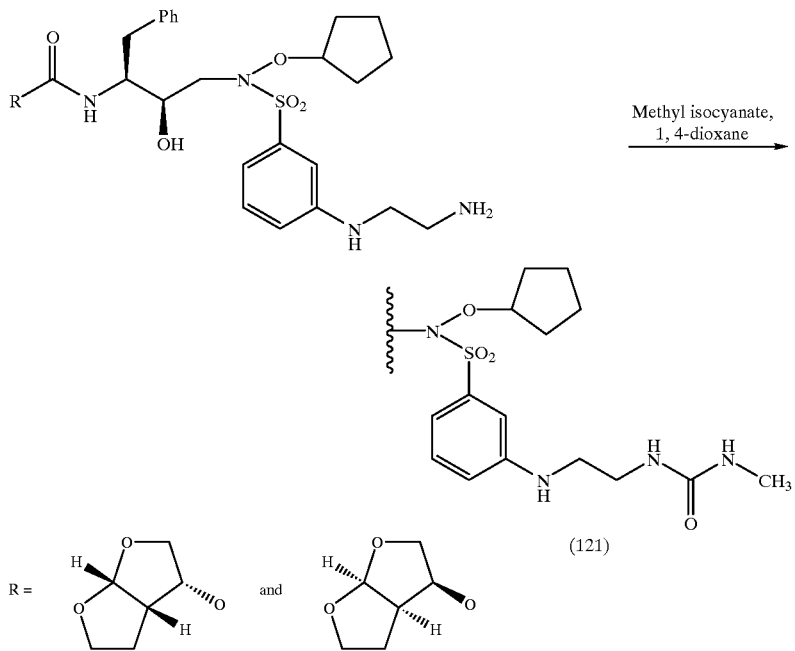

(3R,3aS,6aR)hexahydrofuro[2,3-b]furan-3-yl N-(1S,2R)-1-benzyl-3-[(cyclopentyloxy)(3-[(2-[(methylamino)carbonyl]aminoethyl)amino]phenylsulfonyl)amino]-2-hydroxypropylcarbamate and (3S,3aR,6aS)hexahydrofuro[2,3-b]furan-3-yl N-(1S,2R)-1-benzyl-3-[(cyclopentyloxy)(3-[(2-[(methylamino)carbonyl]amino ethyl)amino]phenylsulfonyl)amino]-2-hydroxypropylcarbamate.

A solution of 33 mg (0.053 mmol) of a 1:1 mixture of (3R,3aS,6aR)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate and (3S,3aR,6aS)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate (Example 83) in 1 mL of anhydrous 1,4-dioxane was treated with 0.003 mL (0.05 mmol) of methyl isocyanate. The resulting solution was stirred at RT. After 2 hours the solution was concentrated in vacuo to afford 35 mg (97%) of the desired product as a white foam. 1H-NMR (CDCl$_3$): 7.43–7.01 (13H), 5.76–4.80 (4H), 4.08–2.70 (18H), 1.90–1.30 (1OH). LCMS(ESI): 676 (M+H).

Example 122

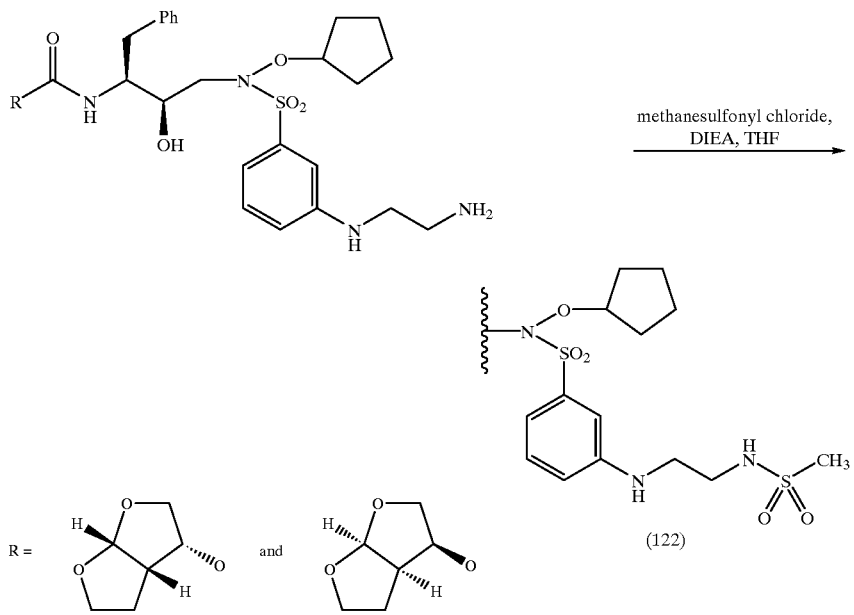

(3R,3aS,6aR)hexahydrofuro[2,3-b]furan-3-yl N-[(1S,2R)-1-benzyl-3-((cyclopentyloxy)[3-(2-[(methylsulfonyl)amino]ethylamino)phenyl]sulfonylamino)-2-hydroxypropyl]carbamate and (3S,3aR,6aS)hexahydrofuro[2,3-b]furan-3-yl N-[(1S,2R)-1-benzyl-3-((cyclopentyloxy)[3-(2-[(methylsulfonyl)amino]ethylamino)phenyl]sulfonylamino)-2-hydroxypropyl]carbamate. A solution of 33 mg (0.053 mmol) of a 1:1 mixture of (3R,3aS,6aR)hexahydrofuro[2,3-b]furan-3-yl N-(1S,2R)-3-[(3-[(2-aminoethyl)amino]phenylsulfonyl) (cyclopentyloxy)amino]-1-benzyl-2-hydroxypropylcarbamate and (3S,3aR,6aS)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate (Example 83) in 2 mL of anhydrous THF at 0° C. was treated with 0.010 mL (0.059 mmol) of N,N-diisopropylethylamine followed by 0.005 mL (0.06 mmol) of methanesulfonyl chloride. The resulting solution was allowed to warm to RT with stirring. After 3 hours the solution was concentrated in vacuo and the residue subjected to flash chromatography (silica gel, 95:5 $CH_2Cl_2$/ 2M $NH_3$ in MeOH) to afford 31 mg (86%) of the desired product as a white foam. 1H-NMR ($CDCl_3$): 7.40–6.81 (12H), 5.62 (1H), 5.43–5.04 (1H), 4.99 (1H), 4.81 (1H), 3.97–2.60 (18H), 1.90–1.30 (1OH). LCMS(ESI): 697 (M+H).

Example 123

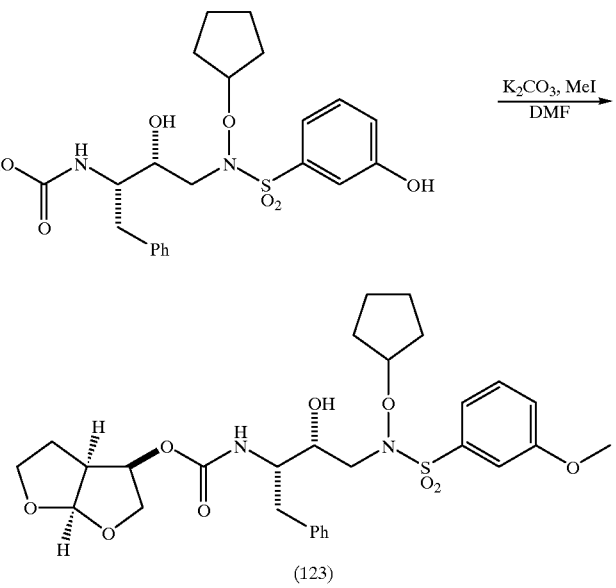

(3R,3aS,6aR)hexahydrofuro[2,3-b]furan-3-yl N-[(1S,2R)-1-benzyl-3-((cyclopentyloxy)[(3-methoxyphenyl) sulfonyl]amino)-2-hydroxypropyl]carbamate (3R,3aS,6aR) hexahydrofuro[2,3-b]furan-3-yl N-((1S,2R)-1-benzyl-3-(cyclopentyloxy)[(3-hydroxyphenyl)sulfonyl]amino-2-hydroxypropyl)carbamate was combined with potassium carbonate (0.86.mmol, 120 mg), iodomethane (0.86 mmol, 0.054 5 mL), and anhydrous DMF (0.5 mL) under nitrogen. The reaction stirred for 3 hours at 50° C. and was concentrated to an oil under vacuum, diluted in ethyl acetate, washed with distilled water and brine, and dried over magnesium sulfate. The crude reaction product was concentrated and purified by silica gel chromatography (1:1/hexanes/ethyl acetate) and yielded 51 mg (>99%) of a fine white powder.; $R_f$=0.15 (1:1 hexanes/ethyl acetate); 1H NMR (CDCl$_3$): δ7.46–7.39 (1H,m), 7.38–7.32 (1H,m), 7.32–7.13 (8H,m), 5.65–5.60 (1H,m), 5.03–4.94 (1H,m), 4.84–4.71 (2H,m), 3.95–3.84 (5H,m), 3.84 15 (3H,s), 3.70–3.61 (2H,m), 3.13 (1H, bs), 3.06–2.72 (5H,m), 1.87–1.69 (4H,m), 1.70–1.54 (4H,m); MS (ESI): M+H=591.

Example 124

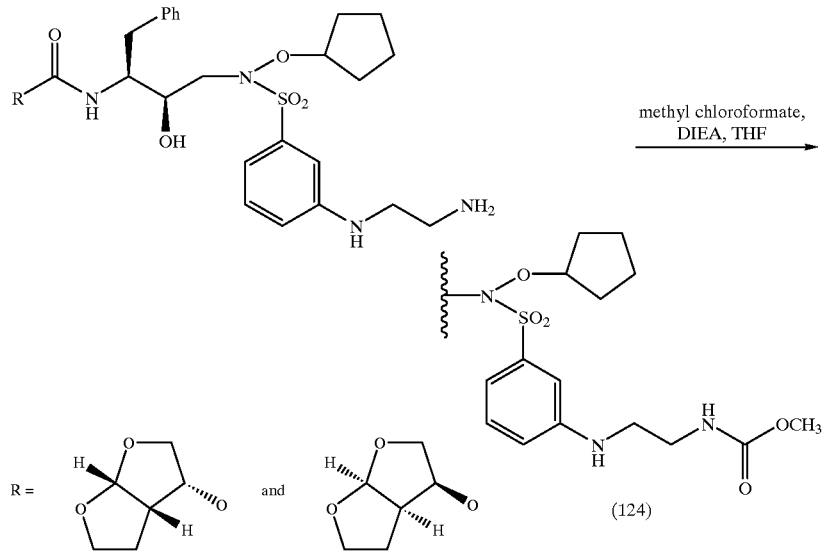

(124)

(3R,3aS, 6aR)hexahydrofuro[2,3-b]furan-3-yl N-[(1S,2R)-1-benzyl-3-((cyclopentyloxy)[3-(2-[(methoxycarbonyl)amino]ethylamino)phenyllsulfonylamino)-2-hydroxypropyl]carbamate and (3S,3aR, 6aS) hexahydrofuro[2,3-b]furan-3-yl N-[(1S,2R)-1-benzyl-3-((cyclopentyloxy)[3-(2-[(methoxycarbonyl)amino]ethylamino)phenyl]sulfonylamino)-2-hydroxypropyl]carbamate. A solution of 33 mg (0.053 mmol) of a 1:1 mixture of (3R,3aS,6aR) hexahydrofuro[2,3-b]furan-3-yl N-(1S,2R)-3-[(3-[(2-aminoethyl)amino]phenylsulfonyl) (cyclopentyloxy)amino]-1-benzyl-2-hydroxypropylcarbamate and (3S,3aR, 6aS)hexahydrofuro[2,3-b]furan-3-yl N-(1S,2R)-3-[(3-[(2-aminoethyl)aminoiphenylsulfonyl)(cyclopentyloxy)amino]-1-benzyl-2-hydroxypropylcarbamate (Example 83) in 2 mL of anhydrous THF at 0° C. was treated with 0.010 mL (0.059 mmol) of N,N-diisopropylethylamine followed by 0.005 mL (0.06 mmol) of methyl chloroformate. The resulting solution was allowed to warm to RT with stirring. After 3 hours the solution was concentrated in vacuo and the residue subjected to flash chromatography (silica gel, 95:5 CH$_2$Cl$_2$/2M NH$_3$ in MeOH) to afford 32 mg (89%) of the desired product as a white foam. 1H-NMR (CDCl$_3$): 7.40–6.81 (12H), 5.61 (1H), 5.40–4.87 (2H), 4.80 (1H), 3.97–2.63 (18H), 1.90–1.30 (1OH). LCMS(ESI): 677 (M+H).

Example 125 (125)

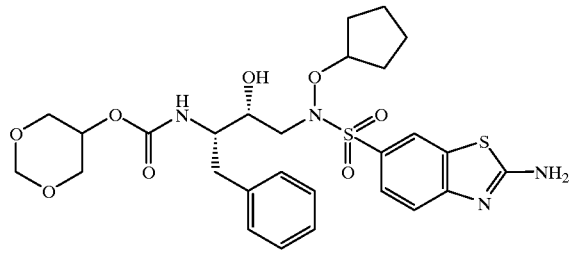

Preparation of 1,3-Dioxane-5-yl N-(1S,2R)-1-benzyl-3-[(cyclopentyloxy)(2-amino)]-benzothiazol-6-ylsulfonyl)amino]-2-hydroxypropylcarbamate Step 1

To a suspension of 2-aminobenzothiazole (4 g, 26.6 mmol) in 20 ml of dichloromethane under nitrogen was added 4 mL of anhydrous DMF. The solution was cooled to −5° C. and triethylamine (7.4 mL, 53.2 mmol, 2.0 eq.) was added. Methanesulfonyl chloride (2.3 mL, 29.3 mmol, 1.1 eq.) was added over 5 minutes followed by an additional 4 mL of dichloromethane. The reaction was warmed to 25° C. After approximately 24 hours at 25° C., the reaction was quenched 0° C. with saturated bicarbonate solution and partitioned between water and ethyl acetate. The aqueous layer was extracted with ethyl acetate and the combined organic layers were washed with water (4X), saturated brine solution, dried over sodium sulfate, filtered and the solvent removed in vacuo to give 930 mg of a residue that was shown by LCMS to contain almost no product. The combined aqueous layers were extracted with excess ethyl acetate. These organic layers were washed with saturated brine solution, dried over sodium sulfate, filtered and the solvent removed in vacuo to give 1.2 g of product that was shown by HPLC and LCMS to be over 97% pure desired product which was used without further purification. LCMS: 229.0(M+H).

Step 2

To 2.4 mL (35 mmol, 20 eq.) of chlorosulfonic acid, stirred under nitrogen at −40° C., was added 2-methanesulfonamidobenzothiazole (Step 1) (400 mg, 1.75 mmol) in small portions over 10 minutes. The suspension was stirred at −400° C. for 5 minutes, then was warmed to 00C for 2.5 hours, then warmed to 25° C. After approximately 4 days at 25° C., the reaction was quenched by adding dropwise to well stirred ice water. A small amount of solid was filtered off and shown by HPLC to contain only a small amount of the desired product. The aqueous layer was extracted with ethyl acetate (2x) and the combined organic layers were washed with saturated brine solution, dried over sodium sulfate, filtered and the solvent removed in vacuo to give 146 mg of the desired material. HPLC showed the material to be ~80% pure, Ret. time=9.42 min. The material was used without further purification.

Step 3

To 64 mg (0.26 mmol) of 2-aminobenzothiazole-6-sulfonyl chloride, (2), was added 102 mg (.26 mmol, 1.0 eq.) of 1,3-Dioxane-5-yl N-(1S,2R)-1-benzyl-3-(cyclopentyloxyamino)2-hydroxypropylcarbamate (Example 55, Step 1) and 7 mg of 4-dimethylaminopyridine. The mixture was dissolved in 3 mL of anhydrous pyridine to give a yellow solution. Solid formed within 5 minutes and the suspension stirred at 25° C., under nitrogen, for approximately 21 hours. The reaction was quenched with saturated sodium bicarbonate solution and ethyl acetate. The solvent removed in vacuo to remove excess pyridine, and the residue was extracted with ethyl acetate (2x). The combined organic layers were washed with saturated brine solution, dried over sodium sulfate, filtered and the solvent was removed in vacuo to give 100 mg of 2-aminobenzothiazole-6-sulfonyl chloride, (2). HPLC showed the material to be 94% pure, Ret. time=8.343 min. The material was used without further purification. 1H NMR (chloroform-D3) 5.71(s, 2H), 8.62-(d, 1H), 7.95 (d, 1H), 8.29 (s, 1H) and LC/MS, M+H=248.9 confirms no methanesulfonyl group present.

Example 126

Step 1

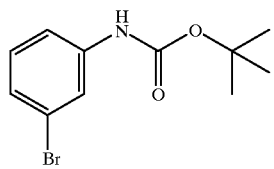

3-Bromo-N-tert-butoxycarbonylaniline. 3-Bromoaniline (0.50 ml, 4.6 mmol) di-tert-butyldicarbonate (1.20 g, 5.5 mmol) and 4-dimethylaminopyridine (0.003 g) were combined in anhydrous CH$_2$Cl$_2$ (10 ml). Solution chilled to 0° C. and triethylamine (1.28 ml, 9.2 mmol) was added. Reaction was allowed to warm to room temperature then was heated to reflux for 1 hour. Reactiom mixture was diluted in EtOAc and washed with sat. NaHCO3, 0.5N KHSO$_4$ and brine. Organic phase was dried with MgSO$_4$ and the solvent was removed in vacuo. Purification by flash chromatography (1:4/EtOAc/Hex to 1:3 to 1:2). Recovered 1.01 g (81%) of the product as a light yellow solid. R$_f$=0.62 (1:4 EtOAc/Hex). $^1$H NMR (CDCl$_3$) 7.68 (1H,s), 7.22–7.10 (3H,m), 6.48 (1H,b), 1.51 (9H,s).

Step 2

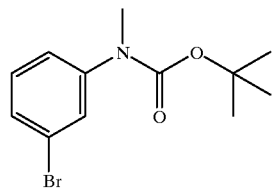

3-Bromo-N-tert-butoxycarbonyl-N-methylaniline. 3-Bromo-N-tert-butoxycarbonylaniline (0.50 g, 1.8 mmol) was dissolved in anhydrous DMF (5 ml). Sodium hydride (0.088 g, 2.2 mmol) was added to the solution and the deprotonation was stirred 10 minutes at room temperature. Methyl iodide (0.137 ml, 2.2 mmol) was added slowly and the reaction was stirred overnight at room temperature. Reaction mixture was diluted in EtOAc and washed with H20 and brine. The organic phase was dried with MgSO$_4$ and the solvent was removed in vacuo to give 0.51 g (96%) of the product cleanly as a light yellow oil. R$_f$=0.63 (1:4 EtOAc/Hex). $^1$H NMR (CDCl$_3$) 7.41 (1H,s), 7.30 (1H,m), 7.20 (2H,m), 3.23 (3H,s), 1.49 (9H,s).

Step 3

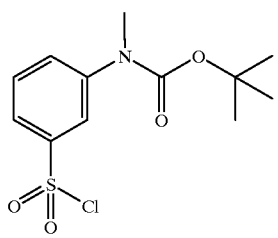

N-tert-Butoxycarbonyl-3-chlorosulfonyl-N-methylaniline. 3-Bromo-N-tert-butoxycarbonyl-N-methylaniline (0.358g, 1.2 mmol) was dissolved in freshly distilled THF (5 ml) under a N2 atmosphere. The solution was chilled to −78° C. and n-butyl lithium (0.750 ml, 2.0 M solution in cyclohexane, 1.5 mmol) was added. After 15 minutes, sulfuryl chloride (0.121 ml, 1.5 mmol) was added and the reaction was allowed to warm to room temperature and stirring was continued overnight. THF was removed by evaporation and the resulting residue was diluted in EtOAc. Organic phase was washed with H$_2$0 and brine before being dried with MgSO$_4$. The solvent was removed in vacuo. Purification by flash chromatography (1:19/EtOAc/Hex gradient to 1:9 and then to 1:4). Recovered 0.089 g (23%) of the product as a colorless oil. Rf=0.14 (1:9 EtOAc/Hex). $^1$H NMR (CDCl$_3$) 7.96 (1H,s), 7.80 (1H,d), 7.68 (1H,d), 7.57 (1H,t), 3.33 (3H,s), 1.50 (9H,s).

Step 4:
(3R, 3aS, 6aR)Hexahydrofuro[2,3b]furan-3-yl-N-(1S,2R)-1-benzyl-3-[(isopropyloxy)[(3-(N-(methyl-tert-Butoxycarbonyl))phenyl) sulfonyl]amino-2-hydroxypropylcarbamate (126)

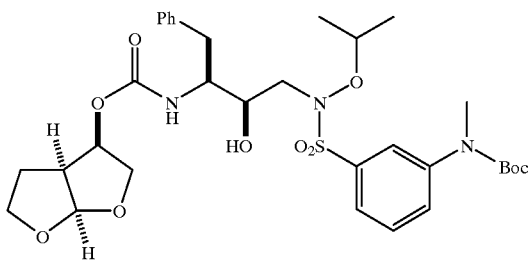

In a dried flask was introduced 1 eq. of (3R,3aS,6aR) Hexahydrofuro[2,3b]furan-3-yl-N-(1S,2R)-1-benzyl-3-[(isopropyloxy) amino]-2-hydroxypropylcarbamate (53.6 mg, 0.14 mmol) in 2 mL of dried pyridine. To this solution was added 1.2 eq. of N-tert-Butoxycarbonyl-3-chlorosulfonyl-N-methylaniline (50 mg, 0.16 mmol) and catalytic amount of N,N-dimethyl aminopyridine. The reaction was continued at room temperature for 24 h. The solvent was evaporated in vacuo to an oil who was solubilized in ethyl acetate washed with 1N hydrochloric acid, and brine. The organic layer was dried over anhydrous magnesium sulfate, filtered and evaporated in vacuo to a residue. The crude material was purified on flash grade silica gel eluting with 50% ethyl acetate in hexane. Fractions containing the product were combined, evaporated in vacuo and dried under high vacuum to provide (3R,3aS,6aR)Hexahydrofuro[2,3b]furan-3-yl-N-(1S,2R)-1-benzyl-3-[(isopropyloxy)[(3-(N-(methyl-tert-Butoxycarbonyl)) phenyl)sulfonyl]amino-2-hydroxy propylcarbamate (29.2 mg, 31%). HPLC showed the material to be 98% pure; Ret. time=12.1 min. IH NMR (CDCl$_3$): 7.09–7.78 (m, 9H), 5.56 (d, 1H), 5.15 (bs, 1H), 4.91 (q, 1H), 4.49 (q, 1H), 3.57–3.88 (m, 5H), 3.24 (s, 3H), 2.96 (m, 2H), 2.72 (m, 1H), 2.56 (m, 1H), 1.42–1.50 (m+s, 13H), 1.19 (d, 6H) and LCMS (ES+), M+H=664.3.

Example 127

(3R,3aS,6aR)Hexahydrofuro[2,3b]furan-3-yl-N-(1S,2R)-1-benzyl-3-[(isopropyloxy)[(3-N-methylphenyl)sulfonyl] amino-2-hydroxypropylcarbamate (127)

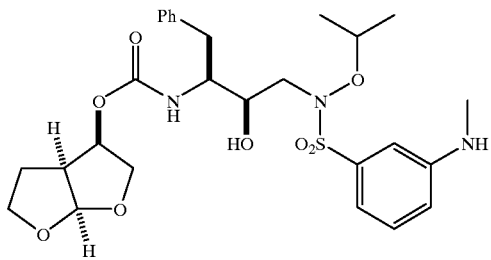

In a dried flask was introduced 1 eq. of (3R,3aS,6aR) Hexahydrofuro[2,3b]furan-3-yl-N-(1S,2R)-1-benzyl-3-[(isopropyloxy)[(3-(N-(methyl-tert-Butoxycarbonyl)) phenyl) sulfonyl]amino-2-hydroxy propylcarbamate (10.8 mg, 0.016 mmol) in 1 mL dichloromethane. To this solution was added 600 μL of trifluoroacetic acid. The reaction was continued at room temperature for 45 min. The solvent was evaporated in vacuo to an oil. The crude material was purified on flash grade silica gel eluting with 50% ethyl acetate in hexane. Fractions containing the product were combined, evaporated in vacuo and dried under high vacuum to provide (3R,3aS,6aR)Hexahydrofuro[2,3b]furan-3-yl-N-(1S,2R)-1-benzyl-3-[(isopropyloxy)[(3-N-methylphenyl)sulfonyl]amino-2-hydroxypropyl carbamate (7.2 mg, 78%). HPLC showed the material to be 98% pure; Ret. time=10.1 min. H$^1$-NMR (CDCl$_3$): 7.09–7.35 (m, 9H), 6.86 (m, 1H), 5.58 (d, 1H), 4.92–4.96 (m, 2H), 4.46–4.50 (m, 2H), 3.56–3.85 (m, 5H), 2.71–2.97 (m+s, 7H), 1.45–1.80 (m, 3H), 1.17 (d, 6H) and LCMS (ES+), M+H= 564.3.

Example 128

(3R,3aS,6aR)hexahydrofuro[2,3b]furan-3-yl-N-(1S,2R)-1-benzyl-3-[(cyclopentyloxy)[(3-(N-(methyl-tert-Butoxycarbonyl))phenyl) sulfonyl]amino-2-hydroxypropylcarbamate (128)

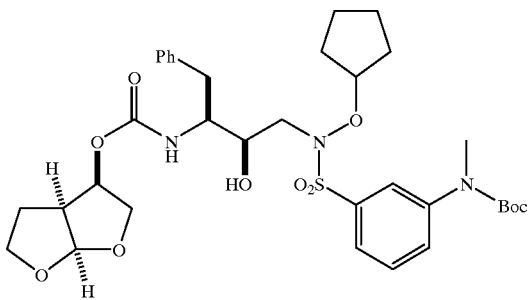

In a dried flask was introduced 1 eq. of (3R,3aS,6aR)Hexa hydrofuro[2,3b]furan-3-yl-N-(1S,2R)-1-benzyl-3-[(cyclopentyloxy) amino]-2-hydroxypropylcarbamate (60 mg, 0.14 mmol) in 2 mL of dried pyridine. To this solution was added 1.3 eq. of N-tert-Butoxycarbonyl-3-chlorosulfonyl-N-methylaniline (57 mg, 0.19 mmol) and catalytic amount of N,N-dimethylaminopyridine. The reaction was continued at room temperature for 24 h. The solvent was evaporated in vacuo to an oil who was solubilized in ethyl acetate washed with 1N hydrochloric acid, and brine. The organic layer was dried over anhydrous magnesium sulfate, filtered and evaporated in vacuo to a residue. The crude material was purified on flash grade silica gel eluting with 50% ethyl acetate in hexane. Fractions containing the product were combined, evaporated in vacuo and dried under high vacuum to provide (3R,3aS,6aR)hexahydrofuro [2,3b]furan-3-yl-N-(1S,2R)-1-benzyl-3-[(cyclopentyloxy) [(3-(N-(methyl-tert-Butoxycarbonyl))phenyl) sulfonyl] amino-2-hydroxypropylcarbamate (26.8 mg, 28%). HPLC showed the material to be 99% pure; Ret. time=12.88 min. H$^1$-NMR (CDCl$_3$): 7.74 (m, 1H), 7.09–7.51 (m, 9H), 5.60 (m, 1H), 5.25 (bs, 1H), 4.94 (q, 1H), 4.77 (q, 1H), 3.71–3.86 (m, 6H), 3.52 (m, 1H), 3.24 (m, 3H), 3.08 (m, 1H), 2.85–2.93 (m, 4H), 2.68 (m, 1H), 1.73–1.83 (m, 5H), 1.42–1.59 (m+s, 12H) and LCMS (ES+), M+H=690.2.

Example 129

Step 1

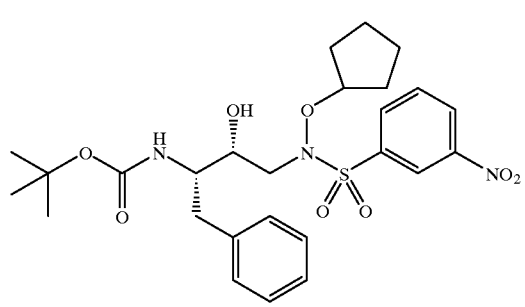

tert-Butyl-N-((1S,2R)-1-benzyl-3-(cyclopentyloxy)[(3-nitrophenyl)sulfonyl]amino-2-hydroxypropyl)carbamate. tert-Butyl-N-((1S,2R)-1-benzyl-3-(cyclopentyloxy)amino-2-hydroxypropyl)carbamate (0.52 g, 1.4 mmol) was combined with 3-nitrobenzenesulfonyl chloride (0.47 g, 2.1 mmol) in freshly distilled THF (5 ml). Diisopropylethylamine (0.74 ml, 4.3 mmol) was added and the reaction was stirred at room temperature overnight. Reaction mixture was diluted in EtOAc and washed with 0.5 N $KHSO_4$, and brine. Organic phase was dried with $MgSO_4$ and solvent was removed in vacuo. Purication by flash chromatography (1:4/EtOAc/Hex gradient to 1:3, to 1:2, to 1:1 and then to 2:1). Recovered 0.44 g (56%) of the product as a white foam. $R_f$=0.45 (2:1 EtOAc/Hex), $^1$H NMR ($CDCl_3$) 8.67 (1H, s), 8.49 (1H, d), 8.08 (1H, d), 7.77 (1H, t), 7.36–7.17 (5H, m), 4.88 (1H,m), 4.62 (1H,b), 3.88–3.71 (2H,m), 3.41 (1H,b), 3.07 (1H,b), 2.98–2.79 (3H,m), 1.92–1.75 (4H,m), 1.73–1.52 (4H,m), 1.45 (9H,s).

Step 2

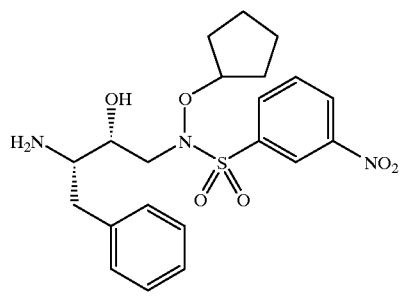

(1S,2R)-1-benzyl-3-(cyclopentyloxy)[(3-nitrophenyl)sulfonyl]amino-2-hydroxypropylamine. tert-Butyl-N-((1S,2R)-1-benzyl-3-(cyclopentyloxy)[(3-nitrophenyl)sulfonyl]amino-2-hydroxypropyl)carbamate (0.34 g, 0.6 mmol) was dissolved in $CH_2Cl_2$ (3 ml). Trifluoroacetic acid was added with stirring and the reaction was stirred 15 minutes at room temperature. The solvent was removed by evaporation and the resulting residue was partitioned between EtOAc and sat. $NaHCO_3$. Organic phase was washed with sat. $NaHCO_3$ and brine then dried with $MgSO_4$. Solvent was removed in vacuo to give 0.27 g (100%) of the product as a white foam. $R_f$=0.11 (2:1 EtOAc/Hex). $^1$H NMR ($CDCl_3$) 8.75 (1H, s), 8.52 (1H, d), 8.19 (1H, d), 7.80 (1H, t), 7.40–7.08 (5H, m), 4.90 (1H,m), 3.80 (1H,m), 3.36–3.14 (2H,m), 3.05 (1H,b), 2.88 (1H,d), 2.48 (1H,m), 1.96–1.75 (4H,m), 1.74–1.50 (4H,m).

Step 3

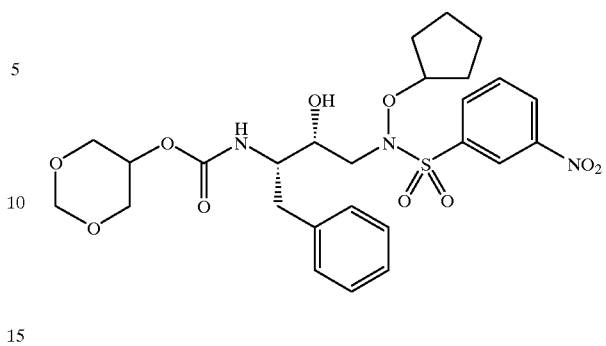

1,3-Dioxan-5-yl-N-(1S,2R)-benzyl-3-(cyclopentyloxy)[(3-nitrophenyl)sulfonyl]amino-2-hydroxypropylcarbamate. (1S,2R)-1-benzyl-3-(cyclopentyloxy)[(3-nitrophenyl)sulfonyl]amino-2-hydroxypropylamine (0.070 g, 0.2 mmol) was combined with 1,3-dioxan-5-yl-(4-nitrophenyl)carbonate (0.066g, 0.2 mmol) in anhydrous DMF (4 ml) under a $N_2$ atmosphere. Triethyl amine (0.045 ml, 0.3 mmol) was added and the reaction was stirred at room temperature for 2 hours. Reaction mixture was diluted in EtOAc and washed with sat. NaHCO3, 0.5N $KHSO_4$ and brine. The organic phase was dried with $MgSO_4$ and solvent was removed in vacuo. Purification by flash chromatography (1:2 EtOAc/Hex to 1:1 to 2:1). Recovered 0.073 g (78%) of the product as a white foam. $R_f$=0.26 (1:1 EtOAc/Hex). $^1$H NMR ($CDCl_3$) 8.66 (1H, s), 8.50 (1H, d), 8.08 (1H, d), 7.77 (1H, t), 7.36–7.13 (5H, m), 5.01 (1H,d), 4.92 (1H,d), 4.88 (1H,m), 4.73 (1H,d), 4.50 (1H,s), 4.00–3.79 (6H,m), 3.13 (1H,m), 3.08–2.88 (2H,m), 2.77 (1H,m), 1.96–1.73 (4H,m), 1.72–1.52 (4H,m).

Step 4:

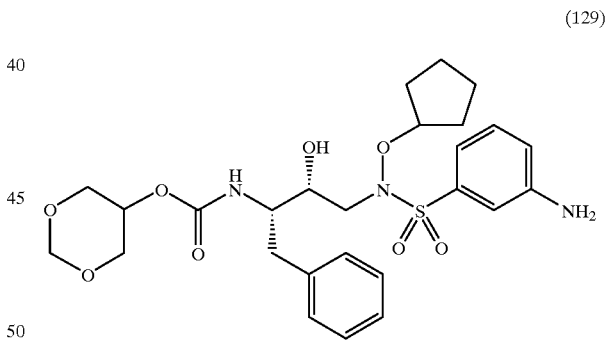

(129)

1,3-Dioxan-5-yl-N-(1S,2R)-benzyl-3-(cyclopentyloxy)[(3-aminophenyl)sulfonyl]amino-2-hydroxypropylcarbamate. 1,3-Dioxan-5-yl-N-(1S,2R)-benzyl-3-(cyclopentyloxy) L(3-nitrophenyl)sulfonyl]amino-2-hydroxypropylcarbamate (0.070 g, 0.1 mmol) was combined with tin chloride dihydrate (0.109 g, 0.5 mmol) is absolute ethanol (10 ml). Reation was heated to reflux and stired for 2.5 hours. Ethanol was removed in vacuo and the material was purified by preparative TLC (2:1/EtOAc/Hex). Recovered 0.045 g (68%) of the product as a colorless residue. $R_f$=0.36 (2:1 EtOAc/Hex). 1H NMR ($CDCl_3$) 7.38–7.18 (6H, m), 7.15 (1H,d), 7.07 (1H,s), 6.85 (1H,d), 5.00 (1H,d), 4.92 (1H,d), 4.83 (1H,m), 4.76 (1H,d), 4.53 (1H,s), 4.05–3.80 (5H,m), 3.73 (1H,m), 3.19 (1H,m), 3.10 (1H,m), 3.00–2.82 (2H,m), 1.91–1.70 (4H,m), 1.69–1.50 (4H,m). LRMS (M+H)$^+$550.3.

Example 130

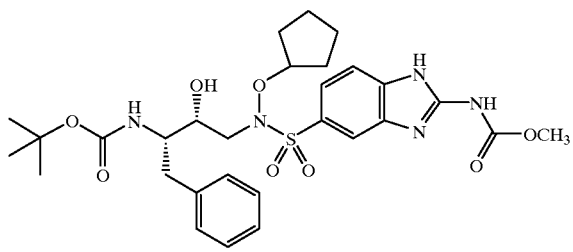

(130)

tert-Butyl-N-((1S,2R)-1-benzyl-3-(cyclopentyloxy) (2-[(methoxycarbonyl)amino]benzimidazol-5-ylsulfonyl) amino-2-hydroxypropyl)carbamate. tert-Butyl-N-((1S,2R)-1-benzyl-3-(cyclopentyloxy)amino-2-hydroxypropyl) carbamate (step 1, Example 54), (0.75 g, 2.1 mmol) was combined with 2-(methoxycarbonyl)amino benzimidazol-5-ylsulfonyl chloride (0.89g, 3.1 mmol) in anhydrous DMF (15 ml) under a $N_2$ atmosphere. Diisopropylethylethyl amine (1.08 ml, 6.2 mmol) was added and the reaction was stirred at room temperature for 24 hours. The reaction mixture was diluted in EtOAc and washed with sat. NaHCO$_{3, 0.5}$N KHSO$_4$ and brine. Organic phase was dried with MgSO$_4$ and solvent was removed in vacuo. Purification by flash chromatography (CH$_2$Cl$_2$ to 1l MeOH in CH$_2$Cl$_2$ to 2% to 3% to 4%). Recovered 0.79 g (62%) of product as a white foam. Rf=0.08 (3% MeOH/CH$_2$Cl$_2$). HPLC $t_R$=10.47 min (C18 column). LRMS (M+H)$^+$618.2.

Example 131

(131)

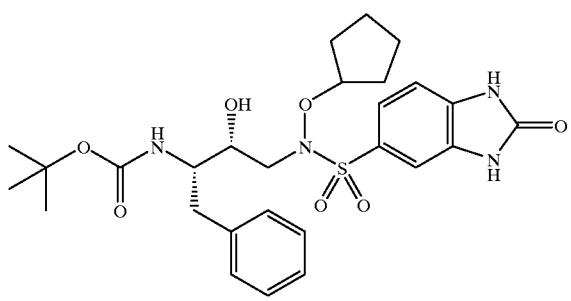

tert-Butyl-N-((1S,2R)-1-benzyl-3-(cyclopentyloxy)(2-oxybenzimidazol-5-ylsulfonyl)amino-2-hydroxypropyl) carbamate. tert-Butyl-N-((1S,2R)-1-benzyl-3-(cyclopentyloxy)amino-2-hydroxypropyl)carbamate (Step 1, Example 54), (0.100 g, 0.3 mmol) was combined with 2-oxobenzimidazol-5-ylsulfonyl chloride (0.070g, 0.3 mmol) in anhydrous DMF (2 ml) under a $N_2$ atmosphere. Diisopropylethylethyl amine (1.08 ml, 6.2 mmol) was added and the reaction was stirred at room temperature overnight. The reaction mixture was diluted in EtOAc and washed with sat. NaHCO3, 0.5N KHSO$_4$ and brine. Organic phase was dried with MgSO$_4$ and solvent was removed in vacuo. Purification by flash chromatography (1:1/EtOAc/Hex to 2:1 to 3:1 to EtOAc). Recovered 0.052 g (54%) of product as a white foam. R$_f$=0.10 (2:1 EtOAC/Hex). HPLC tR=10.0$^8$ min (C18 column). LRMS (M+H)$^+$561.2.

Example 132

(132)

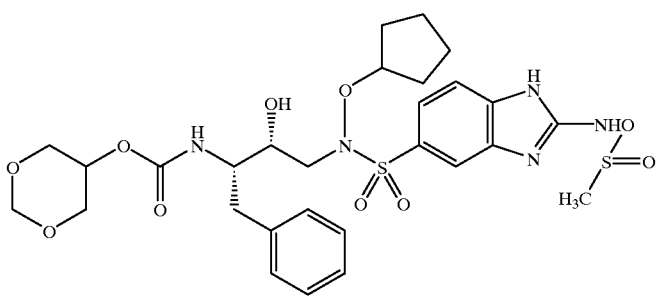

1,3-Dioxan-5-yl-N-((1S,2R)-1-benzyl-3-(cyclopentyloxy) (2-[(methylsulfonyl)amino]benzimidazol-5-ylsulfonyl) amino-2-hydroxypropyl)carbamate. 1,3-Dioxan-5-yl-N-((1S,2R)-1-benzyl-3-(cyclopentyloxy)amino-2-hydroxypropyl)carbamate (Step 1, Example 55), (0.148 g, 0.4 mmol) was combined with 2-[(methylsulfonyl) amino]benzimidazol-5-ylsulfonyl chloride (0.162 g, 0.5 mmol) in anhydrous DMF (4 ml) under a $N_2$ atmosphere. The resulting solution was chilled to 0° C. and diisopropylethylethyl amine (0.196 ml, 1.1 mmol) was added. The reaction was allowed to warm to room temperature and stirred for 24 hours. Reaction mixture was diluted in EtOAc and washed with sat. NaHCO$_{3, 0.5}$N KHSO$_4$ and brine. Organic phase was dried with MgSO$_4$ and solvent was removed in vacuo. Purification by flash chromatography (EtOAc to 2% MeOH/EtOAc to 4%). Recovered 0.159 g (64%) of the product as a white foam. R$_f$=0.48 (5% MeOH/EtOAc). $^1$H NMR (CDCl$_3$) 8.10 (1H,s), 7.67 (1H,d), 7.41 (1H,d), 7.30–7.15 (5H,m), 6.35 (2H,s), 5.14 (1H,d), 4.90 (1H,d), 4.85 (1H,m), 4.72 (1H,d), 4.48 (1H,m), 3.93–3.73 (5H,m), 3.29 (3H,s), 1.89–1.70 (4H,m), 1.69–1.47 (4H,m). LRMS (M+H)$^+$668.0.

Example 133

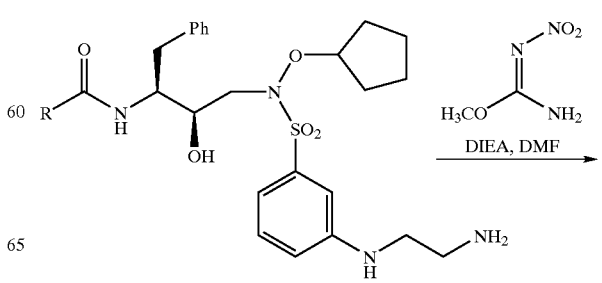

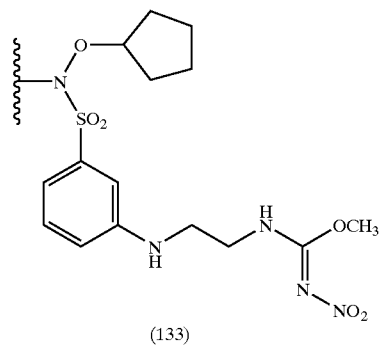

(133)

N-[2-(3-[[(2R,3S)-3-([(3R,3aS,6aR)hexahydrofuro[2,3-b]furan-3-yloxy]carbonylamino)-2-hydroxy-4-phenylbutyl](cyclopentyloxy) amino]sulfonylanilino)ethyl]-O-methyl-N'-(nitro)isourea and N-[2-(3-[[(2R,3S)-3-([(3S,3aR,6aS)hexahydrofuro[2,3-b]furan-3-yloxy]carbonylamino)-2-hydroxy-4-phenylbutyl](cyclopentyloxy) amino]sulfonylanilino)ethyl]-O-methyl-N'-(nitro)isourea. A solution of 25 mg (0.040 mmol) of a 1:1 mixture of (3R,3aS,6aR)hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate and (3S,3aR,6aS)hexahydrofuro[2,3-b]furan-3-yl N-(1S,2R)-3-[(3-[(2-aminoethyl)amino]phenyl sulfonyl)(cyclopentyloxy)amino]-1-benzyl-2-hydroxypropylcarbamate (Example 83) and 0.008 mL (0.048 mmol) of N,N-diisopropyl ethylamine in 1.5 mL of anhydrous DMF was treated with 6 mg (0.05 mmol) of O-methyl-N-nitroisourea (Heyboer et al. Rec. Chim Trav. Pay-Bas (1962), 81, 69–72). The resulting solution was stirred at RT. After 20 hours the solution was concentrated in vacuo and the residue subjected to flash chromatography (silica gel, 85:15 CH$_2$Cl$_2$/2M NH$_3$ in MeOH) to afford 21 mg (72%) of the desired product as a white foam. 1H-NMR (CDCl$_3$): 7.60–7.06 (12H), 5.63–4.65 (4H), 4.10–2.50 (18H), 1.90–1.31 (10H). LCMS(ESI): 721 (M+H).

Example 134

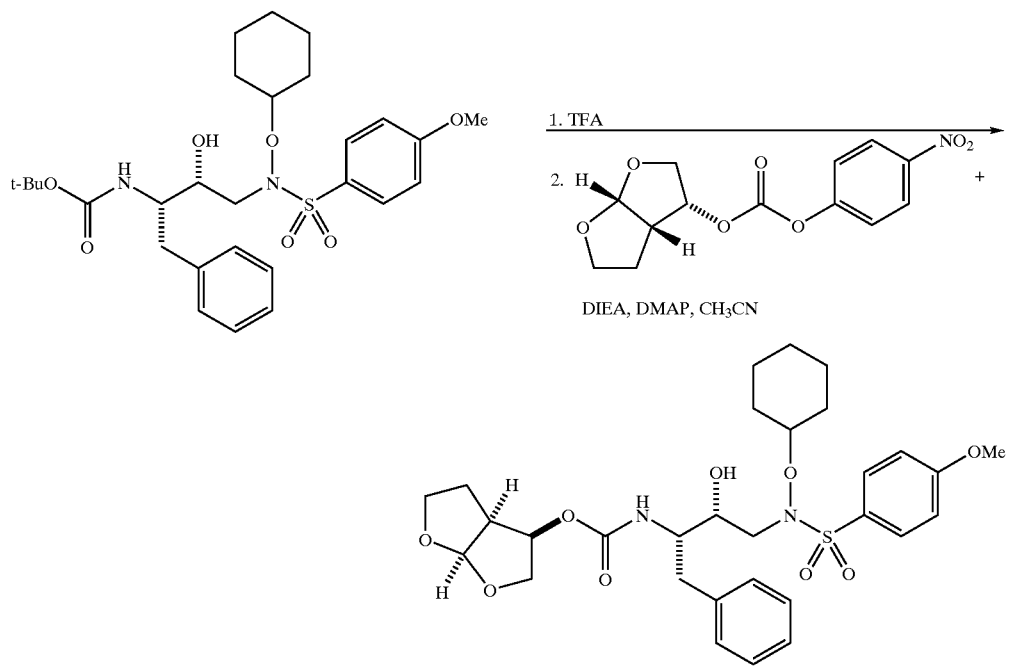

-continued

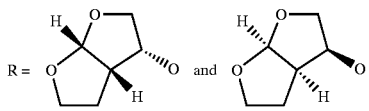

(3R,3aS,6aR)hexahydrofuro[2,3-b]furan-3-yl N-((1S,2R)-1-benzyl-3-(cyclohexyloxy)[(4-methoxyphenyl)sulfonyl]amino-2-hydroxypropyl)carbamate. tert-butyl N-((1S,2R)-1-benzyl-3-(cyclohexyloxy)[(4-methoxyphenyl)sulfonyl]amino-2-hydroxypropyl)carbamate (0.09 mmol, 50 mg) was stirred in 1 mL trifluoroacetic acid (TFA) at room temperature for 5 hours. The TFA was removed under vacuum, and the resulting residue was dissolved in ethyl acetate, washed with 5% aq. potassium carbonate solution, brine, dried over magnesium sulfate, and concentrated to a residue. The resulting free amine, (2R,3aS,6aR) hexahydrofuro[2,3-b]furan-2-yl 4-nitrophenyl carbonate (0.09 mmol, 27 mg), diisopropylethylamine (0.13 mmol, 0.018 mL), a crystal of N,N-dimethylaminopyridine, 4 A molecular sieves and acetonitrile (0.5 mL) were combined and stirred at room temperature for 3 days. The reaction solution was concentrated to a residue, dissolved in ethyl acetate, washed with 1N HCl, 5% aq. potassium carbonate solution, brine, dried over magnesium sulfate, and concentrated under vacuum. The crude residue was purified by crystallization from ether to yield 15 mg (27%) of white crystals. HL-NMR (CDCl$_3$): δ7.71 (2H,d), 7.28–7.16 (6H,m), 6.97 (2H,d), 5.63–5.61

(1H,m), 5.00–4.98 (1H,m), 4.87–4.77 (1H,m), 4.24–δ 4.11 (1H,m), 3.98–3.79 (4H,m), 3.87 (3H,s), 3.72–3.61 (2H,m), 3.05 (1H,bs), 3.05–2.72 (6H,m), 2.10–1.98 (2H,m), 1.78–1.68 (2H,m), 1.37–1.04 (6H,m); MS (ESI): M+H=605.

Example 135

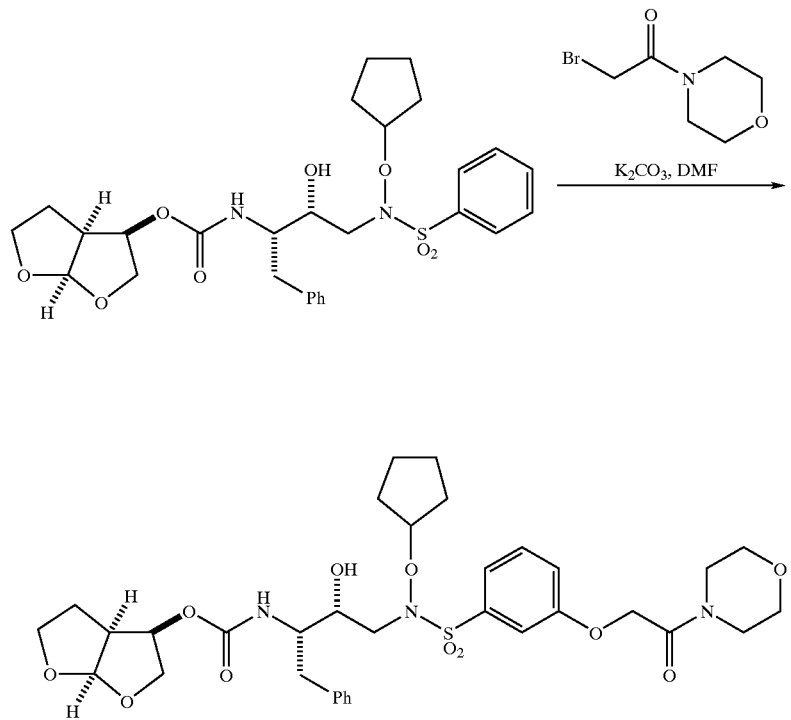

(3R,3aS,6aR)hexahydrofuro[2,3-b]furan-3-yl N-[(1S,2R)-1-benzyl-3-((cyclopentyloxy)[3-(2-morpholino-2-oxoethoxy)phenyl]sulfonylamino)-2-hydroxypropyl] carbamate.

(3R,3aS,6aR)hexahydrofuro[2,3-b]furan-3-yl N-((1S,2R)-1-benzyl-3-(cyclopentyloxy)[(3-hydroxyphenyl)sulfonyl] amino-2-hydroxypropyl)carbamate (0.09 mmol, 50 mg) was combined with 2-bromo-1-morpholino-1-ethanone (0.09 mmol, 18 mg) and potassium carbonate (0.26 mmol, 36 mg), and stirred in anhydrous DMF (1 mL) under nitrogen for 15 hours at room temperature. The reaction was concentrated to a residue, dissolved in ethyl acetate, washed in distilled water and brine, and dried over magnesium sulfate. The dried solution was then concentrated and purified by silica gel flash chromatography (1:1 hexanes/ethyl acetate) to provide 41 mg (67%) of a white solid. R$_f$=0.1 (1: 1 hexanes/ethyl acetate); H1-NMR (CDCl$_3$): δ7.47 (2H,m), 7.38 (1H, m), 7.32–7.14 (7H,m), 5.64 (1H,s), 5.03 (2H,m), 4.91–4.76 (1H,m), 4.78 (2H,s), 3.98–3.89 (2H,m), 3.89–3.77 (2H,m), 3.74–3.63 (8H,m), 3.63–3.52 (2H,m), 3.15 (1H,br.s), 3.08–2.98 (2H,m), 2.98–2.84 (3H,m), 2.84–2.74 (1H,m), 1.89–1.71 (4H,m), 1.71–1.49 (4H,m). MS (ESI): M+H=704.

Example 136

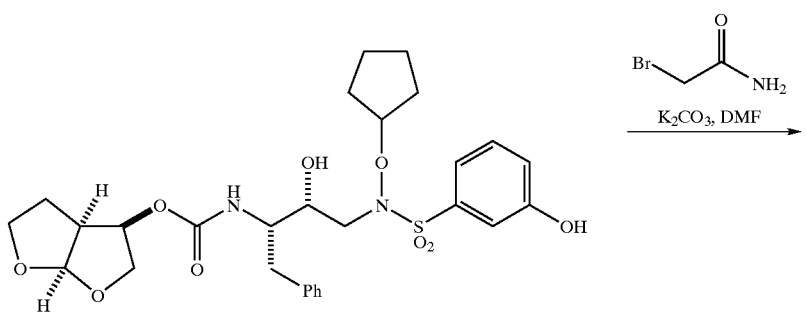

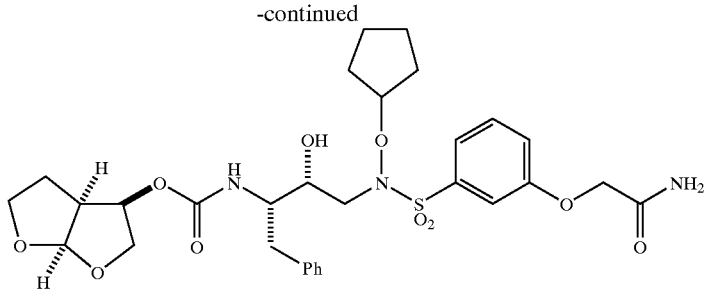

(3R,3aS,6aR)hexahydrofuro[2,3-b]furan-3-yl N-(1S,2R)-3-[[3-(2-amino-2-oxoethoxy)phenyl]sulfonyl(cyclopentyloxy)amino]-1-benzyl-2-hydroxypropylcarbamate. This reaction was set-up, run and purified under the same conditions as for (3R,3aS,6aR)hexahydrofuro[2,3-b]furan-3-yl N-[(1S,2R)-1-benzyl-3-((cyclopentyloxy)[3-(2-morpholino-2-oxoethoxy)phenyl]sulfonylamino)-2-hydroxypropyl]carbamate and generated 44 mg (80%) of a white solid. $R_f$=0.1 (1:1 hexanes/ethyl acetate); H1-NMR (CDCl$_3$): δ7.58–7.42 (2H,m), 7.33–7.06 (8H,m), 6.39 (1H,s), 5.79 (1H,s), 5.63 (1H,s), 5.20–5.12 (1H,m), 5.09–4.99 (1H,m), 4.85 (1H,m), 4.60 (2H,s), 4.0–3.78 (4H,m), 3.71 (2H,m), 3.14 (1H,br.s), 3.09–2.70 (6H,m), 1.93–1.70 (4H,m), 1.70–1.51 (4H,m) MS (ESI): M+H=634.

Example 137

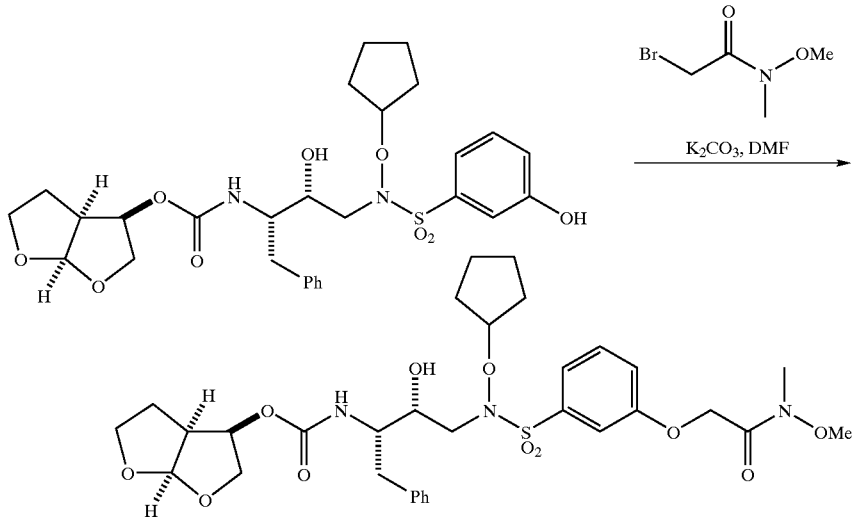

(3R,3aS,6aR)hexahydrofuro[2,3-b]furan-3-yl N-((1S,2R)-1-benzyl-3-(cyclopentyloxy)[(3-2-[methoxy(methyl)amino]-2-oxoethoxyphenyl)sulfonyl]amino-2-hydroxypropyl)carbamate.
(3R,3aS,6aR)hexahydrofuro[2,3-b]furan-3-yl N-((1S,2R)-1-benzyl-3-(cyclopentyloxy)[(3-hydroxyphenyl)sulfonyl]amino-2-hydroxypropyl)carbamate (0.17 mmol, 100 mg), 2-bromo-N-methoxy-N-methylacetamide (0.26 mmol, 43 mg) and excess potassium carbonate were stirred in anhydrous DMF (1 mL) under nitrogen for 20 hours at room temperature. The DMF was removed under vacuum and the residue was dissolved in ethyl acetate. The crude solution was washed with 1N HCl, saturated aqueous sodium bicarbonate and brine, and dried over magnesium sulfate. The dried solution was concentrated to an oil and purified by silica gel flash chromatography (1:1 hexanes/ethyl acetate) to yield 65 mg (55%) of a white solid. $R_f$=0.1 (1:1 hexanes/ethyl acetate); H1-NMR (CDCl$_3$): δ 7.45 (2H,m), 7.26 (5H,m), 7.20 (3H,m), 5.64 (1H,s), 5.09–4.97 (2H,m), 4.91 (2H,s), 4.83 (1H,m), 3.92 (2H,m), 3.78 (3H,s), 3.85–3.74 (2H,m), 3.73–3.59 (2H,m), 3.23 (3H,s), 3.28–3.11 (1H,br.s), 3.06–2.84 (5H,m), 2.75 (1H,m), 1.89–1.72 (4H,m), 1.71–1.48 (4H,m). MS (ESI): M+H=678.

Example 138

Step 1

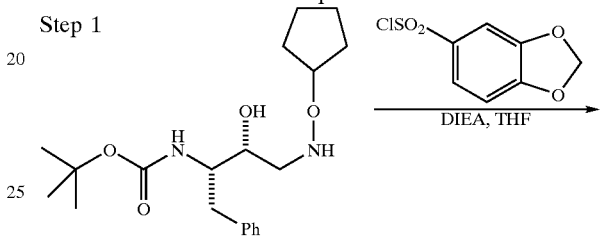

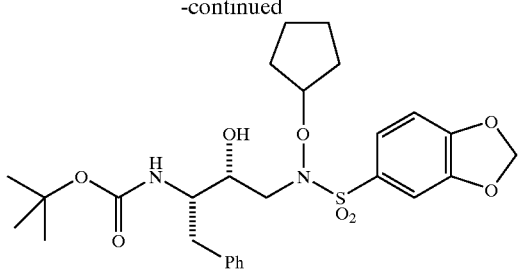

tert-butyl N-(1S,2R)-3-[(1,3-benzodioxol-5-ylsulfonyl)(cyclopentyloxy)amino]-1-benzyl-2-hydroxypropylcarbamate. tert-butyl N-(1S,2R)-1-benzyl-3-[(cyclopentyloxy)amino]-2-hydroxypropylcarbamate (0.19 mmol, 69 mg) was combined with 1,3-benzodioxole-5-sulfonyl chloride (0.23 mmol, 50 mg) and diisopropylethylamine (0.57 mmol, 73 mg) in anhydrous THF (2 mL). The reaction stirred under nitrogen for 72 hours at room temperature. The reaction was diluted with diethyl ether, washed with 1 N HCl, saturated aqueous sodium bicarbonate, brine, and was dried over magnesium sulfate. The crude product was concentrated to an oil and purified by silica gel flash chromatography (5:1 hexanes/ethyl acetate) to provide 82 mg (79w) of a white solid. The 1,3-benzodioxole-5-sulfonyl chloride was synthesized as described in Eur. Pat. Appl. 583960, Feb 23, 1994. $R_f$=0.40 (2:1 hexanes/ethyl acetate); H1-NMR (CDCl$_3$): δ7.37–7.15 (8H,m), 6.89 (1H,d), 6.10 (2H,s), 4.82 (1H,m), 4.60 (1H,m), 3.82 (2H,m), 3.06 (1H, br.s), 2.94 (2H,m), 2.86 (1H,m), 1.90–1.70 (4H,m), 1.65–1.48 (4H,m), 1.35 (9H,s). MS (ESI): M+H=549.

Step 2

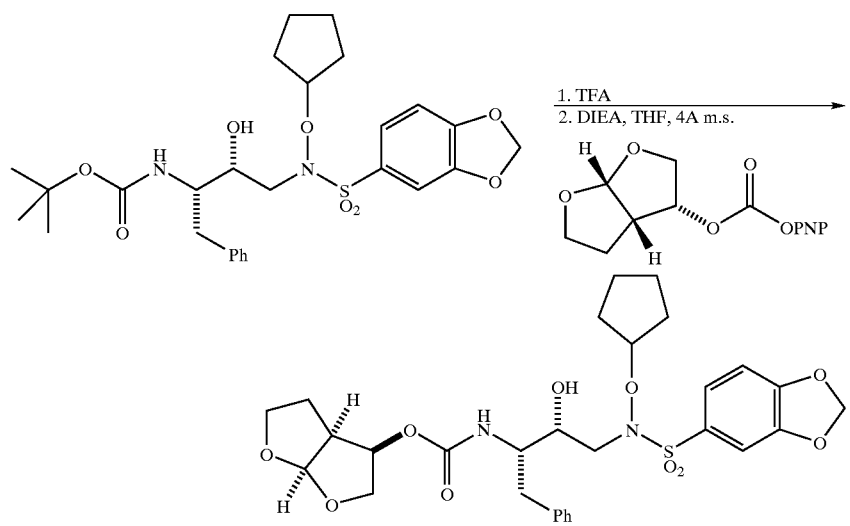

(3R,3aS,6aR)hexahydrofuro[2,3-b]furan-3-yl N-(1S,2R)-3-[(1,3-benzodioxol-5-ylsulfonyl)(cyclopentyloxy)amino]-1-benzyl-2-hydroxypropylcarbamate. tert-butyl N-(1S, 2R)-3-[(1,3-benzodioxol-5-ylsulfonyl)(cyclopentyloxy)amino]-1-benzyl-2-hydroxypropylcarbamate (0.15 mmol, 80 mg) was dissolved in neat trifluoroacetic acid (TFA) and stirred for 2 hours at room temperature. The TFA was removed under vacuum, and the reaction residue was dissolved in ethyl acetate. The reaction solution was washed with 5% aqueous potassium carbonate, brine and dried over magnesium sulfate. The crude solution was concentrated and re-dissolved in 1:1 hexanes/methylene chloride to exchange out the ethyl acetate. The resulting oil was combined with (2R,3aS,6aR) hexahydrofuro[2,3-b]furan-2-yl 4-nitrophenyl carbonate (0.22 mmol, 65 mg), diisopropylethylamine (0.44 mmol, 0.076 mL), 4 A molecular sieves and stirred in anhydrous THF (2 mL) under nitrogen for 15 hours at room temperature. The reaction was diluted with ethyl acetate, washed with 1N HCl, saturated aqueous sodium bicarbonate, brine and was dried over magnesium sulfate. The crude product was purified by silica gel flash chromatography (2:1 hexanes/ethyl acetate) to provide 41 mg (47%) of a white solid. $R_f$=0.20 (1:1 hexanes/ethyl acetate); H1-NMR (CDCl$_3$): δ7.41–7.14 (8H,m), 6.91 (1H,d), 6.12 (2H,s), 5.66 (1H,s), 5.03 (2H,m), 4.84 (2H,m), 3.91 (4H,m), 3.70 (2H, m), 3.12 (1H,s), 3.01 (2H,m), 2.93 (1H,m), 2.84 (2H,m), 1.91–1.71 (4H,m), 1.71–1.49 (4H,m). MS (ESI): M+H=606.

Example 139

Step 1

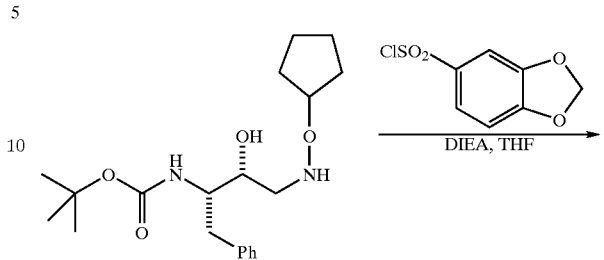

-continued

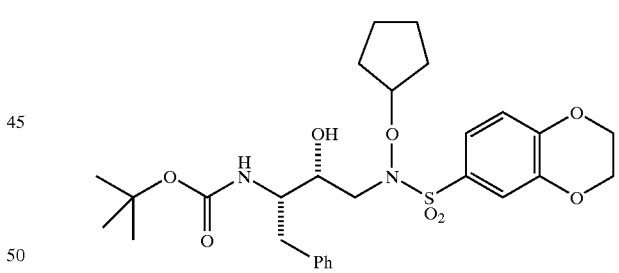

tert-butyl N-(1S, 2R)-1-benzyl-3-[(cyclopentyloxy) (2,3-dihydro-1,4-benzodioxin-6-ylsulfonyl)amino]-2-hydroxypropylcarbamate. This reaction was set-up, run and purified using the same protocol described for tert-butyl N-(1S,2R)-3-[(1,3-benzodioxol-5-ylsulfonyl) (cyclopentyloxy)amino]-1-berizyl-2-hydroxypropylcarbamate. The 1,4-benzodioxan-6-sulfonyl chloride was synthesized according to the procedure described in Eur. Pat. Appl. 583960, Feb 23, 1994. $R_f$=0.40 (2:1 hexanes/ethyl acetate); H1-NMR (CDCl$_3$): δ7.36–7.18 (8H,m), 6.95 (1H,d), 4.82 (1H,m), 4.60 (1H,m), 4.32 (4H, m), 3.82 (2H,m), 3.05 (1H, br.s), 2.93 (2H,m), 2.87 (1H,m), 1.88–1.69 (4H,m), 1.69–1.47 (4H,m), 1.35 (9H,s). MS (ESI): M+H=563.

Step 2

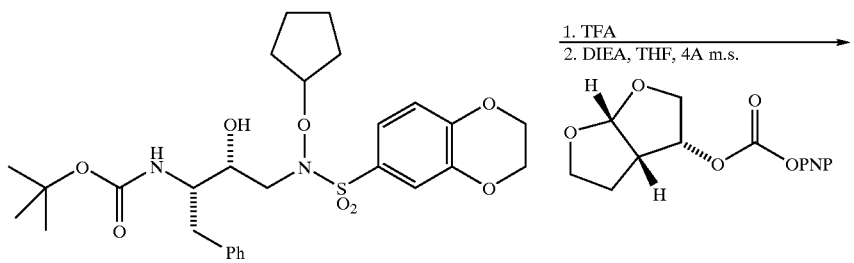

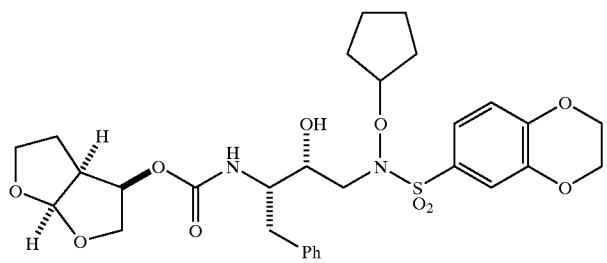

(3R,3aS,6aR)hexahydrofuro[2,3-b]furan-3-yl N-(1S,2R)-1-benzyl-3-[(cyclopentyloxy)(2,3-dihydro-1,4-benzodioxin-6-ylsulfonyl)amino]-2-hydroxypropylcarbamate. This reaction was set-up, run and purified using the same protocol described for (3R,3aS, 6aR)hexahydrofuro[2, 3-b]furan-3-yl N-(1S,2R)-3-[(1,3-benzodioxol-5-ylsulfonyl)(cyclopentyloxy)amino]-1-benzyl-2-hydroxypropylcarbamate. $R_f$=0.20 (1:1 hexanes/ethyl acetate); H1-NMR (CDCl$_3$): δ 7.37–7.12 (8H,m), 6.97 (1H, d), 5.65 (1H,s), 5.03 (2H,m), 5.06–4.77 (2H,m), 4.81 (1H, m), 4.33 (4H,d), 3.91 (4H,m), 3.70 (2H,m), 3.12 (1H,s), 3.07–2.97 (2H,m), 2.93 (2H,m), 2.85 (2H,m), 1.90–1.70 (4H,m), 1.7–1.46 (4H,m). MS (ESI): M+H=619.

Example 140

Step 1

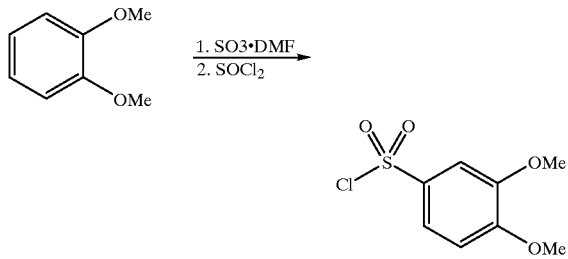

3,4-dimethoxybenzenesulfonyl chloride. 3,4-dimethoxybenzenesulfonyl chloride was synthesized as described in Eur. Pat. Appl. 583960, Feb 23, 1994. $R_f$=0.4 (2:1 hexanes/ethyl acetate). H1-NMR: δ 7.69 (1H,d), 7.45 (1H,m), 7.00 (1H,d), 4.00 (3H,s), 3.98 (3H,s).

Step 2

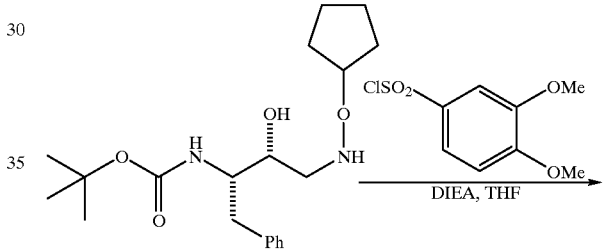

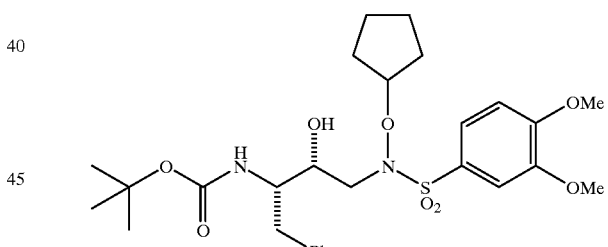

tert-butyl N-((1S,2R)-1-benzyl-3-(cyclopentyloxy)[(3,4-dimethoxyphenyl)sulfonyl]amino-2-hydroxypropyl)carbamate. tert-butyl N-(1S,2R)-1-benzyl-3-[(cyclopentyloxy)amino]-2-hydroxypropylcarbamate (0.41 mmol, 150 mg) was combined with 3,4-dimethoxybenzenesulfonyl chloride (0.82 mmol, 142 mg) and diisopropyl-ethylamine (2.05 mmol, 0.358 mL) in anhydrous THF (1 mL). The reaction was allowed to reflux for 72 hours. The reaction was worked-up by diluting with an equal volume of ethyl acetate, washing with 1N HCl, saturated aq. sodium bicarbonate and brine, and dried over magnesium sulfate. The crude solution was concentrated to an oil and purified by silica gel chromatography (2:1 hexanes/ethyl acetate) yielding 100 mg (43%) of a white solid. $R_f$=0.1 (1:1 hexanes/ethyl acetate); HL-NMR (CDCl$_3$): δ7.41 (1H,d), 7.33–7.17 (7H,m), 6.95 (1H,d), 4.82 (1H,m), 4.52 (1H,m), 3.96 (3H,s), 3.93 (3H,s), 3.80 (2H,m), 3.08 (1H,br.s), 3.00–2.79 (3H,m), 1.90–1.45 (8H,m), 1.32 (9H,s).

Step 3

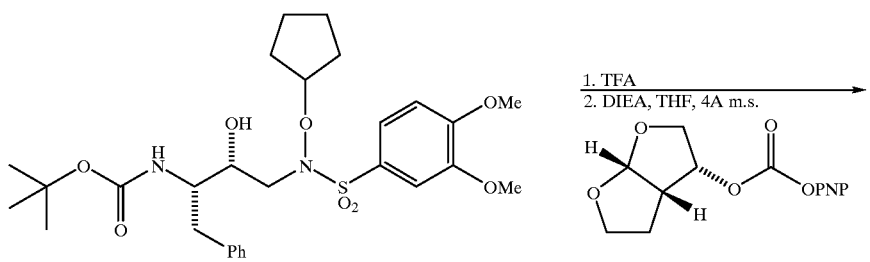

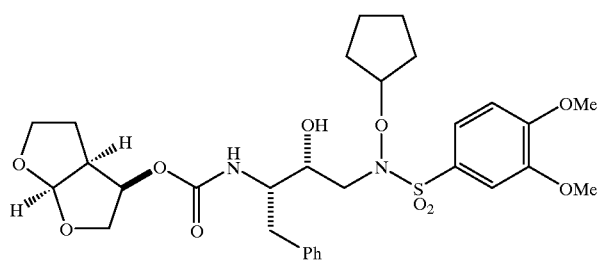

(3R,3aS,6aR)hexahydrofuro[2,3-b]furan-3-yl N-((1S,2R)-1-benzyl-3-(cyclopentyloxy)[(3,4-dimethoxyphenyl)sulfonyl]amino-2-hydroxypropyl)carbamate. This reaction was set-up, run and purified using the same protocol described for (3R,3aS,6aR)hexahydrofuro[2,3-b]furan-3-yl N-(1S,2R)-3-[(1,3-benzodioxol-5-ylsulfonyl)(cyclopentyloxy)amino]-1-benzyl-2-hydroxypropylcarbamate. $R_f$=0.20 (2:1 hexanes/ethyl acetate); H1-NMR (CDCl$_3$): δ 7.42 (1H,d), 7.35–7.14 (8H,m), 6.97 (1H,d), 5.64 (1H,s), 5.00 (1H,m), 4.80 (2H,m), 3.96 (3H,s), 3.93 (3H,s), 3.99–3.80 (4H,m), 3.67 (2H,m), 3.15 (1H,br.s), 3.08–2.98 (2H,m), 2.95–2.75 (3H,m), 1.90–1.71 (4H,m), 1.70–1.43 (4H,m). MS (ESI): M+H=621.

Example 141

(3R,3aS,6aR)hexahydrofuro[2,3-b]furan-3-yl N-((1S,2R)-1-benzyl-3-(cyclopentyloxy)[(4-isopropoxyphenyl)sulfonyl]amino-2-hydroxypropyl)carbamate.

(3R,3aS,6aR)hexahydrofuro[2,3-b]furan-3-yl N-((1S,2R)-1-benzyl-3-(cyclopentyloxy)[(4-hydroxyphenyl)sulfonyl]amino-2-hydroxypropyl)carbamate (0.13 mmol, 75 mg) was combined with 2-bromopropane (0.26 mmol, 0.025 mL), potassium carbonate (0.65 mmol, 90 mg), tetrabutylammonium iodide (5 mg) and anhydrous DMF (1 mL). The reaction stirred under a nitrogen atmosphere at room temperature for 15 hours, then was heated to 50° C. for 3 hours. The reaction mixture was concentrated under vacuum to a residue and diluted with ethyl acetate (2 mL). The reaction was washed in distilled water and brine, and was dried over magnesium sulfate. The dried solution was then concen-

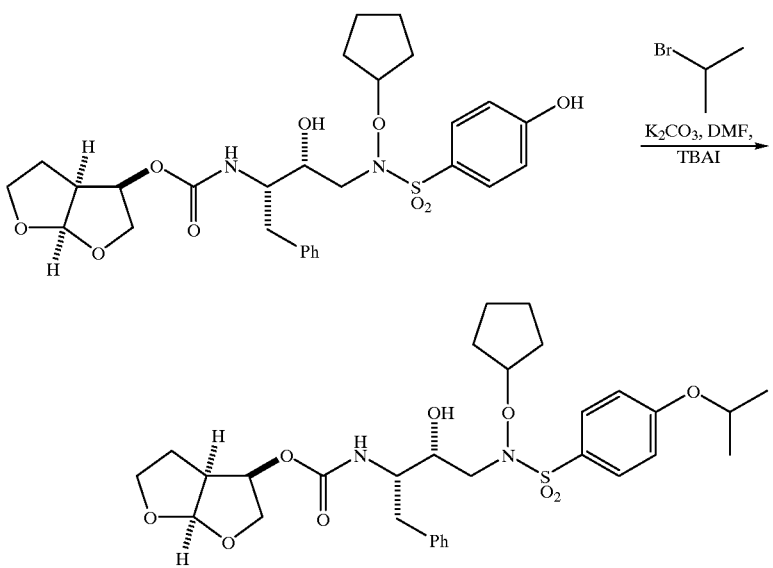

trated to an oil and purified by silica gel chromatography (2:1 hexanes/ethyl acetate) to yield 61 mg (76%) of a white solid. $R_f$=0.50 (2:1 hexanes/ethyl acetate); H1-NMR (CDCl$_3$): δ7.69 (2H,d), 7.33–7.13 (6H,m), 6.96 (2H,d), 5.65 (1H,s), 5.02 (1H,m), 4.86 (1H,m), 4.80 (1H,m), 4.65 (1H, m), 3.99–3.80 (5H,m), 3.69 (2H,m), 3.11 (1H,br.s), 3.09–2.98 (3H,m), 2.91 (1H,m), 2.83 (1H,m), 1.89–1.72 (4H,m), 1.7–1.46 (4H,m), 1.38 (6H,d). MS (ESI): M+H=619.

Example 142

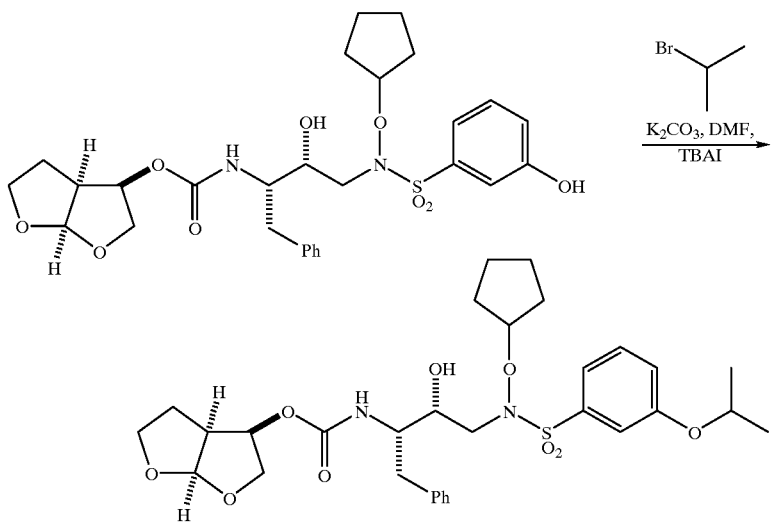

(3R,3aS,6aR)hexahydrofuro[2,3-b]furan-3-yl N-((1S,2R)-1-benzyl-3-(cyclopentyloxy)[(3-isopropoxyphenyl)sulfonyl]amino-2-hydroxypropyl)carbamate. (3R,3aS,6aR)hexahydrofuro [2,3-b]furan-3-yl N-((1S,2R)-1-benzyl-3-(cyclopentyloxy)[(3-hydroxyphenyl)sulfonyl]amino-2-hydroxypropyl)carbamate (0.13 mmol, 75 mg) was combined with 2-bromopropane (0.26 mmol, 0.025 mL), potassium carbonate (0.65 mmol, 90 mg), tetrabutylammonium iodide (5 mg) and anhydrous DMF (1 mL). The reaction was stirred under a nitrogen atmosphere at room temperature for 72 hours. The reaction mixture was concentrated under vacuum to a residue and diluted with ethyl acetate (2 mL). The reaction was washed in distilled water and brine, and was dried over magnesium sulfate. The dried solution was then concentrated to an oil and purified by silica gel chromatography (2:1 hexanes/ethyl acetate) to yield 38 mg (48%) of a white solid. $R_f$=0.40 (2:1 hexanes/ethyl acetate); H1-NMR (CDCl$_3$): δ7.40 (1H,m), 7.33–7.10 (9H,m), 5.63 (1H,s), 5.00 (1H,m), 4.80 (2H,m), 4.58 (1H, m), 3.88 (4H,m), 3.67 (2H,m), 3.13 (1H,br.s), 3.00 (2H,m), 2.94–2.74 (2H,m), 1.88–1.71 (5H,m), 1.69–1.43 (5H,m), 1.35 (6H,d).

Example 143

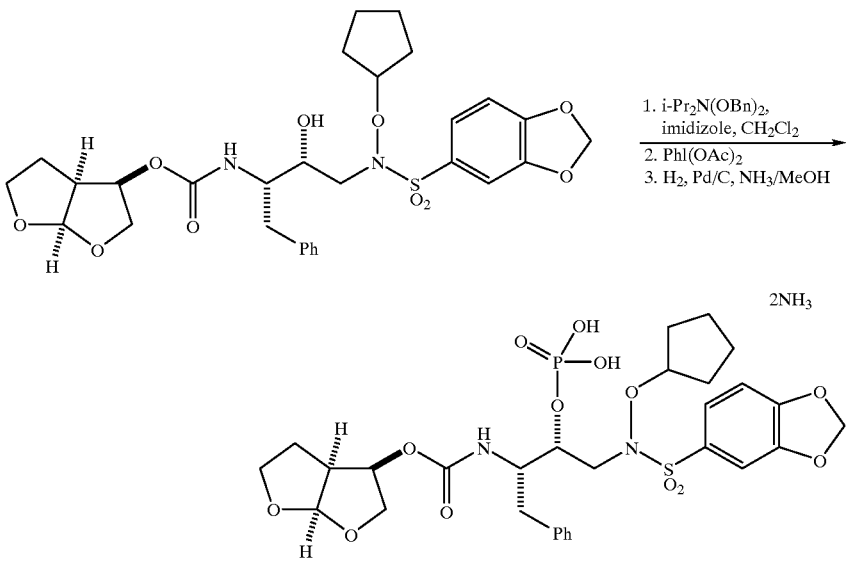

(3R,3aS,6aR)hexahydrofuro[2,3-b]furan-3-yl N-[(1S,2R)-3-[(1,3-benzodioxol-5-ylsulfonyl) (cyclopentyloxy)amino)-1-benzyl-2-(phosphonooxy)propyl]carbamate.

Step 1:

(3R,3aS, 6aR)hexahydrofuro[2,3-b]furan-3-yl N-(1S,2R)-3-[(1,3-benzodioxol-5-ylsulfonyl) (cyclopentyloxy)amino]-1-benzyl-2-hydroxypropylcarbamate (0.38 mmol, 231 mg) was combined with dibenzyl diisopropylphosphoramidite (0.57 mmol, 0.192 mL), imidazole (0.38 mmol, 27 mg) and methylene chloride (5 mL), and stirred for 15 hours at room temperature. The reaction was concentrated to a residue and purified by silica gel chromatography (2:1 hexanes/ethyl acetate) which produced 325 mg of a clear oil.

Step 2

The oil from the previous step was oxidized by combining with iodobenzene diacetate (0.57 mmol, 185 mg) and acetonitrile (10 mL). The reaction was instantaneous and was concentrated to a crude white solid. The product was purified by silica gel chromatography (1:1 hexanes/ethyl acetate) and produced 170 mg of a sticky white residue.

Step 3

The phosphate ester from the previous step was stirred vigorously with 10% Pd/Carbon (34 mg) and methanolic ammonia (2 M in methanol, 2 mL) under a hydrogen atmosphere for 3 hours at room temperature. The reaction was filtered, and the filtrate was concentrated to a residue and crystallized from methylene chloride/diethyl ether. The reaction produced 80 mg (31% - 3 steps) of white crystals. $R_f$=0.20 (1:1 hexanes/ethyl acetate); H1-NMR ($D_2O$): δ 7.38 (1H,m), 7.26–7.05 (6H,m), 6.95 (1H,m), 6.00 (2H,d), 5.51–5.42 (1H,m), 4.78 (1H,m), 4.30 (1H,m), 4.16–3.99 (1H,m), 3.86–3.62 (3H,m), 3.57–3.42 (1H,m), 3.41–3.27 (1H,m), 3.07–2.90 (2H,m), 2.89–2.72 (1H,m), 2.55–2.43 (1H,m), 1.82–1.57 (5H,m), 1.57–1.30 (5H,m), 1.00–0.90 (1H,m). MS (ESI): M+H=685.

(3R,3aS,6aR)hexahydrofuro[2,3-b]furan-3-yl N-[(1S,2R)-1-benzyl-3-[(cyclopentyloxy)(2,3-dihydro-1,4-benzodioxin-6-ylsulfonyl)amino]-2-(phosphonooxy)propyl] carbamate Step 1

(3R,3aS,6aR)hexahydrofuro[2,3-b]furan-3-yl N-(1S,2R)-1-benzyl-3-[(cyclopentyloxy) (2,3-dihydro-1,4-benzodioxin-6-ylsulfonyl)amino]-2-hydroxypropylcarbamate (0.14 mmol, 86 mg) was combined with dibenzyl diisopropylphosphoramidite (0.21 mmol, 0.070 mL), imidazole (0.18 mmol, 13 mg) and methylene chloride (3 mL), and stirred for 20 hours at room temperature. The reaction was concentrated to a residue and purified by silica gel chromatography (2:1 hexanes/ethyl acetate) which produced 100 mg of a clear oil.

Step 2

The oil from the previous step was oxidized by combining with iodobenzene diacetate (0.18 mmol, 56 mg) and acetonitrile (3 mL). The reaction was instantaneous and was concentrated to a crude white solid. The product was purified by silica gel chromatography (1:1 hexanes/ethyl acetate) and produced 65 mg of a white foam.

Step 3

The phosphate ester from the previous step was stirred vigorously with 10% Pd/Carbon (12 mg) and methanolic ammonia (2 M in methanol, 2 mL) under a hydrogen atmosphere for 2 hours at room temperature. The reaction was filtered, and the filtrate was concentrated to a residue and crystallized from methylene chloride/diethyl ether. The crystals were purified by RP HPLC (acetonitrile/water) and produced 20 mg (20% - 3 steps) of a white solid after lyophylization. $R_f$=0.20 (1:1 hexanes/ethyl acetate); H1-NMR ($D_2O$): δ 7.31 (1H,m), 7.26–7.07 (6H,m), 7.03–6.97 (1H,m), 5.52–5.43 (1H,m), 4.78 (1H,m), 4.34–4.15 (5H,m), 4.15–4.00 (1H,m), 3.79–3.65 (3H,m), 3.53–3.41 (1H,m), 3.38–3.23 (1H,m), 3.08–2.92 (2H,m), 2.89–2.71 (1H,m), 2.52–2.43 (1H,m), 1.80–1.57 (5H,m), 1.56–1.33 (5H,m), 0.98–0.88 (1H,m). MS (ESI): M+H=699.

Example 144

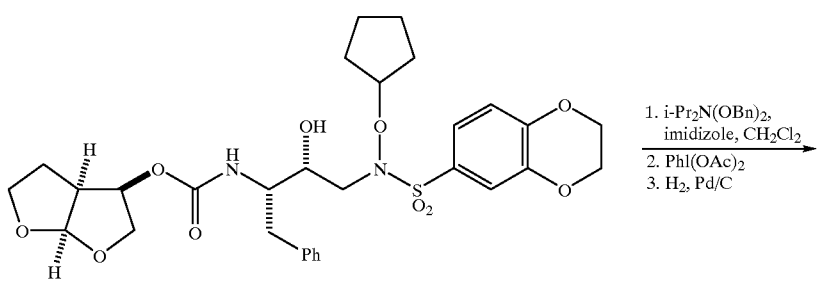

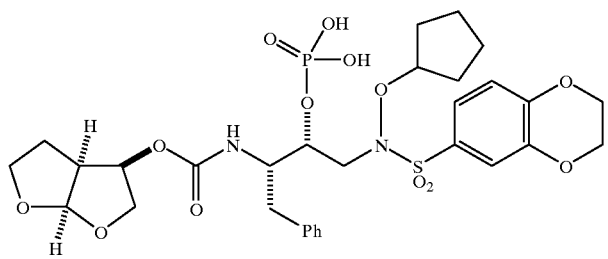

Example 145

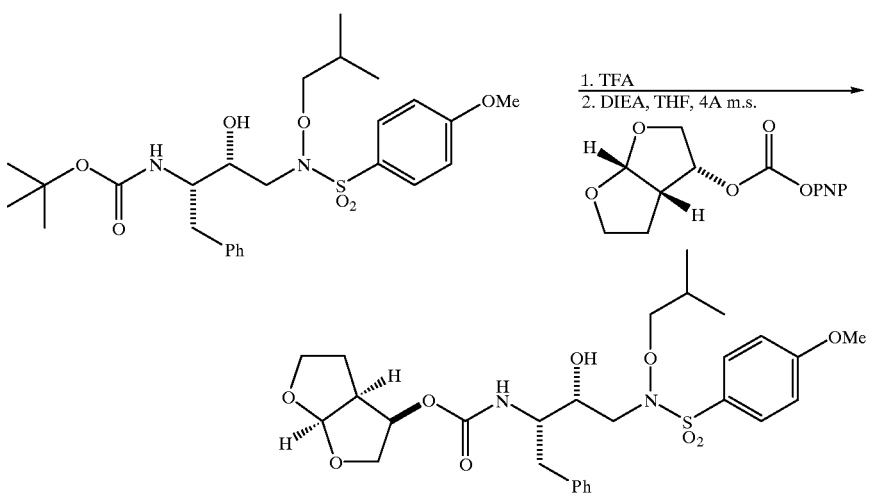

(3R,3aS,6aR)hexahydrofuro[2,3-b]furan-3-yl N-((1S,2R)-1-benzyl-2-hydroxy-3-isobutoxy[(4-methoxyphenyl)sulfonyl]aminopropyl)carbamate. This reaction was set-up, run and purified using the same protocol described for (3R,3aS,6aR)hexahydrofuro[2,3-b]furan-3-yl N-(13,2R)-3-[(1,3-benzodioxol-5-ylsulfonyl) (cyclopentyloxy)amino]-1-benzyl-2-hydroxypropylcarbamate. $R_f$=0.20 (1:1 hexanes/ethyl acetate); H1-NMR (CDCl$_3$): δ 7.74 (2H,d), 7.35–7.12 (6H,m), 7.01 (2H,d), 5.65 (1H,s), 5.03 (1H,m), 4.89 (1H,m), 3.90 (3H,s), 4.03–3.79 (7H,m), 3.70 (2H,m), 3.11 (1H,br.s), 3.04–2.69 (5H,m), 1.86 (1H,m), 0.92 (6H,m). MS (ESI): M+Na=601.

Example 146

Step 1

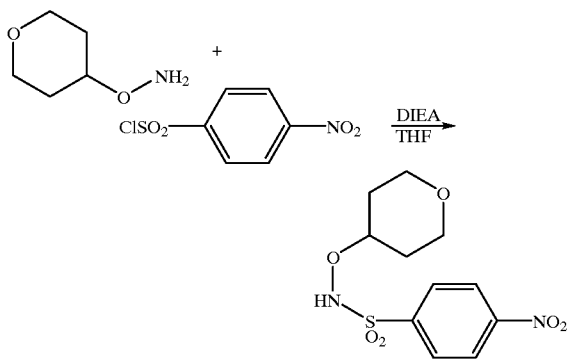

4-nitro-N-(tetrahydro-2H-pyran-4-yloxy)benzenesulfonamide 4-tetrahydropyranoxyhydroxylamine (33.2 mmol, 3.77g) and 4-nitrobenzenesulfonylchloride (38.6 mmol, 8.56 g) were combined in anhydrous THF (100 mL) with diisopropylethylamine (69.3 mmol, 11.2 mL). The reaction was stirred at room temperature for 48 hours. Hydrazine (2 mL) was injected to the stirring solution to break-up the bisarylsulfonamide dimer biproduct. The reaction was stirred for an additional 24 hours. The reaction was diluted in ethyl acetate, washed in brine, filtered to remove insoluble solids and concentrated. The crude was purified by crystallization from hot ethyl acetate to provide 3.5 g (36%) of white crystals. $R_f$=0.3 (2:1 hexanes/ethyl acetate); H1-NMR (CDCl$_3$): δ8.-42 (2H,d), 8.13 (2H,d), 6.93 (1H,s), 4.27 (1H,m), 3.91 (2H,m), 3.45 (2H,m), 2.02 (2H,m), 1.61 (2H,m).

Step 2

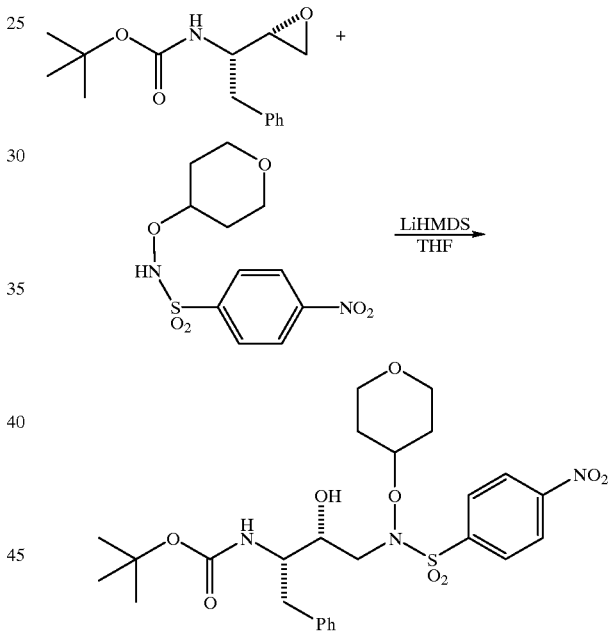

tert-butyl (1S,2R)-1-benzyl-2-hydroxy-3-[[(4-nitrophenyl)sulfonyl](tetrahydro-2H-pyran-4-yloxy)amino]propylcarbamate. 4-nitro-N-(tetrahydro-2H-pyran-4-yloxy)benzenesulfonamide (8.6 mmol, 2.61 g) was combined with tert-butyl N-(1S)-1-[(2S)oxiran-2-yl]-2-phenylethylcarbamate (7.2 mmol, 1.89 g), lithium bis (trimethylsilyl) amide (1.0 M in THF)(1.4 mmol, 1.4 mL) and anhydrous THF (80 mL). The reaction was stirred under nitrogen at room temperature for 96 hours. The reaction was diluted in ethyl acetate (200 mL) and washed with a 5% aqueous solution of potassium carbonate, brine, and was dried over magnesium sulfate. The crude solution was concentrated to a foam and purified by crystallization from diethylether to provide 3.5 g (86%) of light yellow crystals. $R_f$=0.3 (2:1 hexanes/ethyl acetate); H1-NMR (CDCl$_3$): δ8.36 (2H,d), 7.96 (2H,d), 7.33–7.15 (6H,m), 4.55 (1H,m), 4.42 (1H,m), 3.95 (2H,m), 3.77 (2H,m), 3.43 (2H,m), 3.07 (1H,br.s), 2.90 (2H,m), 2.03 (2H,m), 1.65–1.42 (3H,m), 1.32 (9H,s).

Step 3

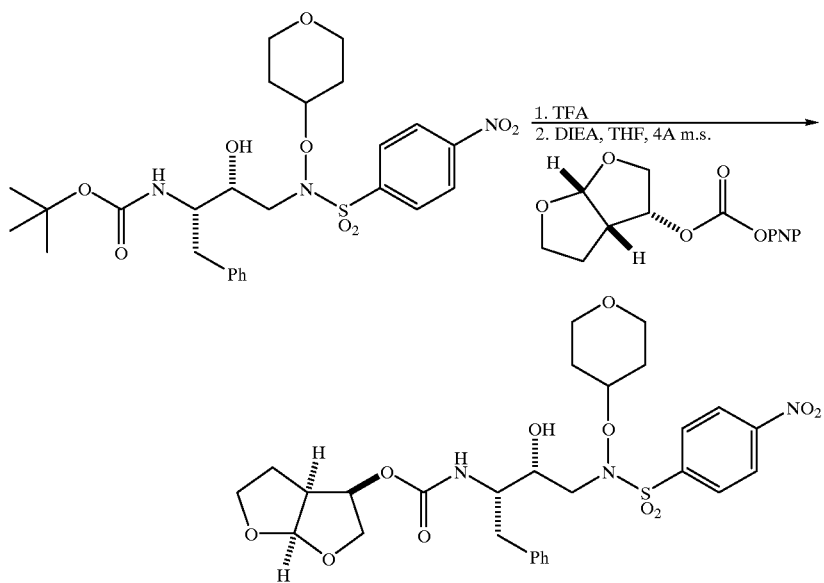

(3R,3aS,6aR)hexahydrofuro[2,3-b]furan-3-yl (1S,2R)-1-benzyl-2-hydroxy-3-[[(4-nitrophenyl)sulfonyl](tetrahydro-2H-pyran-4-yloxy)amino]propylcarbamate. This reaction was set-up, run and purified using the same protocol described for (3R,3aS,6aR)hexahydrofuro[2,3-b]furan-3-yl N-(1S,2R)-3-[(1,3-benzodioxcl-5-ylsulfonyl)(cyclopentyloxy)amino]-1-benzyl-2-hydroxypropylcarbamate. $R_f$=0.1 (1: 1 hexanes/ethyl acetate); H1-NMR (CDCl$_3$): δ 8.38 (2H,d), 7.95 (2H,d), 7.33–7.20 (4H,m), 7.17 (2H,m), 5.64 (1H,s), 5.02 (1H,m), 4.87 (1H,m), 4.45 (1H,m), 4.00–3.77 (6H,m), 3.68 (2H,m), 3.43 (2H,m), 3.31–2.30 (4H,m), 2.05 (2H,m), 1.86 (1H,m), 1.76–1.42 (4H,m).

Step 4:

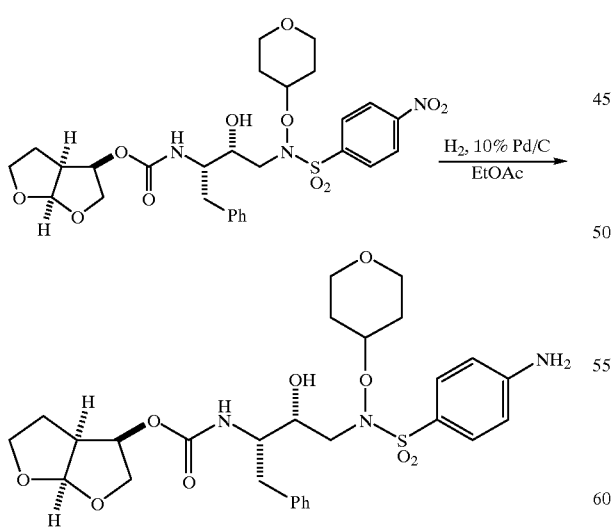

(3R,3aS,6aR)hexahydrofuro[2,3-b]furan-3-yl 3-[[(4-aminophenyl)sulfonyl](tetrahydro-2H-pyran-4-yloxy)amino]-1-benzyl-2-hydroxypropylcarbamate. (3R,3aS,6aR) hexahydrofuro [2,3-b]furan-3-yl (1S,2R)-1-benzyl-2-hydroxy-3-[[(4-nitrophenyl)sulfonyl](tetrahydro-2H-pyran-4-yloxy)amino]propylcarbamate (0.16 mmol, 100 mg) was combined with 10% palladium on carbon (20 mg) and ethyl acetate (2 mL), and the reaction was stirred vigorously under a hydrogen atmosphere for 15 hours. The reaction was filtered and the filtrate was concentrated to an oil. The crude product was purified by crystallization from hexanes/ethyl acetate to provide 30 mg (32%) of fine white crystals. $R_f$=0.5 (ethyl acetate); H1-NMR (CDCl$_3$): δ7.56 (2H,d), 7.33–7.11 (6H,m), 6.72 (2H,d), 5.64 (1H,s), 5.0 (1H,m), 4.83 (1H,m), 4.39 (1H,septet), 4.01–3.78 (6H,m), 3.73–3.59 (2H,m), 3.48–3.33 (2H,m), 3.31–2.28 (2H,br.s), 3.16–2.72 (6H,m), 1.74–1.45 (5H,m). MS (ESI): M+H=592.

Example 147

Step 1

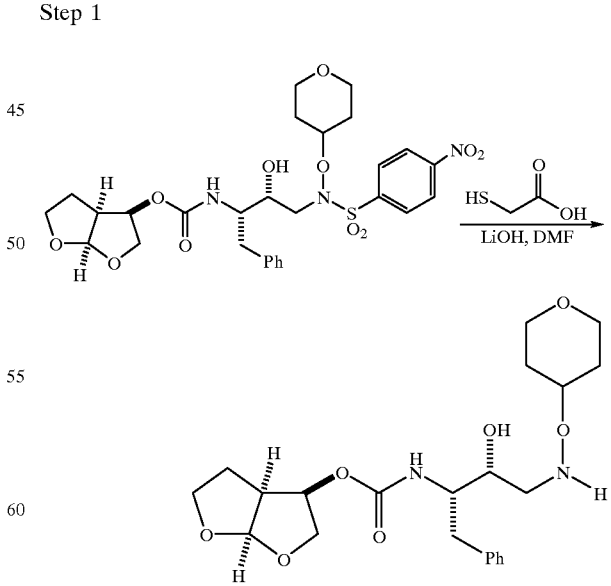

(3R, 3aS, 6aR) hexahydrofuro [2, 3-b]furan-3-yl (1S,2R)-1-benzyl-2-hydroxy-3-[(tetrahydro-2H-pyran-4-yloxy) amino) propylcarbamate. (3R,3aS,6aR)hexahydrofuro[2,3- b]furan-3-yl (1,S2R)-1-benzyl-2-hydroxy-3-[[(4-nitrophenyl)sulfonyl](tetrahydro-2H-pyran-4-yloxy)amino]propylcarbamate (3.62 mmol, 2.25g) was combined with mercaptoacetic acid (7.24 mmol, 0.501 mL), lithium hydroxide (14.5 mmol, 607 mg) and anhydrous DMF (10 mL) and stirred for 2 hours at room temperature under nitrogen. The reaction was concentrated to a red suspension under vacuum and disolved in 700 mL ethyl acetate. The crude solution was washed with distilled water, saturated aqueous sodium bicarbonate, brine and dried over magnesium sulfate. The crude product was concentrated to a yellow solid and purified by silca gel chromatography (10:1 ethyl acetate/methanol) followed by crystallization from methylene chloride/hexanes to provide 650 mg (41%) of white crystals. $R_f$=0.15 (ethyl acetate); H1-NMR (CDCl$_3$): 7.39–7.18 (6H,m), 5.69 (1H,s), 5.08 (2H,m), 4.25 (1H,m), 4.10–3.58 (8H,m), 3.52–3.27 (3H,m), 3.19 (1H,m), 3.03 (1H,br.s), 2.90 (1Hm), 2.71 (1H,m), 2.13–1.80 (3H,m), 1.74–1.29 (4H,m).

Step 2

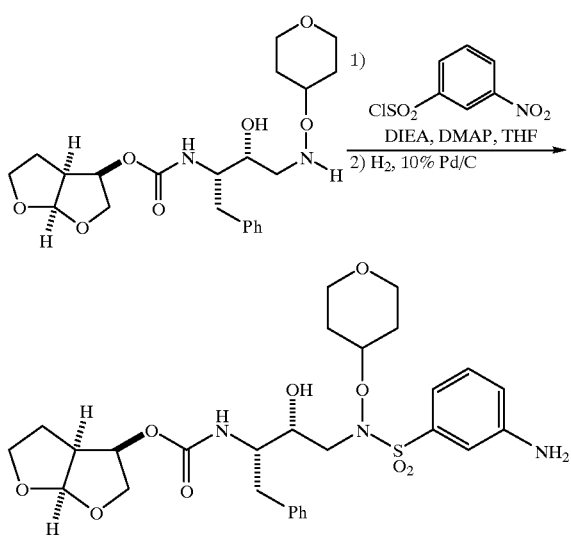

(3R,3aS,6aR)hexahydrofuro[2,3-b]furan-3-yl 3-[[(3-aminophenyl)sulfonyl](tetrahydro-2H-pyran-4-yloxy)amino]-1-benzyl-2-hydroxypropylcarbamate.

Step 1

(3R,3aS,6aR)hexahydrofuro[2,3-b]furan-3-yl (1S,2R)-1-benzyl-2-hydroxy-3-[(tetrahydro-2H-pyran-4-yloxy)amino]propylcarbamate (0.17 mmol, 75 mg) was combined with 3-nitrobenzenesulfonyl chloride (0.26 mmol, 57 mg), diisopropylethylamine (0.69 mmol, 0.120 mL), N,N-dimethylaminopyridine (5 mg), and anhydrous THF (5 mL). The reaction was stirred at 500C for 15 hours under nitrogen. The reaction product was diluted in ethyl acetate (10 mL), washed with 1N HCl, saturated aqueous sodium bicarbonate, brine, and was dried over magnesium sulfate. The crude solution was concentrated under vacuum and purified by silica gel chromatography (1:1 methylene chloride/ethyl acetate) to provide 100 mg (93%) of a white solid.

Step 2

The product of the previous step was combined with 10% palladium on carbon (20 mg) and stirred vigorously in ethyl acetate (2 mL) under hydrogen for 20 hours. The reaction was filtered and concentrated under vacuum. The crude product was purified by crystallization (diethylether/ethyl acetate/hexanes) to yield 40 mg (42%) of white crystals. $R_f$=0.45 (ethyl acetate); H1-NMR (CDCl$_3$): δ7.41–7.02 (10H,m), 6.96 (1H,br.s), 5.62 (1H,s), 5.02 (1H,m), 4.85 (1H,br.s), 4.42 (1H,m), 4.02–3.77 (6H,m), 3.69 (2H,m), 3.48–3.33 (3H,m), 3.22–2.52 (6H,m), 1.87–1.30 (5H,m). MS (ESI): M+H=592.

Example 148

Step 1

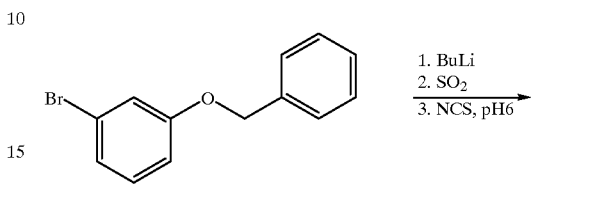

3-benzyloxybenzenesulfonyl chloride

The aryl bromide (12 g, 45.6 mmol) was dissolved in THF (100 mL) and cooled to −78° C. n-Butyl lithium 1.6 M in hexanes (28.5 mL, 45.6 mmol) was injected and the reaction stirred for 1 hr. before being warmed to 0° C. The resulting solution was then transferred to a −78° C. solution of SO$_2$ (41 mL, 913 mmol), Et$_2$O (100 mL) and THF (100 mL). The solution became a yellow suspension immediately upon addition of the aryl lithium. The suspension was warmed to room temperature and stirred for 3 days. The yellow mixture was sparged with nitrogen for 2 hr. The suspension was concentrated and the resulting solid triturated with Et$_2$O to provide 7.23 g of the sulfinate intermediate. The lithium sulfinate was stirred in a bi-phasic mixture of pH 6 aqueous dibasic sodium phosphate buffer (27 g in 200 mL distilled water—adjusted to pH 6 with conc. phosphoric acid) and ethyl acetate (200 mL) and cooled to 0° C. While stirring vigorously, N-chlorosuccinimide (3.80 g, 28.4 mmol) was added. The reaction was immediately warmed to room temperature and the aqueous layer was drained. The organic layer was washed with distilled water, brine and dried over magnesium sulfate. The crude was concentrated to a yellow solid under reduced pressure and washed with Et$_2$O. The product was purified by eluting through a silica gel column with Et$_2$O and resulted in 4.81 g (37%) of the desired product. $R_f$=0.2 (5:1 hexanes/ethyl acetate). H1-NMR: 7.67–7.27 (9H,m), 5.13 (2H,s).

Step 2

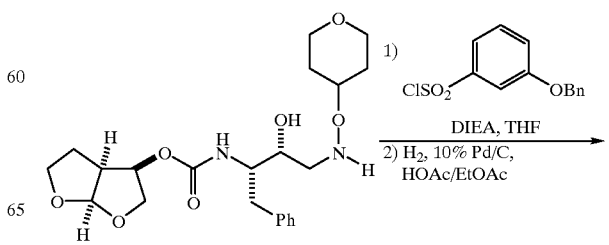

-continued

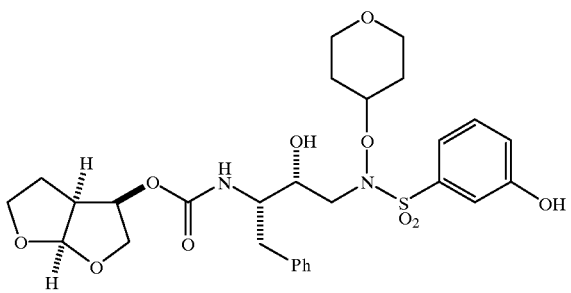

(3R,3aS,6aR)hexahydrofuro[2,3-b]furan-3-yl 1-benzyl-2-hydroxy-3-[[(3-hydroxyphenyl)sulfonyl](tetrahydro-2H-pyran-4-yloxy)amino]propylcarbamate.

Step 1

(3R,3aS,6aR)hexahydrofuro[2,3-b]furan-3-yl (1S,2R)-1-benzyl-2-hydroxy-3-[(tetrahydro-2H-pyran-4-yloxy)amino]propylcarbamate (0.17 mmol, 75 mg) was combined with 3-benzyloxybenzenesulfonyl chloride (0.26 mmol, 73 mg), diisopropylethylamine (0.69 mmol, 0.12 mL) in methylene chloride (2 mL) and allowed to stir for 15 hours at room temperature under nitrogen. The reaction was diluted with ethyl acetate and washed with 1N HCl, 5% aqueous potassium bicarbonate solution, brine and was dried over magnesium sulfate. The solution was concentrated under vacuum and the crude product was purified by silica gel chromatography (1:1 hexanes/ethyl acetate) to provide 60 mg (51%) of a clear oil.

Step 2:

The product of the previous step was stirred vigorously with 10% palladium on carbon (20 mg), acetic acid (0.5 mL), and ethyl acetate (2mL) under hydrogen for 6 hours. The reaction was filtered and concentrated to an oil. The crude product was purified by silica gel chromatography (1:1 hexanes/ethyl acetate), and crystallized from diethylether/hexanes to provide 31 mg (36%) of white crystals. $R_f$=0.2 (1:1 methylene chloride/ethyl acetate); H1-NMR (CDCl$_3$): δ 7.40 (2H,m), 7.32–7.21 (5H,m), 7.17 (3H,m), 6.81 (1H,br.s), 5.69 (1H,s), 5.00 (2H,m), 4.40 (1H,m), 4.02–3.70 (8H,m), 3.48–3.35 (2H,m), 3.23–2.71 (6H,m), 2.04 (2H,m), 1.79–1.67 (1H,m), 1.65–1.42 (3H,m). MS (ESI): M+H=593.

Example 149

Step 1

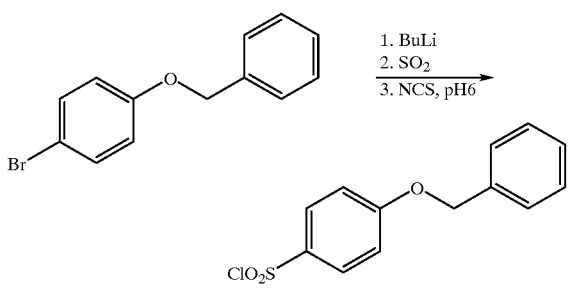

4-benzyloxybenzenesulfonyl chloride. The aryl bromide (12 g, 45.6 mmol) was dissolved in THF (100 mL) and cooled to −78° C. n-Butyl lithium 1.6 M in hexanes (28.5 mL, 45.6 mmol) was injected and the reaction stirred for 1 hr. before being warmed to 0° C. The resulting solution was then transferred to a −78° C. solution of SO$_2$ (41 mL, 913 mmol), Et$_2$O (100 mL) and THF (100 mL). The solution became a yellow suspension immediately upon addition of the aryl lithium. The suspension was warmed to room temperature and sparged with nitrogen for 1 hr. The suspension was concentrated to a yellow solid and triturated with Et$_2$O to provide 6.27 g of the sulfinate intermediate. The lithium sulfinate was stirred in a bi-phasic mixture of pH 6 aqueous dibasic sodium phosphate buffer (27 g in 200 mL distilled water—adjusted to pH 6 with conc. phosphoric acid) and ethyl acetate (200 mL) and cooled to 0° C. While stirring vigorously, N-chlorosuccinimide (3.27 g, 24.7 mmol) was added. The reaction was immediately warmed to room temperature and the aqueous layer was drained. The organic layer was concentrated to a yellow solid under reduced pressure. The crude sulfonyl chloride was purified by silica gel chromatography (5:1 hexanes/ethyl acetate) to provide 3.35g (26%) of an off-white solid. $R_f$=0.2 (5:1 hexanes/ethyl acetate). H1-NMR: δ 7.97 (2H,d), 7.45–7.30 (5H,m), 7.10 (2H,d), 5.16 (2H,s).

Step 2

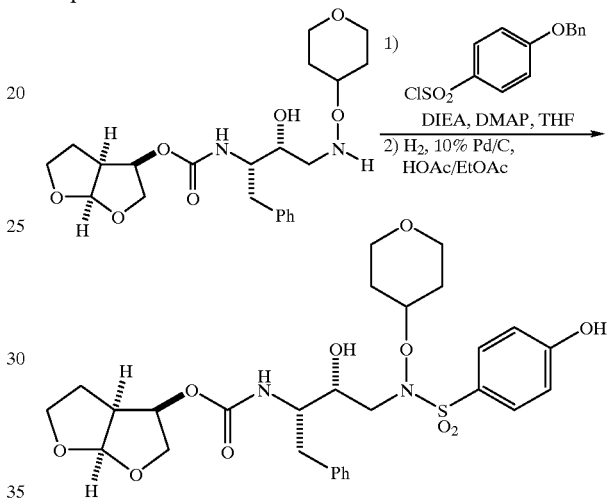

(3R,3aS, 6aR) hexahydrofuro[2,3-b]furan-3-yl 1-benzyl-2-hydroxy-3-[[(4-hydroxyphenyl) sulfonyl](tetrahydro-2H-pyran-4-yloxy) amino]propylcarbamate.

Step 1

(3R,3aS, 6aR) hexahydrofuro[2, 3-b]furan-3-y (1S 2R)-1-benzyl-2-hydroxy-3-[[(tetrahydro-2H-pyran-4-yloxy)amino]propylcarbamate(0.17 mmol, 75 mg) was combined with 4-benzyloxybenzenesulfonyl chloride (0.26 mmol, 73 mg), diisopropylethylamine (0.69 mmol, 0.12 mL), and a few crystals of N,N-dimethylaminopyridine in a 1:1 solution of anhydrous THF/methylene chloride (2 mL) and allowed to stir for 15 hours at room temperature under nitrogen. The reaction was diluted with ethyl acetate and washed with 1N HCl, 5% aqueous potassium carbonate solution, brine and was dried over magnesium sulfate. The solution was concentrated under vacuum and the crude product was purified by silica gel chromatography (1:1 hexanes/ethyl acetate) to provide 50 mg (43%) of a clear oil.

Step 2

The product of the previous step was stirred vigorously with 10% palladium on carbon (10 mg), acetic acid (0.5 mL), and ethyl acetate (2 mL) under hydrogen for 15 hours. The reaction was filtered and concentrated to an oil. The crude product was crystallized from diethylether/hexanes to provide 8 mg (19%) of white crystals. $R_f$=0.2 (1:1 methylene chloride/ethyl acetate); H1-NMR (CDCl$_3$): δ7.66 (2H,d), 7.32–7.12 (6H,m), 6.94 (2H,d), 6.25 (1H,br.s), 5.66 (1H,s), 4.98 (1H,m), 4.76 (1H,m), 4.41 (1H,m), 4.00–3.78 (6H,m), 3.68 (2H,m), 3.51–3.36 (2H,m), 3.29–2.51 (6H,m), 2.12–1.95 (2H,m), 1.69 (1H,m), 1.63–1.45 (2H,m). MS (ESI): M+H=593.

Example 150

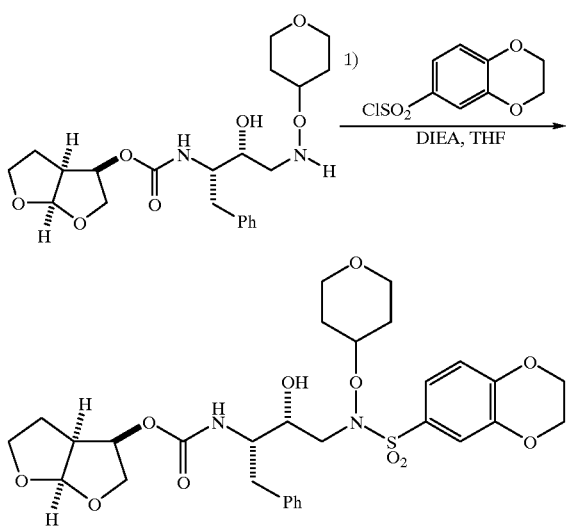

(3R,3aS,6aR)hexahydrofuro[2,3-b]furan-3-yl 1-benzyl-3-[(2,3-dihydro-1,4-benzodioxin-6-ylsulfonyl)(tetrahydro-2H-pyran-4-yloxy)amino]-2-hydroxypropylcarbamate. (3R,3aS,6aR)hexahydrofuro [2,3-b]furan-3-yl (1S,2R)-1-benzyl-2-hydroxy-3-[(tetrahydro-2H-pyran-4-yloxy)amino]propylcarbamate (0.17 mmol, 75 mg) was combined with 1,4-benzodioxan-6-sulfonyl chloride (0.21 mmol, 48 mg), diisopropylethylamine (0.69 mmol, 0.12 mL) in anhydrous THF (2 mL) and allowed to stir for 20 hours at room temperature under nitrogen. The reaction was diluted with diethylether and washed with 1N HCl, 5% aqueous potassium carbonate solution, brine and was dried over magnesium sulfate. The solution was concentrated under vacuum and the crude product was purified by silica gel chromatography (1:1 hexanes/ethyl acetate). The purified oil was lyophylized to provide 13 mg (12%) of a white powder. $R_f$=0.6 (ethyl acetate); H1-NMR (CDCl$_3$) δ 7.37–7.14 (8H, m), 6.98 (1H,d), 5.66 (1H,s), 5.03 (1H,m), 4.83 (1H,m), 4.43 (1H,m), 4.33 (4H,d), 4.03–3.79 (6H,m), 3.70 (2H,m), 3.45 (2H,m), 3.29–2.68 (6H,m), 2.06 (2H,m), 1.74–1.46 (3H,m). MS (ESI): M+H=635.

Example 151

(3R,3aS,6aR)hexahydrofuro[2,3-b]furan-3-yl 3-[(1,3-benzodioxol-5-ylsulfonyl)(tetrahydro-2H-pyran-4-yloxy)amino]-1-benzyl-2-hydroxypropylcarbamate. (3R,3aS,6aR) hexahydrofuro[2,3-b]furan-3-yl (1S,2R)-1-benzyl-2-hydroxy-3-[(tetrahydro-2H-pyran-4-yloxy)amino]propylcarbamate (0.23 mmol, 100 mg) was combined 1,3-benzodioxole-5-sulfonyl chloride (0.28 mmol, 61 mg), diisopropylethylamine (0.69 mmol, 0.12 mL) in anhydrous THF (2 mL) and allowed to stir 72 hours at room temperature under nitrogen. The reaction was diluted with ethyl acetate and washed with 1N HCl, saturated sodium bicarbonate solution, brine and was dried over magnesium sulfate. The solution was concentrated under vacuum and the crude product was purified by silica gel chromatography (1:5 hexanes/ethyl acetate). The purified oil was crystallized to provide 55 mg (39%) of white crystals. $R_f$=0.2 (1:5 hexanes/ethyl acetate); H1-NMR (CDCl$_3$): δ 7.38–7.13 (9H, m), 6.90 (1H,d), 6.10 (2H,s), 5.64 (1H,s), 5.02 (1H,m), 4.82 (1H,m), 4.41 (1H,m), 3.99–3.79 (6H,m), 3.72–3.59 (2H,m), 3.49–3.33 (2H,m), 3.25–2.51 (6H,m), 2.09–1.98 (2H,m), 1.69–1.43 (2H,m). MS (ESI): M+H=621.

Example 152

Step 1

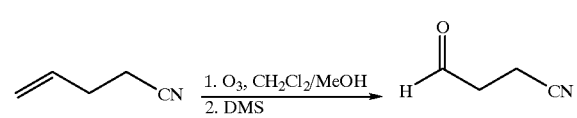

4-oxobutanenitrile. 4-butenenitrile (43.9 mmol, 3.56 grams) was dissolved in 150 mL of a 3:1 methylene chloride/methanol solution, cooled to −78° C., and ozonated until the solution turned blue (15 minutes). The excess ozone was sparged by bubbling nitrogen through the solution while warming to room temperature. Excess dimethylsulfoxide was added and the reaction stirred for 15 hours at room temperature. The reaction was concentrated to a clear liquid, dissolved in ethyl acetate, washed in distilled water, brine and dried over magnesium sulfate. The concentrated crude product was purified by silica gel flash chromatography (2:1 hexanes/ethyl acetate) to provide a brown liquid which was distilled at reduced pressure (150° C/15 mbar) to provide 2.11 grams (58%) of the purified clear liquid. $R_f$=0.2 (2:1 hexanes/ethyl acetate); H1-NMR (CDCl$_3$): δ9.78 (1H, s), 2.90 (2H,m), 2.61 (2H,m).

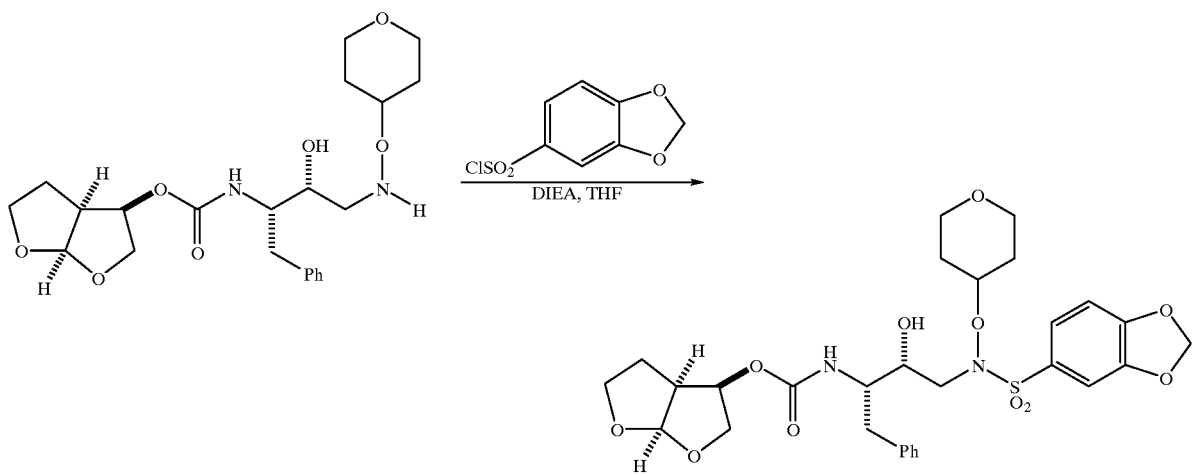

Step 2

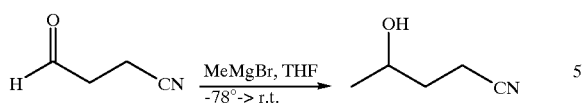

4-hydroxypentanenitrile. The 4-oxobutanenitrile (17.9 mmol, 1.49 grams) was dissolved in anhydrous THF (50 mL) and cooled to −78° C. Methylmagnesium bromide (17.9 mmol, 5.98 mL, 3M in diethyl ether) solution was injected slowly by syringe. The reaction stirred at −78° C. for 15 min. and was warmed to room temperature. The reaction was diluted in methylene chloride (50 mL) and dried over magnesium sulfate. The concentrated crude product was purified by silica gel flash chromatography (4:1 methylene chloride/ethyl acetate) and provided 1.2 grams (67%) of the desire alcohol as a yellow liquid. $R_f$=0.2 (4:1 methylene chloride/ethyl acetate); H1-NMR (CDCl$_3$): δ 3.91 (1H,m), 2.47 (2H,m), 1.86–1.60 (3H,m), 1.23 (3H,m).

Step 3

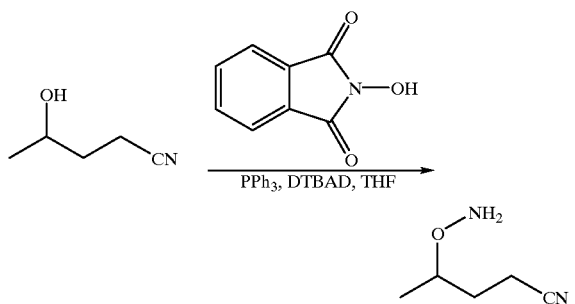

4-(aminooxy)pentanenitrile. A solution of ditertbutylazodicarboxylate (DTBAD) (13.9 mmol, 3.21 grams) in anhydrous THF (20 mL) was canulated dropwise into a stirring slurry of 4-hydroxypentanenitrile (11.6 mmol, 1.15 grams), N-hydroxyphthalimide (11.6 mmol, 1.89 grams), triphenylphosphine (13.9 mmol, 3.65 grams) and anhydrous THF (30 mL). The slurry dissolved on addition and changed color first to orange, then to yellow. The yellow solution stirred at room temperature for 3 hours. The solvent was removed under vacuum and the residue was dissolved in TFA. The reaction stirred in TFA for 2 hours to decompose the DTBAD biproduct. The TFA was removed under vacuum and the crude product was dissolved in ethy acetate, washed in distilled water, 5% aqueous potassium carbonate solution, brine and dried over magnesium sulfate. The crude yellow solid was purified by silica gel flash chromatography (2:1 hexanes/ethyl acetate) and provided 850 mg (32%) of a white crystalline solid. $R_f$=0.3 (2:1 hexanes/ethyl acetate); H-1-NMR (CDCl$_3$): δ7.83 (2H,m), 7.76 (2H,m), 4.39 (1H, m), 2.78 (2H,m), 2.03 (2H,m), 1.41 (3H,d).

Step 4:

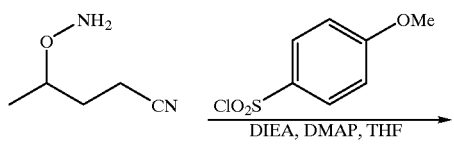

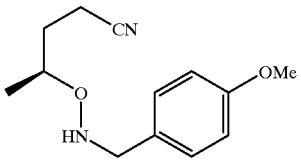

4-{[(4-methoxybenzyl)amino]oxy}pentanenitrile 4-(aminooxy)pentanenitrile (1.3 mmol, 150 mg) and 4-methoxybenzenesulfonylchloride (1.3 mmol, 272 mg) were combined in anhydrous THF with diisopropylethylamine (1.4 mmol, 0.69 mL) and a few crystals of DMAP. The reaction was stirred at 50° C. for 15 hours. The reaction was diluted in diethyl ether, washed with 1N HCl, 1N NaOH and brine and dried over mangesium sulfate. NMR analysis revealed that the isolated crude was the double sulfonyl chloride addition product. The aqueous NaOH fraction was acidified to neutral pH, extracted into ethyl acetate and dried over magnesium sulfate. The solvent was removed under vacuum leaving a very clean 195 mg (52%) crude product. $R_f$=0.4 (1:1 hexanes/ethyl acetate); H1-NMR (CDCl$_3$): δ7.82 (2H,d), 7.01 (2H,d), 6.84 (1H,s), 4.17 (1H,m), 3.88 (3H,s), 2.42 (2H,m), 1.88 (2H,m), 1.23 (3H,d).

Step 5:

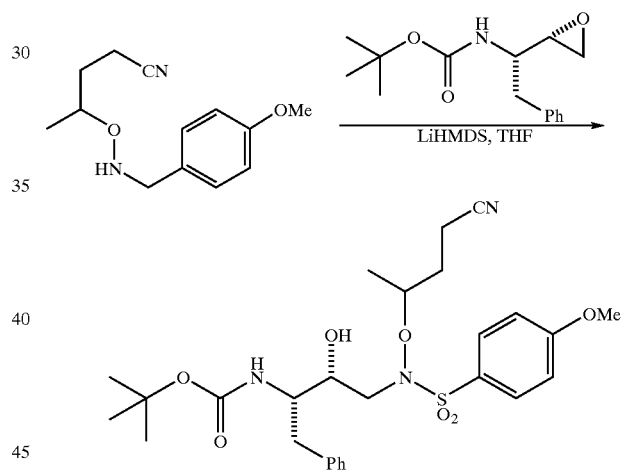

tert-butyl 1-benzyl-3-{(3-cyano-1-methylpropoxy)[(4-methoxyphenyl)sulfonyl]amino}-2-hydroxypropylcarbamate. 4-{[(4-methoxybenzyl)amino]oxy}pentanenitrile (0.69 mmol, 195 mg) was combined with tert-butyl N-(1S)-1-[(2S)oxiran-2-yl]-2-phenylethylcarbamate (0.57 mmol, 151 mg), lithium bis (trimethylsilyl) amide (0.11 mmol, 0.114 mL, 1.0 M in THF) and anhydrous THF (2 mL). The reaction was stirred under nitrogen at room temperature for 20 hours. The reaction was diluted in ethyl acetate (2 mL) and washed with 1N HCl, saturated aqueous sodium bicarbonate, brine, and was dried over magnesium sulfate. The crude solution was concentrated and purified by silica gel flash chromatography (1:1 hexanes/ethyl acetate) and RP HPLC followed by lyophylization to yield 78 mg (25%) of a white solid. $R_f$=0.2 (1:1 hexanes/ethyl acetate); H1-NMR (CDCl$_3$): δ 7.76–7.61 (2H, m), 7.34–7.11 (6H,m), 7.04–6.92 (2H,m), 4.72–4.53 (1H, m), 4.42 (1H, m), 3.89 (3H,s), 3.78 (2H,m), 3.25–2.51 (6H,m), 2.42 (2H,m), 2.02–1.79 (2H, m), 1.43–1.15 (10H, m). MS (ESI): M+H=548.

Example 153

Step 1

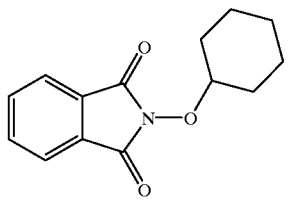

2-(cyclohexyloxy)-1H-isoindole-1,3(2H)-dione. A solution of triphenylphosine (15.53 g, 59.2 mmol), cyclohexanol (6.25 mL, 59.2mmol), and N-hydroxypthalimide (9.66 g, 59.2 mmol) in anhydrous tetrahydrofuran (500 mL) under Argon was treated dropwise over approximately 20 minutes with a solution of di-tert-butyl azodicarboxylate (15.00 g, 65.14 mmol) in tetrahydrofuran (100 mL) with a water bath to control the exotherm. After the reddish color had dissipated, a mixture of di-tert-butyl azodicarboxylate (3.00 g, 13.0 mmol) and triphenylphosine (3.11 g, 11.8 mmol) in anhydrous tetrahydrofuran (50 mL) was added to the reaction mixture and allowed to stir overnight at ambient temperature. After evaporation in vacuo, the residue was treated with trifluoroacetic acid (100 mL) and stirred for 20 minutes. The reaction was evaporated in vacuo and the residue was partitioned between water and dichloromethane. The layers were separated and the aqueous phase was extracted with dichloromethane. The combined organic layers were dried over anhydrous magnesium sulfate, filtered and evaporated in vacuo to a residue. The crude material was purified twice by flash silica gel chromatography eluting with hexane : ethyl acetate (4:1 and 9:1). Pure fractions were concentrated in vacuo to a solid and dried under high vacuum to provide 2-(cyclohexyloxy)-1H-isoindole-1,3(2H)-dione as a solid (10.90 g, 75%).

Step 2

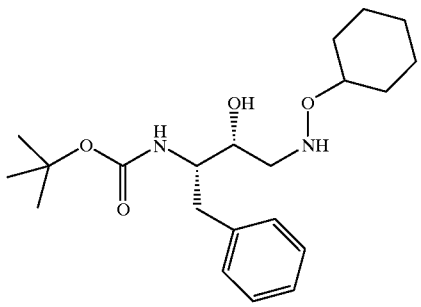

tert-butyl (1S,2R)-1-benzyl-3-[(cyclohexyloxy)amino]-2-hydroxypropylcarbamate. A solution 2-(cyclohexyloxy)-1H-isoindole-1,3(2H)-dione (10.00 g, 40.82 mmol) in anhydrous tetrahydrofuran (100 mL) under Argon was treated with anhydrous hydrazine (1.28 mL, 40.82 mmol). After stirring for approximately two hours, the slurry was treated with additional anhydrous hydrazine (0.13 mL, 4.1 mmol). After stirring an additional hour, the reaction mixture was filtered and washed with a minimum quantity of anhydrous tetrahydrofuran. The filtrate was combined with lithium triflate (5.09 g, 32.7 mmol) and tert-butyl N-(1S)-1-[(2S)oxiran-2-yl]-2-phenylethylcarbamate (8.58 g, 32.6 mmol) and brought to reflux. After heating for 16 hours, additional lithium triflate (5.00 g, 32.1 mmol) was added. The reaction was stirred at reflux for an additional 24 hours and then evaporated in vacuo. The residue was partitioned between ethyl acetate and water. After separating the layers, the organic phase was washed again with water. The aqueous phases were combined and extracted with ethyl acetate. The combined organic phases were washed with brine, dried over anhydrous sodium sulfate, filtered, and evaporated in vacuo. The residue was triturated with diethyl ether and then filtered. The mother liquor was evaporated in vacuo and the residue was triturated again with diethyl ether. The second crop was collected by filtration and the mother liquor was evaporated in vacuo. The residue was dissolved in diethyl ether and placed in the freezer overnight. A third crop was collected by filtration. All three crops were dried under high vacuum to provide tert-butyl (1S,2R)-1-benzyl-3-[(cyclohexyloxy)amino]-2-hydroxypropylcarbamate (4.48 g, 36%) as a solid. H1-NMR (chloroform-D3): 1.34 (m, 14H), 1.52 (m, 1H), 1.72 (m, 2H), 1.95 (m, 2H), 2.97 (m, 4H), 3.25 (m, 1H), 3.67 (m, 1H), 3.83 (m, 1H), 3.92 (m, 1H), 4.32 (b, 1H), 4.61 (d, 1H), 7.26 (m, 5H). MS(ESI): 379(M+H).

Step 3

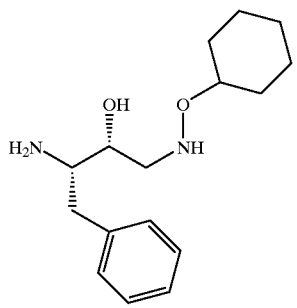

(2R,3S)-3-amino-i-[(cyclohexyloxy) amino]-4-phenyl-2-butanol. A combination of trifluoroacetic acid (20 mL) and tert-butyl (1S, 2R)-1-benzyl-3-[(cyclohexyloxy) amino]-2–15hydroxypropylcarbamate (2.00 g, 5.29 mmol) was stirred under Argon at ambient temperature for approximately 30 minutes. The reaction was evaporated in vacuo and the residue was partitioned between dichloromethane and aqueous sodium hydroxide (1N). After separating the layers, the aqueous phase was extracted with dichioromethane. The combined organic phases were dried over anhydrous sodium sulfate, filtered and evaporated in vacuo to a solid which was dried under high vacuum to provide (2R,3S)-3-amino-1-[(cyclohexyloxy)amino]-4-phenyl-2-butanol (1.426 g, 97%). H1-NMR (chloroform-I) 3): 1.24 (m, SH), 1.58 (m, 4H), 1.73 (m, 2H), 1.95 (m, 2H), 2.51 (m, 1H), 2.97 (m, 2H), 3.16 (m, 2H), 3.33 (m, 1H), 3.57 (m, 1H), 3.77 (m, 1H), 7.26 (m, :H) MS (ESI) 279(M+H)

Step 4:

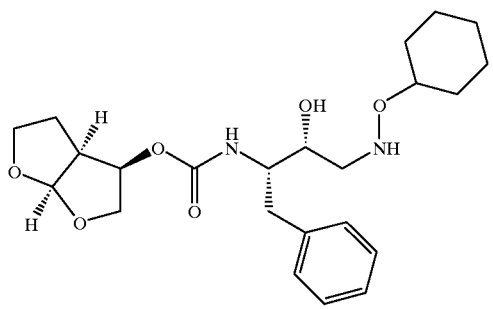

(3R,3aS,6aR)hexahydrofuro[2,3-b]furan-3-yl (1S,2R)-1-benzyl-3-[(cyclohexyloxy)amino]-2-hydroxypropylcarbamate. A mixture of (2R,3aS,6aR)hexahydrofuro[2,3-b]furan-2-yl 4-nitrophenyl carbonate (1.49 g, 4.82 mmol), (2R,3S)-3-amino-1-[(cyclohexyloxy)amino]-4-phenyl-2-butanol (1.341 g, 4.82 mmol) and diisoproylethylamine (0.841 mL, 4.82 mmol) in acetonitrile (15 mL) under Argon was stirred at ambient temperature for 16 hours. The resulting slurry was filtered and washed with cold acetonitrile to provide the first crop of product. The mother liquor was evaporated in vacuo dissolved in ethyl acetate and washed twice with aqueous sodium hydroxide (1N). The combined aqueous phases were extracted with ethyl acetate. The combined organic phases were washed with brine, dried over anhydrous sodium sulfate, filtered and evaporated in vacuo. The residue was triturated with diethyl ether and filtered to provide a second crop of product. The mother liquor was evaporated in vacuo and a third crop was crystallized from the residue dissolved in a minimum quantity of diethyl ether. The three crops were dried under high vacuum to provide (3R,3aS,6aR)hexahydrofuro[2,3-b]furan-3-yl (1S,2R)-1-benzyl-3-[(cyclohexyloxy)amino]-2-hydroxypropylcarbamate (1.555 g, 74%). HL-NMR (chloroform-D3): 1.31 (m, 7H), 1.56 (m, 2H), 1.73 (m, 2H), 1.99 (m, 2H), 2.74 (m, 1H), 2.89 (m, 1H), 3.10 (m, 2H), 3.30 (m, 1H), 3.83 (m, 8H), 5.01 (m, 2H), 5.63 (d, 1H), 7.21 (m, 5H). ). MS(ESI): 456(M+Na).

Step 5:

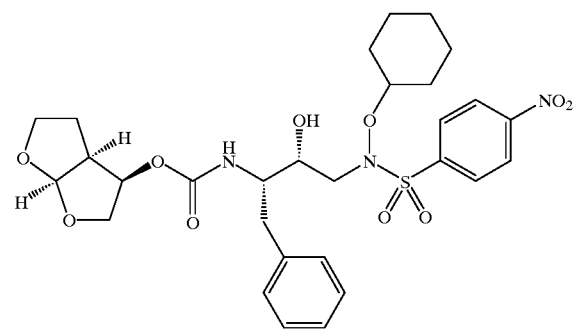

(3R,3aS,6aR)hexahydrofuro[2,3-b]furan-3-yl (1S,2R)-1-benzyl-3-{(cyclohexyloxy)[(4-nitrophenyl)sulfonyl]amino}-2-hydroxypropylcarbamate. A mixture (3R,3aS,6aR)hexahydrofuro [2,3-b]furan-3-yl (1S,2R)-1-benzyl-3-[(cyclohexyloxy)amino]-2-hydroxypropylcarbamate (100 mg, 0.23 mmol), 4-nitrobenzenesuphonyl chloride (61 mg, 0.276 mmol), diisoproylethlylamine (0.048 mL, 0.276 mmol) and 4-dimethylaminopyridine (~1 mg, cat.) was combined in anhydrous tetrahydrofuran (3 mL) and stirred at ambient temperature under an Argon atmosphere for approximately 16 hours. The reaction mixture was evaporated in vacuo and the residue was partitioned between ethyl acetate and aqueous hydrochloric acid (1N). The organic phase was dried over anhydrous magnesium sulfate, filtered and evaporated in vacuo. The residue was purified on flash silica gel eluting with 3:2 hexane : ethyl acetate followed by 1:1 hexane : ethyl acetate. Fractions containing the product were combined, evaporated in vacuo, and triturated with diethyl ether. The solvent was removed and the residual solid was dried under high vacuum to provide (3R,3aS,6aR) hexahydrofuro[2,3-b]furan-3-yl (1S,2R)-1-benzyl-3-{(cyclohexyloxy)[(4-nitrophenyl)sulfonyl]amino}-2-hydroxypropylcarbamate (129 mg, 91%). %). H1-NMR (chloroform-D3): 1.22 (m, 7H), 1.64 (m, 2H), 1.78 (m, 2H), 2.08 (m, 2H), 2.90 (m, 5H), 3.69 (m, 2H), 3.88 (m, 4H), 4.23 (m, 1H), 4.87 (m, 1H), 5.04 (m, 1H), 5.64 (d, 1H), 7.18 (m, 2H), 7.25 (m, 3H), 7.96 (d, 2H), 8.36 (d, 2H). MS(ESI) 642 (M+Na)

Step 6:

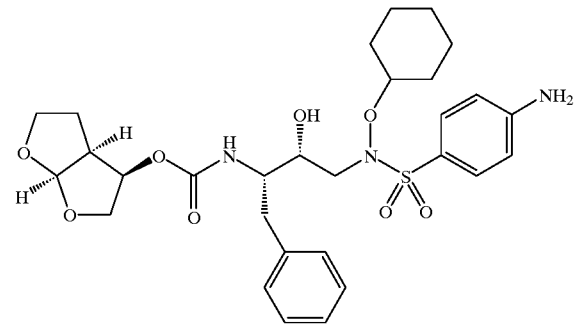

(3R,3aS,6aR)hexahydrofuro[2,3-b]furan-3-yl (1S,2R)-3-[[(4-aminophenyl)sulfonyl](cyclohexyloxy)amino]-1-benzyl-2-hydroxypropylcarbamate. To a solution of (3R, 3aS,6aR)hexahydrofuro[2,3-b]furan-3-yl (1S,2R)-1-benzyl-3-{(cyclohexyloxy)[(4-nitrophenyl)sulfonyl]amino}-2-hydroxypropylcarbamate (115 mg, 0.186 mmol) in a 1:1 mixture of ethanol : ethyl acetate (6 mL) was added Palladium on charcoal (10 wt %, 30 mg). The starting material was reduced under an atmosphere of Hydrogen gas over 16 hrs. The reaction mixture was filtered and evaporated in vacuo. The residue was purified on a preparative TLC plate (20×20 cm, 500 uM) eluting with 3:1 ethyl acetate : hexane. The product band was removed, eluted with 3:1 methylene chloride:methanol, filtered, and evaporated in vacuo. The residue was triturated with water, filtered and dried under high vacuum to provide (3R,3aS,6aR)hexahydrofuro[2,3-b]furan-3-yl (1S,2R)-3-[[(4-aminophenyl)sulfonyl](cyclohexyloxy)amino]-1-benzyl-2-hydroxypropylcarbamate(89 mg, 81%). H1-NMR (chloroform-D3): 1.26 (m, 6H), 1.58 (m, 5H), 2.05 (m, 2H), 2.90 (m, 4H), 3.09 (b, 2H), 3.68 (m, 2H), 3.88 (m, 4H), 4.16 (m, 1H), 4.24 (b, 1H), 4.81 (d, 1H), 5.00 (m, 1H), 5.63 (d, 1H), 6.66 (d, 2H), 7.23 (m, 5H), 7.56 (d, 2H). MS(ESI): 612(M+Na).

Example 154

Step 1

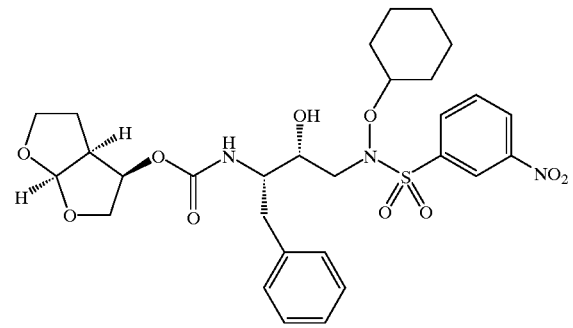

(3R,3aS,6aR)hexahydrofuro[2,3-b]furan-3-yl (1S,2R)-1-benzyl-3-{(cyclohexyloxy)[(3-nitrophenyl)sulfonyl]amino)-2-hydroxypropylcarbamate. A mixture (3R,3aS,6aR)hexahydrofuro[2,3-b]furan-3-yl (1S,2R)-1-benzyl-3-L(cyclohexyloxy)amino]-2-hydroxypropylcarbamate (342 mg, 0.788 mmol), 3-nitrobenzenesuphonyl chloride (175 mg, 0.788 mmol) and diisoproylethylamine (0.137 mL, 0.867 mmol) was combined in anhydrous tetrahydrofuran (10 mL) and stirred at ambient temperature under an Argon atmosphere for approximately 40 hours. The reaction mixture was partitioned between ethyl acetate and aqueous hydrochloric acid (1N). After separating the phases, the aqueous layer was extracted with ethyl acetate. The combined organic phases were washed with brine, dried over anhydrous magnesium sulfate, and evaporate in vacuo. The residue was purified on flash grade silica gel eluting with 1:1 ethyl acetate : hexane. The fractions containing the product were combined, evaporated in vacuo and dried under high vacuum to provide (3R,3aS, 6aR)hexahydrofuro[2,3-b]furan-3-yl (1S,2R)-1-benzyl-3-{(cyclohexyloxy)[(3-nitrophenyl)sulfonyl]amino}-2-hydroxypropylcarbamate (428 mg, 88%) as a foam. H1-NMR (chloroform-D3): 1.29 (m, 6H), 1.57 (m, 3H), 1.76 (m, 2H), 2.08 (m, 2H), 2.91 (m, 4H), 3.10 (b, 1H), 3.68 (m, 2H), 3.88 (m, 4H), 4.25 (m, 1H), 4.83 (d, 1H), 5.00 (m, 1H), 5.64 (d, 1H), 7.22 (m, 5H), 7.76 (m, 1H), 8.07 (d, 1H), 8.50 (d, 1H), 8.66 (s, 1H). MS(ESI): 642(M+Na).

Step 2

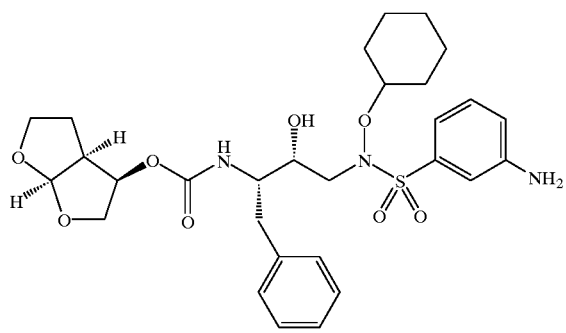

(3R,3aS,6aR)hexahydrofuro[2,3-b]furan-3-yl (1S,2R)-3-[[(3-aminophenyl)sulfonyl](cyclohexyloxy)amino]-1-benzyl-2-hydroxypropylcarbamate. A solution of (3R,3aS, 6aR)hexahydrofuro[2,3-b]furan-3-yl (1S,2R)-1-benzyl-3-{(cyclohexyloxy)[(3-nitrophenyl)sulfonyl]amino}-2-hydroxypropylcarbamate (403 mg, 0.651 mmol) in absolute ethanol (12 mL) was combined with Palladium on carbon (10 wt %, 80 mg) and reduced under a Hydrogen atmosphere for 16 hours. The reaction mixture was filtered and evaporated in vacuo to provide (3R,3aS,6aR)hexahydrofuro[2,3-b]furan-3-yl (1S,2R)-3-[[(3-aminophenyl)sulfonyl](cyclohexyloxy)amino]-1-benzyl-2-hydroxypropylcarbamate (356 mg, 93%) as a foam. A sample of the product (30 mg) was purified on a preparative TLC plate (20×20 cm, 500 uM) eluting with 95:5 dichloromethane:methanol. The product band was removed, eluted with 3:1 methylene chloride : methanol, filtered, and evaporated in vacuo. The residue was triturated with water, filtered and dried under high vacuum to provide (3R,3aS,6aR) hexahydrofuro[2,3-b]furan-3-yl (1S,2R)-3-[[(3-aminophenyl)sulfonyl](cyclohexyloxy)amino]-1-benzyl-2-hydroxypropylcarbamate (18 mg) as a solid. H1-NMR (chloroform-D3): 1.26 (m, 6H), 1.64 (m, 5H), 2.07 (m, 2H), 2.93 (m, 4H), 3.14 (b, 1H), 3.69 (m, 2H), 3.87 (m, 4H), 3.94 (b, 2H), 4.19 (m, 1H), 4.83 (b, 1H), 5.03 (m, 1H), 5.64 (d, 1H), 6.89 (d, 1H), 7.06 (s, 1H), 7.21 (m, 7H). MS(ESI) 612 (M+Na)

Example 155

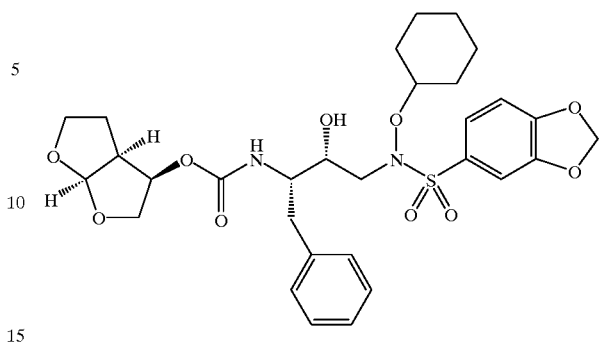

(3R,3aS,6aR)hexahydrofuro[2,3-b]furan-3-yl (1S,2R)-3-[(1,3-benzodioxol-5-ylsulfonyl)(cyclohexyloxy)amino]-1-benzyl-2-hydroxypropylcarbamate. A mixture of (3R,3aS, 6aR)hexahydrofuro[2,3-b]furan-3-yl (1S,2R)-1-benzyl-3-[(cyclohexyloxy)amino]-2-hydroxypropylcarbamate (100 mg, 0.230), 1,3-benzodioxole-5-sulfonyl chloride (Eur. Pat. Appl. 583960, Feb 23, 1994, 56 mg, 0.253 mmol) and diisoproylethylamine (0.042 mL, 0.242 mmol) in anhydrous tetrahydrofuran (3 mL) was stirred at ambient temperature under an Argon atmosphere for 16 hours. A catalytic quantity of dimethylaminopyridine (~1 mg) was added and the reaction was heated at reflux for approximately 2 hours. An additional quantity of 1,3-benzodioxole-5-sulfonyl chloride (11 mg, 0.050 mmol) was added and the reaction was heated for an additional hour. After cooling to ambient temperature, the reaction mixture was partitioned between ethyl acetate and aqueous hydrochloric acid. After separating the phases, the organic layer was washed with brine, dried over anhydrous magnesium sulfate, filtered and evaporated in vacuo. The residue was purified on a preparative TLC plate (20×20 cm, 500 μM) eluting with 1:1 ethyl acetate:hexane. The product band was removed, eluted with 3:1 methylene chloride : methanol, filtered, and evaporated in vacuo. The residue was triturated with water, filtered and dried under high vacuum to provide (3R,3aS,6aR)hexahydrofuro[2,3-b]furan-3-yl (1S,2R)-3-[(1,3-benzodioxol-5-ylsulfonyl)(cyclohexyloxy)amino]-1-benzyl-2-hydroxypropylcarbamate (123 mg, 87%) as a white solid. H1-NMR (chloroform-D3): 1.32 (m, 6H), 1.70 (m, 5H), 2.14 (m, 2H), 3.00 (m, 4H), 3.18 (b, 1H), 3.74 (m, 2H), 3.97 (m, 4H), 4.27 (m, 1H), 4.90 (m, 1H), 5.07 (m, 1H), 5.70 (d, 1H), 6.15 (s, 2H), 6.95 (d, 1H), 7.30 (m, 7H). MS(ESI): 641(M+Na).

Example 156

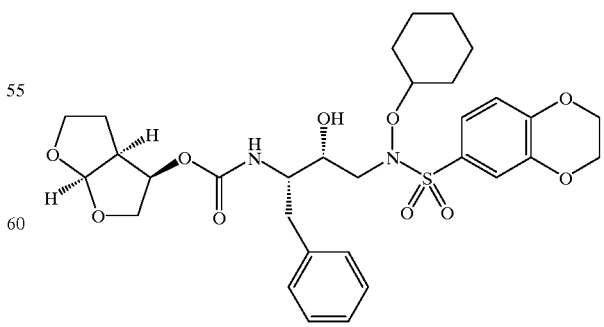

(3R,3aS,6aR)hexahydrofuro[2,3-b]furan-3-yl (1S,2R)-1-benzyl-3-[(cyclohexyloxy)(2,3-dihydro-1,4-benzodioxin-6- ylsulfonyl)amino]-2-hydroxypropylcarbamate. A mixture of 1,4-benzodioxan-6-sulfonyl chloride (Eur. Pat. Appl. 583960, Feb 23, 1994; 60 mg; 0.253 mmol), (3R,3aS,6aR)hexahydrofuro[2,3-b]furan-3-yl (1S,2R)-1-benzyl-3-[(cyclohexyloxy)amino]-2-hydroxypropylcarbamate (100 mg, 0.230 mmol), and diisoproylethylamine (0.042 mL, 0.242 mmol) in anhydrous tetrahydrofuran (3 mL) was stirred at ambient temperature under an Argon atmosphere for 16 hours. A catalytic quantity of dimethylaminopyridine (~1 mg) was added and the reaction was heated at reflux for approximately 2 hours. An additional quantity of 1,4-benzodioxan-6-sulfonyl chloride (12 mg, 0.051 mmol) was added and the reaction was heated for an additional 30 minutes. After cooling to ambient temperature, the reaction mixture was partitioned between ethyl acetate and aqueous hydrochloric acid. After separating the phases, the organic layer was washed with brine, dried over anhydrous magnesium sulfate, filtered and evaporated in vacuo. The residue was purified on a preparative TLC plate (20×20 cm, 500 μM) eluting with 1:1 ethyl acetate:hexane. The product band was removed, eluted with 3:1 methylene chloride:methanol, filtered, and evaporated in vacuo. The residue was triturated with water, filtered and dried under high vacuum to provide (3R,3aS,6aR)hexahydrofuro[2,3-b]furan-3-yl (1S,2R)-1-benzyl-3-[(cyclohexyloxy)(2,3-dihydro-1,4-benzodioxin-6-ylsulfonyl)amino]-2-hydroxypropylcarbamate (125 mg, 86%) as a white solid. HL-NMR (chloroform-D3): 1.20 (m, 6H), 1.60 (m, 5H), 2.07 (m, 2H), 2.90 (m, 4H), 3.09 (b, 1H), 3.67 (m, 2H), 3.90 (m, 4H), 4.23 (m, 1H), 4.31 (m, 4H), 4.82 (d, 1H), 5.01 (m, 1H), 5.64 (d, 1H), 6.95 (d, 1H) 7.25 (m, 7H). MS(ESI): 655(M+Na).

Example 157

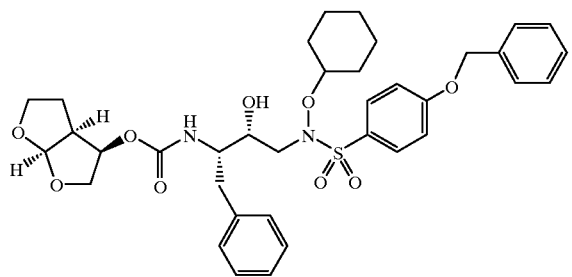

(3R,3aS,6aR)hexahydrofuro[2,3-b]furan-3-yl (1S,2R)-1-benzyl-3-[{[4-(benzyloxy)phenyl]sulfonyl}(cyclohexyloxy)amino]-2-hydroxypropylcarbamate. A mixture of 4-benzyloxybenzenesulfonyl chloride (65 mg; 0.230 mmol), (3R,3aS,6aR)hexahydrofuro[2,3-b]furan-3-yl (1S,2R)-1-benzyl-3-[(cyclohexyloxy)amino]-2-hydroxypropylcarbamate (100 mg, 0.230 mmol), diisopropylethylamine (0.042 mL, 0.242 mmol) and 4-dimethylaminopyridine (~1 mg) in anhydrous tetrahydrofuran (3 mL) was stirred at ambient temperature under an Argon atmosphere for 16 hours. An additional quantity of 4-benzyloxybenzenesulfonyl chloride (13 mg, 0.046 mmol) and 4-dimethylaminopyridine (~1 mg) was added and the reaction was heated at reflux for approximately 2 hours. After cooling to ambient temperature, the reaction mixture was partitioned between ethyl acetate and aqueous hydrochloric acid. The phases were separated and the organic layer was then washed with brine, dried over anhydrous magnesium sulfate, filtered and evaporated in vacuo. The crude product was purified on flash grade silica gel eluting with 1:1 ethyl acetate hexane. Fractions containing the product were combined and evaporated in vacuo and dried under high vacuum to provide (3R,3aS,6aR)hexahydrofuro[2,3-b]furan-3-yl (1S,2R)-1-benzyl-3-[{[4-(benzyloxy)phenyl]sulfonyl}(cyclohexyloxy)amino]-2-hydroxypropylcarbamate (143 mg, 91%). H1-NMR (chloroform-D3): 1.27 (m, 6H), 1.61 (m, 5H), 2.07 (m, 2H), 2.91 (m, 4H), 3.10 (b, 1H), 3.68 (m, 2H), 3.89 (m, 4H), 4.19 (m, 1H), 4.84 (m, 1H), 5.01 (m, 1H), 5.12 (s, 2H), 5.64 (d, 1H), 7.05 (d, 2H), 7.28 (m, 1OH), 7.71 (d, 2H). MS(ESI): 703(M+Na).

Example 158

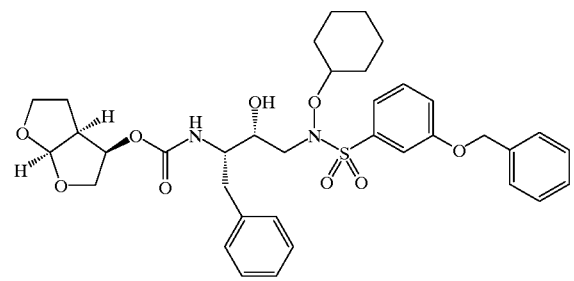

(3R,3aS,6aR)hexahydrofuro[2,3-b]furan-3-yl (1S,2R)-1-benzyl-3-[{[3-(benzyloxy)phenyl]sulfonyl}(cyclohexyloxy)amino]-2-hydroxypropylcarbamate. A mixture of 3-benzyloxybenzenesulfonyl chloride (65 mg; 0.230 mmol), (3R,3aS,6aR)hexahydrofuro[2,3-b]furan-3-yl (1S,2R)-1-benzyl-3-[(cyclohexyloxy)amino]-2-hydroxypropylcarbamate (100 mg, 0.230 mmol) and diisoproylethylamine (0.042 mL, 0.242 mmol) in anhydrous tetrahydrofuran (3 mL) was stirred at ambient temperature under an Argon atmosphere for 16 hours. A catalytic quantity of dimethylaminopyridine (~1 mg) was added and the reaction was heated at reflux for approximately one hour. An additional quantity of 3-benzyloxybenzenesulfonyl chloride (13 mg, 0.046 mmol) was added and the reaction was heated at reflux for approximately 1 hour. After cooling to ambient temperature, the reaction mixture was partitioned between ethyl acetate and aqueous hydrochloric acid. The phases were separated and the organic layer was then washed with brine, dried over anhydrous magnesium sulfate, filtered and evaporated in vacuo. The residue was dried under high vacuum to provide (3R,3aS,6aR)hexahydrofuro[2,3-b]furan-3-yl (1S,2R)-1-benzyl-3-[{[3-(benzyloxy)phenyl]sulfonyl}(cyclohexyloxy)amino]-2-hydroxypropylcarbamate (140 mg, 89%). H1-NMR (chloroform-D3): 1.22 (m, 6H), 1.62 (m, 5H), 2.05 (m, 2H), 2.90 (m, 4H), 3.11 (b, 1H), 3.66 (m, 2H), 3.87 (m, 4H), 4.18 (m, 1H), 4.77 (m, 1H), 4.95 (m, 1H), 5.10 (m, 2H), 5.60 (d, 1H), 7.29 (m, 14H). MS(ESI): 703(M+Na).

Example 159

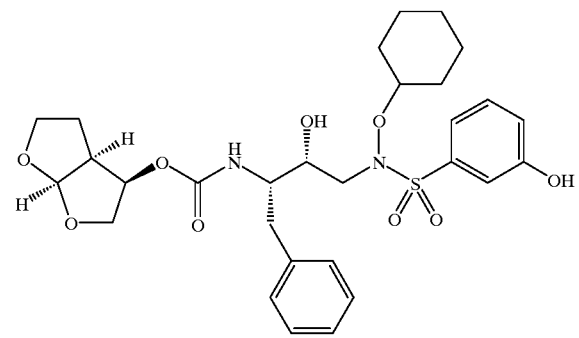

(3R,3aS,6aR)hexahydrofuro[2,3-b]furan-3-yl (1S,2R)-1-benzyl-3-{(cyclohexyloxy)[(3-hydroxyphenyl)sulfonyl]

amino}-2-hydroxypropylcarbamate. A solution of (3R,3aS, 6aR)hexahydrofuro[2,3-b]furan-3-yl (1S,2R)-1-benzyl-3-[([3-(benzyloxy)phenyl]sulfonyl}(cyclohexyloxy)amino]-2-hydroxypropylcarbamate (131 mg, 0.193 mmol) in ethyl acetate (-5 mL) was combined with Palladium on carbon (10 wt %, 25 mg) and reduced under an atmosphere of Hydrogen gas. After stirring for 16 hours, the reaction mixture was filtered and evaporated in vacuo to a residue. The residue was purified on a preparative TLC plate (20×20 cm, 500 μM) eluting with 3:2 ethyl acetate : hexane. The product band was removed, eluted with 3:1 methylene chloride : methanol, filtered, and evaporated in vacuo. The residue was triturated with water, filtered and dried under high vacuum to provide (3R,3aS,6aR)hexahydrofuro[2,3-b]furan-3-yl (1S,2R)-1-benzyl-3-{(cyclohexyloxy)[(3-hydroxyphenyl) sulfonyl]amino}-2-hydroxypropylcarbamate (93 mg, 82%) as a white solid. H1-NMR (chloroform-D3): 1.28 (m, 6H), 1.67 (m, 5H), 2.06 (m, 2H), 2.96 (m, 4H), 3.09 (b, 1H), 3.87 (m, 6H), 4.19 (m, 1H), 5.01 (m, 2H), 5.69 (d, 1H), 6.60 (b, 1H), 7.23 (m, 9H). MS(ESI): 613(M+Na).

Example 160

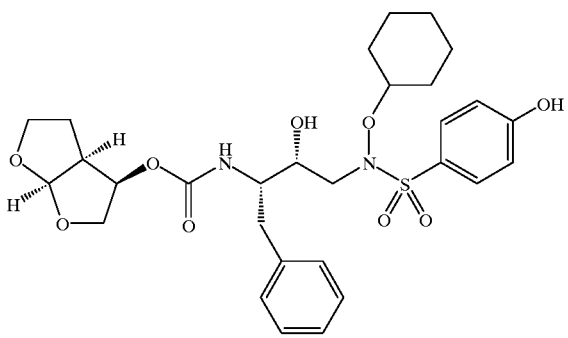

(3R,3aS,6aR)hexahydrofuro[2,3-b]furan-3-yl (1S,2R)-1-benzyl-3-{(cyclohexyloxy)[(4-hydroxyphenyl)sulfonyl] amino}-2-hydroxypropylcarbamate. A solution of (3R,3aS, 6aR)hexahydrofuro[2,3-b]furan-3-yl (1S,2R)-1-benzyl-3-[{ [4-(benzyloxy)phenyl]sulfonyl}(cyclohexyloxy)amino]-2-hydroxypropylcarbamate (140 mg, 0.206 mmol) in ethyl acetate (5 mL) was combined with Palladium on carbon (10 wt %, 28 mg) and reduced under an atmosphere of Hydrogen gas. After stirring for 16 hours, the reaction mixture was filtered and evaporated in vacuo to a residue. The residue was purified on a preparative TLC plate (20×20 cm, 500 μM) eluting with 3:2 ethyl acetate:hexane. The product band was removed, eluted with 4:1 methylene chloride:methanol, filtered, and evaporated in vacuo. The residue was triturated with water, filtered and dried under high vacuum to provide (3R,3aS,6aR)hexahydrofuro[2,3-b]furan-3-yl (1S,2R)-1-benzyl-3-{(cyclohexyloxy)[(4-hydroxyphenyl)sulfonyl] amino}-2-hydroxypropylcarbamate (106 mg, 87%) as a white solid. H1-NMR (chloroform-D3): 1.27 (m, 6H), 1.67 (m, 5H), 2.05 (m, 2H), 2.93 (m, 4H), 3.11 (b, 1H), 3.68 (m, 2H), 3.90 (m, 4H), 4.19 (m, 1H), 4.81 (d, 1H), 4.99 (m, 1H), 5.65 (d, 1H), 6.24 (b, 1H), 6.92 (d, 2H), 7.22 (m, 5H), 7.67 (d, 2H). MS(ESI): 613(M+Na).

Example 161

Step 1

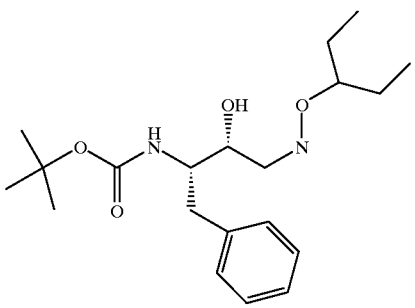

tert-butyl (1S,2R)-1-benzyl-3-[(1-ethylpropoxy) amino]-2-hydroxypropylcarbamate. A solution of 2-(l-ethylpropoxy)-1H-isoindole-1,3(2H)-dione [Synth. Comm., 22(10), 1427–1432 (1992), 10.00 g, 42.9 mmol in anhydrous tetrahydrofuran (100 mL) under Argon was treated with anhydrous hydrazine (1.48 mL, 47.2 mmol) over approximately 5 minutes. The reaction was stirred for 45 minutes and diluted with anhydrous tetrahydrofuran (50 mL). An additional quantity of anhydrous hydrazine (0.888 mL, 28.3 mmol) was added in six increments over 90 minutes. The mixture was filtered washing with tetrahydrofuran (~50 mL). The mother liquor was combined with tert-butyl N-(1S)-1-[(2S)oxiran-2-yl]-2-phenylethylcarbamate (9.03 g, 34.3 mmol) and lithium triflate (5.36 g, 34.3 mmol) and heated to reflux. After stirring for 3.5 days, the reaction was evaporated in vacuo and the residue was partitioned between aqueous potassium carbonate (5% w/v) and ethyl acetate. The aqueous phase was separated and extracted with ethyl acetate. The combined organic layers were washed with saturated brine, dried over magnesium sulfate, filtered and evaporated in vacuo. The residue was purified on flash grade silica gel eluting with 3:1 hexane:ethyl acetate. Fractions containing the product were evaporated in vacuo and dried under high vacuum to tert-butyl (1S,2R)-1-benzyl-3-[(l-ethylpropoxy)amino]-2-hydroxypropylcarbamate (6.425 g, 51%) as a solid. H1-NMR (chloroform-D3): 0.88 (m, 6H), 1.34 (s, 9H), 1.51 (m, 4H), 2.91 (m, 4H), 3.15 (d, 1H), 3.47 (m, 1H), 3.69 (m, 2H), 3.89 (m, 1H), 4.57 (m, 1H), 7.24 (m, 5H). MS(ESI): 389(M+Na).

Step 2

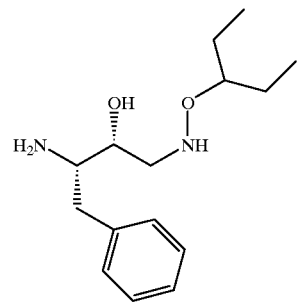

(2R,3S)-3-amino-i-[(1-ethylpropoxy)amino]-4-phenyl-2-butanol. A mixture of tert-butyl (1S,2R)-1-benzyl-3-[(1-ethylpropoxy)amino]-2-hydroxypropylcarbamate (3.285 g, 8.98 mmol) and trifluoroacetic acid (25 mL) was stirred at ambient temperature under Argon for approximately 30 minutes. The reaction was evaporated in vacuo and the residue was partitioned between dichloromethane and aqueous sodium hydroxide (1N). The phases were separated and the aqueous phase was extracted with dichloromethane. The combined organic phases were dried over anhydrous sodium sulfate, filter, evaporated in vacuo and dried under high vacuum to provide (2R,3S)-3-amino-1-[((-ethylpropoxy) amino]-4-phenyl-2-butanol (2.455 g, 100%) as a solid. H1-NMR (chloroform-D3): 0.94 (m, 6H), 1.56 (m, 4H), 2.55 (m, 1H), 3.01 (m, 2H), 3.22 (m, 2H), 3.51 (m, 1H), 3.81 (m, 1H), 7.30 10 (m, 5H). MS (ESI): 267(M+H).

Step 3

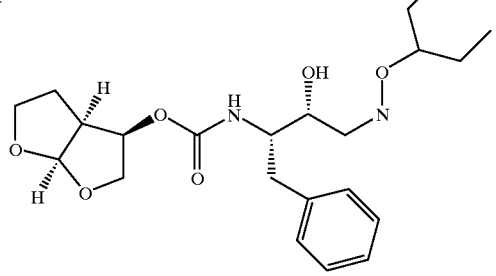

(3R,3aS,6aR)hexahydrofuro[2,3-b]furan-3-yl (1S,2R)-1-benzyl-3-[(1-ethylpropoxy)amino]-2-hydroxypropylcarbamate. A mixture of (2R,3aS,6aR) hexahydrofuro[2,3-b]furan-2-yl 4-nitrophenyl carbonate (2.764 g, 8.94 mmol), (2R,3S)-3-amino-1-[(1-ethylpropoxy) amino]-4-phenyl-2-butanol (2.379 g, 8.94 mmol), and diisoproylethylamine (1.56 mL, 8.94 mmol) in 2 acetonitrile (25 mL) under Argon was stirred at ambient temperature for 16 hours. The reaction mixture was evaporated in vacuo and the residue was partitioned between ethyl acetate and aqueous potassium carbonate (5% w/v). The phases were separated and the organic layer was washed again with aqueous potassium carbonate (5% w/v). The aqueous phases were combined and extracted with ethyl acetate. The combined organic layers were washed with brine, dried over anhydrous magnesium sulfate and evaporated in vacuo. The residue was triturated with diethyl ether and filtered. The mother liquor was evaporated in vacuo and the residue was purified on flash grade silica gel eluting with 1:1 ethyl acetate:hexane. Fractions containing the product were combined and evaporated in vacuo to a solid. Both crops of product were dried under high vacuum to provide (3R,3aS,6aR) hexahydrofuro[2,3-b]furan-3-yl (1s,2R)-1-benzyl-3-[(1-ethylpropoxy)amino]-2-hydroxypropylcarbamate (2.554 g, 68%). H1-NMR (chloroform-D3): 0.88 (m, 6H), 1.52 (m, 7H), 2.77 (m, 1H), 2.91 (m, 2H), 3.07 (m, 1H), 3.16 (m, 1H), 3.37 10 (b, 1H), 3.46 (m, 1H), 3.75 (m, 4H), 3.94 (m, 2H), 4.87 (d, 1H), 5.03 (m, 1H), 5.63 (d, 1H), 7.23 (m, 5H). MS(ESI): 445(M+Na).

Step 4:

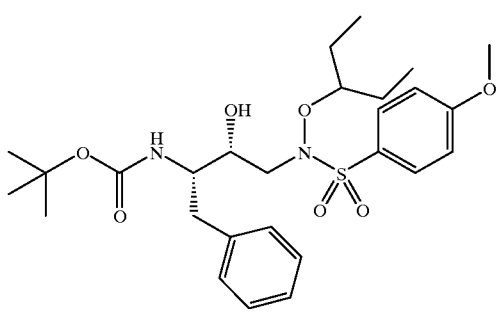

tert-butyl (1S,2R)-1-benzyl-3-{(1-ethylpropoxy)[(4-methoxyphenyl) sulfonyl)amino}-2-hydroxypropylcarbamate. A mixture of tert-butyl (1S,2R)-1-benzyl-3-[(1-ethylpropoxy) amino]-2-hydroxypropylcarbamnate (100 mg, 0.273 mmol), 4-methoxyphenylsulphonyl chloride (57 mg, 0.273 mmol), and diisoproylethylamine (0.0476 mL, 0.273 mmol) in anhydrous tetrahydrofuran (2 mL) was stirred under Argon for 16 hours at ambient temperature. A catalytic quantity of 4-dimethylaminopyridine (~1 mg) was added and the reaction was heated at reflux for approximately two hours. After cooling, the reaction was evaporated in vacuo and the residue was dissolved in ethyl acetate. The solution was washed with aqueous potassium carbonate (5% w/v), aqueous hydrochloric acid (1N) and brine. The organic layer was then dried over anhydrous magnesium sulfate, filtered and evaporated in vacuo. The residue was purified on a preparative TLC plate (20×20 cm, 500 μM) eluting with 95:5 methylene chloride:methanol. The product band was removed, eluted with 4:1 methylene chloride:methanol, filtered, and evaporated in vacuo. The residue was purified again on a preparative TLC plate (20×20 cm, 500 μM) eluting with 95:5 methylene chloride:ethyl acetate. The product band was removed, eluted with 4:1 methylene chloride : methanol, filtered, and evaporated in vacuo to provide tert-butyl (1S,2R)-i-benzyl-3-{(1-ethylpropoxy)[(4-methoxyphenyl)sulfonyl]amino}-2-hydroxypropylcarbamate (103 mg, 70%) as a foam. H1-NMR (chloroform-D3): 0.95 (m, 6H), 1.38 (s, 9H), 1.64 (m, 4H), 3.01 (m, 5H), 3.83 (m, 2H), 3.93 (s, 3H), 4.20 (m, 1H), 4.61 (m, 1H), 7.03 (d, 2H), 7.29 (m, 5H), 7.80 (d, 2H). MS(ESI): 559(M+Na).

Example 162

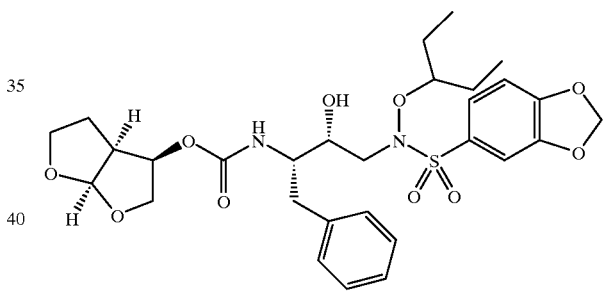

(3R,3aS,6aR)hexahydrofuro[2,3-b]furan-3-yl (1S,2R)-3-[(1,3-benzodioxol-5-ylsulfonyl)(1-ethylpropoxy)amino]-1-benzyl-2-hydroxypropylcarbamate. A mixture of (3R,3aS,6aR)hexahydrofuro[2,3-b]furan-3-yl (1S,2R)-1-benzyl-3-[(l-ethylpropoxy)amino]-2-hydroxypropylcarbamate (0.100 g, 0.237 mmol), 1,3-benzodioxole-5-sulfonyl chloride (52 mg, 0.237 mmol), diisoproylethylamine (0.042 mL, 0.237 mmol) and dimethylaminopyridine (~1 mg) in anhydrous tetrahydrofuran (3 mL) was stirred at ambient temperature over 16 hours under an Argon atmosphere. The reaction was evaporated in vacuo and the residue was partitioned between dichloromethane and aqueous hydrochloric acid (1N). The organic phase was separated and dried over anhydrous magnesium sulfate, filtered and evaporated in vacuo. The residue was purified on a preparative TLC plate (20×20 cm, 500 uM) eluting with 97:3 dichloromethane : methanol. The product band was removed, eluted with 4:1 methylene chloride:methanol, filtered, and evaporated in vacuo. The residue was triturated with water, filtered and dried under high vacuum to provide (3R,3aS,6aR)hexahydrofuro[2,3-b] furan-3-yl (1S,2R)-3-[(1,3-benzodioxol-5-ylsulfonyl)(1-ethylpropoxy)aamino]-1-benzyl-2-hydroxypropylcarbamate (114 mg, 80%) as a white solid. H1-NMR (chloroform-D3):

0.89 (m, - 5 6H), 1.57 (m, 7H), 2.95 (m, 5H), 3.69 (m, 2H), 3.89 (m, 4H), 4.15 (m, 1H), 4.82 (d, 1H), 5.01 (m, 1H), 5.64 (d, 1H), 6.10 (s, 2H), 6.90 (d, 1H), 7.23 (m, 6H), 7.39 (m, 1H). MS(ESI): 629(M+Na).

Example 163

Step 1

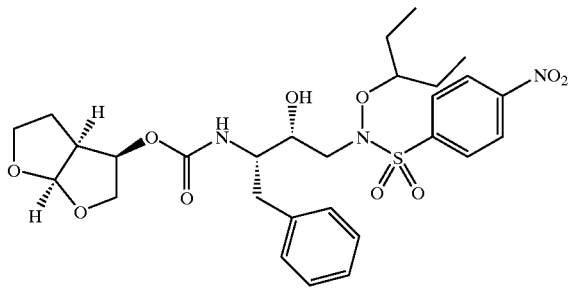

(3R,3aS,6aR)hexahydrofuro[2,3-b]furan-3-yl (1S,2R)-1-benzyl-3-{ (1-ethylpropoxy)[(4-nitrophenyl) sulfonyl amino}-2-hydroxypropylcarbamate. A mixture of (3R,3aS, 6aR)hexahydrofuro[2,3-b]furan-3-yl (1S,2R)-1-benzyl-3-[(1-ethylpropoxy)amino]-2-hydroxypropylcarbamate (200 mg, 0.474 mmol), 4-nitrophenylsulphonyl chloride (105 mg, 0.474 mmol), diisoproylethylamine (0.084 mL, 0.474 mmol) and dimethylaminopyridine (~1 mg) in anhydrous tetrahydrofuran (3 mL) was stirred at ambient temperature over 16 hours under an Argon atmosphere. The reaction was evaporated in vacuo and the residue was partitioned between dichloromethane and aqueous sodium hydrogen sulfate (1N). The phases were separated and the aqueous layer was extracted with dichloromethane. The combined organic phases were dried over anhydrous magnesium sulfate, filtered and evaporated in vacuo. The residue was purified on flash grade silica gel eluting with 1:1 ethyl acetate:hexane. Fractions containing the product were combined, evaporated in vacuo and dried under high vacuum to provide (3R,3aS, 6aR)hexahydrofuro[2,3-b]furan-3-yl (1S,2R)-1-benzyl-3-{ (1-ethylpropoxy)[(4-nitrophenyl)sulfonyl]amino}-2-hydroxypropylcarbamate (254 mg, 88%) as a foam. H1-NMR (chloroform-D3): 0.90 (m, 6H), 1.60 (m, 7H), 2.90 (m, 5H), 3.68 (m, 2H), 3.87 (m, 4H), 4.17 (m, 1H), 4.83 (d, 1H), 5.02 (m, 1H), 5.64 (d, 1H), 7.23 (m, 5H), 7.99 (d, 2H), 8.38 (d, 2H). MS(ESI): 630(M+Na).

Step 2

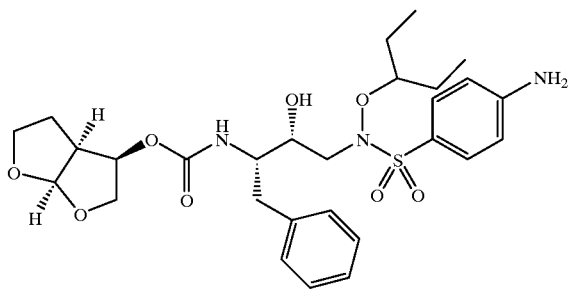

(3R,3aS,6aR)hexahydrofuro[2,3-b]furan-3-yl (1S,2R)-3-[[(4-aminophenyl)sulfonyl](1-ethylpropoxy)amino]-1-benzyl-2-hydroxypropylcarbamate. A solution of (3R,3aS, 6aR)hexahydrofuro[2,3-b]furan-3-yl (1S,2R)-1-benzyl-3-{(1-ethylpropoxy)[(4-nitrophenyl)sulfonyl]amino}-2-hydroxypropylcarbamate (237 mg, 0.390 mmol) in absolute methanol (5 mL) was combined with Palladium on carbon (10 wt %, 50 mg) and reduced under a Hydrogen atmosphere over 16 hours. The reaction was filtered and evaporated in vacuo. The residue was purified on silica gel eluting with 50–60% ethyl acetate in hexane. Fractions containing the product were combined and evaporated in vacuo. The residue was triturated with water, filtered and dried under high vacuum to provide (3R,3aS,6aR)hexahydrofuro[2,3-b] furan-3-yl (1S,2R)-3-[[(4-aminophenyl)sulfonyl](1-ethylpropoxy)amino]-1-benzyl-2-hydroxypropylcarbamate (160 mg, 71%) as a white solid. H1-NMR (chloroform-D3): 0.90 (m, 6H), 1.58 (m, 7H), 2.95 (m, 5H), 3.69 (m, 2H), 3.91 (m, 4H), 4.13 (m, 1H), 4.26 (b, 2H), 4.80 (d, 1H), 5.00 (m, 1H), 5.63 (d, 1H), 6.67 (d, 2H), 7.22 (m, 5H), 7.58 (d, 2H). ). MS(ESI): 600(M+Na).

Example 164

Step 1

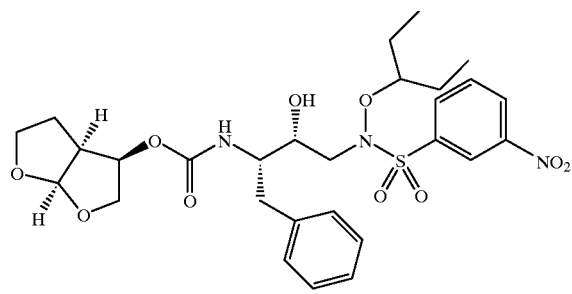

Preparation of (3R,3aS,6aR)hexahydrofuro[2,3-b]furan-3-yl (1S,2R)-1-benzyl-3-{(1-ethylpropoxy)[(3-nitrophenyl) sulfonyl]amino}-2-hydroxypropylcarbamate. A mixture of (3R,3aS,6aR)hexahydrofuro[2,3-b]furan-3-yl (1S,2R)-1-benzyl-3-[(1-ethylpropoxy)amino]-2-hydroxypropylcarbamate (200 mg, 0.474 mmol), 3-nitrophenylsulphonyl chloride (105 mg, 0.474 mmol), diisoproylethylamine (0.084 mL, 0.474 mmol) and dimethylaminopyridine (~1 mg) in anhydrous tetrahydrofuran (3 mL) was stirred at ambient temperature over 16 hours under an Argon atmosphere. The reaction was evaporated in vacuo and the residue was partitioned between dichloromethane and aqueous hydrochloric acid (1N). After separating the phases, the aqueous layer was extracted with dichloromethane. The combined organic phases were dried over anhydrous magnesium sulfate, filtered and evaporated in vacuo. The residue was purified on flash grade silica gel eluting with 1:1 ethyl acetate : hexane. Fractions containing the product were combined, evaporated in vacuo and dried under high vacuum to provide (3R,3aS,6aR)hexahydrofuro [2,3-b]furan-3-yl (1S,2R)-1-benzyl-3-{(1-ethylpropoxy)[(3-nitrophenyl)sulfonyl]amino}-2-hydroxypropylcarbamate (246 mg, 86%). H1-NMR (chloroform-D3): 0.98 (m, 6H), 1.68 (m, 7H), 2.99 (m, 5H), 3.73 (m, 2H), 3.96 (m, 4H), 4.27 (m, 1H), 4.86 (d, 1H), 5.07 (m, 1H), 5.69 (d, 1H), 7.27 (m, 5H), 7.84 (m, 1H), 8.16 (d, 1H), 8.57 (d, 1H), 8.76 (s, 1H). MS (ESI): 630(M+Na).

Step 2

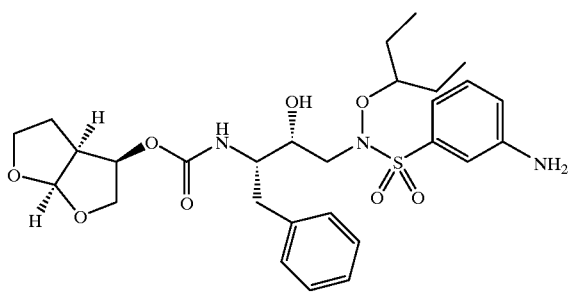

(3R,3aS,6aR)hexahydrofuro[2,3-b]furan-3-yl (1S,2R)-3-[[(3-aminophenyl)sulfonyl](1-ethylpropoxy)amino]-1-benzyl-2-hydroxypropylcarbamate. A solution of (3R,3aS,6aR)hexahydrofuro[2,3-b]furan-3-yl (1S,2R)-1-benzyl-3-{(1-ethylpropoxy)[(3-nitrophenyl)sulfonyl]amino}-2-hydroxypropylcarbamate (239 mg, 0.394 mmol) in absolute ethanol (3 mL) was combined with Palladium on carbon (10 wt %, 25 mg) and reduced under a Hydrogen atmosphere over 16 hours. The reaction was filtered and evaporated in vacuo. The residue was purified on flash grade silica gel eluting with 3:2 ethyl acetate : hexane. Fractions containing the product were combined and evaporated in vacuo. The residue was triturated with water, filtered and dried under high vacuum to provide (3R,3aS,6aR)hexahydrofuro[2,3-b]furan-3-yl (1S,2R)-3-[[(3-aminophenyl)sulfonyl](1-ethylpropoxy)amino]-1-benzyl-2-hydroxypropylcarbamate (153 mg, 67%) as a white solid. H1-NMR (chloroform-D3): 0.96 (m, 6H), 1.62 (m, 7H), 3.05 (m, 5H), 3.76 (m, 2H), 3.96 (m, 6H), 4.19 (m, 1H), 4.88 (m, 1H), 5.07 (m, 1H), 5.69 (d, 1H), 6.95 (d, 1H), 7.14 (s, 1H), 7.28 (m, 7H). MS(ESI): 600(M+Na).

Example 165

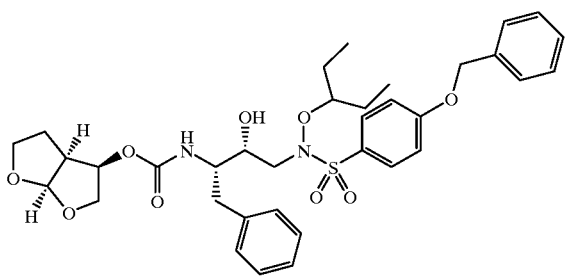

(3R,3aS,6aR)hexahydrofuro[2,3-b]furan-3-yl (1S,2R)-1-benzyl-3-[{[4-(benzyloxy)phenyl]sulfonyl}(1-ethylpropoxy)amino]-2-hydroxypropylcarbamate. A mixture of (3R,3aS, 6aR)hexahydrofuro[2,3-b]furan-3-yl (1S,2R)-1-benzyl-3-[(1-ethylpropoxy)amino]-2-hydroxypropylcarbamate (200 mg, 0.474 mmol), 4-benzyloxybenzenesulphonyl chloride (134 mg, 0.474 mmol), diisoproylethylamine (0.083 mL, 0.474 mmol) and dimethylaminopyridine (1 mg) in anhydrous tetrahydrofuran (3 mL) was stirred at ambient temperature over 16 hours under an Argon atmosphere. The reaction mixture was warmed to 55° C. and an additional quantity of dimethylaminopyridine (~2 mg) was added. After stirring for 2 hours, the reaction was evaporated in vacuo and the residue was partitioned between dichloromethane and aqueous sodium hydrogen sulfate (1N). After separating the phases, the aqueous layer was extracted with dichloromethane. The combined organic phases were dried over anhydrous magnesium sulfate, filtered and evaporated in vacuo. The residue was purified on flash grade silica gel eluting with 3:2 ethyl acetate : hexane. Fractions containing the product were combined, evaporated in vacuo, and dried under high vacuum to provide (3R,3aS,6aR)hexahydrofuro[2,3-b]furan-3-yl (1S,2R)-1-benzyl-3-[{[4-(benzyloxy)phenyl]sulfonyl}(1-ethylpropoxy)amino]-2-hydroxypropylcarbamate (235 mg, 74%) as a foam. H1-NMR (chloroform-D3): 0.94 (m, 6H), 1.62 (m, 7H), 3.05 (m, 5H), 3.74 (m, 2H), 3.98 (m, 4H), 4.18 (m, 1H), 4.88 (d, 1H), 5.08 (m, 1H), 5.19 (s, 2H), 5.70 (d, 1H), 7.13 (d, 2H), 7.34 (m, 10H), 7.80 (d, 2H). MS(ESI): 691(M+Na).

Example 166

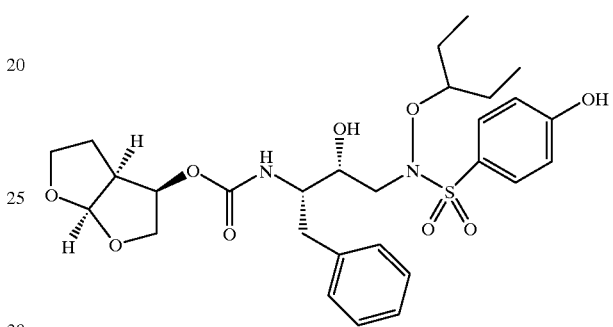

(3R,3aS, 6aR) hexahydrofuro [2,3-b]furan-3-yl (1S,2R)-1-benzyl-3-{ (1-ethylpropoxy)[(4-hydroxyphenyl) sulfonyl]] amino}-2-hydroxypropylcarbamate. A solution of (3R,3aS, 6aR)hexahydrofuro[2,3-b]furan-3-yl (1S,2R)-1-benzyl-3-[{[4-(benzyloxy)phenyl]sulfonyl}(1-ethylpropoxy)amino]-2-hydroxypropylcarbamate (222 mg, 0.384 mmol) in 3:1 absolute ethanol:ethyl acetate was combined with Palladium on carbon (10 wt %, 44 mg) and reduced under an atmosphere of Hydrogen gas over 16 hours. The reaction was filtered and evaporated in vacuo. The residue was purified on flash grade silica gel eluting with 3:2 ethyl acetate:hexane. Fractions containing the product were combined and evaporated in vacuo. The residue was triturated with water, filtered and dried under high vacuum to provide (3R,3aS,6aR) hexahydrofuro[2,3-b]furan-3-yl (1S,2R)-1-benzyl-3-{(1-ethylpropoxy)[(4-hydroxyphenyl)sulfonyl]amino}-2-hydroxypropylcarbamate (103 mg, 46%) as a white solid. H1-NMR (chloroform-D3): 0.91 (m, 6H), 1.61 (m, 7H), 2.93 (m, 5H), 3.70 (m, 2H), 3.92 (m, 4H), 4.17 (m, 1H), 4.79 (d, 1H), 5.01 (m, 1H), 5.66 (d, 1H), 6.12 (s, 1H), 6.94 (d, 2H), 7.26 (m, 5H), 7.72 (d, 2H). MS(ESI): 601(M+Na).

Example 167

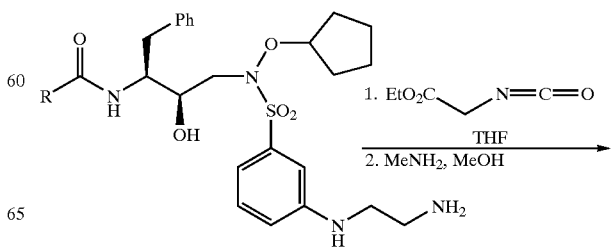

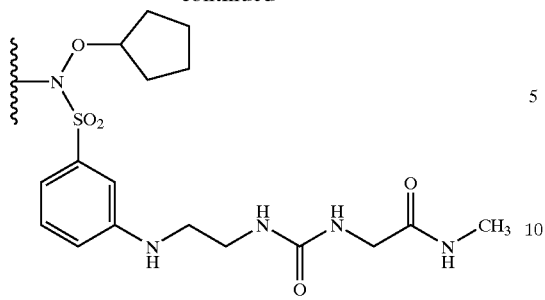

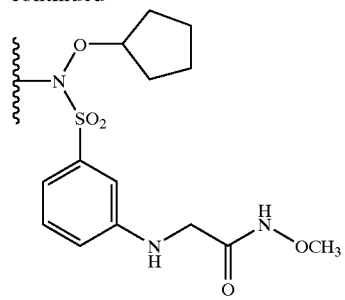

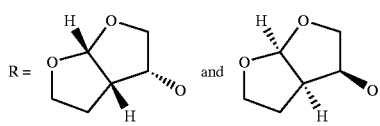

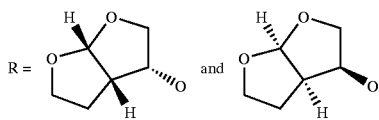

(3R,3aS,6aR)hexahydrofuro[2,3-b]furan-3-yl N-[(1S,2R)-1-benzyl-3-((cyclopentyloxy)[3-([(2-[methylamino]-2-oxoethylamino)carbonylamino]ethylamino)phenyl]sulfonylamino) -2-hydroxypropyl]carbamate and (3S,3aR,6aS)hexahydrofuro[2,3-b]furan-3-yl N-[(1S,2R)-1-benzyl-3-((cyclopentyloxy)[3-([(2-[methylamino]-2-oxoethylamino)carbonylamino]ethylamino)phenyl]sulfonylamino) -2-hydroxypropyl]carbamate. A solution of 30 mg (0.048 mmol) of a 1:1 mixture of (3R,3aS,6aR) hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate and (3S,3aR,6aS) hexahydrofuro[2,3-b]furan-3-yl N-(1S,2R)-3-[(3-[(2-aminoethyl)amino]phenylsulfonyl)(cyclopentyloxy)amino]-1-benzyl-2-hydroxypropylcarbamate in 2 mL of anhydrous THF was treated with 6.0 μL (0.05 mmol) of ethyl isocyanatoacetate. After stirring at RT for 2.5 hours the solution was concentrated in vacuo. The residue was dissolved in 3 mL of 2M NH$_3$/MeOH and the solution stirred at RT. After 18 hours the solution was concentrated to dryness and the residue subjected to flash chromatography (silica gel, 9:1 CH$_2$Cl$_2$/2M NH$_3$ in MeOH) to afford 23 mg (66%) of the desired product as a white foam, 1H-NMR (CDCl$_3$): 7.38–7.07 (10H), 6.88 (2H), 6.39 (1H), 6.16–5.88 (2H), 5.68 (1H), 5.09 (1H), 4.84 (1H), 4.17–2.59 (20H), 2.10–1.25 (1OH). MS(ESI): 733 (M+H).

(3R,3aS,6aR)hexahydrofuro[2,3-b]furan-3-yl N-[(1S,2R)-1-benzyl-3-((cyclopentyloxy)[3-(2-[methoxyamino]-2-oxoethylamino)phenyl]sulfonylamino)-2-hydroxypropyl] carbamate and (3S,3aR,6aS)hexahydrofuro[2,3-b]furan-3-yl N-[(1S,2R)-1-benzyl-3-((cyclopentyloxy)[3-(2-[methoxyamino]-2-oxoethylamino)phenyl]sulfonylamino)-2-hydroxypropyl]carbamate. A solution of 0.100 g (0.174 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 44 mg (0.26 mmol) of N-methoxybromoacetamide (prepared in a manner analogous to N-methoxy-N-methylbromoacetamide, example 88), and 0.045 mL (0.26 mmol) of N,N-diisopropylethylamine in 5 mL of anhydrous DMF was heated to 80° C. with stirring in a sealed tube. The reaction progress was monitored by HPLC (C18, H$_2$O/MeCN/0.1% TFA). In order to push the reaction further toward completion, additional 1.5 equivalent portions of N-methoxybromoacetamide and N,N-diisopropylethylamine were added after 4 hours and 3 days. After a total reaction time of 4 days the solution was cooled to RT and concentrated in vacuo. The residue was subjected to flash chromatography (SiO$_2$, 93:7 CH$_2$Cl$_2$/2M NH$_3$ in MeOH) to afford 16 mg (14%) of the desired product as a white foam. 1H-NMR (CDCl$_3$): 7.36–7.00 (9H), 6.85 (2H), 5.60 (1H), 5.20–4.82 (2H), 4.75(2H), 4.10–3.43 (10H), 3.21–2.45 (6H), 1.90–1.39 (10H). MS(ESI): 663(M+H).

Example 168

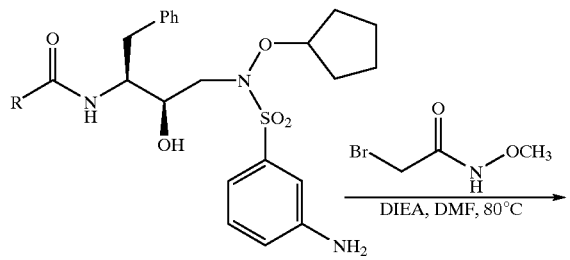

Example 169

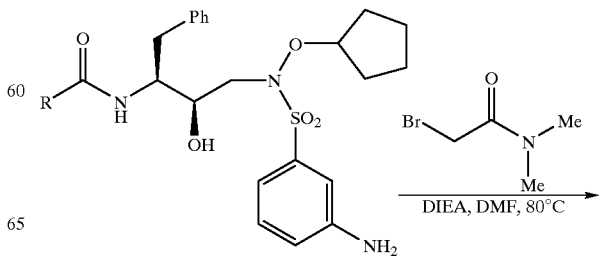

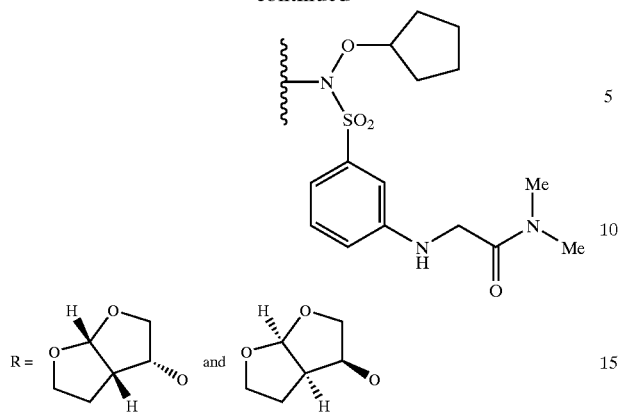
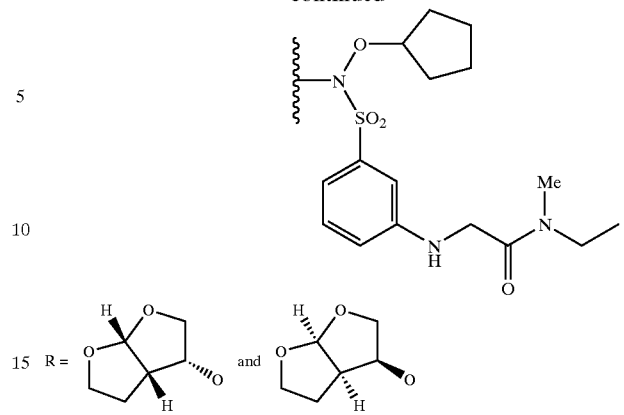

(3R,3aS,6aR)hexahydrofuro[2,3-b]furan-3-yl N-[(1S,2R)-1-benzyl-3-((cyclopentyloxy)[3-(2-[dimethylamino]-2-oxoethylamino)phenyl)sulfonylamino)-2-hydroxypropyl]carbamate and (3S,3aR,6aS)hexahydrofuro[2,3-b]furan-3-yl N-[(1S,2R)-1-benzyl-3-((cyclopentyloxy)[3-(2-[dimethylamino]-2-oxoethylamino)phenyl]sulfonylamino)-2-hydroxypropyl]carbamate. A solution of 0.100 g (0.174 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 32 mg (0.19 mmol) of N,N-dimethylbromoacetamide (prepared in a manner analogous to N-methoxy-N-methylbromoacetamide, example 88), and 0.033 mL (0.19 mmol) of N,N-diisopropylethylamine in 3 mL of anhydrous DMF was heated to 80° C. with stirring in a sealed tube. The reaction progress was monitored by HPLC (C18, H$_2$O/MeCN/0.1% TFA). In order to push the reaction further toward completion, additional 1.1 equivalent portions of N,N-dimethylbromoacetamide and N,N-diisopropylethylamine were added after 18 hours and 42 hours. After a total reaction time of 3 days the solution was cooled to RT and concentrated in vacuo. The residue was dissolved in EtOAc and the solution washed with aqueous brine (3x), dried over MgSO$_4$, and concentrated. The crude product was purified by flash chromatography (SiO$_2$, EtOAc) to afford 53 mg (46%) of the desired product as a light yellow foam. 1H-NMR (CDCl$_3$): 7.32–7.14 (8H), 7.10 (1H), 6.93 (1H), 6.86 (1H), 5.61 (1H), 4.96 (1H), 4.91–4.77 (2H), 3.92–3.55 (7H), 3.23–2.77 (12H), 1.86–1.38 (1OH). MS(ESI): 661(M+H).

(3R,3aS,6aR)hexahydrofuro[2,3-b]furan-3-yl N-[(1S,2R)-1-benzyl-3-((cyclopentyloxy)[3-(2-[ethyl(methyl)amino]-2-oxoethylamino)phenyl]sulfonylamino)-2-hydroxypropyl]carbamate and (3S,3aR,6aS)hexahydrofuro[2,3-b]furan-3-yl N-[(1S,2R)-1-benzyl-3-((cyclopentyloxy)[3-(2-[ethyl(methyl)amino]-2-oxoethylamino)phenyl]sulfonylamino)-2-hydroxypropyl]carbamate. A solution of 0.100 g (0.174 mmol) of a 1:1 mixture of (3R,3aS,6aR)hexahydrofuro[2,3-b]furan-3-yl N-((1S,2R)-1-benzyl-3-(cyclopentyloxy)[(3-aminophenyl)sulfonyl]amino-2-hydroxypropyl)carbamate and (3S,3aR,6aS)hexahydrofuro[2,3-b]furan-3-yl N-((1S,2R)-1-benzyl-3-(cyclopentyloxy)[(3-aminophenyl)sulfonyl]amino-2-hydroxypropyl)carbamate (see example 31), 34 mg (0.19 mmol) of N-ethyl-N-methylacetamide (prepared in a manner analogous to N-methoxy-N-methylbromoacetamide, example 88), and 0.033 mL (0.19 mmol) of N,N-diisopropylethylamine in 3 mL of anhydrous DMF was heated to 80° C. with stirring in a sealed tube. The reaction progress was monitored by HPLC (C18, H$_2$O/MeCN/0.1% TFA). In order to push the reaction further toward completion, additional 1.1 equivalent portions of N-ethyl-N-methylacetamide and N,N-diisopropylethylamine were added after 18 hours and 42 hours. After a total reaction time of 3 days the solution was cooled to RT and concentrated in vacuo. The residue was dissolved in EtOAc and the solution washed with aqueous brine (3x), dried over MgSO$_4$, and concentrated. The crude product was purified by flash chromatography (SiO$_2$, EtOAc) to afford 61 mg (52%) of the desired product as a light yellow foam. 1H-NMR (CDCl$_3$): 7.32–7.14 (1H), 7.09 (1H), 6.91 (1H), 6.85 (1H), 5.62 (1H), 5.01–4.77 (3H), 3.95–3.53 (7H), 3.48 (1H), 3.34 (1H), 3.23–2.75 (9H), 1.88–1.41 (1OH), 1.27–1.08 (3H). MS(ESI): 675(M+H).

Example 170

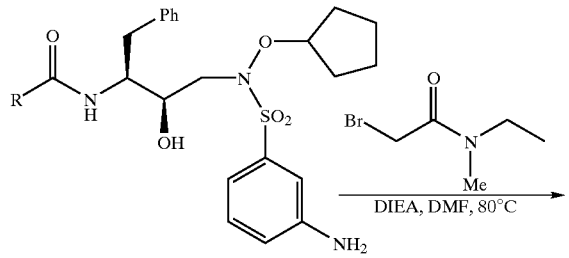

Example 171

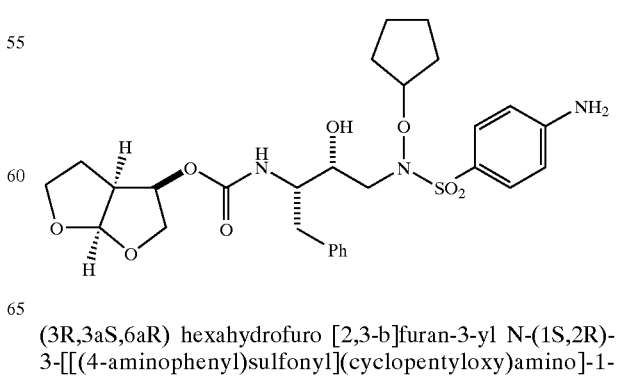

(3R,3aS,6aR) hexahydrofuro [2,3-b]furan-3-yl N-(1S,2R)-3-[[(4-aminophenyl)sulfonyl](cyclopentyloxy)amino]-1- benzyl-2-hydroxypropyl carbamate. This material was obtained in an analogous manner to Example 77, but p-nitrobenzenesulfonyl chloride was used instead of meta nitrobenzenesulfonyl chloride.

MS: 598 (M+Na), NMR (chloroform-d): 1.2–2.0 (m), 2.75–3.2 (m), 3.6 (dd), 3.7–4.0 (m), 4.2 (s), 4.75 (m), 4.85 (m), 5.0 (m), 5.62 (d), 6.65 (d), 7.2–7.3 (m), 7.55 (d).

Example 172

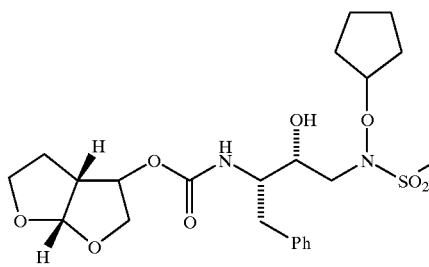

(3S,3aR,6aS) hexahydrofuro [2,3-b]furan-3-yl N-(1S,2R)-3-[[(4-aminophenyl)sulfonyl](cyclopentyloxy)amino]-1-benzyl-2-hydroxypropyl carbamate. This material was obtained in an analogous manner to Example 77, but p-nitrobenzenesulfonyl chloride was used instead of meta nitrobenzenesulfonyl chloride and the starting scaffold was that used in Example 39 (oposite stereochemistry at the furanylfuran ring system).

MS: 598 (M+Na). ), NMR (chloroform-d): 1.2–2.0 (m), 2.75–3.2 (m), 3.6 (dd), 3.7–4.0 (m), 4.2 (s), 4.75 (m), 4.95 (m), 5.1 (m), 5.8 (d), 6.65 (d), 7.2–7.3 (m), 7.55 (d).

Example 173

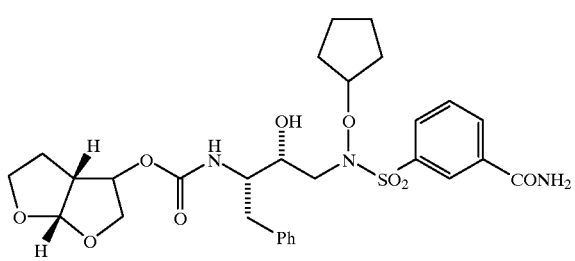

Step 1
(3R,3aS,6aR) hexahydrofuro [2,3-b]furan-3-yl N-(1S,2R)-3-[[(3-cyanophenyl)sulfonyl](cyclopentyloxy)amino]-1-benzyl-2-hydroxypropyl carbamate. In a dried flask was introduced 1 eq. of (3R,3aS,6aR)Hexahydrofuro[2,3b]furan-3-yl-N-(1S,2R)-1-benzyl-3-[(cyclopentyloxy)amino]-2-hydroxypropylcarbamate (53.6 mg, 0.127 mmol) in 2 mL of dried pyridine. To this solution was added 1.2 eq. of the m-cyanophenyl sulfonyl chloride (31 mg, 0.153 mmol). This was followed by the addition of catalytic DMAP (1 mg). The reaction was continued at room temperature for 24 h. The solvent was evaporated in vacuo to an oil who was solubilized in ethyl acetate and then washed with 1N hydrochloric acid, and brine. The organic layer was dried over anhydrous magnesium sulfate, filtered and evaporated in vacuo to a residue. The crude material was purified on flash grade silica gel eluting with 50% ethyl acetate in hexane. Fractions containing the product were combined, evaporated in vacuo and dried under high vacuum to provide (3R,3aS,6aR)Hexahydrofuro[2,3b]furan-3-yl-N-(1S,2R)-1-benzyl-3-(cyclopentyloxy)[(m-cyanophenyl)sulfonyl]amino-2-hydroxypropyl carbamate (31 mg, 42%). HPLC showed the material to be 98% pure; Ret. time 12.1 min, tlc in 50% ethyl acetate/ Hexanes indicated an Rf of 0,3 and LCMS (ES+), M+H=586.3 (M+H).

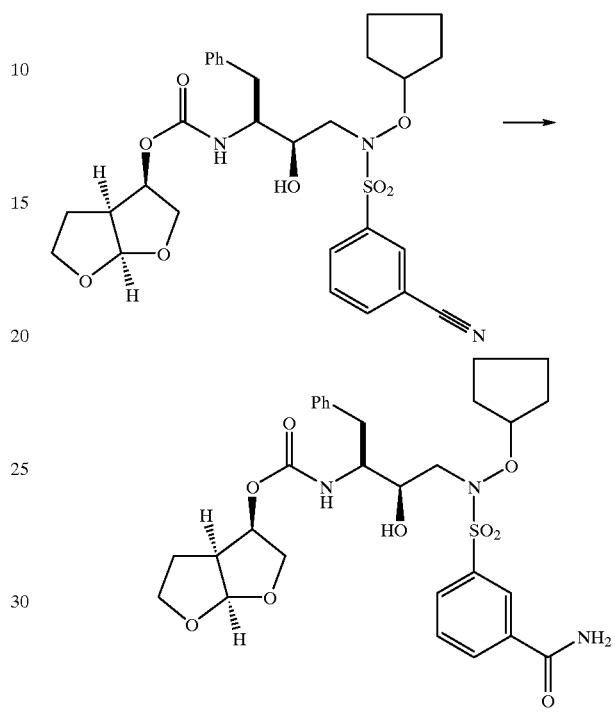

Step 2
(3R,3aS,6aR) hexahydrofuro [2,3-b]furan-3-yl N-(1S,2R)-3-[[(3-carbamoylphenyl)sulfonyl](cyclopentyloxy)amino]-1-benzyl-2-hydroxypropyl carbamate. In a flask was introduced 1 eq. (3R,3aS,6aR)Hexahydrofuro[2,3b]furan-3-yl-N-(1S,2R)-1-benzyl-3-[(cyclopentyloxy)[(m-cyanophenyl)sulfonyl]amino-2-hydroxypropyl carbamate (28 mg, 0.048 mmol) in 1 mL acetone. To this solution was added: lurea hydroperoxide (4EQ., 18 mg, 0.19 mmol), $K_2CO_3$ (0.1 EQ., 0.7 mg), and the 1 mL $H_2O$. The reaction was continued at room temperature for 5 h. The solvent was evaporated in vacuo to an oil who was solubilized in ethyl acetate and then washed with and brine. The organic layer was dried over anhydrous magnesium sulfate, filtered and evaporated in vacuo to a residue. The crude material was purified on flash grade silica gel eluting with ethyl acetate. Fractions containing the product were combined, evaporated in vacuo and dried under high vacuum to provide (3R,3aS,6aR) Hexahydrofuro[2,3b]furan-3-yl-N-(1S,2R)-1-benzyl-3-[(cyclopentyloxy)[(m-phenyl-carboxamide)sulfonyl]amino-2-hydroxypropyl carbamate (20.2 mg). HPLC showed the material to be 98% pure; Ret. time=10.68 min, tlc in ethyl acetate indicated an Rf of 0.5 and LCMS (ES+), M+H= 604.3 (M+H).

Example 173

Tablet Formulation

The following formulations A, B and C are prepared by wet granulation of the ingredients with a solution of povidone, followed by addition of magnesium stearate and compression.

|  | mg/tablet |
| --- | --- |
| Formulation A | |
| Active Ingredient | 250 |
| Lactose B.P. | 210 |
| Povidone B.P. | 15 |
| Sodium Starch Glycollate | 20 |
| Magnesium Stearate | 5 |
| | 500 |
| Formulation B | |
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
| | 500 |
| Formulation C | |
| Active Ingredient | 250 |
| Lactose B.P. | 200 |
| Starch | 50 |
| Povidone | 5 |
| Magnesium Stearate | 4 |
| | 359 |

The following formulations, D and E, are prepared by direct compression of the admixed ingredients. The lactose in formulation E is of the direct compression type (Dairy Crest-"Zeparox").

|  | mg/tablet |
| --- | --- |
| Formulation D | |
| Active Ingredient | 250 |
| Pregelatinized Starch NF15 | 150 |
| | 400 |
| Formulation E | |
| Active Ingredient | 250 |
| Lactose B.P. | 150 |
| Avicel | 100 |
| | 500 |

Formulation F (Controlled Release Formulation)

The formulation is prepared by wet granulation of the ingredients with a solution of povidone followed by the addition of magnesium stearate and compression.

|  | mg/tablet |
| --- | --- |
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
| | 700 |

Drug release takes place over a period of about 6–8 hours and is complete after 12 hours.

Example 174

Capsule Formulations

Formulation A

A capsule formulation is prepared by admixing the ingredients of formulation D in Example 134 above and filling into a two-part hard gelatin capsule. Formulation B (infra) is prepared in a similar manner.

|  | mg/capsule |
| --- | --- |
| Formulation B | |
| Active Ingredient | 250 |
| Lactose B.P. | 143 |
| Sodium Starch Glycollate | 25 |
| Magnesium Stearate | 2 |
| | 420 |
| Formulation C | |
| Active Ingredient | 250 |
| Macrogel 4000 B.P. | 350 |
| | 600 |

Capsules of formulation C are prepared by melting the Macrogel 4000 B.P., dispersing the active ingredient in the melt and filling the melt into a two-part hard gelatin capsule.

| Formulation D | mg/capsule |
| --- | --- |
| Active Ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

| Formulation E | mg/capsule |
| --- | --- |
| Active Ingredient | 150.0 |
| Vitamin E TPGS | 400.0 |
| Polyethylene Glycol 400 NF | 200.5 |
| Propylene Glycol USP | 39.5 |

Four (4) kilograms (kg) of Vitamin E TPGS (obtained from Eastman Chemical Co.) was heated at 50° C. until liquefied. To the liquified Vitamin E TPGS, 2.005 kg of polyethylene glycol 400 (PEG400) (low aldehyde, <10 ppm, obtained from Union Carbide or Dow Chemical Co.) heated to 50° C. was added and mixed until a homogeneous solution was formed. The resultant solution was heated to 65° C. 1.5 kg of active ingredient was dissolved in the liquefied solution of Vitamin E TPGS and PEG 400.0.395 kg of propylene glycol at room temperature was added and mixed until a homogenous solution was formed. The solution was cooled to 28–35° C. The solution was then de-gassed. The mixture was preferably encapsulated at 28–35° C. at a fill weight equivalent to 150 mg of volatiles-free compound, into Size 12 oblong, white opaque soft gelatin capsules using a capsule filling machine. The capsule shells were dried to a constant fill moisture of 3–6% water and a shell hardness of 7–10 newtons, and placed in a suitable container.

Formulation F (Controlled Release Capsule)

The following controlled release capsule formulation is prepared by extruding ingredients a,b, and c using an extruder, followed by spheronization of the extrudate and drying. The dried pellets are then coated with release-controlling membrane (d) and filled into a two-piece, hard gelatin capsule.

|  | mg/capsule |
|---|---|
| (a) Active Ingredient | 250 |
| (b) Microcrystalline Cellulose | 125 |
| (c) Lactose B.P. | 125 |
| (d) Ethyl Cellulose | 13 |
|  | 513 |

Example 175

| Injectable Formulation Formulation A | |
|---|---|
| Active Ingredient | 200 mg |
| Hydro chloric Acid Solution 0.1M or Sodium Hydroxide Solution 0.1M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate.

The batch is then made up to volume with water and filtered through a sterile micropore filter into a sterile 10 ml amber glass vial (type 1) and sealed with sterile closures and overseals.

| Formulation B | |
|---|---|
| Active Ingredient | 125 mg |

Sterile, Pyrogen-free, pH 7 Phosphate Buffer, q.s. to 25 ml

Example 176

| Intramuscular Injection | |
|---|---|
| Active Ingredient | 200 mg |
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

Example 177

| Syrup Formulation | |
|---|---|
| Active Ingredient | 250 mg |
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

Example 178

| Suppository Formulation | mg/capsule suppository |
|---|---|
| Active Ingredient | 250 |
| Hard Fat, B.P. (Witepsol H15-Dynamit Nobel) | 1770 |
|  | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250um stainless steel screen and, with continuous stirring, is allowed to cool to 45° C. At a temperature of 38° C. to 40° C., 2.02 g of the mixture is filled into suitable, 2 ml plastic molds. The suppositories are allowed to cool to room temperature.

Example 179

| Pessary Formulation | mg/pessary |
|---|---|
| Active Ingredient | 250 |
| Anhydrate Dextrose | 380 |
| Potato Starch | 363 |
| Magnesium Stearate | 7 |
|  | 1000 |

The above ingredients are mixed directly to form a pessary.

Example 180

Anti-Viral Activity

We measured the enzyme inhibition constants of the compounds listed in Table I against HIV-1 protease using the methods of:

Maschera, B., Darby, G., Palú, G., Wright, L. L., Tisdale, M., Myers, R., Blair, E. D. and Furfine, E. S., Human Immunodefficiency Virus: Mutations in the Viral Protease that Confer Resistance to Saquinavir Increase the Dissociation Rate Constant for the Protease-Saquinavir Complex, *J. Biol. Chem.*, 271 33231–33235 (1996); and Toth, M. V. and Marshall, G. R. (1990) *Int. J. Peptide Protein Res.* 36, 544–550.

Antiviral activity assay in MT4 cells

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of $5 \times 10^5$ cells/ml. Cell aliquots were infected by the addition of HIV-1 (strain IIIB) diluted to give a viral multiplicity of infection of $100 \times TCID_{50}$. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted 6-fold with fresh medium, and 125 pl of the cell suspension was added to each well of the plate containing prediluted compound. Plates were then placed in a tissue culture incubator with humidified 5% $CO_2$ for 5 days. At the end of the incubation period, 27 μl of 5% Nonidet-40 was added to each well of the incubation plate. After thorough mixing with a Costar multitip pipetter, 60 Al of the mixture was transferred to filter-bottomed 96-well plates. The plates were analyzed in an automated assay instrument (Screen Machine, Idexx Laboratories). The assay makes use of a propidium iodide dye to estimate the DNA content of each well.

REFERENCES

1. Averett, D. R. 1989. Anti-HIV compound assessment by two novel high capacity assays. *J. Virol. Methods* 23: 263–276.
2. Schwartz, O., et al. 1988. A rapid and simple calorimetric test for the study of anti-HIV agents. *AIDS Res. and Human Retroviruses*, 4(6):441–447.
3. Daluge, S. M., et al. 1994. 5-chloro-2'3'-deoxy-3'fluorouridine (935U83), a selective anti-human immunodeficiency virus agent with an improved metabolic and toxicological profile. *Antimicro. Agents and Chemother.*, 38 (7):1590–1603.

The anti-viral potency of the compounds of Table 1 in MT-4 cells was determined using the above technique. The results are shown in Table 2 as $IC_{50}$ values expressed in μM.

In Table 2, the following classifications have been employed:

"A": $K_i$ of less than 1 nM;
"B": $K_i$ between 1 and 10 nM;
"C": $K_i$ between 10 and 100 nM;
"D": $K_i$ greater than 100 nM;
"E": $IC_{50}$ of 0.1 μM or less;
"F": $IC_{50}$ between 0.1 and 0.5 μM;
"G": $IC_{50}$ between 0.5 and 1.0 μM;
"H": $IC_{50}$ greater than 1.0 μM.

The designation "NA" is used where a given compound was not tested.

The designation ">" is used where a given Ki or $IC_{50}$ for a compound is greater than the range given for the designated letters.

TABLE 2

| Compound | Ki (enzyme) [nM] IC50 (MT-4 cells) [μM] | Compound | Ki (enzyme) [nM] IC50 (MT-4 cells) [μM] |
|---|---|---|---|
| 1 | C H | 19 | C H |
| 2 | C H | 20 | B H |
| 3 | C H | 21 | C H |
| 4 | C H | 22 | B H |
| 5 | B G | 23 | B H |
| 6 | C H | 24 | A H |
| 7 | B H | 25 | A G |
| 8 | A G | 26 | B H |
| 9 | B >E | 27 | A G |
| 11 | B H | 28 | A F |
| 12 | >B NA | 29 | A E |
| 13 | C NA | 30 | A F |
| 14 | A F | 31 | A E |
| 15 | B H | 32 | A E |
| 16 | C H | 33 | A E |
| 17 | C H | 34 | A F |
| 18 | B >G | 35 | A >G |
| 36 | A E | 55 | A E |
| 37 | A E | 56 | A F |
| 38 | A E | 57 | A E |
| 39 | A F | 58 | A F |
| 40 | A E | 59 | A E |
| 41 | A E | 60 | A F |
| 42 | A NA | 61 | B G |
| 43 | A NA | 62 | B H |
| 44 | A E | 63 | B NA |
| 45 | A E | 64 | A H |
| 46 | A E | 65 | A F |
| 47 | A G | 66 | A E |
| 48 | A F | 67 | A F |
| 49 | A E | 68 | A E |
| 50 | A E | 69 | A F |
| 51 | A F | 70 | A >F |
| 52 | A E | 71 | A E |
| 53 | A E | 72 | B G |
| 54 | A E | 73 | A E |
| 74 | A E | 100 | C F |

TABLE 2-continued

| Compound | Ki (enzyme) [nM] IC50 (MT-4 cells) [μM] | Compound | Ki (enzyme) [nM] IC50 (MT-4 cells) [μM] |
|---|---|---|---|
| 75 | A >F | 103 | A E |
| 76 | A F | 104 | A E |
| 77 | A E | 105 | A E |
| 78 | A E | 106 | A F |
| 79 | A F | 107 | A NA |
| 83 | A F | 108 | C >F |
| 84 | A NA | 109 | C >E |
| 85 | A NA | 110 | A F |
| 86 | A E | 111 | B H |
| 87 | A E | 112 | B H |
| 88 | A E | 113 | A E |
| 89 | A NA | 114 | A E |
| 90 | A E | 115 | D G |
| 91 | A NA | 116 | D G |
| 92 | A NA | 117 | D G |
| 97 | A E | 118 | D G |
| 98 | A NA | 119 | D H |
| 99 | A NA | | |
| 120 | NA NA | 137 | A E |
| 121 | A F | 138 | A E |
| 122 | A E | 139 | A E |
| 123 | A E | 140 | A E |
| 124 | A E | 141 | A H |
| 125 | A E | 142 | A F |
| 126 | D H | 143 | A E |
| 127 | A E | 144 | A E |
| 128 | D H | 145 | A E |
| 129 | NA NA | 146 | A E |
| 130 | A E | 147 | A E |
| 131 | A E | 148 | A E |
| 132 | A E | 149 | A E |
| 133 | A F | 150 | A E |
| 134 | A E | 151 | A E |
| 135 | B E | 152 | C G |
| 136 | A E | 153 | A E |
| 154 | A E | 164 | A E |
| 155 | A E | 165 | NA NA |
| 156 | A E | 166 | A E |
| 157 | NA NA | 167 | A F |
| 158 | NA NA | 168 | A E |
| 159 | A E | 169 | A E |
| 160 | A E | 170 | A E |
| 161 | B H | 171 | A E |
| 162 | A E | 172 | A E |
| 163 | A E | 173 | A E |

As demonstrated above, all of the compounds tested displayed inhibitory and anti-viral activity. Moreover, several of these compounds exhibited activity levels far greater than those of known HIV protease inhibitors. While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

We claim:

1. A compound of formula (I):

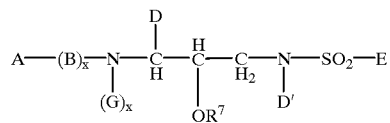

or a pharmaceutically acceptable salt or ester thereof, wherein:

A is selected from H; Ht; —$R^1$-Ht; —$R^1$—$C_1$-$C_6$ alkyl, which is optionally substituted with one or more groups independently selected from hydroxy, $C_1$-$C_4$ alkoxy, Ht, —O-Ht, —$NR^2$—CO—N$(R^2)_2$ or —CO—N$(R^2)_2$; —$R^1$—$C_2$-$C_6$ alkenyl, which is optionally substituted with one or more groups independently selected from hydroxy, $C_1$-$C_4$ alkoxy, Ht, —O-Ht, —$NR^2$—CO—N$(R^2)_2$ or —CO—N$(R^2)_2$; or $R^7$;

each $R^1$ is independently selected from —C(O)—, —S(O)$_2$—, —C(O)—C(O)—, —O—C(O)—, —O—S(O)$_2$, —$NR^2$—S(O)$_2$—, —$NR^2$—C(O)— or —$NR^2$—C(O)—C(O)—;

each Ht is independently selected from $C_3$-$C_7$ cycloalkyl; $C_5$-$C_7$ cycloalkenyl; $C_6$-$C_{10}$ aryl; or a 5–7 membered saturated or unsaturated heterocycle, containing one or more heteroatoms selected from a group consisting of N, N($R^2$), O, S and S(O)$_n$; wherein said aryl or said heterocycle is optionally fused to Q; and wherein any member of said Ht is optionally substituted with one or more substituents independently selected from oxo, —O$R^2$, S$R^2$, —$R^2$, —N($R^2$) ($R^2$), —$R^2$—OH, —CN, —CO$_2R^2$, —C(O)—N$(R^2)_2$, —S(O)$_2$—N$(R^2)_2$, —N($R^2$)—C(O)—$R^2$, —C(O)—$R^2$, —S(O)$_n$—$R^2$, —OCF$_3$, —S(O)$_n$—Q, methylenedioxy, —N(R$^2$)—S(O)$_2$(R$^2$), halo, —CF$_3$, —NO$_2$, Q, —OQ, —OR$^7$, —SR$^7$, —R$^7$, —N(R$^2$)(R$^7$) or —N(R$^7$)$_2$;

each R$^2$ is independently selected from H, Ht or C$_1$–C$_6$ alkyl optionally substituted with Q or R$^{10}$;

B, when present, is —N(R$^2$)—C(R$^3$)$_2$—C(O)—;

each x is independently 0 or 1;

each R$^3$ is independently selected from H, Ht, C$_1$–C$_6$ alkyl, C$_2$–C$_6$ alkenyl, C$_3$–C$_6$ cycloalkyl or C$_5$–C$_6$ cycloalkenyl; wherein any member of said R$^3$, except H, is optionally substituted with one or more substituents selected from —OR$^2$, —C(O)—NH—R$^2$, —S(O)$_n$—N(R$^2$)(R$^2$), Ht, —CN, —SR$^2$, —CO$_2$R$^2$, NR$^2$—C(O)—R$^2$;

each n is independently 1 or 2;

G, when present, is selected from H, R$^7$ or C$_1$–C$_4$ alkyl, or, when G is C$_1$–C$_4$ alkyl, G and R$^7$ are bound to one another either directly or through a C$_1$–C$_3$ linker to form a heterocyclic ring; or when G is not present, then the nitrogen to which G is attached is bound directly to the R$^7$ group in —OR$^7$ in formula I with the concomitant displacement of one —ZM group from R$^7$;

D is selected from a 3–7 membered saturated, partially saturated or unsaturated carbocyclic ring system; C$_1$–C$_6$ alkyl or C$_2$–C$_4$ alkenyl, which is optionally substituted with one or more 3–7 membered saturated, partially saturated or unsaturated carbocyclic ring systems; C$_3$–C$_6$ cycloalkyl or C$_5$–C$_6$ cycloalkenyl, which is optionally substituted with or fused to a 3–7 membered saturated, partially saturated or unsaturated carbocyclic ring system;

each Q is independently selected from a 3–7 membered saturated, partially saturated or unsaturated carbocyclic ring system; or a 5–7 membered saturated, partially saturated or unsaturated heterocyclic ring containing one or more heteroatoms selected from O, N, S, S(O)$_n$ or N(R$^2$); wherein Q is optionally substituted with one or more groups selected from oxo, —OR$^2$, —R$^2$, —N(R$^2$)$_2$, —N(R$^2$)—C(O)—R$^2$, —R$^2$—, —CN, —CO$_2$R$^2$, —C(O)—N(R$^2$)$_2$, halo or —CF$_3$;

D' is selected from —OR$^{10}$, —N=R$^{10}$ or —N(R$^{10}$)—N(R$^{10}$)—R$^1$—R$^3$;

E is Ht; O-Ht; —Ht-Ht; —O—R$^3$; —N(R$^2$)(R$^3$); C$_1$–C$_6$ alkyl, which is optionally substituted with one or more groups selected from R$^4$ or Ht; C$_2$–C$_6$ alkenyl, which is optionally substituted with one or more groups selected from R$^4$ or Ht; C$_3$–C$_6$ saturated carbocycle, which is optionally substituted with one or more groups selected from R$^4$ or Ht; or C$_5$–C$_6$ unsaturated carbocycle, which is optionally substituted with one or more groups selected from R$^4$ or Ht;

each R$^4$ is independently selected from —OR$^2$, —SR$^2$, —C(O)—NHR$^2$, —S(O)$_2$—NHR$^2$, halo, —NR$^2$—C(O)—R$^2$, —N(R$^2$)$_2$ or —CN;

each R$^7$ is independently selected from hydrogen,

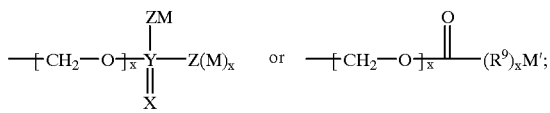

wherein each M is independently selected from H, Li, Na, K, Mg, Ca, Ba, —N(R$^2$)$_4$, C$_1$–C$_{12}$-alkyl, C$_2$–C$_{12}$-alkenyl, or —R$^6$; wherein 1 to 4 —CH$_2$ radicals of the alkyl or alkenyl group, other than the —CH$_2$ that is bound to Z, is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, —R$^2$, N(R$^2$)$_2$, N(R$^2$)$_3$, R$^2$OH, —CN, —CO$_2$R$^2$, —C(O)—N(R$^2$)$_2$, S(O)$_2$—N(R$^2$)$_2$, N(R$^2$)—C(O)—R$_2$, C(O)R$^2$, —S(O)$_n$—R$^2$, OCF$_3$, —S(O)$_n$—R$^6$, N(R$^2$)—S(O)$_2$(R$^2$), halo, —CF$_3$, or —NO$_2$;

M' is H, C$_1$–C$_{12}$-alkyl, C$_2$–C$_{12}$-alkenyl, or —R$^6$; wherein 1 to 4 —CH$_2$ radicals of the alkyl or alkenyl group is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, —R$^2$, —N(R$^2$)$_2$, N(R$^2$)$_3$, —R$^2$OH, —CN, —CO$_2$R$^2$, —C(O)—N(R$^2$)$_2$, —S(O)$_2$—N(R$_2$)$_2$, —N(R$^2$)—S(O)$_2$(R$^2$), halo, —CF$_3$, or —NO$_2$;

Z is O, S, N(R$^2$)$_2$, or, when M is not present, H;

Y is P or S;

X is O or S;

R$^9$ is C(R$^2$)$_2$, O or N(R$^2$); and wherein when Y is S, Z is not S;

R$^6$ is a 5–6 membered saturated, partially saturated or unsaturated carbocyclic or heterocyclic ring system, or an 8–10 membered saturated, partially saturated or unsaturated bicyclic ring system; wherein any of said heterocyclic ring systems contains one or more heteroatoms selected from O, N, S, S(O)$_n$ or N(R$^2$); and wherein any of said ring systems optionally contains 1 to 4 substituents independently selected from OH, C$_1$–C$_4$ alkyl, O-C$_1$–C$_4$ alkyl or O—C(O)—C$_1$–C$_4$ alkyl;

R$^8$ is selected from C$_1$–C$_8$ alkyl, C$_3$–C$_7$ alkyl or cyano substituted C$_2$–C$_6$ alkenyl; and R$^{10}$ is selected from C$_1$–C$_8$ alkyl, C$_2$–C$_6$ alkenyl, C$_6$–C$_{14}$ aryl or Ht, wherein R$^{10}$ optionally contains up to three substituents independently selected from —R$^3$, —CN, —SR$^5$, —SOR$^5$, —SO$_2$R$^5$,—SR—NR$^5$—C(O)R$^6$, —NR$^5$—(SO$_2$)R$^5$, —C(O)N(R$^5$)$_2$, —C(S)N(R$^5$)$_2$, —S(O)$_2$N(R$^5$)$_2$, —C(O)R$^6$, —C(S)R$^6$, —N(R$^5$)$_2$, —NR$^5$—C(O)R$^5$,—NR$^5$—C(O)OR$^5$,—NR$^5$—C(O)N(R$^5$)$_2$, —NR$^5$—C(S)R$^5$, —NR$^5$—C(S)OR$^5$, —NR$^5$—C(S)N(R$^5$)$_2$, —NR$^5$—C[=N(R$^5$)]—N(R$^5$)$_2$, —NH—C[=N—NO$_2$[—NH$_2$, —NH—C[=N—NO$_2$]—OR$^5$, —N(R$^8$)$_2$—C(O)R$^8$, —NH—C[=N—NO$_2$]—NH$_2$, —NH—C[=N—NO$_2$]—OR$^5$, —N(R$^8$)$_2$—C(O)R$^8$, —OC(O)R$^6$, —OC(O)N(R$^5$)$_2$, —OC(S)N(R$^5$)$_2$, wherein any one of the —CH$_2$ groups of said alkyl or alkenyl chains of R$^{10}$ may be optionally replaced by O, S, SO, SO$_2$, C(O) or NR$^5$;

wherein each R$^5$ is independently selected from hydrogen, C$_1$–C$_8$ alkyl, C$_2$–C$_8$ alkenyl, C$_2$–C$_8$ alkynyl or Ht, wherein each R$^5$, except for hydrogen, is optionally substituted with —CF3, —PO$_3$R$^3$, azido or halo.

2. The compound according to claim 1 or a pharmaceutically acceptable salt or ester thereof, wherein at least one R$^7$ is selected from:

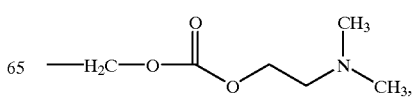

275

-continued

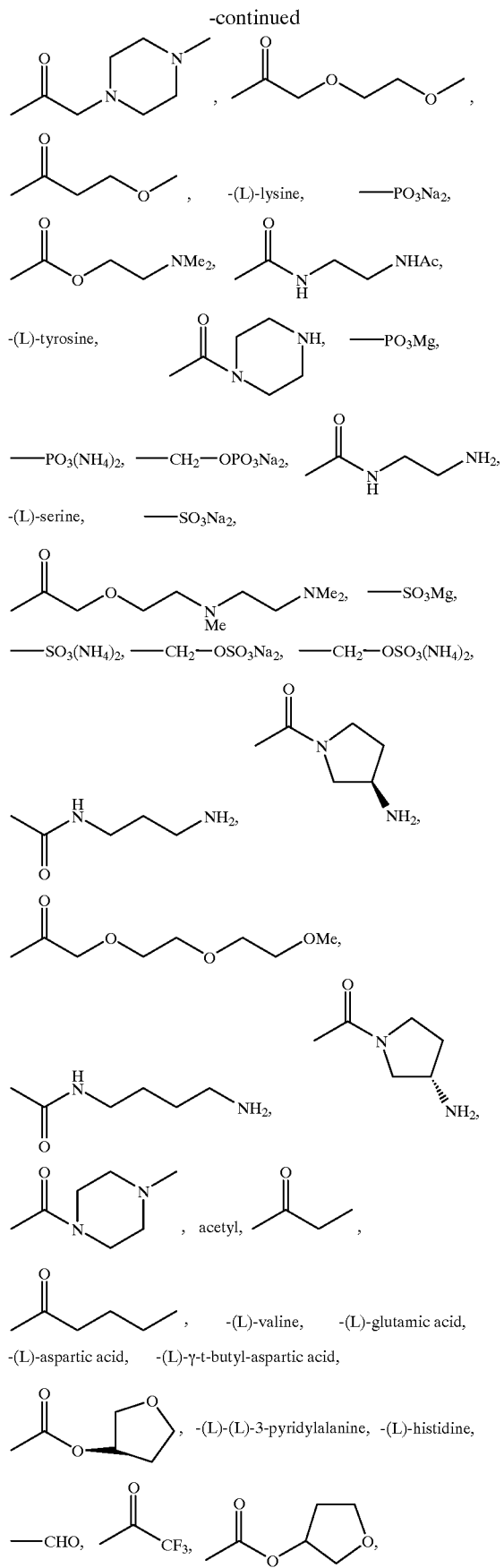

-(L)-lysine, —PO₃Na₂,

-(L)-tyrosine,

—PO₃Mg,

—PO₃(NH₄)₂, —CH₂—OPO₃Na₂,

-(L)-serine, —SO₃Na₂,

—SO₃(NH₄)₂, —CH₂—OSO₃Na₂, —CH₂—OSO₃(NH₄)₂,

, acetyl,

, -(L)-valine, -(L)-glutamic acid,

-(L)-aspartic acid, -(L)-γ-t-butyl-aspartic acid,

, -(L)-(L)-3-pyridylalanine, -(L)-histidine,

—CHO,

276

-continued

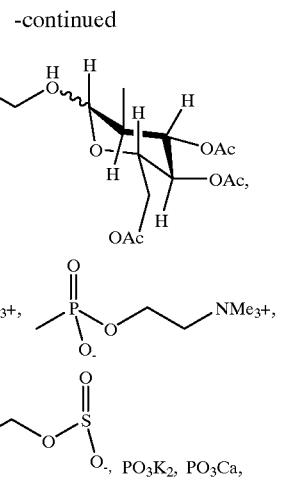

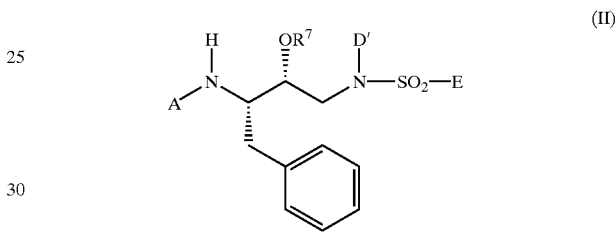

$PO_3$-spermine, $PO_3$-(spermidine)$_2$ or $PO_3$-(meglamine)$_2$.

3. A compound of formula (II):

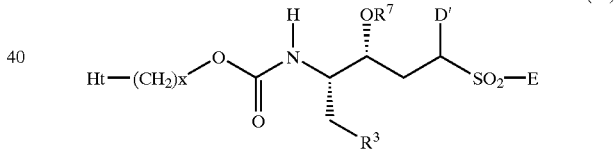

(II)

wherein A, $R^7$, D' and E are as defined in claim 1; or a pharmaceutically acceptable salt or ester thereof.

4. A compound of formula (III):

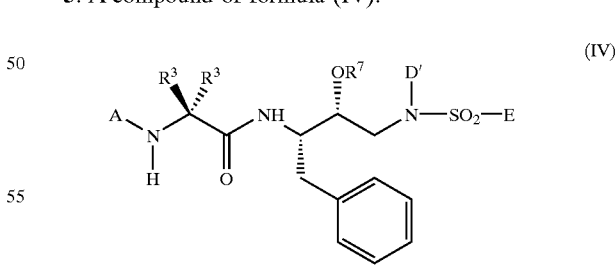

(III)

wherein Ht, x, $R^3$, $R^7$, D' and E are as defined in claim 1; or a pharmaceutically acceptable salt or ester thereof.

5. A compound of formula (IV):

(IV)

wherein A, $R^3$, $R^7$, D' and E are as defined in claim 1; or a pharmaceutically acceptable salt or ester thereof.

6. The compound according to claim 3 or a pharmaceutically acceptable salt or ester thereof, wherein:
  A is —C(O)Ht;
  D' is —O—$R^{10}$;
  E is $C_6$–$C_{10}$ aryl optionally substituted with one or more substituents selected from oxo, —$OR^2$, $SR^2$, —$R^2$, —N(R²)₂, —R²—OH, —CN, —CO₂R², —C(O)—N(R²)₂, —S(O)₂—N(R²)₂, —N(R²)—C(O)—R², —C(O)—R², —S(O)ₙ—R², —OCF₃, —S(O)ₙ-Q, methylenedioxy, —N(R²)—S(O)₂(R²), halo, —CF₃, —NO₂, Q, —OQ, —OR⁷, —SR⁷, —R⁷, —N(R²)(R⁷) or —N(R⁷)₂; or a 5-membered heterocyclic ring containing one S and optionally containing N as an additional heteroatom, wherein said heterocyclic ring is optionally substituted with one to two groups independently selected from —CH₃, R⁴, or Ht.

7. The compound according to claim 3 or a pharmaceutically acceptable salt or ester thereof, wherein:
E is a 5-membered heterocyclic ring containing one S and optionally containing N as an additional heteroatom, wherein said heterocyclic ring is optionally substituted with one to two groups independently selected from —CH₃, R⁴, or Ht.

8. The compound according to claim 3 or a pharmaceutically acceptable salt or ester thereof, wherein:
in —OR⁷ group shown in formula II is —PO(OM)₂ or C(O)CH₂OCH₂CH₂OCH₂CH₂OCH₃ and both R⁷ in —N(R⁷)₂ are H; or R⁷ in —OR⁷ group shown in formula II is C(O)CH₂OCH₂CH₂OCH₃, one R⁷ in —N(R⁷)₂ is C(O)CH₂OCH₂CH₂OCH₃ and the other is H; and
wherein M is H, Li, Na, K or C₁–C₄ alkyl.

9. The compound according to claim 1, having formula (V):

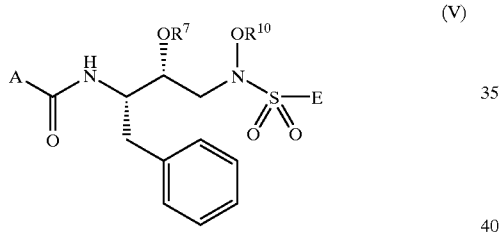

wherein A, R⁷, R¹⁰ and E are as defined in claim 1; or a pharmaceutically acceptable salt or ester thereof.

10. A compound of formula (VI):

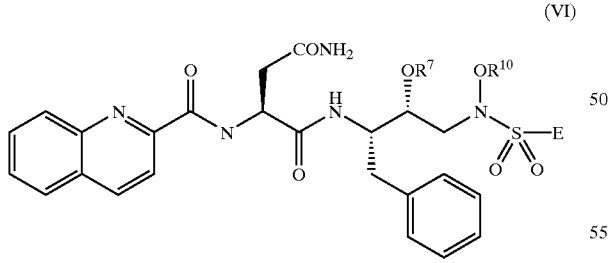

or a pharmaceutically acceptable salt or ester thereof, wherein:
R¹⁰ and R⁷ are as defined in claim 1;
E is C₆–C₁₄ aryl, optionally substituted with one or more groups selected from the group consisting of nitro, oxo, alkoxy, amino, hydroxyamino; heterocyclcyl, optionally substituted with one or more groups selected from the group consisting of nitro, oxo, alkoxy, amino, hydroxyamino or N(CO)OCH₃.

11. A compound of formula (VII):

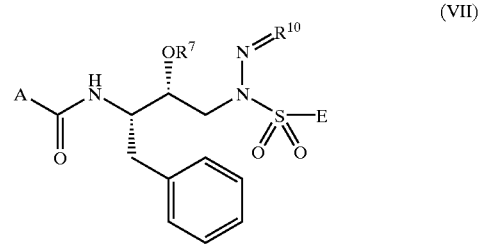

wherein A, E, R⁷ and R¹⁰ are as defined in claim 1; or a pharmaceutically acceptable salt or ester thereof.

12. A compound of formula (VIII):

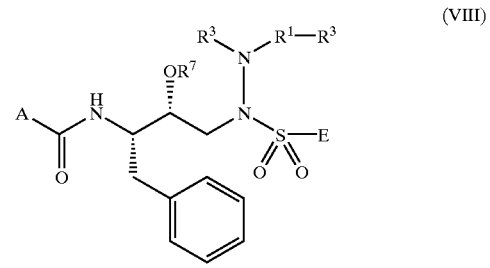

wherein A, R¹, R³, R⁷ and E are as defined in claim 1; or a pharmaceutically acceptable salt or ester thereof.

13. A compound selected from:

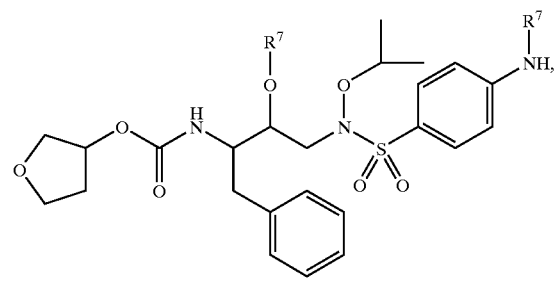

wherein R⁷ is as defined in claim 1 or a pharmaceutically acceptable salt or ester thereof.

14. A compound selected from:
(3R,3aS,6aR)hexahydrofuro[2,3-b]furan-3-yl N-((1S,2R)-1-benzyl-3-(cyclopentyloxy)[(3-[2-(dimethylamino)ethyl]aminophenyl)sulfonyl]amino-2-hydroxypropyl)carbamate;

(3S,3aR,6aS)hexahydrofuro[2,3-b]furan-3-yl N-((1S,2R)-1-benzyl-3-(cyclopentyloxy)[(3-[2-(dimethylamino)ethyl]aminophenyl) sulfonyl]amino-2-hydroxypropyl) carbamate;

(3R,3aS,6aR)Hexahydrofuro[2,3-b]furan-3-yl-N-((1S,2R)-1-benzyl-3-(cyclopentyloxy)(2-[(methylsulfonyl)amino]benzimidazol-5-ylsulfonyl)amino-2-hydroxypropyl)carbamate;

(3R,3aS,6aR hexahydrofuro [2,3-b]furan-3-yl N-(1S,2R)-3-[[(3-N-methylaminophenyl)sulfonyl](cyclopentyloxy)amino]-1-benzyl-2-hydroxypropylcarbamate;

1,3-Dioxan-5-yl N-(1S,2R)-1-benzyl-3-[(cyclopentyloxy) (2-{(methoxycarbonyl)amino]-1H-benzimidazol-5-ylsulfonyl) amino]-2-hydroxypropylcarbamate;

(3R,3aS,6aR hexahydrofuro[2,3-b]furan-3-yl N-(1S,2R)-1-benzyl-2-hydroxy-3-[[(4-methoxyphenyl) sulfonyl] (tetrahydro-2H-pyran-4-yloxy amino [propylcarbamate;

(3R,3aS,6aR hexahydrofuro[2,3-b]furan-3-yl N-(1S,2R)-3-[[(3-aminophenyl)sulfonyl](cyclopentyloxy)amino]-1-benzyl-2-hydroxypropylcarbamate;

(3R,3aS,6aR)hexahydrofuro[2,3-b]furan-3-yl N-[(1S,2R)-1-benzyl-3-((cyclopentyloxy)[3-(2-[methoxy (methyl)amino]-2-oxoethylamino) phenyl] sulfonylamino)-2-hydroxypropyl]carbamate;

(3R,3aS,6aR)hexahydrofuro[2,3-b]furan-3-yl N-[(1S,2R)-1-benzyl-4-(cyclopentyloxy)-2-hydroxy-4-(6-quinoxalinyl sulfonyl)butyl]carbamate;

(3R,3aS,6aR)hexahydrofuro[2,3-b]furan-3-yl N-((1S,2R)-1-benzyl-3-(cyclopentyloxy)[(4-methoxyphenyl) sulfonyl]amino-2-hydroxypropyl)carbamate;

(3R,3aS,6aR)hexahydrofuro[2,3-b]furan-3-yl N-[(1S,2R)-1-benzyl-3-((cyclopentyloxy)[3-(2-[(methylsulfonyl)amino]ethylamino)phenyl] sulfonylamino)-2-hydroxypropyl]carbamate;

(3R,3aS,6aR)hexahydrofuro[2,3-b]furan-3-yl N-(1S,2R)-3-[[(3-N-methylaminophenyl)sulfonyl] (cyclopentyloxy)amino]-1-benzyl-2-hydroxypropylcarbamate, phosphate ester;

(3R,3aS,6aR hexahydrofuro[2,3-b]furan-3-yl N-(1S,2R)-3-[[(3-aminophenyl)sulfonyl](cyclopentyloxy)amino]-1-benzyl-2-hydroxypropylcarbamate phosphate ester;

(3R,3aS,6aR) hexahydrofuro [2,3-b]furan-3-yl N-(1S,2R)-3-[[(4-aminophenyl)sulfonyl](cyclopentyloxy) amino]-1-benzyl-2-hydroxypropyl carbamate;

(3R,3aS,6aR)hexahydrofuro[2,3-b]furan-3-yl (1S,2R)-1-benzyl-3-{(1-ethylpropoxy)[(4-hydroxyphenyl) sulfonyl]amino}-2-hydroxypropylcarbamate;

(3R,3aS,6aR)hexahydrofuro[2,3-b]furan-3-yl (1S,2R)-3-[(1,3-benzodioxol-5-ylsulfonyl)(1-ethylpropoxy) amino]-1-benzyl-2-hydroxypropylcarbamate;

(3R,3aS,6aR)hexahydrofuro[2,3-b]furan-3-yl N-[(1S,2R)-3-[(1,3-benzodioxol-5-ylsulfonyl) (cyclopentyloxy) amino]-1-benzyl-2-(phosphonooxy) propyl]carbamate;

(3R,3aS,6aR)hexahydrofuro[2,3-b]furan-3-yl (1S,2R)-3-[(1,3-benzodioxol-5-ylsulfonyl)(cyclohexyloxy) amino]-1-benzyl -2-hydroxypropylcarbamate;

(3R,3aS,6aR)hexahydrofuro[2,3-b]furan-3-yl 3-[(1,3-benzodioxol-5-ylsulfonyl)(tetrahydro-2H-pyran-4-yloxy)amino]-1-benzyl-2-hydroxypropylcarbamate;

(3R,3aS,6aR)hexahydrofuro[2,3-b]furan-3-yl N-[(1S,2R)-3-[(1,3-benzodioxol-5-ylsulfonyl) (cyclopentyloxy)amino]-1-benzyl-2-(phosphonooxy) propyl]carbamate; or a pharmaceutically acceptable salt or ester thereof.

15. The compound according to claim 1 or a pharmaceutically acceptable salt or ester thereof wherein said compound has a molecular weight less than or equal to about 700 g/mol.

16. The compound according to claim 15 or a pharmaceutically acceptable salt or ester thereof wherein said compound has a molecular weight less than or equal to about 600 g/mol.

17. A pharmaceutical composition comprising a compound according to any one of claims 1–14 or a pharmaceutically acceptable salt or ester thereof together with a acceptable carrier therefore.

18. The pharmaceutical composition according to claim 17, further comprising an antiviral agent other than a compound according to claims 1–14.

19. A pharmaceutical composition according to claim 17 or 18 in the form of a tablet or capsule.

20. A method of treating a patient infected with a retrovirus that depends upon an aspartyl protease for an obligatory event in its life cycle comprising the step of administering to said patient an effective antiviral treatment amount of a compound according to any one of claims 1–14 or a pharmaceutically acceptable salt or ester thereof.

21. The method according to claim 20 wherein the retrovirus is HIV.

22. The method according to claim 20 wherein said of administering comprises oral administration of administration by injection.

23. The method according to claim 21 wherein said step of administering comprises oral administration or administration by injection.

24. A method of inhibiting aspartyl protease in a patient in need thereof comprising the step of administering to said patient a compound according to any one of claims 1–14 or a pharmaceutically acceptable salt or ester thereof.

25. A method of treating a patient diagnosed with AIDS, AIDS related complex (ARC), progressive generalized lymphadenopathy (PGL), Kaposi's sarcoma, thrombocytopenic purpura, AIDS-related neurological conditions, AIDS dementia complex, HIV-associated multiple sclerosis, tropical paraperesis, anti-HIV antibody-positive conditions or HIV-positive conditions, comprising the step of administering to said patient a compound according to any one of claims 1–14 or a pharmaceutically acceptable salt or ester thereof.

* * * * *